US012766189B2

(12) United States Patent
Tursi et al.

(10) Patent No.: US 12,766,189 B2
(45) Date of Patent: *Oct. 20, 2026

(54) METHODS OF TREATING PLANTAR FIBROMATOSIS

(71) Applicant: Endo Biologics Limited, Dublin (IE)

(72) Inventors: James P. Tursi, Moorestown, NJ (US); Luis A. Ortega, Manheim, PA (US); Qinfang Xiang, West Chester, PA (US); Saji Vijayan, Chester Springs, PA (US); Jeffrey David Lehrman, Fort Collins, CO (US); David Hernandez, Lititz, PA (US)

(73) Assignee: Endo Biologics Limited, Dublin (IE)

( * ) Notice: Subject to any disclaimer, the term of this patent is extended or adjusted under 35 U.S.C. 154(b) by 10 days.

This patent is subject to a terminal disclaimer.

(21) Appl. No.: 19/288,073

(22) Filed: Aug. 1, 2025

(65) Prior Publication Data

US 2026/0091092 A1 Apr. 2, 2026

Related U.S. Application Data

(60) Provisional application No. 63/764,721, filed on Feb. 28, 2025, provisional application No. 63/678,664, filed on Aug. 2, 2024.

(51) Int. Cl.

| | |
|---|---|
| ***A61K 38/48*** | (2006.01) |
| ***A61K 9/00*** | (2006.01) |
| ***A61P 19/04*** | (2006.01) |
| ***A61P 35/00*** | (2006.01) |

(52) U.S. Cl.

CPC ........ *A61K 38/4886* (2013.01); *A61K 9/0019* (2013.01); *A61P 19/04* (2018.01); *A61P 35/00* (2018.01); *C12Y 304/24003* (2013.01)

(58) Field of Classification Search

CPC .............. A61K 38/4886; A61K 9/0019; C12Y 304/24003

See application file for complete search history.

(56) References Cited

U.S. PATENT DOCUMENTS

| | | | |
|---|---|---|---|
| 7,811,560 | B2 | 10/2010 | Sabatino et al. |
| 9,636,385 | B2 | 5/2017 | Honkanen |
| 9,744,138 | B2 | 8/2017 | Leppert et al. |
| 9,757,435 | B2 | 9/2017 | Herber |

FOREIGN PATENT DOCUMENTS

| | | | |
|---|---|---|---|
| WO | 2012/125948 | A1 | 9/2012 |
| WO | 2012/155212 | A1 | 11/2012 |
| WO | 2020/058755 | A1 | 3/2020 |

OTHER PUBLICATIONS

Mahmoud et al. The successful use of collagenase for Ledderhose disease (plantar fibromatosis) in a paediatric patient: a case report. Journal of Surgical Case Reports. 2021;2:1-3.*

Hwang et al. Follow-up of clinical and sonographic features after extracorporeal shock wave therapy in painful plantar fibromatosis. PLoS One. 2020; 15(8):e0237447.*

Warwick et al. Collagenase Clostridium histolyticum: emerging practice patterns and treatment advances. Journal of Plastic Surgery and Hand Surgery. 2016;50(5):251-261.*

McCaffery et al. The Numeric Pain Rating Scale Instructions. www.rehabmeasures.org. 1989;1.*

Adnane et al. Continuous phenobarbital treatment and palmoplantar fibromatosis. World Journal of Advanced Research and Reviews. 2020;05(02):060-066.*

Budiman-Mak et al., "A review of the foot function index and the foot function index-revised", J. Foot Ankle Res., 2013, 6(1), 5.

Budiman-Mak et al., "The Foot Function Index: A Measure of Foot Pain and Disability", J. Clin. Epidemiol., 1991, 44(6), 561-570.

Gisslow et al., "A Rapid Sensitive Collagenase Assay", Anal. Biochem., 1975, 68, 70-78.

Robertson et al., "A Reproducible Quantitative Collagenase Radiofibril Assay", Clinica Chemica Acta, 1972, 42, 43-45.

Sakamoto et al., "A new method for the Assay of Tissue Collagenase (36297)", 1972.

Worthington Biochemical Corp. Assay (www_worthington-biochem_com/CLS/assay), accessed Jul. 3, 2019.

American College of Foot and Ankle Surgeons, "Plantar Fibroma", 2010, 2 pages.

Endo, "Endo Presents New Investigational Collagenase Clostridium Histolyticum Data at the American Podiatric Medical Association Annual Scientific Meeting", Jul. 29, 2021, Retrieved from https://investor.endo.com/2021-07-29-Endo-Presents-New-Investigational-Collagenase-Clostridium-Histolyticum-Data-at-the-American-Podiatric-Medical-Association-Annual-Scientific-Meeting#, pp. 1-5.

Akdag et al., "Dupuytren-Like Contracture of the Foot: Ledderhose Disease," Surg J (N Y), vol. 2, Issue 3, 2016, pp. e102-e104.

Allen et al., "Soft-tissue tumors of the sole; with special reference to plantar fibromatosis," J Bone Joint Surg Am, vol. 37, 1955, pp. 14-26.

Aviles et al., "Plantar fibromatosis," Surgery, vol. 69, 1971, pp. 117-120.

Carroll et al., "Plantar Fibromatosis: Pathophysiology, Surgical and Nonsurgical Therapies: An Evidence-Based Review," Foot Ankle Spec, vol. 11, Issue 2, 2018, pp. 168-176.

Cavolo et al., "Dupuytren's disease of the plantar fascia," J Foot Surg, vol. 21, 1982, pp. 12-15.

De Bree et al., "Incidence and treatment of recurrent plantar fibromatosis by surgery and postoperative radiotherapy," Am J Surg, vol. 187, Issue 1, 2004, pp. 33-38.

DeVitis et al., "Unusual Intranodular Collagenase Injection: A Case of Bilateral Ledderhose Disease", Plast Reconstr Surg Glob Open, Apr. 27, 2020, vol. 8, 1-3.

Downey et al., "Point-Counterpoint: Is conservative care the best approach for plantar fibromatosis?," Podiatry Today, vol. 26, 2013, pp. 36-42.

Draghi et al., "Imaging of plantar fascia disorders: findings on plain radiography, ultrasound and magnetic resonance imaging," Insights Imaging, vol. 8, Issue 1, 2017, pp. 69-78.

(Continued)

*Primary Examiner* — Lynn Y Fan

(74) *Attorney, Agent, or Firm* — BakerHostetler

(57) ABSTRACT

Disclosed herein are methods of treating plantar fibromatosis in a subject or a population of subjects.

13 Claims, 44 Drawing Sheets

Specification includes a Sequence Listing.

(56) References Cited

OTHER PUBLICATIONS

Fausto de Souza et al., "Ledderhose diease an unusual presentation," J Clin Aesthet Dermatol, vol. 3, Issue 9, 2010, pp. 45-47.
Fuiano et al., "Current concepts about treatment options of plantar fibromatosis: A systematic review of the literature," Foot Ankle Surg, vol. 25, Issue 5, 2019, pp. 559-564.
Gordon, "Dupuytren's contracture: plantar involvement," Br J Plast Surg, vol. 17, 1964, pp. 421-423.
Greenfield et al., "Ultrasound-Guided Collagenase Injection Therapy of Recurrent Plantar Fibromatosis: A Case Report", Foot and Ankle Orthopaedics 2023, 8(4): 1-5.
Griffith et al., "Sonography of plantar fibromatosis," AJR Am J Roentgenol, vol. 179, Issue 5, 2002, pp. 1167-1172.
Gudmundsson et al., "Association of Morbus Ledderhose with Dupuytren's contracture," Foot Ankle Int, vol. 34, 2013, pp. 841-845.
Haedicke et al, "Plantar fibromatosis: an isolated disease," Plast Reconstr Surg, vol. 82, Issue 2, 1989, pp. 296-300.
Hammoudeh, "Collagenase Clostridium histolyticum injection for plantar fibromatosis (Ledderhose disease)," Plast Reconstr Surg, vol. 134, Issue 3, 2014, pp. 497e-498e.
Heyd et al., "Radiation therapy for early stages of morbus Ledderhose," Strahlenther Onkol, vol. 186, Issue 1, 2010, pp. 24-29.
Johnston et al., "Plantar fibromatosis: literature review and a unique case report," J Foot Surg, vol. 31, 1992, pp. 400-406.
Keller et al., "The preparation of purified collagenase," Archives of Biochemistry and Biophysics, vol. 101, Issue 1, Apr. 1963, pp. 81-87.
Lehrman et al, "The Effects of Collagenase Clostridium histolyticum on Plantar Fibromatosis: A Case Study", The Journal of Foot and Ankle Surgery, 2019, 58: 1281-1284.
McNally et al., "Plantar fascia: imaging diagnosis and guided treatment," Semin Musculoskelet Radiol, vol. 14, Issue 3, 2010, pp. 334-343.
Moon et al., "Plantar Fibromatosis Clinical Presentation," Medscape. Updated Jul. 10, 2018. Accessed Oct. 29, 2019.
Pentland et al., "Plantar fibromatosis responds to intralesional steroids," J Am Acad Dermatol, vol. 12, 1985, pp. 212-214.
Sammarco et al., "Classification and treatment of plantar fibromatosis," Foot Ankle Int, vol. 21, 2000, pp. 563-569.
Seegenschmiedt et al., "Radiation therapy for shingles—Indication and clinical results", vol. 179, 2003, pp. 847-853.
Syed et al., "In vitro study of novel collagenase (Xiaflex®) on Dupuytren's disease fibroblasts displays unique drug related properties," PLoS One, vol. 7, Issue 2, 2012, e31430, pp. 1-22.
Tabchi et al., Crozer Keystone Health System, "The Effects of Collagenase Clostridium histolyticum on Plantar fibromatosis: A Case Study", Poster Presentation; Feb. 2015.
Traore et al., "Collagenase Clostridium histolyticum in the management of Peyronie's disease: a review of the evidence", Therapeutic Advances in Urology, 2016, vol. 8, No. 3, 192-202.
Van der Veer et al., "Recurrence of plantar fibromatosis after plantar fasciectomy: single-center long-term results", Plast Reconstr Surg, vol. 122, Issue 2, 2008, 486-491.
Veith et al., "Plantar fibromatosis—topical review," Foot Ankle Int, vol. 34, Issue 12, 2013, pp. 1742-1746.
Wapner et al,, "Plantar fibromatosis: a review of primary and recurrent surgical treatment," Foot Ankle Int, vol. 16, Issue 9, 1995, pp. 548-551.
Xiaflex [US Prescribing Information], Malvern, PA, Endo Pharmaceuticals Inc., Nov. 2019, 43pp.
Young et al., "The etiology, evaluation, and management of plantar fibromatosis," Orthop Res Rev, vol. 11, 2018, pp. 1-7.

* cited by examiner

Day 1

Day 22

FIG. 28
EN3835
70
65
60
55
50
45
40
35
30
Day 1
Day 15
Day 29
Day 43
Day 57
Day 117
Day 197
Day 237

FIG. 37

Please choose the response below that best describes your foot pain in the past 24 hours.

| | | | | | | | | | | |
|---|---|---|---|---|---|---|---|---|---|---|
| ☐ 0 | ☐ 1 | ☐ 2 | ☐ 3 | ☐ 4 | ☐ 5 | ☐ 6 | ☐ 7 | ☐ 8 | ☐ 9 | ☐ 10 |
| No pain | | | | | | | | | | Worst pain imaginable |

FIG. 38

Please choose the response below that best represents your foot pain immediately before taking rescue medication.

| | | | | | | | | | | |
|---|---|---|---|---|---|---|---|---|---|---|
| ☐<br>0 | ☐<br>1 | ☐<br>2 | ☐<br>3 | ☐<br>4 | ☐<br>5 | ☐<br>6 | ☐<br>7 | ☐<br>8 | ☐<br>9 | ☐<br>10 |

No pain

Worst pain imaginable

FIG. 39

The Activity Limitation Subscale is provided below. Please choose the best number to indicate how often you performed the following activities in the past week because of your feet.

A. In the past week, how much of the time did you:

| | | | | | |
|---|---|---|---|---|---|
| 1. Stay indoors most of the day because of foot problems? | 0 Never | 1 Rarely | 2 Sometimes | 3 Often | 4 Always |
| 2. Stay off one or both of your feet most of the day because of foot problems? | 0 Never | 1 Rarely | 2 Sometimes | 3 Often | 4 Always |
| 3. Limit your activities because of your foot problems? | 0 Never | 1 Rarely | 2 Sometimes | 3 Often | 4 Always |

FIG. 40

The Difficulty Subscale is provided below. Please choose the best number to indicate how much difficulty you experienced because of your feet when performing these activities in the past week.

B. In the past week, how much difficulty did you have:

| | | | | | |
|---|---|---|---|---|---|
| 1. Walking around the house? | 0 No difficulty | 1 A little difficulty | 2 Some difficulty | 3 Much difficulty | 4 A lot of difficulty |
| 2. Walking outside on uneven ground? | 0 No difficulty | 1 A little difficulty | 2 Some difficulty | 3 Much difficulty | 4 A lot of difficulty |
| 3. Walking four or more blocks? | 0 No difficulty | 1 A little difficulty | 2 Some difficulty | 3 Much difficulty | 4 A lot of difficulty |
| 4. Climbing stairs? | 0 No difficulty | 1 A little difficulty | 2 Some difficulty | 3 Much difficulty | 4 A lot of difficulty |
| 5. Descending stairs? | 0 No difficulty | 1 A little difficulty | 2 Some difficulty | 3 Much difficulty | 4 A lot of difficulty |
| 6. Standing on tiptoes? | 0 No difficulty | 1 A little difficulty | 2 Some difficulty | 3 Much difficulty | 4 A lot of difficulty |
| 7. Getting out of a chair? | 0 No difficulty | 1 A little difficulty | 2 Some difficulty | 3 Much difficulty | 4 A lot of difficulty |
| 8. Climbing up or down curbs? | 0 No difficulty | 1 A little difficulty | 2 Some difficulty | 3 Much difficulty | 4 A lot of difficulty |
| 9. Walking or running fast? | 0 No difficulty | 1 A little difficulty | 2 Some difficulty | 3 Much difficulty | 4 A lot of difficulty |

FIG. 41

The Pain Subscale is provided below. Please choose the best number to indicate the severity of your foot pain during the past week in the following situations.

C. In the past week, how severe was your foot pain:

| | | | | | |
|---|---|---|---|---|---|
| 1. At its worst? | 0 None | 1 Mild | 2 Moderate | 3 Severe | 4 Extreme |
| 2. Before you get up in the morning? | 0 None | 1 Mild | 2 Moderate | 3 Severe | 4 Extreme |
| 3. When you walk barefoot? | 0 None | 1 Mild | 2 Moderate | 3 Severe | 4 Extreme |
| 4. When you stand barefoot? | 0 None | 1 Mild | 2 Moderate | 3 Severe | 4 Extreme |
| 5. When you walk wearing shoes? | 0 None | 1 Mild | 2 Moderate | 3 Severe | 4 Extreme |
| 6. When you stand wearing shoes? | 0 None | 1 Mild | 2 Moderate | 3 Severe | 4 Extreme |
| 7. When you walk wearing orthotics? ☐ Do not wear orthotics | 0 None | 1 Mild | 2 Moderate | 3 Severe | 4 Extreme |
| 8. When you stand wearing orthotics? ☐ Do not wear orthotics | 0 None | 1 Mild | 2 Moderate | 3 Severe | 4 Extreme |
| 9. At the end of the day? | 0 None | 1 Mild | 2 Moderate | 3 Severe | 4 Extreme |

METHODS OF TREATING PLANTAR FIBROMATOSIS

CROSS REFERENCE TO RELATED APPLICATIONS

This application claims priority to U.S. Provisional Application No. 63/678,664, filed on Aug. 2, 2024, and U.S. Provisional Application No. 63/764,721, filed on Feb. 28, 2025, the disclosure of which are hereby incorporated by reference in their entirety.

SEQUENCE LISTING

The instant application contains a Sequence Listing which is being submitted herewith electronically in XML format and is hereby incorporated by reference in its entirety. Said XML copy, created on Jul. 25, 2025, is named 117326.000627_SL.xml and is 8,704 bytes in size.

FILED OF THE INVENTION

Disclosed herein are methods of treating plantar fibromatosis and the use of collagenase in the treatment of plantar fibromatosis.

BACKGROUND OF THE INVENTION

Plantar fibromatosis is a rare pathology of the plantar aponeurosis characterized by disordered fibrous tissue and subsequent formation of nodules of the feet. Specifically, the disease is characterized by nodules in the medial or central plantar fascia, which are formed by excess collagen leading to fibrotic tissue. Plantar fibromatosis presents bilaterally in 25% of patients with males predominantly affected. Symptoms range from local pressure and distention, to tender erythematous lesions that can affect the patient's ability to bear weight and walk. The primary symptom most patients experience is a slow-growing lump along the medial longitudinal arch, which becomes painful and causes swelling as it enlarges. In rare cases, the fibromatosis leads to toe contractures, which potentially can lead to shrinkage and sclerosis of the fascia. The condition reduces quality of life and can cause functional disability, leading to severe impairment in some patients.

Because there is no available therapy that addresses the pathophysiology of plantar fibromatosis to date, disease progression cannot be prevented. Current treatment of plantar fibromatosis is aimed at symptom relief and is adapted to the severity of the disease. Nonsurgical treatment options are available for the less painful stages of the disease. If pain reduction cannot be achieved and a stage of strong fibroblast activity has been reached, other therapeutic options such as X-ray irradiation and surgery are considered. The long-term safety of radiation therapy has not been established and the risk of malignant changes at the radiation site is not known. Surgical treatment is the only indicated treatment option in cases of persistent pain, but the recurrence rate is relatively high (between 60% and 100%) and the postsurgical burden to patients is significant due to tenderness and prolonged recovery.

SUMMARY OF THE INVENTION

Disclosed herein are methods of treating moderate to severe plantar fibromatosis in a subject or a population of subjects, the methods comprising:

- intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.45 mg to about 1.35 mg and the treating comprises:
- a reduction from baseline as measured on a foot function index (FFI) pain sub scale;
- a reduction from baseline as measured on a FFI combined pain and difficulty subscale;
- an improvement from baseline as measured on a patient global impression of change (PGIC)-PF overall scale;
- a reduction from baseline as measured on a FFI total composite score;
- an improvement from baseline as measured on a subject satisfaction with treatment scale;
- a reduction from baseline in LSM FFI Foot Pain score;
- a reduction from baseline in combined FFI pain and difficulty score;
- or any combination thereof.

Disclosed herein are methods of treating moderate to severe plantar fibromatosis in a subject or population of subjects by administering a collagenase enzyme at a dose of about 0.45 mg to about 1.35 mg per nodule, the collagenase enzyme comprising:

- means for breaking down collagen type I, collagen type III, and combinations thereof,
- wherein the treating comprises:
- a reduction from baseline as measured on a foot function index (FFI) pain sub scale;
- at a reduction from baseline as measured on a FFI combined pain and difficulty subscale;
- an improvement from baseline as measured on a patient global impression of change (PGIC)-PF overall scale;
- a reduction from baseline as measured on a FFI total composite score;
- an improvement from baseline as measured on a subject satisfaction with treatment scale;
- a reduction from baseline in LSM FFI Foot Pain score;
- a reduction from baseline in combined FFI pain and difficulty score;
- or any combination thereof.

Disclosed herein are methods of treating moderate to severe plantar fibromatosis in a subject or a population of subjects, the methods comprising:

- intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.6 mg, and the treating comprises:
- a reduction from baseline in the weekly mean of the average daily pain (ADP) score;
- a reduction from baseline in the FFI Difficulty Subscale score of the FFI;
- a reduction from baseline on the FFI Activity Limitation Subscale score;
- a reduction from baseline in the weekly mean of the ADP score;
- a reduction from baseline on the FFI Pain Subscale score;
- a reduction from baseline on the FFI Total score;
- an improvement from baseline on the PGIS PF Overall score;
- an improvement from baseline on the PGIS Foot Pain Subscale;

an improvement from baseline on the PGIS Difficulty Subscale;
an improvement from baseline on the PGIS Activity Limitation Subscale;
an improvement from baseline in nodule consistency (firmness);
a reduction from baseline in the nodular hardness;
a reduction from baseline in LSM FFI Foot Pain score;
a reduction from baseline in combined FFI pain and difficulty score;
or any combination thereof.

Disclosed herein are methods of treating moderate to severe plantar fibromatosis in a subject or a population of subjects by administering a collagenase enzyme at a dose of about 0.6 mg per nodule, the collagenase enzyme comprising:

means for breaking down collagen type I, collagen type III, and combinations thereof'
wherein the treating comprises:
a reduction from baseline in the weekly mean of the average daily pain (ADP) score;
a reduction from baseline in the FFI Difficulty Subscale score of the FFI;
a reduction from baseline on the FFI Activity Limitation Subscale score;
a reduction from baseline in the weekly mean of the ADP score;
a reduction from baseline on the FFI Pain Subscale score;
a reduction from baseline on the FFI Total score;
an improvement from baseline on the PGIS PF Overall score;
an improvement from baseline on the PGIS Foot Pain Subscale;
an improvement from baseline on the PGIS Difficulty Subscale;
an improvement from baseline on the PGIS Activity Limitation Subscale;
an improvement from baseline in nodule consistency (firmness);
a reduction from baseline in the nodular hardness;
a reduction from baseline in LSM FFI Foot Pain score;
a reduction from baseline in combined FFI pain and difficulty score;
or any combination thereof.

Disclosed herein are methods of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.45 mg to about 1.35 mg and the treating comprises:
a reduction from baseline as measured on a foot function index (FFI) pain sub scale;
a reduction from baseline as measured on a FFI combined pain and difficulty subscale;
an improvement from baseline as measured on a patient global impression of change (PGIC)-PF overall scale;
a reduction from baseline as measured on a FFI total composite score;
an improvement from baseline as measured on a subject satisfaction with treatment scale;
a reduction from baseline in LSM FFI Foot Pain score;
a reduction from baseline in combined FFI pain and Difficulty score;

an improvement from baseline in nodule consistency;
a reduction from baseline in the nodular hardness;
or any combination thereof.

Disclosed herein are methods of treating moderate to severe plantar fibromatosis in a subject or a population of subjects by administering a collagenase enzyme at a dose of about 0.45 mg to about 1.35 mg per nodule, the collagenase enzyme comprising:

means for breaking down collagen type I, collagen type III, and combinations thereof,
wherein the treating comprises:
a reduction from baseline as measured on a foot function index (FFI) pain sub scale;
a reduction from baseline as measured on a FFI combined pain and difficulty subscale;
an improvement from baseline as measured on a patient global impression of change (PGIC)-PF overall scale;
a reduction from baseline as measured on a FFI total composite score;
an improvement from baseline as measured on a subject satisfaction with treatment scale;
a reduction from baseline in LSM FFI Foot Pain score;
a reduction from baseline in combined FFI pain and Difficulty score;
an improvement from baseline in nodule consistency;
a reduction from baseline in the nodular hardness;
or any combination thereof.

Disclosed herein are methods of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.45 mg to about 1.35 mg and the treating comprises:
an improvement from baseline in nodule consistency;
a reduction from baseline in the nodular hardness;
or a combination thereof.

Disclosed herein are methods of treating moderate to severe plantar fibromatosis in a subject or a population of subjects by administering a collagenase enzyme at a dose of about 0.45 mg to about 1.35 mg per nodule, the collagenase enzyme comprising:

means for breaking down collagen type I, collagen type III, and combinations thereof,
wherein the treating comprises:
an improvement from baseline in nodule consistency;
a reduction from baseline in the nodular hardness;
or a combination thereof.

Disclosed herein are methods of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.6 mg, and the treating comprises:

an improvement from baseline in nodule consistency;
a reduction from baseline in the nodular hardness;
or a combination thereof.

Disclosed herein are methods of treating moderate to severe plantar fibromatosis in a subject or a population of subjects by administering a collagenase enzyme at a dose of about 0.6 mg per nodule, the collagenase enzyme comprising:

means for breaking down collagen type I, collagen type III, and combinations thereof' wherein the treating comprises:

an improvement from baseline in nodule consistency;

a reduction from baseline in the nodular hardness;

or a combination thereof.

Disclosed herein are methods of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.45 mg to about 1.35 mg and the treating comprises:

a reduction from baseline as measured on a foot function index (FFI) pain sub scale;

a reduction from baseline as measured on a FFI combined pain and difficulty subscale;

a reduction from baseline in LSM FFI Foot Pain score;

a reduction from baseline in combined FFI pain and Difficulty score;

or any combination thereof.

Disclosed herein are methods of treating moderate to severe plantar fibromatosis in a subject or a population of subjects by administering a collagenase enzyme at a dose of about 0.45 mg to about 1.35 mg per nodule, the collagenase enzyme comprising:

means for breaking down collagen type I, collagen type III, and combinations thereof, wherein the treating comprises:

a reduction from baseline as measured on a foot function index (FFI) pain sub scale;

a reduction from baseline as measured on a FFI combined pain and difficulty subscale;

a reduction from baseline in LSM FFI Foot Pain score;

a reduction from baseline in combined FFI pain and Difficulty score;

or any combination thereof.

Disclosed herein are methods of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.6 mg, and the treating comprises:

a reduction from baseline in the weekly mean of the average daily pain (ADP) score;

a reduction from baseline in the weekly mean of the ADP score;

a reduction from baseline on the FFI Pain Subscale score;

an improvement from baseline on the PGIS Foot Pain Subscale;

a reduction from baseline in LSM FFI Foot Pain score;

a reduction from baseline in combined FFI pain and Difficulty score;

or any combination thereof.

Disclosed herein are methods of treating moderate to severe plantar fibromatosis in a subject or a population of subjects by administering a collagenase enzyme at a dose of about 0.6 mg per nodule, the collagenase enzyme comprising:

means for breaking down collagen type I, collagen type III, and combinations thereof' wherein the treating comprises:

a reduction from baseline in the weekly mean of the average daily pain (ADP) score;

a reduction from baseline in the weekly mean of the ADP score;

a reduction from baseline on the FFI Pain Subscale score;

an improvement from baseline on the PGIS Foot Pain Subscale;

a reduction from baseline in LSM FFI Foot Pain score;

a reduction from baseline in combined FFI pain and Difficulty score;

or any combination thereof.

Disclosed herein are methods of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.45 mg to about 1.35 mg and the treating comprises:

an improvement from baseline as measured on a patient global impression of change (PGIC)-PF overall scale;

a reduction from baseline as measured on a FFI total composite score;

an improvement from baseline as measured on a subject satisfaction with treatment scale;

or any combination thereof.

Disclosed herein are methods of treating moderate to severe plantar fibromatosis in a subject or a population of subjects by administering a collagenase enzyme at a dose of about 0.45 mg to about 1.35 mg per nodule, the collagenase enzyme comprising:

means for breaking down collagen type I, collagen type III, and combinations thereof, wherein the treating comprises:

an improvement from baseline as measured on a patient global impression of change (PGIC)-PF overall scale;

a reduction from baseline as measured on a FFI total composite score;

an improvement from baseline as measured on a subject satisfaction with treatment scale;

or any combination thereof.

Disclosed herein are methods of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.6 mg, and the treating comprises:

a reduction from baseline in the FFI Difficulty Subscale score of the FFI;

a reduction from baseline on the FFI Activity Limitation Subscale score;

a reduction from baseline on the FFI Total score;

an improvement from baseline on the PGIS PF Overall score;

an improvement from baseline on the PGIS Difficulty Subscale;

an improvement from baseline on the PGIS Activity Limitation Subscale;

or any combination thereof.

Disclosed herein are methods of treating moderate to severe plantar fibromatosis in a subject or a population of subjects by administering a collagenase enzyme at a dose of about 0.6 mg per nodule, the collagenase enzyme comprising:

means for breaking down collagen type I, collagen type III, and combinations thereof' wherein the treating comprises:

a reduction from baseline in the FFI Difficulty Subscale score of the FFI;

a reduction from baseline on the FFI Activity Limitation Subscale score;

a reduction from baseline on the FFI Total score;

an improvement from baseline on the PGIS PF Overall score;

an improvement from baseline on the PGIS Difficulty Subscale;

an improvement from baseline on the PGIS Activity Limitation Subscale;

or any combination thereof.

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments of the methods; however, the methods are not limited to the specific embodiments disclosed. In the drawings:

FIG. 1A illustrates the dosing schedule and timing of ultrasounds (US). FIG. 1B illustrates the timing of the various assessments during the Initial Treatment Period.

FIG. 7A: Day 1; FIG. 7B: Day 22.

FIG. 13A—Periphery of nodule when nodule's largest diameter is length. FIG. 13B—Periphery of nodule when nodule's largest diameter is width.

FIG. 13C—Periphery of nodule when nodule's largest diameter is length. FIG. 13D—Periphery of nodule when nodule's largest diameter is width. FIG. 13E—Periphery of nodule when nodule's largest diameter is length. FIG. 13F—Periphery of nodule when nodule's largest diameter is width.

FIG. 37 illustrates an exemplary Pain Intensity Numeric Rating Scale (NRS)—Daily Scale.

FIG. 38 illustrates an exemplary Pain Intensity NRS—Before Taking Rescue Medication Scale.

FIG. 39 illustrates an exemplary Foot Function Index (FFI) Activity Limitation Subscale.

FIG. 40 illustrates an exemplary FFI Difficulty Subscale.

FIG. 41 illustrates an exemplary FFI Pain Subscale.

DETAILED DESCRIPTION OF ILLUSTRATIVE EMBODIMENTS

Figure 1A:
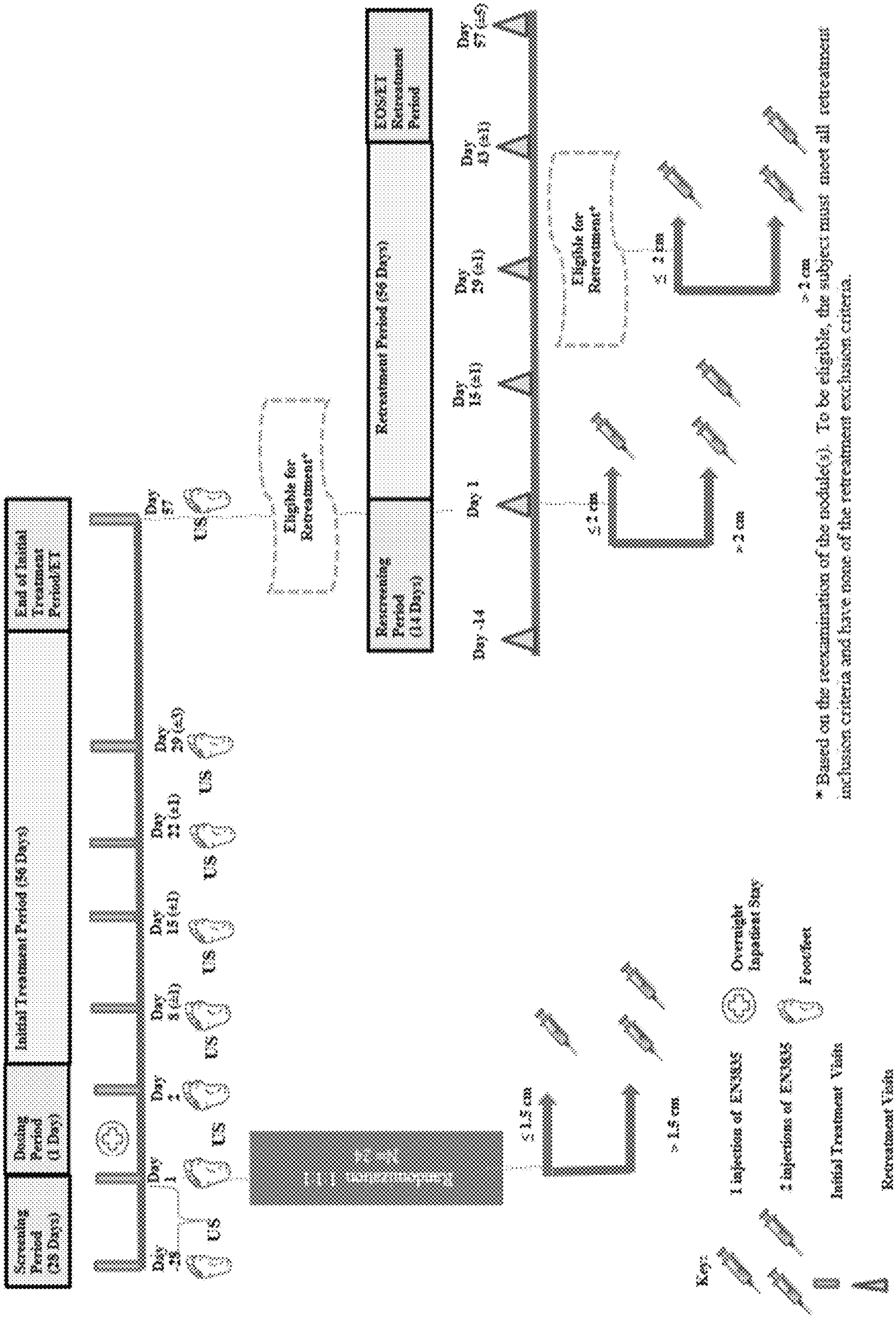
FIG. 1A and FIG. 1B illustrate the Study Design for Study 105.
Figure 1B:
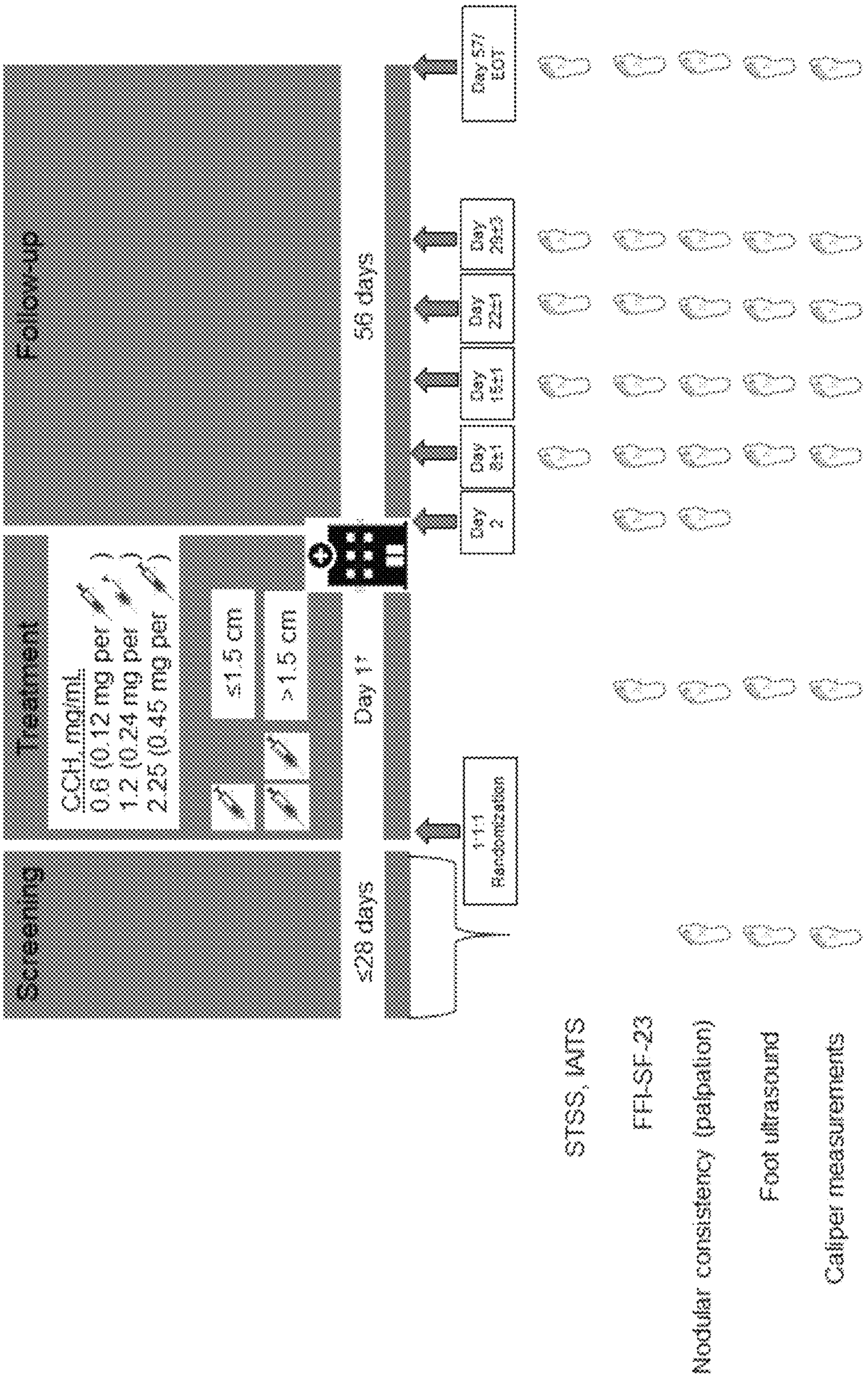
Figure 2A:
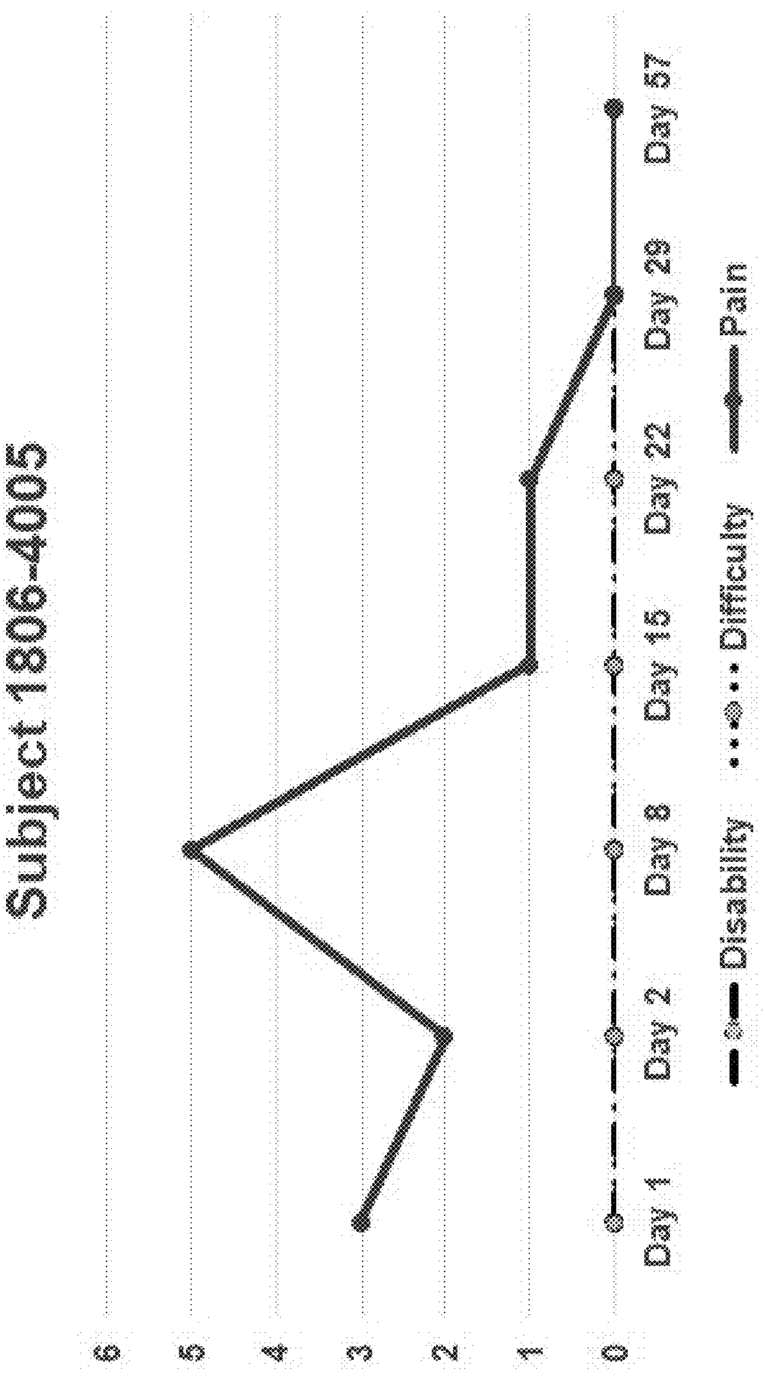
FIG. 2A and FIG. 2B illustrate Foot Function Index-Short Form-23 (FFI-SF-23) graphs of subjects having a nodule≤1.5 cm in size after receiving the following dose of collagenase: 0.6 mg/mL, 0.12 mg, 1 injection (0.2 mL).
Figure 2B:
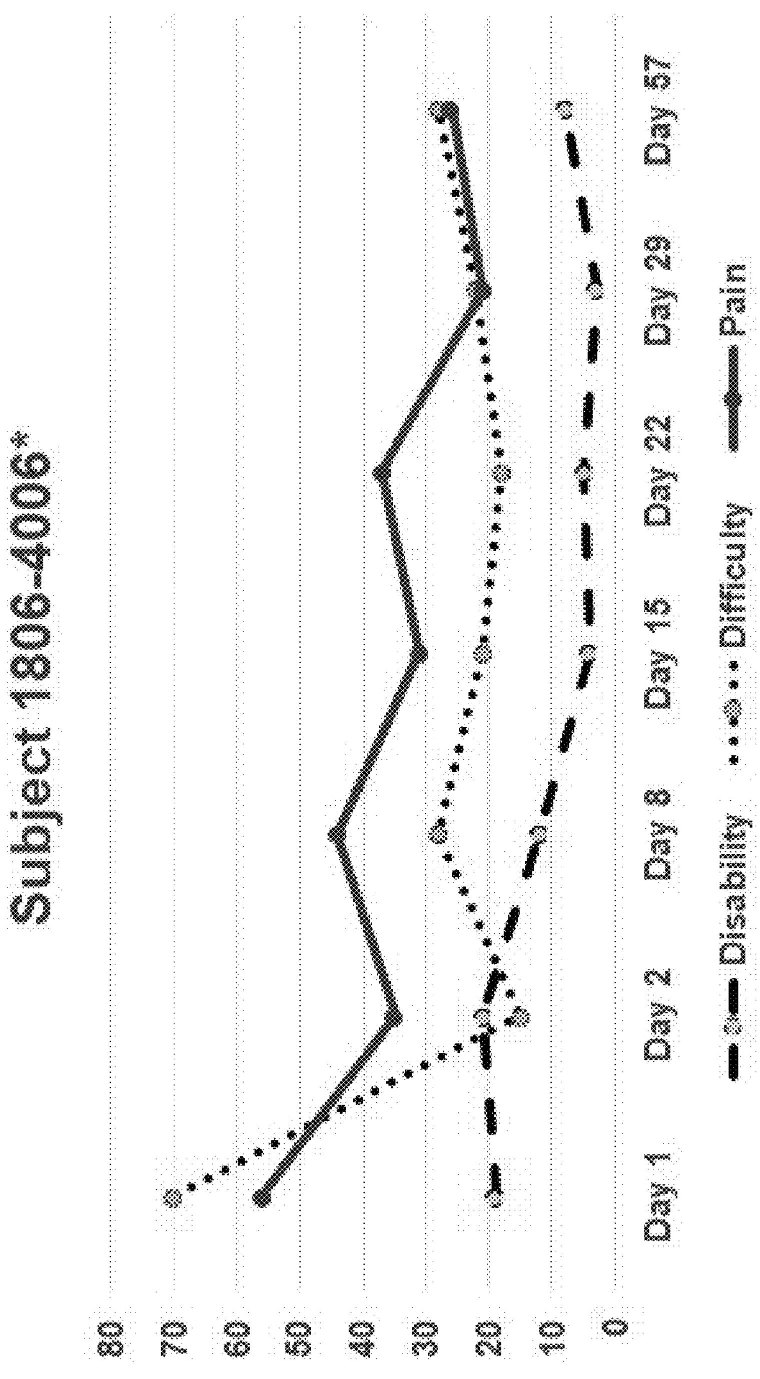
Figure 3A:
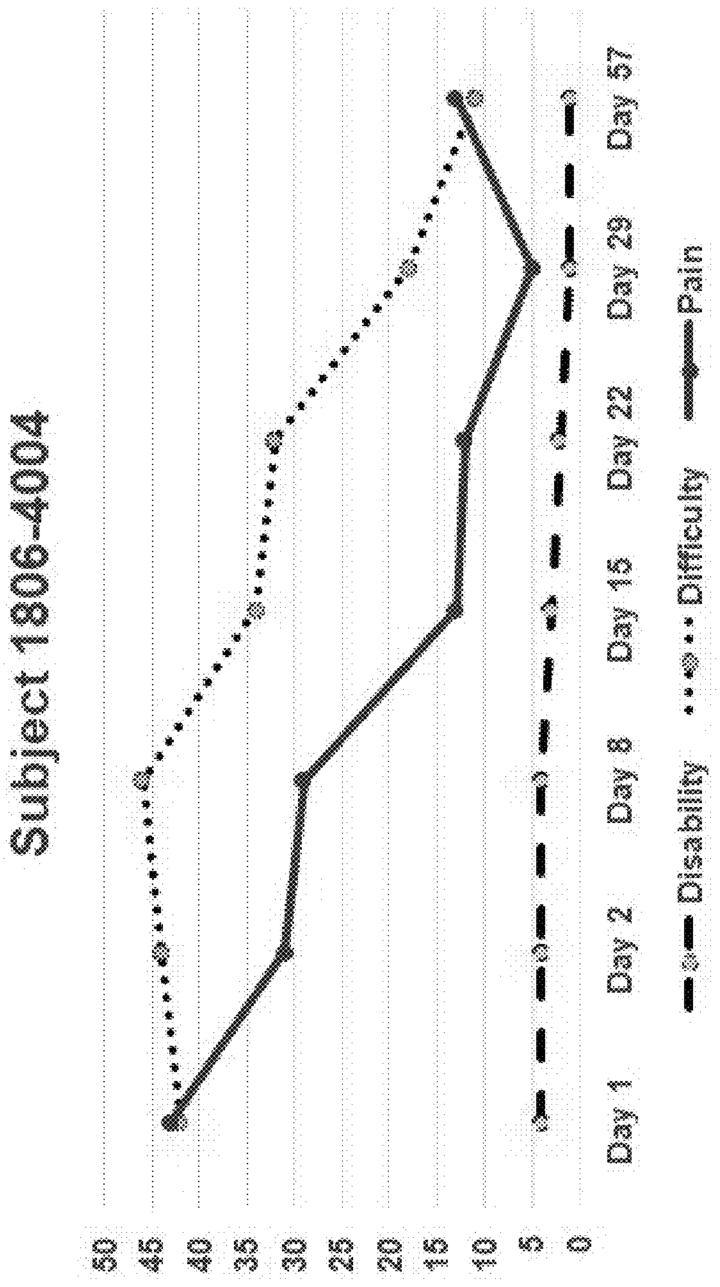
FIG. 3A and FIG. 3B illustrate FFI-SF-23 graphs of subjects having a nodule≤1.5 cm in size after receiving the following dose of collagenase: 1.2 mg/mL, 0.24 mg, 1 injection (0.2 mL).
Figure 3B:
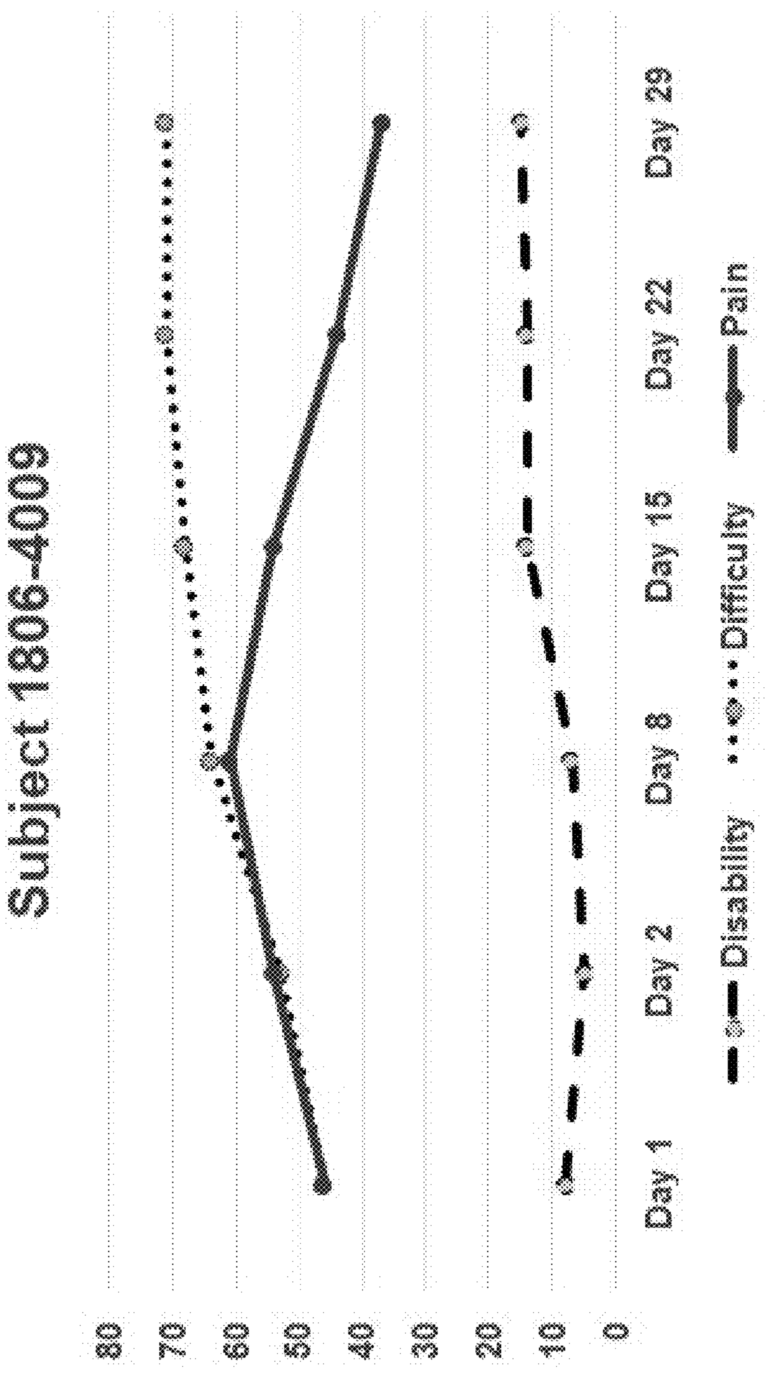
Figure 4:
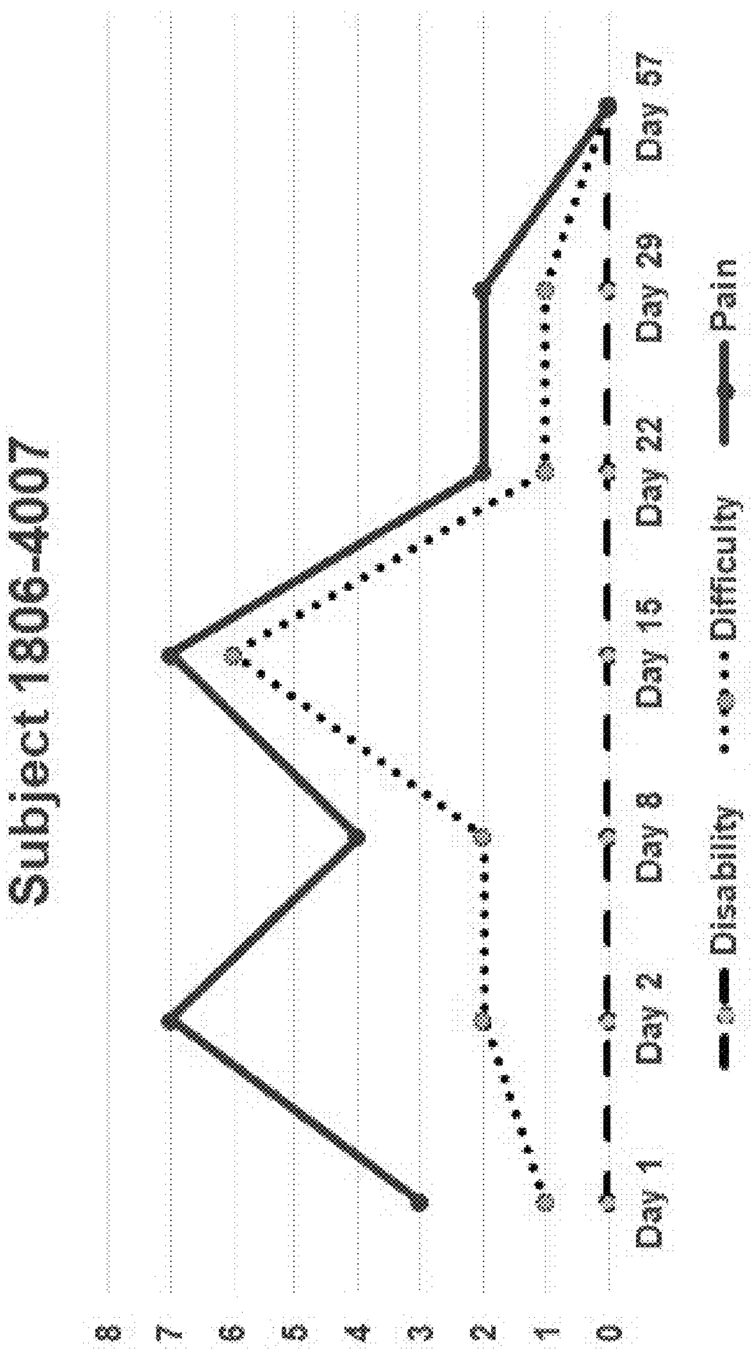
FIG. 4 illustrates a FFI-SF-23 graph of a subject having a nodule≤1.5 cm in size after receiving the following dose of collagenase: 2.25 mg/mL, 0.45 mg, 1 injection (0.2 mL).
Figure 5:
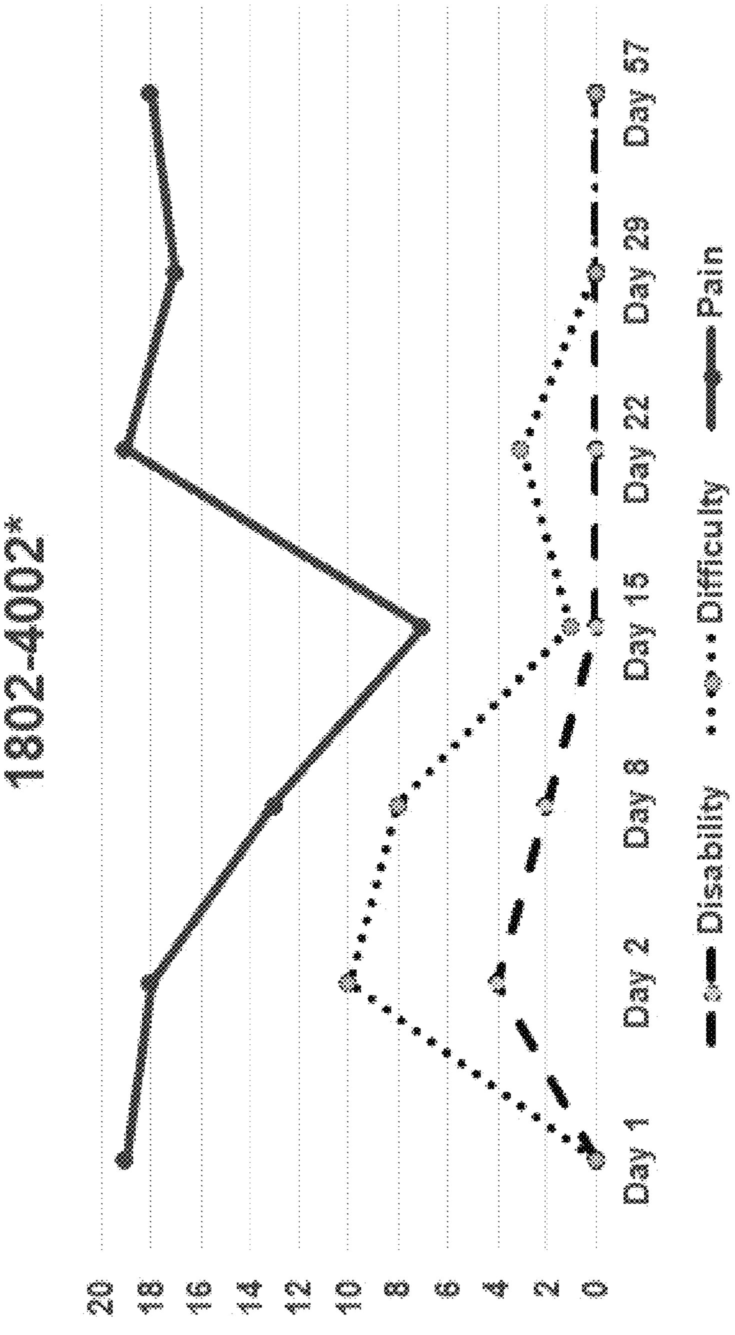
FIG. 5 illustrates a FFI-SF-23 graph of a subject having a nodule >1.5 cm in size after receiving the following dose of collagenase: 0.6 mg/mL, 0.24 mg, 2 injections (0.2 mL each).
Figure 6:
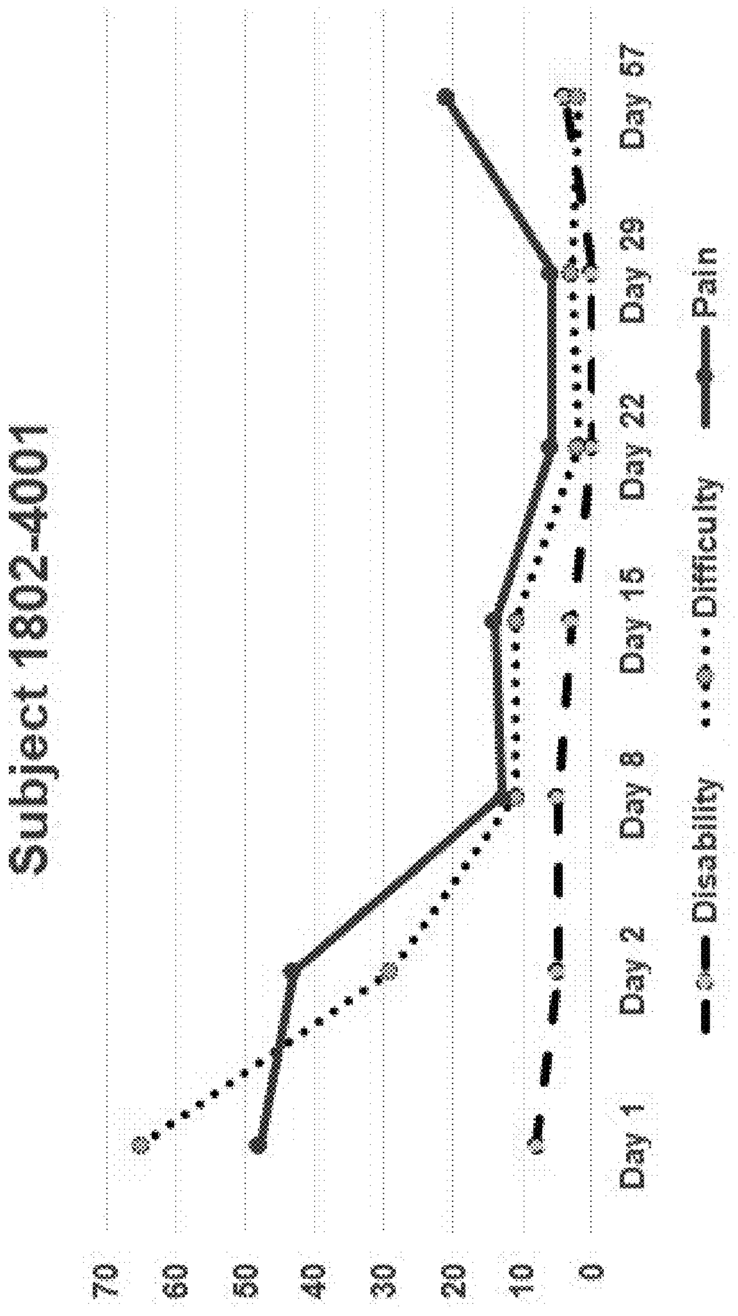
FIG. 6 illustrates a FFI-SF-23 graph of a subject having a nodule >1.5 cm in size after receiving the following dose of collagenase: 1.2 mg/mL, 0.48 mg, 2 injections (0.2 mL each).
Figure 7A:
FIG. 7A and FIG. 7B illustrate ultrasound images from a subject having a nodule >1.5 cm in size after receiving the following dose of collagenase: 2.25 mg/mL, 0.9 mg, 2 injections (0.2 mL each).
Figure 7B:
Figure 8A:
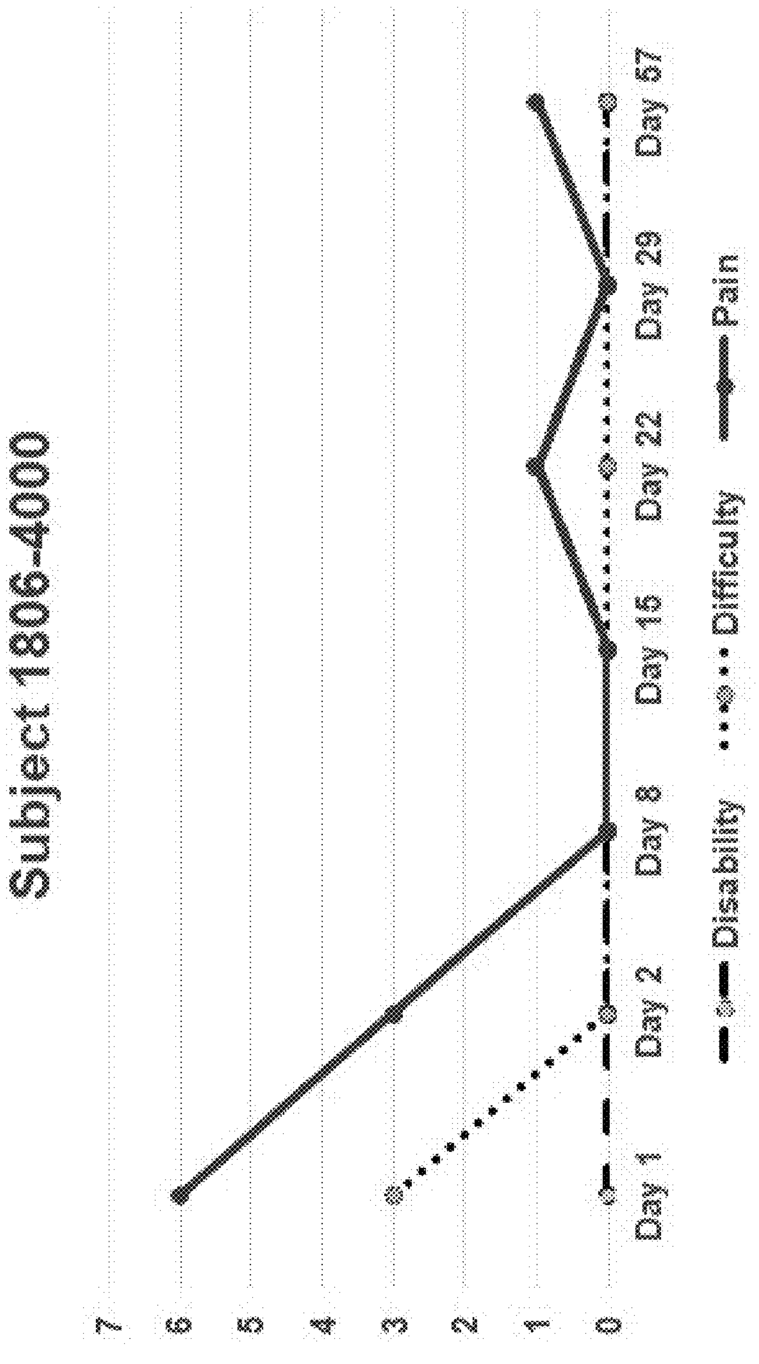
FIG. 8A and FIG. 8B illustrate FFI-SF-23 graphs of subjects having a nodule >1.5 cm in size after receiving the following dose of collagenase: 2.25 mg/mL, 0.9 mg, 2 injections (0.2 mL each).
Figure 8B:
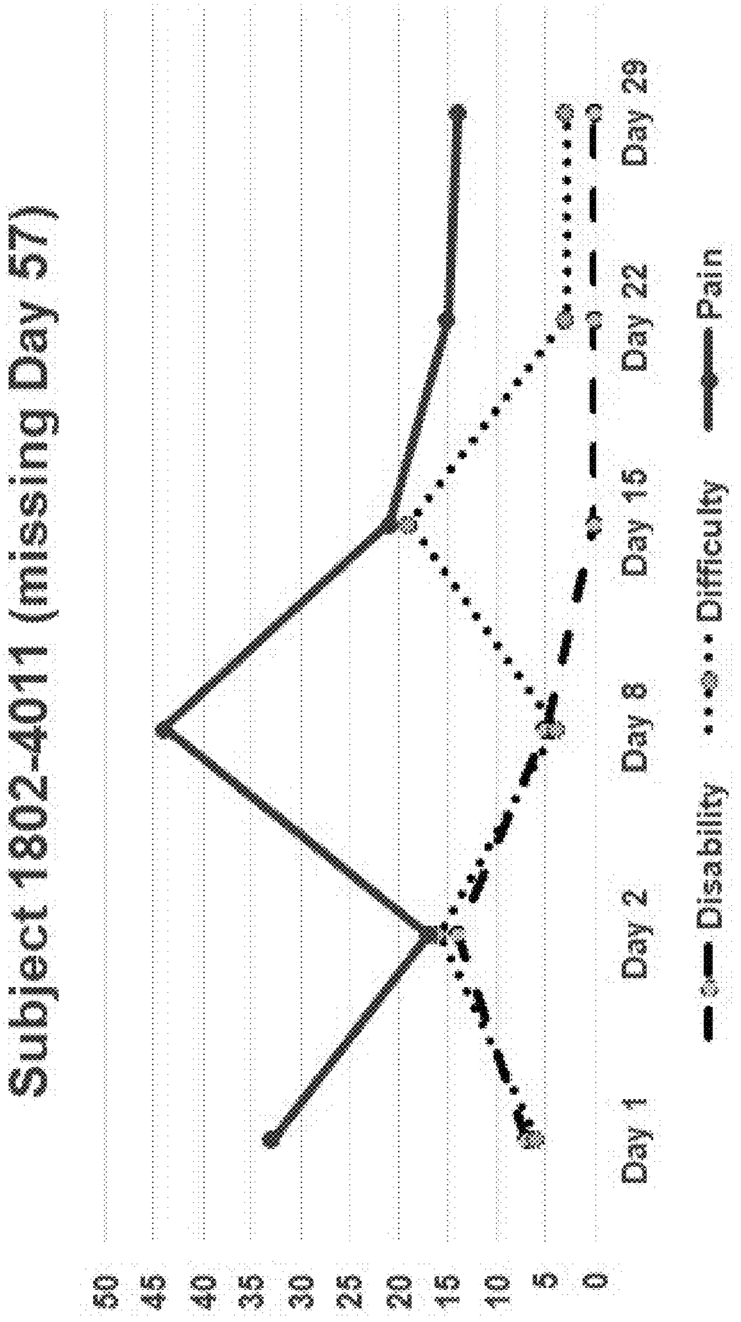

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

Unless specifically stated otherwise, any description as to a possible mechanism or mode of action or reason for improvement is meant to be illustrative only, and the disclosed methods are not to be constrained by the correctness or incorrectness of any such suggested mechanism or mode of action or reason for improvement.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, the singular forms "a," "an," and "the" include the plural.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

The term "comprising" is intended to include examples encompassed by the terms "consisting essentially of" and "consisting of"; similarly, the term "consisting essentially of" is intended to include examples encompassed by the term "consisting of."

"Treat," "treatment," and like terms include one or more of the following: reducing pain as measured on an Average Daily Pain score, reducing the consistency of one or more plantar fibromatosis nodules, reducing the size of one or more plantar fibromatosis nodules, reducing foot function index (FFI) composite score, reducing FFI total score, reducing FFI pain subscale score, reducing FFI difficulty subscale score, reducing FFI disability subscale score, reducing FFI activity limitation subscale score, increasing Subject Satisfaction With Treatment Scale Score, increasing Investigator Assessment of Improvement with Treatment Scale Score, increasing Clinician Global Impression of Change Scale score, reducing PGIS Foot Pain Subscale score, increasing PGIC Foot Pain Subscale score, reducing PGIS Difficulty Subscale score, increasing PGIC Difficulty Subscale score, reducing PGIS Activity Limitation Subscale score, increasing PGIC Activity Limitation Subscale score, reducing PGIS-PF Overall score, increasing PGIC PF Overall score, reducing Pain Intensity NRS score, eliminating one or more plantar fibromatosis nodules, reducing and/or eliminating the severity and/or frequency of one or more plantar fibromatosis nodules, reducing and/or eliminating the underlying cause of one or more plantar fibromatosis nodules, reducing and/or eliminating the likelihood of one or more plantar fibromatosis nodules, reducing and/or eliminating pain and discomfort caused by one or more plantar fibromatosis nodules, improving the subject's ability to stand, walk, and/or place weight on the foot, and inducing and/or improving the subject's overall comfort. The disclosed methods encompass the treatment of all or a portion of a subject's total number of plantar fibromatosis nodules.

As used herein, "administering" and similar terms indicate a procedure by which the pharmaceutical formulation is injected into a subject such that the plantar fibromatosis nodules are contacted with the pharmaceutical formulation.

The term "biosimilar" (of an approved reference product/biological drug, i.e., reference listed drug) refers to a biological product that is highly similar to the reference product notwithstanding minor differences in clinically inactive components with no clinically meaningful differences between the biosimilar and the reference product in terms of safety, purity and potency, based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biosimilar. The biosimilar may be an interchangeable product that may be substituted for the reference product at the pharmacy without the intervention of the prescribing healthcare professional. To meet the additional standard of "interchangeability," the biosimilar is to be expected to produce the same clinical result as the reference product in any given patient and, if the biosimilar is administered more than once to an individual, the risk in terms of safety or diminished efficacy of alternating or switching between the use of the biosimilar and the reference product is not greater than the risk of using the reference product without such alternation or switch. The biosimilar utilizes the same mechanisms of action for the proposed conditions of use to the extent the mechanisms are known for the reference product. The condition or conditions of use prescribed, recommended, or suggested in the labeling proposed for the biosimilar have been previously approved for the reference product. The route of administration, the dosage form, and/or the strength of the biosimilar are the same as those of the reference product and the biosimilar is manufactured, processed, packed or held in a facility that meets standards designed to assure that the biosimilar continues to be safe, pure and potent. The biosimilar may include minor modifications in the amino acid sequence when compared to the reference product, such as N- or C-terminal truncations that are not expected to change the biosimilar performance.

"Potency" as used herein refers to the level of collagenase activity per mg of material as determined by one or more enzyme assays, including those described in the Examples section herein.

Plantar fibromatosis (PF), as used herein, includes, for example, plantar fibroma and the following:

- Ledderhose disease—often used synonymously with plantar fibromatosis. Ledderhose disease is described as consisting of one or more small, round or flattened hard nodules that are generally located on the medial side of the sole. These lesions are typically present in middle-aged or elderly individuals.
- Superficial PF—appears as one or more limited, flat nodules of fibrous consistency and variable size. They are most commonly located on the plantar aspect of the anteromedial portion of the heel pad.
- Hamartomatous PF—appear as raised cerebriform soft-to-firm exophytic plantar masses and are covered by pink, lightly dark, or normal-colored skin.
- Juvenile aponeurotic fibroma—may appear in a localized form affecting adults, or a diffuse variety observed in children. It is more common in males than in females, and the hard nodules grow slowly and adhere to deep structures.

The progression pattern of plantar fibromatosis generally follows the following 3 stages: 1) a proliferative phase with increased fibroblast activity and cellular proliferation; 2) an active or involutional stage, where the nodules are formed and collagen is deposited; and 3) a residual stage in which the fibroblast activity is diminished, and reduced collagen maturation and contracture take place. The disclosed methods can be used to treat plantar fibromatosis at any of these stages.

The term "subject" as used herein is intended to mean any animal, in particular, mammals. The methods are applicable to human and nonhuman animals, although most preferably with humans. "Subject" and "patient" can be used interchangeably herein.

The term "treatment session" is synonymous with "treatment visit" and "treatment cycle" and includes a single visit to a doctor's office in which the pharmaceutical formulation is administered.

The phrase "moderate to severe plantar fibromatosis" refers to a score of greater than or equal to 5 on the NRS scale.

Disclosed herein are methods of treating moderate to severe plantar fibromatosis in a subject or a population of subjects, the methods comprising:

- intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.45 mg to about 1.35 mg and the treating comprises:
- a reduction from baseline as measured on a foot function index (FFI) pain sub scale;
- a reduction from baseline as measured on a FFI combined pain and difficulty subscale;
- an improvement from baseline as measured on a patient global impression of change (PGIC)-PF overall scale;
- a reduction from baseline as measured on a FFI total composite score;
- an improvement from baseline as measured on a subject satisfaction with treatment scale;
- a reduction from baseline in LSM FFI Foot Pain score;
- a reduction from baseline in combined FFI pain and difficulty score;
- an improvement from baseline in nodule consistency (firmness);
- a reduction from baseline in the nodular hardness;
- a reduction from baseline as measured at day 57 on a foot function index (FFI) pain subscale;
- a reduction from baseline as measured at day 57 on a FFI combined pain and difficulty subscale;
- an improvement from baseline as measured at day 57 on a patient global impression of change (PGIC)-PF overall scale;
- a reduction from baseline as measured at day 57 on a FFI total composite score;
- an improvement from baseline as measured at day 57 on a subject satisfaction with treatment scale;
- a reduction from baseline as measured at day 57 in LSM FFI Foot Pain score;
- a reduction from baseline as measured at day 57 in combined FFI pain and difficulty score;
- an improvement from baseline as measured at day 57 in nodule consistency (firmness);
- a reduction from baseline as measured at day 57 in the nodular hardness;
- at least a 1 point reduction from baseline as measured on a foot function index (FFI) pain subscale;
- at least a 1 point reduction from baseline as measured on a FFI combined pain and difficulty subscale;
- at least a 1 level improvement from baseline as measured on a patient global impression of change (PGIC)-PF overall scale;
- at least a 1 point reduction from baseline as measured on a FFI total composite score;
- at least a 1 level improvement from baseline as measured on a subject satisfaction with treatment scale;
- at least a 1 point reduction from baseline in LSM FFI Foot Pain score;
- at least a 1 point reduction from baseline in combined FFI pain and difficulty score;
- at least a 1 point improvement from baseline in nodule consistency (firmness);
- at least a 1 point reduction from baseline in the nodular hardness;
- at least a 1 point reduction from baseline as measured at day 57 on a foot function index (FFI) pain sub scale;
- at least a 1 point reduction from baseline as measured at day 57 on a FFI combined pain and difficulty subscale;
- at least a 1 level improvement from baseline as measured at day 57 on a patient global impression of change (PGIC)-PF overall scale;
- at least a 1 point reduction from baseline as measured at day 57 on a FFI total composite score;
- at least a 1 level improvement from baseline as measured at day 57 on a subject satisfaction with treatment scale;
- at least a 1 point reduction from baseline as measured at day 57 in LSM FFI Foot Pain score;
- at least a 1 point reduction from baseline as measured at day 57 in combined FFI pain and difficulty score;
- at least a 1 point improvement from baseline as measured at day 57 in nodule consistency (firmness);
- at least a 1 point reduction from baseline as measured at day 57 in the nodular hardness;
- or any combination thereof.

The collagenase can comprise collagenase I activity, collagenase II activity, or a mixture of collagenase I activity and collagenase II activity. In some embodiments, the collagenase comprises collagenase I activity. In some embodiments, the collagenase comprises collagenase II activity. In some embodiments, the collagenase comprises a mixture of collagenase I activity and collagenase II activity. The collagenase can be a single enzyme that has both collagenase I activity and collagenase II activity. Alternatively, the collagenase can be separate enzymes, one having collagenase I activity and one having collagenase II activity.

"Collagenase I activity," as used herein, refers to the activity of Class I Collagenases, which exhibit high collagenolytic activity and low peptidase activity, making them particularly effective at breaking down collagen and gelatin substrates. They show a preference for collagen and gelatin as a substrate. "Collagenase II activity," as used herein, refers to the activity of Class II Collagenases, which exhibit low collagenolytic activity and higher peptidase activity, meaning it is more efficient at cleaving small peptides. Class I and II collagenases work synergistically to degrade native collagen. Class I and II collagenases have complementary activity that enhances overall collagen breakdown.

Any of the herein disclosed collagenases can be used in the methods. In some embodiments, the collagenase comprises a mixture of collagenase I and collagenase II. In some embodiments, the collagenase comprises collagenase *Clostridium histolyticum* (CCH).

In some embodiments, the subject has an NRS score of greater than or equal to 5 to less than or equal to 10.

In some embodiments, prior to the injecting, the plantar fibromatosis nodules are hard or firm.

In some embodiments, prior to the injecting, the subject had an NRS score of greater than or equal to 5 to less than or equal to 10 and the plantar fibromatosis nodules are hard or firm.

In some embodiments, prior to the injecting, the subject had an NRS score of less than 10, the subject did not have moderately firm nodule(s), or the subject had an NRS score less than 10 and the subject did not have moderately firm nodule(s).

In some embodiments, prior to the injecting, the subject had a baseline FFI Difficulty Subscale score of ≥18, a baseline FFI Pain Subscale score of ≥18, or a baseline FFI Difficulty Subscale score of ≥18 and a baseline FFI Pain Subscale score of ≥18.

In some embodiments, prior to the injecting, the subject had: an NRS score of greater than or equal to 5 to less than or equal to 10; a baseline FFI Difficulty Subscale score of ≥18, a baseline FFI Pain Subscale score of ≥18, or a baseline FFI Difficulty Subscale score of >18 and a baseline FFI Pain Subscale score of ≥18; and hard or firm plantar fibromatosis nodules.

The dose of collagenase administered per nodule in a single treatment session depends, in part, on the number of nodules, the size of the nodules, the severity of the plantar fibromatosis, the volume administered per injection, and the anticipated number of treatment sessions. Suitable doses of collagenase administered per nodule in a single treatment session include, for example, about 0.45 mg, about 0.50 mg, about 0.55 mg, about 0.60 mg, about 0.70 mg, about 0.80 mg, about 0.90 mg, about 1.0 mg, about 1.1 mg, about 1.2 mg, about 1.3, or about 1.35 mg. In some embodiments, a dose of about 0.45 mg collagenase is administered per nodule per treatment session. In some embodiments, a dose of about 0.60 mg collagenase is administered per nodule per treatment session. In some embodiments, a dose of about 0.90 mg of collagenase is administered per nodule per treatment session. In some embodiments, a dose of about 1.0 mg of collagenase is administered per nodule per treatment session. In some embodiments, a dose of about 1.25 mg of collagenase is administered per nodule per treatment session. In some embodiments, a dose of about 1.35 mg of collagenase is administered per nodule per treatment session.

In some embodiments, about 0.45 mg to about 1.35 mg of collagenase is administered per nodule in a first treatment session. In some embodiments, about 0.45 mg to about 0.9 mg of collagenase is administered per nodule in a first treatment session.

The amount of collagenase administered per nodule in a subsequent treatment session (or multiple subsequent treatment sessions) can be greater than, less than, or the same as the amount of collagenase administered per nodule in the first treatment session. In some embodiments, about 0.45 mg to about 1.35 mg of collagenase is administered per nodule in a subsequent treatment session. In some embodiments, about 0.45 mg to about 0.9 mg of collagenase is administered per nodule in a subsequent treatment session.

In some embodiments, about 0.45 mg to about 0.90 mg of collagenase is administered per nodule in a first treatment session and about 0.45 mg to about 0.9 mg of collagenase is administered per nodule in a subsequent treatment session. In some embodiments, about 0.45 mg to about 1.35 mg of collagenase is administered per nodule in a first treatment session and about 0.45 mg to about 1.35 mg of collagenase is administered per nodule in a subsequent treatment session.

Subsequent treatment sessions can be initiated, for example, 1 week, 2 weeks, 3 weeks, 4 weeks, 5 weeks, or more than 5 weeks after the previous treatment session began. A subsequent treatment session can be initiated, for example, 1 week, 2 weeks, 3 weeks, 4 weeks, 5 weeks, or more than 5 weeks after the first treatment session began (e.g., Day 1 of the first treatment session). The subsequent treatment sessions can be initiated 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, or more than 35 days after the previous treatment session, such as the first treatment session, began. In some embodiments, the subsequent treatment session can begin on Day 21, Day 22, Day 23, Day 24, Day 25, Day 26, Day 27, Day 28, Day 29, Day 30, Day 31, Day 32, Day 33, Day 34, or Day 35 when the first treatment session began on Day 1. In some embodiments, the first treatment session can begin on Day 1 and the subsequent treatment session can begin on Day 29.

A dose of about 0.45 mg of collagenase can be administered per treatment session to each nodule having a palpable size of <about 2 cm. In some embodiments, the dose of about 0.45 mg of collagenase is administered in a single injection to each nodule having a palpable size of <about 2 cm.

A dose of about 0.9 mg of collagenase is administered per treatment session to each nodule having a palpable size of >about 2 cm to <about 4 cm. In some embodiments, the dose of about 0.9 mg of collagenase is administered in two injections of about 0.45 mg per injection to each nodule having a palpable size of >about 2 cm to <about 4 cm.

A dose of about 1.35 mg of collagenase is administered per treatment session to each nodule having a palpable size of >about 4 cm. In some embodiments, the dose of about 1.35 mg of collagenase is administered in three injections of about 0.45 mg per injection to each nodule having a palpable size of >about 4 cm.

Also disclosed herein are methods of treating moderate to severe plantar fibromatosis in a subject or a population of subjects by administering a collagenase enzyme at a dose of about 0.45 mg to about 1.35 mg per nodule, the collagenase enzyme comprising:

means for breaking down collagen type I, collagen type III, and combinations thereof, wherein the treating comprises:

a reduction from baseline as measured on a foot function index (FFI) pain sub scale;

a reduction from baseline as measured on a FFI combined pain and difficulty subscale;

an improvement from baseline as measured on a patient global impression of change (PGIC)-PF overall scale;

a reduction from baseline as measured on a FFI total composite score;

an improvement from baseline as measured on a subject satisfaction with treatment scale;

a reduction from baseline in LSM FFI Foot Pain score;

a reduction from baseline in combined FFI pain and difficulty score;

an improvement from baseline in nodule consistency (firmness);

a reduction from baseline in the nodular hardness;

a reduction from baseline as measured at day 57 on a foot function index (FFI) pain subscale;

a reduction from baseline as measured at day 57 on a FFI combined pain and difficulty subscale;

an improvement from baseline as measured at day 57 on a patient global impression of change (PGIC)-PF overall scale;

a reduction from baseline as measured at day 57 on a FFI total composite score;

an improvement from baseline as measured at day 57 on a subject satisfaction with treatment scale;

a reduction from baseline as measured at day 57 in LSM FFI Foot Pain score;

a reduction from baseline as measured at day 57 in combined FFI pain and difficulty score;

an improvement from baseline as measured at day 57 in nodule consistency (firmness);

a reduction from baseline as measured at day 57 in the nodular hardness;

at least a 1 point reduction from baseline as measured on a foot function index (FFI) pain subscale;

at least a 1 point reduction from baseline as measured on a FFI combined pain and difficulty subscale;

at least a 1 level improvement from baseline as measured on a patient global impression of change (PGIC)-PF overall scale;

at least a 1 point reduction from baseline as measured on a FFI total composite score;

at least a 1 level improvement from baseline as measured on a subject satisfaction with treatment scale;

at least a 1 point reduction from baseline in LSM FFI Foot Pain score;

at least a 1 point reduction from baseline in combined FFI pain and difficulty score;
at least a 1 point improvement from baseline in nodule consistency (firmness);
at least a 1 point reduction from baseline in the nodular hardness;
at least a 1 point reduction from baseline as measured at day 57 on a foot function index (FFI) pain sub scale;
at least a 1 point reduction from baseline as measured at day 57 on a FFI combined pain and difficulty subscale;
at least a 1 level improvement from baseline as measured at day 57 on a patient global impression of change (PGIC)-PF overall scale;
at least a 1 point reduction from baseline as measured at day 57 on a FFI total composite score;
at least a 1 level improvement from baseline as measured at day 57 on a subject satisfaction with treatment scale;
at least a 1 point reduction from baseline as measured at day 57 in LSM FFI Foot Pain score;
at least a 1 point reduction from baseline as measured at day 57 in combined FFI pain and difficulty score;
at least a 1 point improvement from baseline as measured at day 57 in nodule consistency (firmness);
at least a 1 point reduction from baseline as measured at day 57 in the nodular hardness;
or any combination thereof.

In some embodiments, the collagenase comprises means for digesting native collagen fibrils under physiological conditions of pH, temperature and ionic strength, and which act by cleaving the helical part of the collagen molecule. In certain aspects, the collagenase has means for cleaving polypeptide chains that make up the collagen triple helix structure at various loci thereby leading to solubilization from the collagen fibril. The collagenases described herein may have means to cleave Type I collagen and/or Type III collagen by binding the Type I and/or Type III collagen, unwinding the local triple helix, and sequential cutting of individual chains inside the catalytic cleft.

In some embodiments, the subject has an NRS score of greater than or equal to 5 to less than or equal to 10.

In some embodiments, prior to the injecting, the plantar fibromatosis nodules are hard or firm.

In some embodiments, prior to the injecting, the subject had an NRS score of greater than or equal to 5 to less than or equal to 10 and the plantar fibromatosis nodules are hard or firm.

In some embodiments, prior to the injecting, the subject had an NRS score less than 10, the subject did not have moderately firm nodule(s), or the subject had an NRS score less than 10 and the subject did not have moderately firm nodule(s).

In some embodiments, prior to the injecting, the subject had a baseline FFI Difficulty Subscale score of ≥18, a baseline FFI Pain Subscale score of ≥18, or a baseline FFI Difficulty Subscale score of ≥18 and a baseline FFI Pain Subscale score of ≥18.

In some embodiments, prior to the injecting, the subject had: an NRS score of greater than or equal to 5 to less than or equal to 10; a baseline FFI Difficulty Subscale score of ≥18, a baseline FFI Pain Subscale score of ≥18, or a baseline FFI Difficulty Subscale score of ≥18 and a baseline FFI Pain Subscale score of ≥18; and hard or firm plantar fibromatosis nodules.

The dose of collagenase administered per nodule in a single treatment session depends, in part, on the number of nodules, the size of the nodules, the severity of the plantar fibromatosis, the volume administered per injection, and the anticipated number of treatment sessions. Suitable doses of collagenase administered per nodule in a single treatment session include, for example, about 0.45 mg, about 0.50 mg, about 0.55 mg, about 0.60 mg, about 0.70 mg, about 0.80 mg, about 0.90 mg, about 1.0 mg, about 1.1 mg, about 1.2 mg, about 1.3, or about 1.35 mg. In some embodiments, a dose of about 0.45 mg collagenase is administered per nodule per treatment session. In some embodiments, a dose of about 0.6 mg collagenase is administered per nodule per treatment session. In some embodiments, a dose of about 0.90 mg of collagenase is administered per nodule per treatment session. In some embodiments, a dose of about 1.0 mg of collagenase is administered per nodule per treatment session. In some embodiments, a dose of about 1.25 mg of collagenase is administered per nodule per treatment session. In some embodiments, a dose of about 1.35 mg of collagenase is administered per nodule per treatment session.

In some embodiments, about 0.45 mg to about 1.35 mg of collagenase is administered per nodule in a first treatment session. In some embodiments, about 0.45 mg to about 0.9 mg of collagenase is administered per nodule in a first treatment session.

The amount of collagenase administered per nodule in a subsequent treatment session (or multiple subsequent treatment sessions) can be greater than, less than, or the same as the amount of collagenase administered per nodule in the first treatment session. In some embodiments, about 0.45 mg to about 1.35 mg of collagenase is administered per nodule in a subsequent treatment session. In some embodiments, about 0.45 mg to about 0.9 mg of collagenase is administered per nodule in a subsequent treatment session.

In some embodiments, about 0.45 mg to about 0.90 mg of collagenase is administered per nodule in a first treatment session and about 0.45 mg to about 0.9 mg of collagenase is administered per nodule in a subsequent treatment session. In some embodiments, about 0.45 mg to about 1.35 mg of collagenase is administered per nodule in a first treatment session and about 0.45 mg to about 1.35 mg of collagenase is administered per nodule in a subsequent treatment session.

Subsequent treatment sessions can be initiated, for example, 1 week, 2 weeks, 3 weeks, 4 weeks, 5 weeks, or more than 5 weeks after the previous treatment session began. A subsequent treatment session can be initiated, for example, 1 week, 2 weeks, 3 weeks, 4 weeks, 5 weeks, or more than 5 weeks after the first treatment session began (e.g., Day 1 of the first treatment session). The subsequent treatment sessions can be initiated 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, or more than 35 days after the previous treatment session, such as the first treatment session, began. In some embodiments, the subsequent treatment session can begin on Day 21, Day 22, Day 23, Day 24, Day 25, Day 26, Day 27, Day 28, Day 29, Day 30, Day 31, Day 32, Day 33, Day 34, or Day 35 when the first treatment session began on Day 1. In some embodiments, the first treatment session can begin on Day 1 and the subsequent treatment session can begin on Day 29.

A dose of about 0.45 mg of collagenase can be administered per treatment session to each nodule having a palpable size of <about 2 cm. In some embodiments, the dose of about 0.45 mg of collagenase is administered in a single injection to each nodule having a palpable size of <about 2 cm.

A dose of about 0.9 mg of collagenase is administered per treatment session to each nodule having a palpable size of >about 2 cm to <about 4 cm. In some embodiments, the dose of about 0.9 mg of collagenase is administered in two injections of about 0.45 mg per injection to each nodule having a palpable size of >about 2 cm to <about 4 cm.

A dose of about 1.35 mg of collagenase is administered per treatment session to each nodule having a palpable size of >about 4 cm. In some embodiments, the dose of about 1.35 mg of collagenase is administered in three injections of about 0.45 mg per injection to each nodule having a palpable size of >about 4 cm.

Disclosed herein are methods of treating moderate to severe plantar fibromatosis in a subject or a population of subjects, the methods comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.6 mg, and the treating comprises:

a reduction from baseline in the weekly mean of the average daily pain (ADP) score;
a reduction from baseline in the FFI Difficulty Subscale score of the FFI;
a reduction from baseline on the FFI Activity Limitation Subscale score;
a reduction from baseline on the FFI Pain Subscale score;
a reduction from baseline on the FFI Total score;
an improvement from baseline on the PGIS PF Overall score;
an improvement from baseline on the PGIS Foot Pain Subscale;
an improvement baseline on the PGIS Difficulty Subscale;
an improvement from baseline on the PGIS Activity Limitation Subscale;
an improvement from baseline in nodule consistency (firmness);
a reduction from baseline in the nodular hardness;
a reduction from baseline in LSM FFI Foot Pain score;
a reduction from baseline in combined FFI pain and difficulty score;
a reduction from baseline as measured at week 12 in the weekly mean of the ADP score;
a reduction from baseline as measured at day 85 in the FFI Difficulty Subscale score of the FFI;
a reduction from baseline as measured at day 85 on the FFI Activity Limitation Subscale score;
a reduction from baseline as measured at day 85 on the FFI Pain Subscale score;
a reduction from baseline as measured at day 85 on the FFI Total score;
an improvement from baseline as measured at day 85 on the PGIS PF Overall score;
an improvement from baseline as measured at day 85 on the PGIS Foot Pain Subscale;
an improvement from baseline as measured at day 85 on the PGIS Difficulty Subscale;
an improvement from baseline as measured at day 85 on the PGIS Activity Limitation Subscale;
an improvement from baseline as measured at day 85 in nodule consistency (firmness);
a reduction from baseline as measured at day 85 in the nodular hardness;
a reduction from baseline as measured at day 85 in LSM FFI Foot Pain score;
a reduction from baseline as measured at day 85 in combined FFI pain and difficulty score;
at least a 0.5 point reduction from baseline in the weekly mean of the ADP score;
at least a 1 point reduction from baseline in the weekly mean of the ADP score;
at least a 1 point reduction from baseline in the FFI Difficulty Subscale score of the FFI;
at least a 1 point reduction from baseline on the FFI Activity Limitation Subscale score;
at least a 1 point reduction from baseline on the FFI Pain Subscale score;
at least a 1 point reduction from baseline on the FFI Total score;
at least a 1 level change from baseline on the PGIS PF Overall score;
at least a 1 level change from baseline on the PGIS Foot Pain Subscale;
at least a 1 level change from baseline on the PGIS Difficulty Subscale;
at least a 1 level change from baseline on the PGIS Activity Limitation Subscale;
at least a 1 level change from baseline in nodule consistency (firmness);
at least a 1 point reduction from baseline in the nodular hardness;
at least a 1 point reduction from baseline in LSM FFI Foot Pain score;
at least a 1 point reduction from baseline in combined FFI pain and difficulty score;
at least a 0.5 point reduction from baseline as measured at week 12 in the weekly mean of the ADP score;
at least a 1 point reduction from baseline as measured at week 12 in the weekly mean of the ADP score;
at least a 1 point reduction from baseline as measured at day 85 in the FFI Difficulty Subscale score of the FFI;
at least a 1 point reduction from baseline as measured at day 85 on the FFI Activity Limitation Subscale score;
at least a 1 point reduction from baseline as measured at day 85 on the FFI Pain Subscale score;
at least a 1 point reduction from baseline as measured at day 85 on the FFI Total score;
at least a 1 level change from baseline as measured at day 85 on the PGIS PF Overall score;
at least a 1 level change from baseline as measured at day 85 on the PGIS Foot Pain Subscale;
at least a 1 level change from baseline as measured at day 85 on the PGIS Difficulty Subscale;
at least a 1 level change from baseline as measured at day 85 on the PGIS Activity Limitation Subscale;
at least a 1 level change from baseline as measured at day 85 in nodule consistency (firmness);
at least a 1 point reduction from baseline as measured at day 85 in the nodular hardness;
at least a 1 point reduction from baseline as measured at day 85 in LSM FFI Foot Pain score;
at least a 1 point reduction from baseline as measured at day 85 in combined FFI pain and difficulty score;
or any combination thereof.

The collagenase can comprise collagenase I activity, collagenase II activity, or a mixture of collagenase I activity and collagenase II activity. In some embodiments, the collagenase comprises collagenase I activity. In some embodiments, the collagenase comprises collagenase II activity. In some embodiments, the collagenase comprises a mixture of collagenase I activity and collagenase II activity. The collagenase can be a single enzyme that has both collagenase I activity and collagenase II activity. Alternatively, the collagenase can be separate enzymes, one having collagenase I activity and one having collagenase II activity.

Any of the herein disclosed collagenases can be used in the methods. In some embodiments, the collagenase comprises a mixture of collagenase I and collagenase II. In some embodiments, the collagenase comprises collagenase *Clostridium histolyticum* (CCH).

In some embodiments, the subject has an NRS score of greater than or equal to 5 to less than or equal to 9.

In some embodiments, prior to the injecting, the plantar fibromatosis nodules are hard or firm.

In some embodiments, prior to the injecting, the subject had an NRS score of greater than or equal to 5 to less than or equal to 9 and the plantar fibromatosis nodules are hard or firm.

In some embodiments, prior to the injecting, the subject had an NRS score less than or equal to 9, the subject did not have moderately firm nodule(s), or the subject had an NRS score less than or equal to 9 and the subject did not have moderately firm nodule(s).

In some embodiments, prior to the injecting, the subject or population of subjects had a baseline FFI Difficulty Subscale score of ≥18, a baseline FFI Pain Subscale score of ≥18, or a baseline FFI Difficulty Subscale score of ≥18 and a baseline FFI Pain Subscale score of ≥18.

In some embodiments, prior to the injecting, the subject had: an NRS score of greater than or equal to 5 to less than or equal to 9; a baseline FFI Difficulty Subscale score of ≥18, a baseline FFI Pain Subscale score of ≥18, or a baseline FFI Difficulty Subscale score of ≥18 and a baseline FFI Pain Subscale score of ≥18; and hard or firm plantar fibromatosis nodules.

In some embodiments, about 0.6 mg of collagenase is administered per nodule in a first treatment session. The amount of collagenase administered per nodule in a subsequent treatment session (or multiple subsequent treatment sessions) can be greater than, less than, or the same as the amount of collagenase administered per nodule in the first treatment session. In some embodiments, about 0.6 mg of collagenase is administered per nodule in a subsequent treatment session. The total amount of collagenase administered in the one or more treatment sessions can be 0.6 mg to 2.4 mg.

Subsequent treatment sessions can be initiated, for example, 1 week, 2 weeks, 3 weeks, 4 weeks, 5 weeks, or more than 5 weeks after the previous treatment session began. A subsequent treatment session can be initiated, for example, 1 week, 2 weeks, 3 weeks, 4 weeks, 5 weeks, or more than 5 weeks after the first treatment session began (e.g., Day 1 of the first treatment session). The subsequent treatment sessions can be initiated 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, or more than 35 days after the previous treatment session, such as the first treatment session, began. In some embodiments, the subsequent treatment session can begin on Day 21, Day 22, Day 23, Day 24, Day 25, Day 26, Day 27, Day 28, Day 29, Day 30, Day 31, Day 32, Day 33, Day 34, or Day 35 when the first treatment session began on Day 1. In some embodiments, the first treatment session can begin on Day 1 and the subsequent treatment session can begin on Day 29.

The plantar fibromatosis nodule can be less than or equal to 4 cm in size. In some embodiments, the methods comprise administering a single injection of the collagenase to any nodule that is less than 2 cm in size. In some embodiments, the methods comprise administering two injections of the collagenase to any nodule that is greater than 2 cm but less than 4 cm in size. Each of the two injections can comprise 0.3 mg of the collagenase.

Also disclosed are methods of treating moderate to severe plantar fibromatosis in a subject or a population of subjects by administering a collagenase enzyme at a dose of about 0.6 mg per nodule, the collagenase enzyme comprising:

means for breaking down collagen type I, collagen type III, and combinations thereof' wherein the treating comprises:

a reduction from baseline in the weekly mean of the average daily pain (ADP) score;

a reduction from baseline in the FFI Difficulty Subscale score of the FFI;

a reduction from baseline on the FFI Activity Limitation Subscale score;

a reduction from baseline in the weekly mean of the ADP score;

a reduction from baseline on the FFI Pain Subscale score;

a reduction from baseline on the FFI Total score;

an improvement from baseline on the PGIS PF Overall score;

an improvement from baseline on the PGIS Foot Pain Subscale;

an improvement baseline on the PGIS Difficulty Subscale;

an improvement from baseline on the PGIS Activity Limitation Subscale;

an improvement from baseline in nodule consistency (firmness);

a reduction from baseline in the nodular hardness;

a reduction from baseline in LSM FFI Foot Pain score;

a reduction from baseline in combined FFI pain and difficulty score;

a reduction from baseline as measured at week 12 in the weekly mean of the ADP score;

a reduction from baseline as measured at day 85 in the FFI Difficulty Subscale score of the FFI;

a reduction from baseline as measured at day 85 on the FFI Activity Limitation Subscale score;

a reduction from baseline as measured at day 85 on the FFI Pain Subscale score;

a reduction from baseline as measured at day 85 on the FFI Total score;

an improvement from baseline as measured at day 85 on the PGIS PF Overall score;

an improvement from baseline as measured at day 85 on the PGIS Foot Pain Subscale;

an improvement from baseline as measured at day 85 on the PGIS Difficulty Subscale;

an improvement from baseline as measured at day 85 on the PGIS Activity Limitation Subscale;

an improvement from baseline as measured at day 85 in nodule consistency (firmness);

a reduction from baseline as measured at day 85 in the nodular hardness;

a reduction from baseline as measured at day 85 in LSM FFI Foot Pain score;

a reduction from baseline as measured at day 85 in combined FFI pain and difficulty score;

at least a 0.5 point reduction from baseline in the weekly mean of the ADP score;

at least a 1 point reduction from baseline in the weekly mean of the ADP score;

at least a 1 point reduction from baseline in the FFI Difficulty Subscale score of the FFI;

at least a 1 point reduction from baseline on the FFI Activity Limitation Subscale score;
at least a 1 point reduction from baseline on the FFI Pain Subscale score;
at least a 1 point reduction from baseline on the FFI Total score;
at least a 1 level change from baseline on the PGIS PF Overall score;
at least a 1 level change from baseline on the PGIS Foot Pain Subscale;
at least a 1 level change from baseline on the PGIS Difficulty Subscale;
at least a 1 level change from baseline on the PGIS Activity Limitation Subscale;
at least a 1 level change from baseline in nodule consistency (firmness);
at least a 1 point reduction from baseline in the nodular hardness;
at least a 1 point reduction from baseline in LSM FFI Foot Pain score;
at least a 1 point reduction from baseline in combined FFI pain and difficulty score;
at least a 0.5 point reduction from baseline as measured at week 12 in the weekly mean of the ADP score;
at least a 1 point reduction from baseline as measured at week 12 in the weekly mean of the ADP score;
at least a 1 point reduction from baseline as measured at day 85 in the FFI Difficulty Subscale score of the FFI;
at least a 1 point reduction from baseline as measured at day 85 on the FFI Activity Limitation Subscale score;
at least a 1 point reduction from baseline as measured at day 85 on the FFI Pain Subscale score;
at least a 1 point reduction from baseline as measured at day 85 on the FFI Total score;
at least a 1 level change from baseline as measured at day 85 on the PGIS PF Overall score;
at least a 1 level change from baseline as measured at day 85 on the PGIS Foot Pain Subscale;
at least a 1 level change from baseline as measured at day 85 on the PGIS Difficulty Subscale;
at least a 1 level change from baseline as measured at day 85 on the PGIS Activity Limitation Subscale;
at least a 1 level change from baseline as measured at day 85 in nodule consistency (firmness);
at least a 1 point reduction from baseline as measured at day 85 in the nodular hardness;
at least a 1 point reduction from baseline as measured at day 85 in LSM FFI Foot Pain score;
at least a 1 point reduction from baseline as measured at day 85 in combined FFI pain and difficulty score;
or any combination thereof.

In some embodiments, the subject has an NRS score of greater than or equal to 5 to less than or equal to 9.

In some embodiments, prior to the injecting, the plantar fibromatosis nodules are hard or firm.

In some embodiments, prior to the injecting, the subject had an NRS score of greater than or equal to 5 to less than or equal to 9 and the plantar fibromatosis nodules are hard or firm.

In some embodiments, prior to the injecting, the subject had an NRS score less than or equal to 9, the subject did not have moderately firm nodule(s), or the subject had an NRS score less than or equal to 9 and the subject did not have moderately firm nodule(s).

In some embodiments, prior to the injecting, the subject or population of subjects had a baseline FFI Difficulty Subscale score of ≥18, a baseline FFI Pain Subscale score of ≥18, or a baseline FFI Difficulty Subscale score of ≥18 and a baseline FFI Pain Subscale score of ≥18.

In some embodiments, prior to the injecting, the subject had: an NRS score of greater than or equal to 5 to less than or equal to 9; a baseline FFI Difficulty Subscale score of ≥18, a baseline FFI Pain Subscale score of ≥18, or a baseline FFI Difficulty Subscale score of ≥18 and a baseline FFI Pain Subscale score of ≥18; and hard or firm plantar fibromatosis nodules.

In some embodiments, about 0.6 mg of collagenase is administered per nodule in a first treatment session. The amount of collagenase administered per nodule in a subsequent treatment session (or multiple subsequent treatment sessions) can be greater than, less than, or the same as the amount of collagenase administered per nodule in the first treatment session. In some embodiments, about 0.6 mg of collagenase is administered per nodule in a subsequent treatment session. The total amount of collagenase administered in the one or more treatment sessions can be 0.6 mg to 2.4 mg.

Subsequent treatment sessions can be initiated, for example, 1 week, 2 weeks, 3 weeks, 4 weeks, 5 weeks, or more than 5 weeks after the previous treatment session began. A subsequent treatment session can be initiated, for example, 1 week, 2 weeks, 3 weeks, 4 weeks, 5 weeks, or more than 5 weeks after the first treatment session began (e.g., Day 1 of the first treatment session). The subsequent treatment sessions can be initiated 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, or more than 35 days after the previous treatment session, such as the first treatment session, began. In some embodiments, the subsequent treatment session can begin on Day 21, Day 22, Day 23, Day 24, Day 25, Day 26, Day 27, Day 28, Day 29, Day 30, Day 31, Day 32, Day 33, Day 34, or Day 35 when the first treatment session began on Day 1. In some embodiments, the first treatment session can begin on Day 1 and the subsequent treatment session can begin on Day 29.

The plantar fibromatosis nodule can be less than or equal to 4 cm in size. In some embodiments, the methods comprise administering a single injection of the collagenase to any nodule that is less than 2 cm in size. In some embodiments, the methods comprise administering two injections of the collagenase to any nodule that is greater than 2 cm but less than 4 cm in size. Each of the two injections can comprise 0.3 mg of the collagenase.

The "collagenase" (also referred to as "collagenase enzyme" herein) used in each of the disclosed methods refers to any of the following: (a) collagenase (including mutants) having activity as defined by EC 3.4.24.3 (www.brenda-enzymes.org/enzyme.php?ecno=3.4.24.3 (accessed Aug. 24, 2020); (b) collagenase produced by fermentation of *Clostridium histolyticum* (also known as *Hathewaya histolytica*); (c) CCH (as described herein); (d) collagenase having at least 50% sequence alignment with collagenase I (also referred as class I collagenase) as determined by BLAST; (e) collagenase having at least 50% sequence alignment with collagenase II (also referred as class II collagenase) as determined by BLAST; (f) collagenase produced by fermentation of other source organisms (i.e., non-*Clostridium histolyticum*), e.g., mammalian, crustacean, fungal, bacterial, or microbial collagenase; (g) collagenase obtained by recombinant techniques; (h) collagenase with a molecular mass from about 65 kDa to about 130 kDa; (i) collagenase designated as collagenase I (col I) or collagenase II (col II); (j) mixtures of collagenase I and II;

(k) collagenase from strain JCM 1403 (ATCC 19401) or derivatives thereof; (l) collagenase from strain ATCC 21000 or derivatives thereof; (m) collagenase from ATCC 69334 or derivatives thereof; (n) collagenase from *C. perfringens*; (o) collagenase from *Vibrio alginolyticus*; (p) collagenase from *Streptomyces*; (q) collagenase from *Pseudomonas*; (r) collagenase from *Achromobacter iophagus*; (s) collagenase described by Worthington Biochemical Corp. (www.Worthington-biochem.com; "Product Highlights"); (t) collagenase described by Sigma-Aldrich (www.sigma-aldrich.com); (u) collagenase having one or more of the following characteristics:

- $V_{max}$ ($min^{-1}$) of about 0.08 to 7.70 (SRC assay; as described in Int'l Pub. No. WO2020/058755), or about 0.3 to 30.5 (GPA assay; as described in Int'l Pub. No. WO2020/058755);
- $K_M$ of about 4.1 to 410 nM (SRC assay), or about 0.03 to 3.1 mM (GPA assay);
- $K_{cat}$ ($sec^{-1}$) of about 1.1 to 107 (SRC assay), or about 93 to 9,179 (GPA assay);
- $1/K_{cat}$ (microseconds) of about 376 to 37,222 (SRC assay), or about 4 to 428 (GPA assay);
- $K_{cat}/K_M$ ($mM^{-1}$ $sec^{-1}$) of about 5,140 to 508,814 (SRC assay), or about 60 to 5,934 (GPA assay);
- A molecular mass from about 60 kDa to about 130 kDa, or about 70 kDa to about 130 kDa, or about 80 kDa to about 120 kDa, or about 90 kDa to about 120 kDa, or about 100 kDa to about 110 kDa;
- A purity by area of at least 80% as measured by reverse phase HPLC (high pressure liquid chromatography);
- Potency (i.e., specific activity) of about 500 to about 30,000 SRC units/mg;
- Potency of about 5,000 to about 30,000 f-SRC units/mg;
- Potency of about 10,000 to about 400,000 GPA units/mg;
- Potency of about 175,000 to about 500,000 f-GPA units/mg;
- Potency of about 5,000 to about 25,000 ABC units/mg;
- Less than or equal to 1% by area of an impurity selected from the group consisting of clostripain, gelatinase, and leupeptin; or
- Less than or equal to 1 cfu/mL bioburden.

wherein:

- $V_{max}$=maximal rate
- $K_M$=[Substrate] at 50% of $V_{max}$
- $K_{cat}$=molecules of substrate cleaved per second
- $1/K_{cat}$=The microseconds required to cleave a molecule of substrate;

(v) collagenase described by Nordmark Arzneimittel GmbH & Co. KG; (w) collagenase from strain 004; (x) equivalents or mixtures of any of the foregoing; (y) biosimilars of collagenase component of XIAFLEX® or biosimilars of XIAFLEX®; (z) ColQ1 from *Bacillus cereus*; (aa) a collagenase from family M9, for example subfamily M9A or M9B, as described in ebi.ac.uk/merops/cgi-bin/famsum?family-m09b, or (bb) collagenase derived from *Clostridium histolyticum* either by fermentation or through recombinant expression in a suitable host cell. Non-limiting examples of collagenases that may be used in the disclosure herein are described in U.S. Pat. Nos. 7,811,560, 9,757,435, 9,744,138, and Int'l Pub. No. WO2012/125948.

The collagenase can have type I collagenase activity and type II collagenase activity, wherein:

the type I collagenase activity has one or more of the following characteristics based on the SRC microplate assay

- $V_{max}$: About 0.08 to 7.70 $min^{-1}$
- $K_M$: About 4.1 to 410 nanoMolar
- $K_{cat}$: About 1.1 to 107 $sec^{-1}$
- $1/K_{cat}$: About 376 to 37,222 microseconds
- $K_{cat}/K_M$: About 5,140 to 508,814 $mM^{-1}$ $sec^{-1}$ and the type II collagenase activity has one or more of the following characteristics based on the GPA microplate assay

- $V_{max}$: About 0.3 to 30.5 $min^{-1}$
- $K_M$: About 0.03 to 3.1 mM
- $K_{cat}$: About 93 to 9,179 $sec^{-1}$
- $1/K_{cat}$: About 4 to 428 microseconds
- $K_{cat}/K_M$: About 60 to 5,934 $mM^{-1}$ $sec^{-1}$ The collagenase can have type I collagenase activity and type II collagenase activity, wherein:

the type I collagenase activity has one or more of the following characteristics based on the SRC microplate assay

- $V_{max}$: About 3.8 $min^{-1}$
- $K_M$: About $2.07\times10^4$ mM
- $K_{cat}$: About 53 $sec^{-1}$
- $1/K_{cat}$: About 18,799 microseconds
- $K_{cat}/K_M$: About 256,977 $mM^{-1}$ $sec^{-1}$ and the type II collagenase activity has one or more of the following characteristics based on the GPA microplate assay

- $V_{max}$: About 15.4 $min^{-1}$
- $K_M$: About 1.6 mM
- $K_{cat}$: About 4,636 $sec^{-1}$
- $1/K_{cat}$: About 216 microseconds
- $K_{cat}/K_M$: About 2,997 $mM^{-1}$ $sec^{-1}$ The collagenase can comprise a collagenase I. A suitable collagenase I includes, for example, a collagenase I comprising an amino acid sequence having 90%, 91%, 92%, 93%, 94%, 95%, 96%, 97%, 98%, 99%, or 100% sequence identity to the amino acid sequence of SEQ ID NO: 1. In some aspects, the collagenase I comprises the amino acid sequence of SEQ ID NO: 1.

The collagenase can comprise a collagenase II. A suitable collagenase II includes, for example, a collagenase II comprising an amino acid sequence having 90%, 91%, 92%, 93%, 94%, 95%, 96%, 97%, 98%, 99%, or 100% sequence identity to the amino acid sequence of SEQ ID NO: 2. In some aspects, the collagenase II comprises the amino acid sequence of SEQ ID NO: 2.

TABLE 1

| Sequences | |
|---|---|
| Collagenase I | IANTNSEKYDFEYLNGLSYTELTNLIKNIKWNQINGLFNYSTGSQKFFG |
| (SEQ ID NO: 1) | DKNRVQAIINALQESGRTYTANDMKGIETFTEVLRAGFYLGYYNDGLSY |
| Activator | LNDRNFQDKCIPAMIAIQKNPNFKLGTAVQDEVITSLGKLIGNASANAE |
| domain is | VVNNCVPVLKQFRENLNQYAPDYVKGTAVNELIKGIEFDFSGAAYEKDV |
| underlined; | KTMPWYGKIDPFINELKALGLYGNITSATEWASDVGIYYLSKFGLYSTN |
| peptidase | RNDIVQSLEKAVDMYKYGKIAFVAMERITWDYDGIGSNGKKV**DHDKFLD** |
| domain is bold; | **DAEKHYLPKTYTFDNGTFIIRAGEKVSEEKIKRLYWASREVKSQFHRVV** |
| and collagen | **GNDKALEVGNADDVLTMKIFNSPEEYKFNTNINGVSTDNGGLYIEPRGT** |

TABLE 1-continued

| | Sequences |
|---|---|
| recruitment domains (PKD & CBD) are in bold underline. | FYTYERTPQQSIFSLEELFRHEYTHYLQARYLVDGLWGQGPFYEKNRLT<br>WFDEGTAEFFAGSTRTSGVLPRKSILGYLAKDKVDHRYSLKKTLNSGYD<br>DSDWMFYNYGFAVAHYLYEKDMPTFIKMNKAILNTDVKSYDEIIKKLSD<br>DANKNTEYQNHIQELADKYQGAGIPLVSDDYLKDHGYKKASEVYSEISK<br>AASLTNTSVTAEKSQYFNTFTLRGTYTGETSKGEFKDWDEMSKKLDGTL<br>ESLAKNSWSGYKTLTAYFTNYRVTSDNKVQYDVVFHGVLTDNADISNNK<br>APIAKVTGPSTGAVGRNIEFSGKDSKDEDGKIVSYDWDFGDGATSRGKN<br>SVHAYKKTGTYNVTLKVTDDKGATATESFTIEIKNEDTTTPITKEMEPN<br>DDIKEANGPIVEGVTVKGDLNGSDDADTFYFDVKEDGDVTIELPYSGSS<br>NFTWLVYKEGDDQNHIASGIDKNNSKVGTFKATKGRHYVFIYKHDSASN<br>ISYSLNIKGLGNEKLKEKENNDSSDKATVIPNFNTTMQGSLLGDDSRDY<br>YSFEVKEEGEVNIELDKKDEFGVTWTLHPESNINDRITYGQVDGNKVSN<br>KVKLRPGKYYLLVYKYSGSGNYELRVNK |
| Collagenase II (SEQ ID NO: 2) Activator domain is underlined; peptidase domain is bold; and collagen recruitment domains (PKD & CBD) are in bold underline. | AVDKNNATAAVQNESKRYTVSYLKTLNYYDLVDLLVKTEIENLPDLFQY<br>SSDAKEFYGNKTRMSFIMDEIGRRAPQYTEIDHKGIPTLVEVVRAGFYL<br>GFHNKELNEINKRSFKERVIPSILAIQKNPNFKLGTEVQDKIVSATGLL<br>AGNETAPPEVVNNFTPIIQDCIKNMDRYALDDLKSKALFNVLAAPTYDI<br>TEYLRATKEKPENTPWYGKIDGFINELKKLALYGKINDNNSWIIDNGIY<br>HIAPLGKLHSNNKIGIETLTEVMKIYPYLSMQHLQSADQIERHYDSKDA<br>EGNKIPLDKFKKEGKEKYCPKTYTFDDGKVIIKAGARVEEEKVKRLYWA<br>SKEVNSQFFRVYGIDKPLEEGNPDDILTMVIYNSPEEYKLNSVLYGYDT<br>NNGGMYIEPDGTFFTYERKAEESTYTLEELFRHEYTHYLQGRYAVPGQW<br>GRTKLYDNDRLTWYEEGGAELFAGSTRTSGILPRKSIVSNIHNTTRNNR<br>YKLSDTVHSKYGASFEFYNYACMFMDYMYNKDMGILNKLNDLAKNNDVD<br>GYDNYIRDLSSNHALNDKYQDHMQERIDNYENLTVPFVADDYLVRHAYK<br>NPNEIYSEISEVAKLKDAKSEVKKSQYFSTFTLRGSYTGGASKGKLEDQ<br>KAMNKFIDDSLKKLDTYSWSGYKTLTAYFTNYKVDSSNRVTYDVVFHGY<br>LPNEGDSKNSLPYGKINGTYKGTEKEKIKFSSEGSFDPDGKIVSYEWDF<br>GDGNKSNEENPEHSYDKVGTYTVKLKVTDDKGESSVSTTTAEIKDLSEN<br>KLPVIYMHVPKSGALNQKVVFYGKGTYDPDGSIAGYQWDFGDGSDFSSE<br>QNPSHVYTKKGEYTVTLRVMDSSGQMSEKTMKIKITDPVYPIGTEKEPN<br>NSKETASGPIVPGIPVSGTIENTSDQDYFYFDVITPGEVKIDINKLGYG<br>GATWVVYDENNNAVSYATDDGQNLSGKFKADKPGRYYIHLYMFNGSYMP<br>YRINIEGSVGR |

The collagenase can comprise a mixture of collagenase I and collagenase II. The collagenase can comprise, for example, a mixture of a collagenase I comprising an amino acid sequence having 90%, 91%, 92%, 93%, 94%, 95%, 96%, 97%, 98%, 99%, or 100% sequence identity to the amino acid sequence of SEQ ID NO: 1 and a collagenase II comprising an amino acid sequence having 90%, 91%, 92%, 93%, 94%, 95%, 96%, 97%, 98%, 99%, or 100% sequence identity to the amino acid sequence of SEQ ID NO: 2. In some aspects, the collagenase comprises a mixture of the collagenase I comprising the amino acid sequence of SEQ ID NO: 1 and the collagenase II comprising the amino acid sequence of SEQ ID NO: 2. Suitable mixtures of the collagenase I and collagenase II include, for example, a collagenase I:collagenase II mass ratio of 0.1:1, 0.25:1, 0.5:1, 0.75:1, 1:1, 1.1:1, 1.25:1, 1.5:1, 1.75:1, 2:1, 1:0.1, 1:0.25, 1:0.5; 1:0.75, 1:1.1, 1:1.25, 1:1.5, 1:1.75, or 1:2. Each of the collagenase I and collagenase II may have a purity of at least 80%, 85%, 90%, 91%, 92%, 93%, 94%, 95%, 96%, 97%, 98%, 99%, or 100% as measured by, for example, reverse phase HPLC.

The collagenase can comprise collagenase *Clostridium histolyticum* (CCH). "CCH," as used herein, refers to collagenase *Clostridium histolyticum* containing a mixture of collagenase I (SEQ ID NO: 1) and collagenase II (SEQ ID NO: 2) in an approximate 1:1 mass ratio. CCH is obtained by the fermentation of *Clostridium histolyticum* (also known as *Hathewaya histolytica*).

The collagenase I and collagenase II can have the following characteristics:

Collagenase I (SRC microplate assay)
- $V_{max}$: About 0.08 to 7.70 $min^{-1}$
- $K_M$: About 4.1 to 410 nanoMolar
- $K_{cat}$: About 1.1 to 107 $sec^{-1}$
- $1/K_{cat}$: About 376 to 37,222 microseconds
- $Kcal/K_M$: About 5,140 to 508,814 $mM^{-1}$ $sec^{-1}$ Collagenase II (GPA microplate assay)
- $V_{max}$: About 0.3 to 30.5 $min^{-1}$
- $K_M$: About 0.03 to 3.1 mM
- $K_{cat}$: About 93 to 9,179 $sec^{-1}$
- $1/K_{cat}$: About 4 to 428 microseconds
- $K_{cat}/K_M$: About 60 to 5,934 $mM^{-1}$ $sec^{-1}$ The collagenase I and collagenase II can have the following characteristics:

Collagenase I (SRC assay):
- $V_{max}$: About 3.8 $min^{-1}$
- $K_M$: About $2.07\times10^4$ mM
- $K_{cat}$: About 53 $sec^{-1}$
- $1/K_{cat}$: About 18,799 microseconds
- $K_{cat}/K_M$: About 256,977 $mM^{-1}$ $sec^{-1}$ Collagenase II (GPA assay):
- $V_{max}$: About 15.4 $min^{-1}$
- $K_M$: About 1.6 mM
- $K_{cat}$: About 4,636 $sec^{-1}$
- $1/K_{cat}$: About 216 microseconds
- $K_{cat}/K_M$: About 2,997 $mM^{-1}$ $sec^{-1}$ Any of the disclosed methods can be used to treat plantar fibromatosis in one or both of the subject's feet. In some embodiments, the subject can have a single nodule in one foot or a single nodule in each foot. In some embodiments, the subject can have multiple nodules in one foot. In some embodiments, the subject can have a single nodule in one foot and multiple nodules in the other foot. In some embodiments, the subject can have multiple nodules in both feet. Accordingly, the disclosed methods can comprise administering a pharmaceutical formulation comprising collagenase into one or more plantar fibromatosis nodules in one or both of the subject's feet to thereby treat the plantar fibromatosis.

Suitable methods of administering the pharmaceutical formulation comprising collagenase include, for example, one or more intralesional injections of the pharmaceutical formulation into each of the one or more nodules. The number of intralesional injections depends, in part, on the number of nodules, the size of the nodule(s), and the number of anticipated treatment sessions. The methods can comprise one, two, three, four, five, six, seven, eight, nine, ten, or more than ten intralesional injections of the pharmaceutical formulation into each of the one or more nodules.

The disclosed methods can comprise administering the pharmaceutical composition during a single treatment session or during multiple treatment sessions. The number of treatment sessions will depend, in part, on the size and severity of the nodules/plantar fibromatosis as well as the response to the first or subsequent treatment sessions. The methods can comprise administering the pharmaceutical composition during one, two, three, four, five, six, seven, eight, nine, ten, or more than ten treatment sessions. The intralesional injections of the pharmaceutical formulation into each of the one or more nodules can be administered in a single treatment session, over multiple treatment sessions, or in each treatment session. For example, two injections can be given in a single treatment session, one injection can be given in a first treatment session and one injection can be given in a second treatment session, or two injections can be given in a first treatment session and two injections can be given in a second treatment session.

Subsequent treatment sessions can be initiated, for example, 1 week, 2 weeks, 3 weeks, 4 weeks, 5 weeks, or more than 5 weeks after the previous treatment session began. A subsequent treatment session can be initiated, for example, 1 week, 2 weeks, 3 weeks, 4 weeks, 5 weeks, or more than 5 weeks after the first treatment session began (e.g., Day 1 of the first treatment session). The subsequent treatment sessions can be initiated 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, or more than 35 days after the previous treatment session, such as the first treatment session, began. In some embodiments, the subsequent treatment session can begin on Day 21, Day 22, Day 23, Day 24, Day 25, Day 26, Day 27, Day 28, Day 29, Day 30, Day 31, Day 32, Day 33, Day 34, or Day 35 when the first treatment session began on Day 1. In some embodiments, the first treatment session can begin on Day 1 and the subsequent treatment session can begin on Day 29.

The collagenase I may have a potency of about 500 SRC units/mg to about 30,000 SRC units/mg. In some embodiments, the potency is about 500 SRC units/mg to about 25,000 SRC units/mg, or about 500 SRC units/mg to about 20,000 SRC units/mg, or about 500 SRC units/mg to about 15,000 SRC units/mg, or about 500 SRC units/mg to about 12,500 SRC units/mg, or about 500 SRC units/mg to about 10,000 SRC units/mg, or about 500 SRC units/mg to about 7,500 SRC units/mg, or about 500 SRC units/mg to about 5,000 SRC units/mg, or about 500 SRC units/mg to about 2,500 SRC units/mg, or about 500 SRC units/mg to about 2,000 SRC units/mg, or about 500 SRC units/mg to about 1,000 SRC units/mg, wherein "mg" refers to the amount of collagenase I present in a composition (as distinct from excipients and other constituents).

Suitable amounts of collagenase I administered per nodule in a single treatment session include about 5 SRC units to about 180,000 SRC units. In some embodiments, about 5 SRC units, about 25 SRC units, about 35 SRC units, about 50 SRC units, about 60 SRC units, about 75 SRC units, about 100 SRC units, about 200 SRC units, about 225 SRC units, about 250 SRC units, about 450 SRC units, about 500 SRC units, about 675 SRC units, about 750 SRC units, about 1,000 SRC units, about 2,100 SRC units, about 2,500 SRC units, about 3,600 SRC units, about 5,000 SRC units, about 10,000 SRC units, about 13,500 SRC units, about 15,000 SRC units, about 25,000 SRC units, about 27,000 SRC units, about 40,500 SRC units, about 50,000 SRC units, about 75,000 SRC units, about 100,000 SRC units, about 150,000 SRC units, about 175,000 SRC units, about 180,000 SRC units are administered per nodule in a single treatment session. In some embodiments, about 60 SRC units to about 40,500 SRC units are administered per nodule in a single treatment session.

The collagenase I may have a potency of about 5,000 f-SRC units/mg to about 30,000 f-SRC units/mg. In some embodiments, the potency is about 5,000 f-SRC units/mg to about 25,000 f-SRC units/mg, or about 5,000 f-SRC units/mg to about 20,000 f-SRC units/mg, or about 5,000 f-SRC units/mg to about 15,000 f-SRC units/mg, or about 5,000 f-SRC units/mg to about 12,500 f-SRC units/mg, or about 5,000 f-SRC units/mg to about 10,000 f-SRC units/mg, or about 5,000 f-SRC units/mg to about 7,500 f-SRC units/mg, wherein "mg" refers to the amount of collagenase I present in a composition (as distinct from excipients and other constituents).

Suitable amounts of collagenase I administered per nodule in a single treatment session include about 50 f-SRC units to about 180,000 f-SRC units. In some embodiments, about 50 f-SRC units, about 75 f-SRC units, about 100 f-SRC units, about 150 f-SRC units, about 200 f-SRC units, about 250 f-SRC units, about 350 f-SRC units, about 500 f-SRC units, about 600 f-SRC units, about 750 f-SRC units, about 1,000 f-SRC units, about 1,500 f-SRC units, about 2,000 f-SRC units, about 2,100 f-SRC units, about 2,250 f-SRC units, about 2,500 f-SRC units, about 3,600 f-SRC units, about 4,500 f-SRC units, about 5,000 f-SRC units, about 6,750 f-SRC units, about 7,500 f-SRC units, about 10,000 f-SRC units, about 13,500 f-SRC units, about 15,000 f-SRC units, about 20,000 f-SRC units, about 25,000 f-SRC units, about 27,000 f-SRC units, about 40,500 f-SRC units, about 50,000 f-SRC units, about 100,000 f-SRC units, about 150,000 f-SRC units, about 180,000 f-SRC units are administered per nodule in a single treatment session. In some embodiments, about 600 f-SRC units to about 40,500 f-SRC units are administered per nodule in a single treatment session.

The collagenase II may have a potency of about 10,000 GPA units/mg to about 400,000 GPA units/mg, or about 10,000 GPA units/mg to about 350,000 GPA units/mg, or about 10,000 GPA units/mg to about 300,000 GPA units/mg, or about 10,000 GPA units/mg to about 250,000 GPA units/mg, or about 10,000 GPA units/mg to about 200,000 GPA units/mg, or about 10,000 GPA units/mg to about 150,000 GPA units/mg, wherein "mg" refers to the amount of collagenase II present in a composition (as distinct from excipients and other constituents).

Suitable amounts of collagenase II administered per nodule in a single treatment session include about 1,000 GPA units to about 2,400,000 GPA units. In some embodiments, about 1,000 GPA units, about 2,500 GPA units, about 5,000 GPA units, about 7,000 GPA units, about 10,000 GPA units, about 12,000 GPA units, about 15,000 GPA units, about 25,000 GPA units, about 28,000 GPA units, about 45,000 GPA units, about 48,000 GPA units, about 50,000 GPA units, about 75,000 GPA units, about 90,000 GPA units, about 100,000 GPA units, about 135,000 GPA units, about 150,000 GPA units, about 180,000 GPA units, about 200,000 GPA units, about 250,000 GPA units, about 300,000 GPA units, about 360,000 GPA units, about 400,000 GPA units, about 500,000 GPA units, about 540,000 GPA units, about 600,000 GPA units, about 1,000,000 GPA units, about 2,000,000 GPA units, about 2,400,000 GPA units are administered per nodule in a single treatment session. In some embodiments, about 12,000 GPA units to about 540,000 GPA units are administered per nodule in a single treatment session.

The collagenase II may have a potency of about 175,000 f-GPA units/mg to about 500,000 f-GPA units/mg, or about 175,000 f-GPA units/mg to about 450,000 f-GPA units/mg, or about 175,000 f-GPA units/mg to about 400,000 f-GPA units/mg, or about 175,000 f-GPA units/mg to about 350,000 f-GPA units/mg, or about 175,000 f-GPA units/mg to about 300,000 f-GPA units/mg, or about 175,000 f-GPA units/mg to about 250,000 f-GPA units/mg, or about 175,000 f-GPA units/mg to about 200,000 f-GPA units/mg, wherein "mg" refers to the amount of collagenase II present in a composition (as distinct from excipients and other constituents).

Suitable amounts of collagenase II administered per nodule in a single treatment session include about 1,750 f-GPA units to about 3,000,000 f-GPA units. In some embodiments, about 1,750 f-GPA units, about 2,500 f-GPA units, about 5,000 f-GPA units, about 7,000 f-GPA units, about 10,000 f-GPA units, about 12,250 f-GPA units, about 15,000 f-GPA units, about 21,000 f-GPA units, about 25,000 f-GPA units, about 28,000 f-GPA units, about 35,000 f-GPA units, about 50,000 f-GPA units, about 60,000 f-GPA units, about 75,000 f-GPA units, about 78,750 f-GPA units, about 100,000 f-GPA units, about 150,000 f-GPA units, about 157,500 f-GPA units, about 200,000 f-GPA units, about 225,000 f-GPA units, about 236,250 f-GPA units, about 250,000 f-GPA units, about 300,000 f-GPA units, about 400,000 f-GPA units, about 450,000 f-GPA units, about 500,000 f-GPA units, about 600,000 f-GPA units, about 675,000 f-GPA units, about 1,000,000 f-GPA units, about 2,000,000 f-GPA units, about 3,000,000 f-GPA units are administered per nodule in a single treatment session. In some embodiments, about 21,000 f-GPA units to about 675,000 f-GPA units are administered per nodule in a single treatment session.

The collagenase I and/or collagenase II can have a potency of about 5,000 BTC units/mg to about 25,000 BTC units/mg, or about 5,000 BTC units/mg to about 20,000 BTC units/mg, or about 5,000 BTC units/mg to about 17,500 BTC units/mg, or about 5,000 BTC units/mg to about 15,000 BTC units/mg, or about 5,000 BTC units/mg to about 10,000 BTC units/mg, or about 5,000 BTC units/mg to about 7,500 BTC units/mg, wherein "mg" refers to the amount of collagenase(s) present in a composition (as distinct from excipients and other constituents).

Suitable amounts of collagenase I and/or collagenase II administered per nodule in a single treatment session include about 50 BTC units to about 150,000 BTC units. In some embodiments, about 50 BTC units, about 100 BTC units, about 150 BTC units, about 200 BTC units, about 250 BTC units, about 350 BTC units, about 500 BTC units, about 600 BTC units, about 750 BTC units, about 1,000 BTC units, about 1,250 BTC units, about 1,500 BTC units, about 1,750 BTC units, about 2,000 BTC units, about 2,250 BTC units, about 2,500 BTC units, about 3,000 BTC units, about 4,500 BTC units, about 5,000 BTC units, about 6,750 BTC units, about 10,000 BTC units, about 11,250 BTC units, about 15,000 BTC units, about 22,500 BTC units, about 25,000 BTC units, about 33,750 BTC units, about 50,000 BTC units, about 100,000 BTC units, about 150,000 BTC units are administered per nodule in a single treatment session. In some embodiments, about 600 BTC units to about 33,750 BTC units are administered per nodule in a single treatment session.

The collagenase I and/or collagenase II can have a potency of about 5,000 ABC units/mg to about 25,000 ABC units/mg, or about 5,000 ABC units/mg to about 20,000 ABC units/mg, or about 5,000 ABC units/mg to about 17,500 ABC units/mg, or about 5,000 ABC units/mg to about 15,000 ABC units/mg, or about 5,000 ABC units/mg to about 12,500 ABC units/mg, or about 5,000 ABC units/mg to about 10,000 ABC units/mg, or about 5,000 ABC units/mg to about 7,500 ABC units/mg, wherein "mg" refers to the amount of collagenase(s) present in a composition (as distinct from excipients and other constituents).

Suitable amounts of collagenase I and/or collagenase II administered per nodule in a single treatment session include about 50 ABC units to about 150,000 ABC units. In some embodiments, about 50 ABC units, about 100 ABC units, about 150 ABC units, about 200 ABC units, about 250 ABC units, about 350 ABC units, about 500 ABC units, about 600 ABC units, about 750 ABC units, about 1,000 ABC units, about 1,250 ABC units, about 1,500 ABC units, about 1,750 ABC units, about 2,000 ABC units, about 2,250 ABC units, about 2,500 ABC units, about 3,000 ABC units, about 4,500 ABC units, about 5,000 ABC units, about 6,750 ABC units, about 10,000 ABC units, about 11,250 ABC units, about 15,000 ABC units, about 22,500 ABC units, about 25,000 ABC units, about 33,750 ABC units, about 50,000 ABC units, about 100,000 ABC units, about 150,000 ABC units are administered per nodule in a single treatment session. In some embodiments, about 600 ABC units to about 33,750 ABC units are administered per nodule in a single treatment session.

The size of the nodule can be the largest of the length or width as measured by any measurement technique. In some embodiments, the length and/or width is measured by caliper. In some embodiments, the length and/or width is measured by ultrasound.

Suitable concentrations of the collagenase in the pharmaceutical formulation include about 0.01 mg/ml, about 0.025 mg/ml, about 0.050 mg/ml, about 0.075 mg/ml, about 0.1 mg/ml, about 0.125 mg/ml, about 0.150 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.25 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3.0 mg/ml, about 4.0 mg/ml, about 5.0 mg/ml, about 6.0 mg/ml, about 7.0 mg/ml, about 8.0 mg/ml, about 9.0 mg/ml, about 10.0 mg/ml, or greater than about 10.0 mg/ml. The concentration of collagenase in the pharmaceutical formulation can be from about 0.01 mg/ml to about 10.0 mg/ml, from about 0.01 mg/ml to about 5.0 mg/ml, from about 0.01 mg/ml to about 2.5 mg/ml, from about 0.01 mg/ml to about 1.0 mg/ml, from about 0.01 mg/ml to about 0.5 mg/ml, from about 0.01 mg/ml to about 0.1 mg/ml, from about 0.05 mg/ml to about 10.0 mg/ml, from about 0.1 mg/ml to about 10 mg/ml, from about 0.5 mg/ml to about 10 mg/ml, from about 1.0 mg/ml to about 10 mg/ml, from about 2.5 mg/ml to about 10 mg/ml, or from about 5.0 mg/ml to about 10 mg/ml. The collagenase can have a concentration of about 0.6 mg/ml to about 2.25 mg/ml. In some embodiments, the collagenase can have a concentration of about 0.6 mg/ml. In some embodiments, the collagenase can have a concentration of about 1.2 mg/ml. In some embodiments, the collagenase can have a concentration of about 2.25 mg/ml.

Suitable volumes of each injection include, for example, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, or greater than about 1.0 ml. In some embodiments, each injection has a volume of about 0.1 ml to 0.3 ml. In some embodiments, each injection has a volume of about 0.2 ml.

A total volume of about 0.1 ml to about 1.0 ml can be administered to each nodule. In some embodiments, a total volume of about 0.2 ml to about 0.6 ml can be administered to each nodule. A total volume of about 0.2 ml can be administered to each nodule. A total volume of about 0.3 ml can be administered to each nodule. A total volume of about 0.4 ml can be administered to each nodule. A total volume of about 0.5 ml can be administered to each nodule. A total volume of about 0.6 ml can be administered to each nodule.

The pharmaceutical formulation can comprise the collagenase and a pharmaceutically acceptable carrier. As used herein, "pharmaceutically acceptable carrier" or "pharmaceutical acceptable excipient" includes any material which, when combined with the collagenase, allows the collagenase to retain its biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for parenteral administration are phosphate buffered saline or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000). In some embodiments, the pharmaceutical formulation is XIAFLEX®. In some embodiments, the pharmaceutical formulation comprises 0.9% sodium chloride and 0.03% calcium chloride dihydrate in water.

The treating can comprise a reduction in consistency by palpation of one or more of the nodules. Reduction in consistency by palpation includes an at least one level reduction on the scale of 0-4 from Baseline, with Hard (no give) being assigned a value of 4, Firm Throughout (a little resistance) being assigned a value of 3, Moderately Firm (some resistance) being assigned a value of 2, Soft (no resistance) being assigned a value of 1, and non-palpable being assigned a value of 0. In some embodiments, for example, the reduction in consistency comprises a reduction from Hard (4) to Firm Throughout (3). In some embodiments, for example, the reduction in consistency comprises a reduction from Hard (4) to Soft (1). The consistency and hardness of the nodules, before and/or after treatment, can be determined by palpation and/or durometer measurements.

The treating can comprise a reduction in size of one or more of the nodules. Suitable reductions in size include, for example, a 1%, 5%, 10%, 15%, 20%, 25%, 30%, 35%, 40%, 45%, 50%, or greater than 50% reduction in size compared to the size of the nodule at baseline. The size of the nodules, before and/or after treatment, can be determined by caliper measurements.

The following assessments/scales can be used to assess the treatment:

- Average Daily Pain (ADP) score, in which the subject's score on the Pain Intensity NRS is taken daily and then averaged to determine a weekly mean of ADP scores on the Pain Intensity NRS.
- Foot Function Index (FFI), including the Long Form (LF), Revised Long Form (FFI-R Long Form), Revised Short Form (FFI-R Short Form), Short Form (SF), Short Form-23 (as described herein), FFI-PF-May 2021 (as described herein), and modifications of the FFI scales (as described in Budiman-Mak E, et al., A review of the foot function index and the foot function index-revised. *J Foot Ankle Res.* 2013; 6 (1): 5; Budiman-Mak E, et al., The Foot Function Index: a measure of foot pain and disability. *J Clin Epidemiol.* 1991; 44 (6): 561-570.). The Foot Function Index Short Form-23 (FFI-SF-23), can include:
  - The foot pain subscale of the FFI-SF-23 (9 items), ranging from 0 ("No Pain") to 10 ("Worst Pain Imaginable"). Higher scores indicate greater impairment.
  - The difficulty subscale (9 items) of the FFI-SF-23, ranging from 0 ("No Difficulty") to 10 ("So Difficult Unable"). Higher scores indicate greater impairment.
  - The disability subscale (5 items) of the FFI-SF-23, ranging from 0 ("None of the Time") to 10 ("All of the Time"). Higher scores indicate greater impairment.
- The FFI-PF-May 2021 can include:
  - The pain subscale (9 items), ranging from 0 ("none") to 4 ("extreme").
  - The difficulty subscale (9 items), ranging from 0 ("no difficulty") to 4 ("a lot of difficulty").
  - The activity limitation subscale (3 items), ranging from 0 ("never") to 4 ("always").
- Subject Satisfaction With Treatment Scale, which is a 5-point scale ranging from −2 ("Very Dissatisfied") to +2 ("Very Satisfied").
- Investigator Assessment of Improvement with Treatment Scale, which is a 7-point scale ranging from −3 ("Very Much Worse") to +3 ("Very Much Improvement").

The treating can comprise a reduction in foot function index (FFI) composite score, FFI total score, or both. Methods of calculating the FFI composite score and total score are described in the Examples herein.

The treating can comprise a reduction in FFI pain subscale score, FFI difficulty subscale score, FFI disability subscale score, or any combination thereof. Methods of calculating the FFI-SF-23 subscale score values are described in the Examples herein.

The treating can comprise a reduction in FFI pain subscale score, FFI difficulty subscale score, FFI activity limitation subscale score, or any combination thereof. Methods of calculating the FFI-PF-May2021 subscale score values are described in the Examples herein.

The treating can comprise an increase in the Subject Satisfaction With Treatment Scale. A responder is defined as a subject with a response of "Quite Satisfied" or "Very Satisfied" in the Subject Satisfaction with treatment scale during evaluation of each treated nodule. Methods of calculating the Subject Satisfaction With Treatment Scale are described in the Examples herein.

The treating can comprise an increase in the Investigator Assessment of Improvement with Treatment Scale. A responder is defined as a subject with a response of "Minimal Improvement", "Much Improvement" or "Very Much Improvement" in the Investigator Assessment of Improvement Scale during evaluation of each treated nodule. Methods of calculating the Investigator Assessment of Improvement with Treatment Scale are described in the Examples herein.

The treating can comprise an increase in the Clinician Global Impression of Change Scale. A responder is defined as a subject with a response of "Minimal Improvement", "Much Improvement" or "Very Much Improvement" in the Investigator Assessment of Improvement Scale during evaluation of each treated nodule. Methods of calculating the Clinician Global Impression of Change Scale are described in the Examples herein.

The treating can comprise any combination of:

a reduction in consistency of one or more of the nodules;
a reduction in size of one or more of the nodules;
a reduction in foot function index (FFI) composite score;
a reduction in FFI total score;
a reduction in FFI pain subscale score;
a reduction in FFI difficulty subscale score;
a reduction in FFI disability subscale score;
a reduction in FFI activity limitation subscale score;
a reduction in PGIS Foot Pain Subscale score;
an increase in PGIC Foot Pain Subscale score;
a reduction in PGIS Difficulty Subscale score;
an increase in PGIC Difficulty Subscale score;
a reduction in PGIS Activity Limitation Subscale score;
an increase in PGIC Activity Limitation Subscale score;
a reduction in PGIS-PF Overall score;
an increase in PGIC PF Overall score;
a reduction in Pain Intensity NRS score;
eliminating one or more plantar fibromatosis nodules,
an increase in Subject Satisfaction With Treatment Scale; and
an increase in Investigator Assessment of Improvement with Treatment Scale;
an increase in Clinician Global Impression of Change Scale;
a reduction in LSM FFI Foot Pain score; and
a reduction in combined FFI pain and difficulty score.

Also disclosed herein is the use of collagenase in the preparation of a medicament for treating plantar fibromatosis in a subject, wherein the medicament is prepared for injection into one or more plantar fibromatosis nodules in the subject's foot.

Collagenase for use in treating plantar fibromatosis in a subject is also provided, wherein the collagenase is injected into one or more plantar fibromatosis nodules in the subject's foot to thereby treat the plantar fibromatosis.

EMBODIMENTS

The following list of embodiments is intended to complement, rather than displace or supersede, the previous descriptions.

1A. A method of treating moderate to severe plantar fibromatosis in a subject or a population of subjects, the method comprising:
intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.45 mg to about 1.35 mg and the treating comprises:
a reduction from baseline as measured on a foot function index (FFI) pain sub scale;
a reduction from baseline as measured on a FFI combined pain and difficulty subscale;
an improvement from baseline as measured on a patient global impression of change (PGIC)-PF overall scale;
a reduction from baseline as measured on a FFI total composite score;
an improvement from baseline as measured on a subject satisfaction with treatment scale;
a reduction from baseline in LSM FFI Foot Pain score;
a reduction from baseline in combined FFI pain and Difficulty score;
an improvement from baseline in nodule consistency;
a reduction from baseline in the nodular hardness;
or any combination thereof.

2A. The method of embodiment 1A, wherein the collagenase comprises collagenase I activity, collagenase II activity, or a mixture of collagenase I activity and collagenase II activity.

3A. The method of embodiment 1A or 2A, wherein the collagenase comprises a mixture of collagenase I activity and collagenase II activity.

4A. A method of treating moderate to severe plantar fibromatosis in a subject or a population of subjects by administering a collagenase enzyme at a dose of about 0.45 mg to about 1.35 mg per nodule, the collagenase enzyme comprising:
means for breaking down collagen type I, collagen type III, and combinations thereof,
wherein the treating comprises:
a reduction from baseline as measured on a foot function index (FFI) pain sub scale;
a reduction from baseline as measured on a FFI combined pain and difficulty subscale;
an improvement from baseline as measured on a patient global impression of change (PGIC)-PF overall scale;
a reduction from baseline as measured on a FFI total composite score;
an improvement from baseline as measured on a subject satisfaction with treatment scale;
a reduction from baseline in LSM FFI Foot Pain score;
a reduction from baseline in combined FFI pain and Difficulty score;
an improvement from baseline in nodule consistency;
a reduction from baseline in the nodular hardness;
or any combination thereof.

5A. The method of any one of the previous embodiments, wherein the reduction or improvement occurs at Day 57 or earlier.

6A. The method of any one of the previous embodiments, wherein the reduction or improvement is an at least 1 point reduction from baseline or an at least 1 point improvement from baseline.

7A. The method of any one of the previous embodiments, wherein the subject had an NRS score of ≥5 and <10 prior to treatment.

8A. The method of any one of the previous embodiments, wherein, prior to the injecting, the plantar fibromatosis nodules are hard or firm.

9A. The method of any one of the previous embodiments, wherein, prior to injecting, the subject had an NRS score of less than 10 and did not have moderately firm plantar fibromatosis nodule(s).

10A. The method of any one of the previous embodiments, wherein the collagenase has a concentration of about 0.6 mg/ml to about 2.25 mg/ml.

11A. The method of any one of the previous embodiments, wherein the collagenase has a potency of about 500 SRC units/mg to about 30,000 SRC units/mg.

12A. The method of any one of the previous embodiments, wherein about 5 SRC units to about 180,000 SRC units of collagenase are administered per nodule.

13A. The method of any one of the previous embodiments, wherein the collagenase has a potency of about 10,000 GPA units/mg to about 400,000 GPA units/mg.

14A. The method of any one of the previous embodiments, wherein about 1,000 GPA units to about 2,400,000 GPA units of collagenase are administered per nodule.

15A. A method of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.6 mg, and the treating comprises:

a reduction from baseline in the weekly mean of the average daily pain (ADP) score;

a reduction from baseline in the FFI Difficulty Subscale score of the FFI;

a reduction from baseline on the FFI Activity Limitation Subscale score;

a reduction from baseline in the weekly mean of the ADP score;

a reduction from baseline on the FFI Pain Subscale score;

a reduction from baseline on the FFI Total score;

an improvement from baseline on the PGIS PF Overall score;

an improvement from baseline on the PGIS Foot Pain Subscale;

an improvement from baseline on the PGIS Difficulty Subscale;

an improvement from baseline on the PGIS Activity Limitation Subscale;

an improvement from baseline in nodule consistency (firmness);

a reduction from baseline in the nodular hardness;

a reduction from baseline in LSM FFI Foot Pain score;

a reduction from baseline in combined FFI pain and Difficulty score;

or any combination thereof.

16A. The method of embodiment 15A, wherein the collagenase comprises collagenase I activity, collagenase II activity, or a mixture of collagenase I activity and collagenase II activity.

17A. The method of embodiment 15A or 16A, wherein the collagenase comprises a mixture of collagenase I activity and collagenase II activity.

18A. A method of treating moderate to severe plantar fibromatosis in a subject or a population of subjects by administering a collagenase enzyme at a dose of about 0.6 mg per nodule, the collagenase enzyme comprising:

means for breaking down collagen type I, collagen type III, and combinations thereof' wherein the treating comprises:

a reduction from baseline in the weekly mean of the average daily pain (ADP) score;

a reduction from baseline in the FFI Difficulty Subscale score of the FFI;

a reduction from baseline on the FFI Activity Limitation Subscale score;

a reduction from baseline in the weekly mean of the ADP score;

a reduction from baseline on the FFI Pain Subscale score;

a reduction from baseline on the FFI Total score;

an improvement from baseline on the PGIS PF Overall score;

an improvement from baseline on the PGIS Foot Pain Subscale;

an improvement from baseline on the PGIS Difficulty Subscale;

an improvement from baseline on the PGIS Activity Limitation Subscale;

an improvement from baseline in nodule consistency (firmness);

a reduction from baseline in the nodular hardness;

a reduction from baseline in LSM FFI Foot Pain score;

a reduction from baseline in combined FFI pain and Difficulty score;

or any combination thereof.

19A. The method of any one of embodiments 15A-18A, wherein the reduction or improvement occurs at Day 85 or earlier.

20A. The method of any one of embodiments 15A-19A, wherein the reduction or improvement is an at least 1 point reduction from baseline or an at least 1 point improvement from baseline.

21A. The method of any one of embodiments 15A-20A, wherein the subject had an NRS score of 5 to 9 prior to treatment.

22A. The method of embodiment 21A, wherein the subject had an average daily pain (ADP) score on the Pain Intensity NRS of 5 to 9 during the 7 days prior to treatment.

23A. The method of any one of embodiments 15A-22A, wherein, prior to the injecting, the plantar fibromatosis nodules are hard or firm.

24A. The method of any one of embodiments 15A-23A, wherein, prior to injecting, the subject had an NRS score of less than or equal to 9 and did not have moderately firm plantar fibromatosis nodule(s).

25A. The method of any one of embodiments 15A-24A, wherein the plantar fibromatosis nodule is less than or equal to 4 cm in size.

26A. The method of embodiment 25A, comprising administering a single injection of the collagenase to any nodule that is less than 2 cm in size.

27A. The method of embodiment 25A, comprising administering two injections of the collagenase to any nodule that is greater than 2 cm but less than 4 cm in size.

28A. The method of embodiment 27A, wherein each of the two injections comprises 0.3 mg of the collagenase.

29A. The method of any one of embodiments 15A-28A, wherein the collagenase has a concentration of about 0.6 mg/ml to about 2.25 mg/ml.

30A. The method of any one of embodiments 15A-29A, wherein the collagenase has a potency of about 500 SRC units/mg to about 30,000 SRC units/mg.

31A. The method of any one of embodiments 15A-30A, wherein about 5 SRC units to about 180,000 SRC units of collagenase are administered per nodule.

32A. The method of any one of embodiments 15A-31A, wherein the collagenase has a potency of about 10,000 GPA units/mg to about 400,000 GPA units/mg.

33A. The method of any one of embodiments 15A-32A, wherein about 1,000 GPA units to about 2,400,000 GPA units of collagenase are administered per nodule.

34A. The method of any one of the previous embodiments, wherein the reduction in FFI Foot Pain score, the reduction in combined FFI pain and Difficulty score, or the reduction in FFI Foot Pain score and the reduction in combined FFI pain and Difficulty score occurred over 57 days.

35A. The method of any one of the previous embodiments, wherein the population of subjects treated with the collagenase exhibit greater proportions of CGIC score and nodule consistency responders as compared to a population of subjects treated with placebo.

The following list of additional embodiments is intended to complement, rather than displace or supersede, the previous descriptions.

1B. A method of treating moderate to severe plantar fibromatosis in a subject or a population of subjects, the method comprising:
intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.45 mg to about 1.35 mg and the treating comprises:
an improvement from baseline in nodule consistency;
a reduction from baseline in the nodular hardness;
or a combination thereof.

2B. The method of embodiment 1B, wherein the reduction or improvement occurs at Day 57 or earlier.

3B. The method of embodiment 1B, wherein the reduction or improvement is an at least 1 point reduction from baseline or an at least 1 point improvement from baseline.

4B. The method of embodiment 1B, wherein the collagenase comprises collagenase I activity, collagenase II activity, or a mixture of collagenase I activity and collagenase II activity.

5B. The method of embodiment 1B, wherein the subject has an NRS score of ≥5 and <10 prior to treatment.

6B. The method of embodiment 1B, wherein, prior to the injecting, the plantar fibromatosis nodules are hard or firm.

7B. The method of embodiment 1B, wherein, prior to injecting, the subject had an NRS score of less than 10 and did not have moderately firm plantar fibromatosis nodule(s).

8B. The method of embodiment 1B, wherein the collagenase has a concentration of about 0.6 mg/ml to about 2.25 mg/ml.

9B. The method of embodiment 1B, wherein the collagenase has a potency of about 500 SRC units/mg to about 30,000 SRC units/mg.

10B. The method of embodiment 1B, wherein about 5 SRC units to about 180,000 SRC units of collagenase are administered per nodule.

11B. The method of embodiment 1B, wherein the collagenase has a potency of about 10,000 GPA units/mg to about 400,000 GPA units/mg.

12B. The method of embodiment 1B, wherein about 1,000 GPA units to about 2,400,000 GPA units of collagenase are administered per nodule.

13B. A method of treating moderate to severe plantar fibromatosis in a subject or a population of subjects, the method comprising:
intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.6 mg, and the treating comprises:
an improvement from baseline in nodule consistency;
a reduction from baseline in the nodular hardness;
or a combination thereof.

14B. The method of embodiment 13B, wherein the reduction or improvement occurs at Day 85 or earlier.

15B. The method of embodiment 13B, wherein the reduction or improvement is an at least 1 point reduction from baseline or an at least 1 point improvement from baseline.

16B. The method of embodiment 13B, wherein the collagenase comprises collagenase I activity, collagenase II activity, or a mixture of collagenase I activity and collagenase II activity.

17B. The method of embodiment 13B, wherein the subject had an NRS score of 5 to 9 prior to treatment.

18B. The method of embodiment 13B, wherein the subject had an average daily pain (ADP) score on the Pain Intensity NRS of 5 to 9 during the 7 days prior to treatment.

19B. The method of embodiment 13B, wherein, prior to the injecting, the plantar fibromatosis nodules are hard or firm.

20B. The method of embodiment 13B, wherein, prior to injecting, the subject had an NRS score of less than or equal to 9 and did not have moderately firm plantar fibromatosis nodule(s).

21B. The method of embodiment 13B, wherein the plantar fibromatosis nodule is less than or equal to 4 cm in size.

22B. The method of embodiment 21B, comprising administering a single injection of the collagenase to any nodule that is less than 2 cm in size.

23B. The method of embodiment 21B, comprising administering two injections of the collagenase to any nodule that is greater than 2 cm but less than 4 cm in size.

24B. The method of embodiment 23B, wherein each of the two injections comprises 0.3 mg of the collagenase.

25B. The method of embodiment 13B, wherein the collagenase has a concentration of about 0.6 mg/ml to about 2.25 mg/ml.

26B. The method of embodiment 13B, wherein the collagenase has a potency of about 500 SRC units/mg to about 30,000 SRC units/mg.

27B. The method of embodiment 13B, wherein about 5 SRC units to about 180,000 SRC units of collagenase are administered per nodule.

28B. The method of embodiment 13B, wherein the collagenase has a potency of about 10,000 GPA units/mg to about 400,000 GPA units/mg.

29B. The method of embodiment 13B, wherein about 1,000 GPA units to about 2,400,000 GPA units of collagenase are administered per nodule.

The following list of additional embodiments is intended to complement, rather than displace or supersede, the previous descriptions.

1C. A method of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.45 mg to about 1.35 mg and the treating comprises:

a reduction from baseline as measured on a foot function index (FFI) pain sub scale;

a reduction from baseline as measured on a FFI combined pain and difficulty subscale;

a reduction from baseline in LSM FFI Foot Pain score;

a reduction from baseline in combined FFI pain and Difficulty score;

or any combination thereof.

2C. The method of embodiment 1C, wherein the reduction or improvement occurs at Day 57 or earlier.

3C. The method of embodiment 1C, wherein the reduction or improvement is an at least 1 point reduction from baseline or an at least 1 point improvement from baseline.

4C. The method of embodiment 1C, wherein the collagenase comprises collagenase I activity, collagenase II activity, or a mixture of collagenase I activity and collagenase II activity.

5C. The method of embodiment 1C, wherein the subject has an NRS score of ≥5 and <10 prior to treatment.

6C. The method of embodiment 1C, wherein, prior to the injecting, the plantar fibromatosis nodules are hard or firm.

7C. The method of embodiment 1C, wherein, prior to injecting, the subject had an NRS score of less than 10 and did not have moderately firm plantar fibromatosis nodule(s).

8C. The method of embodiment 1C, wherein the collagenase has a concentration of about 0.6 mg/ml to about 2.25 mg/ml.

9C. The method of embodiment 1C, wherein the collagenase has a potency of about 500 SRC units/mg to about 30,000 SRC units/mg.

10C. The method of embodiment 1C, wherein about 5 SRC units to about 180,000 SRC units of collagenase are administered per nodule.

11C. The method of embodiment 1C, wherein the collagenase has a potency of about 10,000 GPA units/mg to about 400,000 GPA units/mg.

12C. The method of embodiment 1C, wherein about 1,000 GPA units to about 2,400,000 GPA units of collagenase are administered per nodule.

13C. A method of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.6 mg, and the treating comprises:

a reduction from baseline in the weekly mean of the average daily pain (ADP) score;

a reduction from baseline in the weekly mean of the ADP score;

a reduction from baseline on the FFI Pain Subscale score;

an improvement from baseline on the PGIS Foot Pain Subscale;

a reduction from baseline in LSM FFI Foot Pain score;

a reduction from baseline in combined FFI pain and Difficulty score;

or any combination thereof.

14C. The method of embodiment 13C, wherein the reduction or improvement occurs at Day 85 or earlier.

15C. The method of embodiment 13C, wherein the reduction or improvement is an at least 1 point reduction from baseline or an at least 1 point improvement from baseline.

16C. The method of embodiment 13C, wherein the collagenase comprises collagenase I activity, collagenase II activity, or a mixture of collagenase I activity and collagenase II activity.

17C. The method of embodiment 13C, wherein the subject had an NRS score of 5 to 9 prior to treatment.

18C. The method of embodiment 13C, wherein the subject had an average daily pain (ADP) score on the Pain Intensity NRS of 5 to 9 during the 7 days prior to treatment.

19C. The method of embodiment 13C, wherein, prior to the injecting, the plantar fibromatosis nodules are hard or firm.

20C. The method of embodiment 13C, wherein, prior to injecting, the subject had an NRS score of less than or equal to 9 and did not have moderately firm plantar fibromatosis nodule(s).

21C. The method of embodiment 13C, wherein the plantar fibromatosis nodule is less than or equal to 4 cm in size.

22C. The method of embodiment 21C, comprising administering a single injection of the collagenase to any nodule that is less than 2 cm in size.

23C. The method of embodiment 21C, comprising administering two injections of the collagenase to any nodule that is greater than 2 cm but less than 4 cm in size.

24C. The method of embodiment 23C, wherein each of the two injections comprises 0.3 mg of the collagenase.

25C. The method of embodiment 13C, wherein the collagenase has a concentration of about 0.6 mg/ml to about 2.25 mg/ml.

26C. The method of embodiment 13C, wherein the collagenase has a potency of about 500 SRC units/mg to about 30,000 SRC units/mg.

27C. The method of embodiment 13C, wherein about 5 SRC units to about 180,000 SRC units of collagenase are administered per nodule.

28C. The method of embodiment 13C, wherein the collagenase has a potency of about 10,000 GPA units/mg to about 400,000 GPA units/mg.

29C. The method of embodiment 13C, wherein about 1,000 GPA units to about 2,400,000 GPA units of collagenase are administered per nodule.

The following list of additional embodiments is intended to complement, rather than displace or supersede, the previous descriptions.

1D. A method of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.45 mg to about 1.35 mg and the treating comprises:

an improvement from baseline as measured on a patient global impression of change (PGIC)-PF overall scale;

a reduction from baseline as measured on a FFI total composite score;

an improvement from baseline as measured on a subject satisfaction with treatment scale;

or any combination thereof.

2D. The method of embodiment 1D, wherein the reduction or improvement occurs at Day 57 or earlier.

3D. The method of embodiment 1D, wherein the reduction or improvement is an at least 1 point reduction from baseline or an at least 1 point improvement from baseline.

4D. The method of embodiment 1D, wherein the collagenase comprises collagenase I activity, collagenase II activity, or a mixture of collagenase I activity and collagenase II activity.

5D. The method of embodiment 1D, wherein the subject has an NRS score of ≥5 and <10 prior to treatment.

6D. The method of embodiment 1D, wherein, prior to the injecting, the plantar fibromatosis nodules are hard or firm.

7D. The method of embodiment 1D, wherein, prior to injecting, the subject had an NRS score of less than 10 and did not have moderately firm plantar fibromatosis nodule(s).

8D. The method of embodiment 1D, wherein the collagenase has a concentration of about 0.6 mg/ml to about 2.25 mg/ml.

9D. The method of embodiment 1D, wherein the collagenase has a potency of about 500 SRC units/mg to about 30,000 SRC units/mg.

10D. The method of embodiment 1D, wherein about 5 SRC units to about 180,000 SRC units of collagenase are administered per nodule.

11D. The method of embodiment 1D, wherein the collagenase has a potency of about 10,000 GPA units/mg to about 400,000 GPA units/mg.

12D. The method of embodiment 1D, wherein about 1,000 GPA units to about 2,400,000 GPA units of collagenase are administered per nodule.

13D. A method of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the dose of collagenase administered per nodule comprises about 0.6 mg, and the treating comprises:

a reduction from baseline in the FFI Difficulty Subscale score of the FFI;

a reduction from baseline on the FFI Activity Limitation Subscale score;

a reduction from baseline on the FFI Total score;

an improvement from baseline on the PGIS PF Overall score;

an improvement from baseline on the PGIS Difficulty Subscale;

an improvement from baseline on the PGIS Activity Limitation Subscale;

or any combination thereof.

14D. The method of embodiment 13D, wherein the reduction or improvement occurs at Day 85 or earlier.

15D. The method of embodiment 13D, wherein the reduction or improvement is an at least 1 point reduction from baseline or an at least 1 point improvement from baseline.

16D. The method of embodiment 13D, wherein the collagenase comprises collagenase I activity, collagenase II activity, or a mixture of collagenase I activity and collagenase II activity.

17D. The method of embodiment 13D, wherein the subject had an NRS score of 5 to 9 prior to treatment.

18D. The method of embodiment 13D, wherein the subject had an average daily pain (ADP) score on the Pain Intensity NRS of 5 to 9 during the 7 days prior to treatment.

19D. The method of embodiment 13D, wherein, prior to the injecting, the plantar fibromatosis nodules are hard or firm.

20D. The method of embodiment 13D, wherein, prior to injecting, the subject had an NRS score of less than or equal to 9 and did not have moderately firm plantar fibromatosis nodule(s).

21D. The method of embodiment 13D, wherein the plantar fibromatosis nodule is less than or equal to 4 cm in size.

22D. The method of embodiment 21D, comprising administering a single injection of the collagenase to any nodule that is less than 2 cm in size.

23D. The method of embodiment 21D, comprising administering two injections of the collagenase to any nodule that is greater than 2 cm but less than 4 cm in size.

24D. The method of embodiment 23D, wherein each of the two injections comprises 0.3 mg of the collagenase.

25D. The method of embodiment 13D, wherein the collagenase has a concentration of about 0.6 mg/ml to about 2.25 mg/ml.

26D. The method of embodiment 13D, wherein the collagenase has a potency of about 500 SRC units/mg to about 30,000 SRC units/mg.

27D. The method of embodiment 13D, wherein about 5 SRC units to about 180,000 SRC units of collagenase are administered per nodule.

28D. The method of embodiment 13D, wherein the collagenase has a potency of about 10,000 GPA units/mg to about 400,000 GPA units/mg.

29D. The method of embodiment 13D, wherein about 1,000 GPA units to about 2,400,000 GPA units of collagenase are administered per nodule.

EXAMPLES

The following examples are provided to further describe some of the embodiments disclosed herein. The examples are intended to illustrate, not to limit, the disclosed embodiments.

Example 1—Enzyme Assays

Collagenase I Potency as Measured by SRC Assay (Cuvette)

The SRC assay is primarily used to measure the potency of collagenase I. The general methodology is as follows. Leucine standards and collagenase sample solutions are prepared. The first step of the assay involves an enzymatic reaction in which soluble rat-tail tendon collagen (SRC) is digested by the collagenase. The second step involves the subsequent measurement of liberated peptide fragments/amino acids with the fluorogenic derivative fluorescamine. The assay follows the methodology below, but a person of ordinary skill in the art will appreciate that certain modifications (e.g., dilution concentrations and times) may be made.

Collagenase and leucine standard samples are treated with reagents in order to tag the generated GPA with fluorescamine. The leucine standards and collagenase samples are allowed to incubate at room temperature for 10 minutes prior to determining the fluorescence of each solution at 392 and 480 nm excitation and emission wavelengths, respectively. The resulting slopes of the leucine and collagenase sample curves are then used to calculate potency units as follows:

$$\text{Potency } (f\text{-}SRC \text{ units/mg} = (M_{Sample}/M_{Leucine}) \times (DF/T) \times CF$$

where:

$M_{sample}$=Slope of the collagenase sample potency curve $M_{Leucine}$=Slope of the leucine standard curve DF=Dilution Factor (1500 μL/100 mL=15)

T=Reaction time (2.5 hr×60 min/1 hr=150 min)

CF=Conversion factor (1000 μg/1 mg=1000)

An exemplary SRC assay is set forth below:

Buffers and Reagents

The following buffers/reagents are used:

1. F-TC Assay Buffer, pH 7.2 (22g HEPES [4-(2-Hydroxyethyl)-1-piperazineethanesulfonic acid], 4.4 g calcium acetate)
2. F-Enzyme Buffer, pH 7.2
3. 200 mM Borate, pH 9.0
4. 10 mM Leucine Stock Solution
5. 1 mM Leucine Working Stock Solution
6. 1 mM Fluorescamine Solution in Acetone
7. 2 mg/mL Rat Tail Collagen in 0.02N acetic acid Preparation of Solutions Solutions are prepared as follows:

F-TC Assay Buffer: Dissolve 22 g HEPES and 4.4 g calcium acetate in approximately 900 mL of water. Adjust pH to 7.2 with sodium hydroxide and QS to 1 L with water. Store at 2-8° C.

F-Enzyme Buffer: Dilute F-TC Assay Buffer by combining 4 mL with 16 mL water. Store at 2-8° C.

10 mM Leucine Stock Solution: Dissolve 65.5 mg of leucine in 50 mL of water. Leucine must be weighed directly into a 100 mL (or equivalent) glass beaker on the scale. Weigh out approximately 65 mg (target weight) of leucine into the beaker. Based on the weight of leucine weighed, calculate the amount of water to add to the beaker using the equation below. Add the calculated volume of water to the beaker and mix thoroughly to ensure the leucine is fully dissolved. Dispense into 1 mL aliquots. Store at less than or equal to −20° C.

$$V2(\text{mL}) = C2(\text{mg}) \times \frac{V1(50 \text{ mL})}{C1(65.5 \text{ mg})}$$

Where:

C2=mass of leucine weighed (mg)

V1=50 (mL of water)

C1=65.5 (mg of leucine)

V2=volume of water needed to produce a 10 mM stock solution (mL)

1 mM Leucine Working Stock Solution: Thaw a vial of 10 mM Leucine Stock Solution and dilute to 1 mM by combining 150 μL with 1350 μL water. Mix well prior to use.

0.5 N HCl: Dilute HCl to 0.5 N with water and mix well. Store at room temperature. Alternatively, commercially available 0.5 N HCl may be used.

0.02 N Acetic Acid: Combine 1 mL of 1 N Acetic Acid with 49 mL of water and mix well. Store at room temperature.

200 mM Borate, pH 9.0: Dissolve 2.4 g boric acid in approximately 150 mL water. Adjust the pH to 9.0 using sodium hydroxide. QS to 200 mL with water and mix well. Store at 2-8° C.

1 mM Fluorescamine Solution: Dissolve 15 mg of fluorescamine with 50 mL acetone and swirl to dissolve. Store at 2-8° C. protected from light.

Substrate Solution (2 mg/mL Rat Tail Collagen): Dilute sock rat tail collagen to 2 mg/mL with 0.02 N acetic acid. Store at 2-8° C.

The leucine standard curve is prepared according to the following table.

TABLE 2

Preparation of the leucine standard curve

| Reagent | L1 | L2 | L3 | L4 | L5 | L6 |
|---|---|---|---|---|---|---|
| Leucine Conc. (μM) | 0 | 70 | 140 | 210 | 280 | 350 |
| Water (μL) | 1000 | 930 | 860 | 790 | 720 | 650 |
| 1 mM Leucine (μL) | 0 | 70 | 140 | 210 | 280 | 350 |

100 μL of each Leucine Standard is then transferred into separate centrifuge tubes for detection of fluorescamine.

Collagenase Sample and Blanks Preparation

The sample is diluted to 0.01 mg/mL with F-Enzyme Buffer in two stages vortexed gently to mix. The following is an example dilution scheme:

$$1.\ 100\ \mu\text{L} \times 1.0\ \text{mg/mL} \rightarrow 1000\ \mu\text{L} = 0.1\ \text{mg/mL}$$

$$2.\ 100\ \mu\text{L} \times 0.1\ \text{mg/mL} \rightarrow 1000\ \mu\text{L} = 0.01\ \text{mg/mL}$$

The diluted samples are maintained at room temperature until use.

Blanks are prepared according to the following table by first combining the sample and 0.5 N hydrochloric acid to inactivate the enzyme prior to addition of buffers and substrate.

Collagenase samples in labeled tubes according to the following table. Tubes 1, 2, 4 and 6 are prepared from one preparation and tubes 3, 5 and 7 from the duplicate preparation.

TABLE 3

Blank and Collagenase Sample Preparations

| Preparation | Tube(s) | 0.5N HCl (μL) | F-Enzyme Buffer (μL) | F-TC Buffer (μL) | 2 mg/mL RTC (μL) | Sample (μL) |
|---|---|---|---|---|---|---|
| Blank | 1 | 750 | 137.5 | 375 | 187.5 | 50.0 |
| Potency Curve | 2-3 | — | 167.5 | 375 | 187.5 | 20.0 |

TABLE 3-continued

| Blank and Collagenase Sample Preparations | | | | | | |
|---|---|---|---|---|---|---|
| Preparation | Tube(s) | 0.5N HCl (µL) | F-Enzyme Buffer (µL) | F-TC Buffer (µL) | 2 mg/mL RTC (µL) | Sample (µL) |
| | 4-5 | — | 152.5 | 375 | 187.5 | 35.0 |
| | 6-7 | — | 137.5 | 375 | 187.5 | 50.0 |

The tubes are capped and vortexed gently to mix. The potency curve preparations are incubated in a 25° C.±3° C. water bath for 2.5 hours. At the end of incubation, the potency curve tubes are removed from the water bath. 750 µL of 0.5 N HCl is added to each preparation and vortexed thoroughly to mix. The preparations may be stored at 2-8° C. for up to 22 hours prior to detection.

Detection/Fluorometer Setup

The leucine standards are prepared as described above.

The luminescence spectrometer is set up with the following instrument parameters. The fluorescence of each preparation is read with 1 hour of derivatization.

TABLE 4

| Parameters and Settings | |
|---|---|
| Parameter | Setting |
| Excitation Wavelength | 392 nm |
| Emission Wavelength | 480 nm |
| Integration | 5.0 sec. |
| Slits (Ex & Em) | 5.0 nm (band pass) |
| Path Length | 3 mm |

Calculations

The concentration of each leucine standard (X-axis) is plotted against the fluorescence response at 480 nm (Y-axis). The slope (m), coefficient of determination ($R^2$), and the mean fluorescence of each duplicate preparation are determined. Do not force through zero. The net fluorescence of each collagenase sample preparation is calculated as follows:

$$F(\text{net}) = \text{Mean Collagenase Sample } (EM_{480}) - \text{Blank } (EM_{480})$$

The amount of the collagenase sample in each preparation is plotted (X-axis) against the net fluorescence (Y-axis). The slopes (m) and coefficient of determination ($R^2$) are determined. Do not force through zero.

The potency of the collagenase is determined as follows:

$$\text{Potency } (f\text{-}SRC \text{ units/mg}) = (M_{Sample}/M_{Leucine}) \times (DF/T) \times CF$$

Where:

$M_{Sample}$=Slope of the collagenase sample potency curve $M_{Leucine}$=Slope of the leucine standard curve DF=Dilution Factor (1500 µL/100 mL=15)

T=Reaction time (2.5 hr×60 min/1 hr=150 min)

CF=Conversion factor (1000 µg/1 mg=1000)

The above SRC assay may be employed to analyze the potency of any collagenase.

SRC Microplate Assay for the Determination of Collagenase I Activity in a Collagenase Sample This method is similar to the SRC assay above, except it is performed in a microplate. Like the SRC assay above, the microplate assay measures the collagenase activity towards soluble rat-tail collagen (SRC) substrate (hereafter, "substrate"). The assay follows the methodology below, but a person of ordinary skill in the art will appreciate that certain modifications may be made.

Buffers and Reagents

The following buffers and reagents are used:

1. Soluble Rat Collagen Substrate (BD Biosciences 354236)
2. Tripeptide GPA (Bachem H3615 or equivalent)
3. Fluorescamine (Acros 191675000 or equivalent)
4. Purified Water (Millipore, Milli-Q-Plus 18.2 MΩ system or equivalent)
5. 1 M HEPES buffer (Gibco 15630-080 or equivalent)
6. 1 M Calcium Acetate ($Ca(C_2H_3O_2)_2$) (Emerald Biosciences EBS-100-CAAC or equivalent)
7. Surfact-Amps 20™ (10% Tween solution) (Pierce Cat. #28320 or equivalent)
8. 1.0 N Acetic acid (Sigma 318590 or equivalent)
9. 0.5 N Hydrochloric Acid (VWR 101223-134 or equivalent)
10. Boric acid (Sigma B7660 or equivalent)
11. 2.5 N Sodium hydroxide (J.T Baker 5666-02 or equivalent)
12. Acetone (Sigma 270725 or equivalent)

Preparation of Solutions

Preparation of assay buffer (50 mM HEPES pH 7.1/0.05% Tween 20/5 mM ($Ca(C_2H_3O_2)_2$): An amount of 50 mL 1 M HEPES is pipetted into 800 mL DI water. 5 mL 1 M ($Ca(C_2H_3O_2)_2$) and 5 mL Surfact-Amps (10% Tween 20) are added. The pH is checked and adjusted to 7.1±0.1 if necessary. A sufficient quantity of water is added to adjust the volume to 1 L and the solution is filtered through a 0.22 micron filter. This assay buffer can be stored at room temperature for up to 3 months.

Preparation of 0.1 N NaOH: An amount of 2 mL of 2.5 N NaOH is added into 48 mL DI water. This solution can be stored at room temperature for up to 3 months.

Preparation of 4 mg/mL tripeptide GPA stock: An amount of 400 mg (±1 mg) of GPA tripeptide is dissolved into 10 mL 0.1 N NaOH and vortexed until totally dissolved. A sufficient quantity of assay buffer is added to make the volume 100 mL and the solution is dispensed into 0.5 mL aliquots and stored at −70° C. The 4 mg/mL tripeptide GPA stock can be stored at −70° C. for up to one year.

Preparation of 0.02 N acetic acid: An amount of 1 mL of 1.0 N acetic acid is added to 40 mL of purified water. A sufficient amount of purified water is added to adjust the volume to 50 mL. This solution can be stored at room temperature for up to 1 year.

Preparation of 2 mg/mL SRC substrate stock solution: An amount of 23.3 mL 0.02 N acetic acid is added directly to the vial in which substrate is supplied (supplied in one non-limiting example as 100 mg SRC at 3.75 mg/mL). Other concentrations of SRC substrate may be used. The calculation is below:

$$100 \text{ mg} \div 3.75 \text{ mg/mL} = 26.7 \text{ mL};$$

$$\text{Total vol(mL)} = (3.75 \text{ mg/mL} \times 26.7 \text{ mL})/2 \text{ mg/mL};$$

$$\text{Total vol(50.0 mL)} - 26.7 \text{ mL} = 23.3 \text{ mL}$$

The solutions are mixed thoroughly by inversion and can be stored at 2-8° C. for up to 3 months.

Preparation of 0.6 mg/mL SRC substrate working solution: An amount of 4.2 mL of assay buffer is added to a 15 mL conical tube. Then, 1.8 mL of 2 mg/mL SRC substrate stock solution is added and the solution is mixed by inversion. This solution should be prepared immediately before addition to plate.

Preparation of 120 mM Boric Acid pH 9.0: An amount of 7.4 g (±0.5 g) of the boric acid is dissolved in 800 mL DI water. The solution is titrated with NaOH to pH 9.0 and sufficient DI water is added to adjust the volume to 1 L. This solution can be stored at room temperature for up to 3 months.

Preparation of 1 mM Fluorescamine in Acetone: An amount of 28±2 mg Fluorescamine is dissolved in 100 mL acetone. This solution needs to be freshly prepared and protected from light and moisture.

Preparation of Tripeptide GPA Standard and Serial Dilution

A 0.08 mg/mL (329 UM) tripeptide GPA standard is prepared by making a 50-fold dilution of the 4 mg/mL tripeptide GPA stock in assay buffer (for example, 20 μL 4 mg/mL GPA in 980 μL assay buffer). In the assay plate, row A, 200 μL of 329 μM tripeptide GPA standard is pipetted into A1 and A7. An amount of 100 μL assay buffer is pipetted into A2-A6 and A8-A12.

For the tripeptide GPA standard serial dilution, an amount of 100 μL is transferred from A1 into A2, mixed, an amount of 100 μL is transferred from A2 into A3, and repeated until A5. An amount of 100 μL is taken out from A5 well so that its final volume is 100 μL. The A6 well contains buffer only.

For the second tripeptide GPA standard serial dilution, an amount of 100 μL is transferred from A7 into A8, mixed, an amount of 100 μL is transferred from A8 into A9, and repeated until A11. An amount of 100 μL is taken out from All well so that its final volume is 100 μL. The A12 well contains buffer only.

Preparation of Collagenase Test Samples

For collagenase samples (e.g., a lyophilized collagenase drug product), the sample is allowed to come to room temperature for at least 10 minutes and reconstituted to form a 3.0 μg/mL stock solution. Different concentrations may be used. A test collagenase sample (T1A) is prepared from the stock solution by diluting with assay buffer. The procedure is repeated to prepare triplicate test samples (TIA, T1B, TIC).

DISCUSSION

In this method, 50 μL of increasing concentrations of the test collagenase samples are mixed with 50 μL of excess substrate (0.2 mg/mL final concentration) in a 96-well plate. An amount of 50 μL of assay buffer is added to rows C-G in a U-bottomed, 96 well polypropylene reaction plate. 150 μL of collagenase samples are pipetted into row B. Then, a 1/1.5 serial dilution is performed using a multi-channel pipette, by transferring 100 μL of collagenase sample from row B into row C, mixing and repeating the process until row G is reached. An amount of 100 μL is removed and discarded from row G. The Blank is prepared in row H by pipetting 50 μL assay buffer to row H. This row contains no enzyme. The following table contains the final collagenase concentrations after adding 50 μL substrate to row B through row H.

TABLE 5

| Assay Target Concentrations After Substrate Addition | | |
|---|---|---|
| Row | Dilution | Collagenase (ng/ml) |
| A | N/A | N/A |
| B | Stock | 1500 |
| C | 1/1.5 | 100 |
| D | 1/2.3 | 667 |
| E | 1/3.4 | 444 |
| F | 1/5.1 | 296 |
| G | 1/7.6 | 198 |
| H-Blank | N/A | 0 |

Collagenase Reaction

The incubator and temperature probe are turned on to a temperature 22±1° C. prior to the addition of substrate to the plates. An amount of 50 μL 0.6 mg/mL SRC substrate is added to each well from row B to row H, added column by column then mixed. The reaction start time begins after the substrate is added to the first column. The plate is covered and placed in the 22±1° C. incubator for a total reaction time of 45±5 minutes. To quench the reaction, 100 μL of 0.5 N HCl is added into each well of the dilution plate, column by column, and mixed. Reaction time ends after the HCl is added to the first column.

Detection

An amount of 195 μL of 120 mM Borate pH 9.0 is added to each well of a Microplate Greiner polypropylene black reading plate. 30 μL of the quenched reaction mixture is transferred from the reaction plate into the corresponding wells of the reading plate and mixed well. Then, 75 μL of 1 mM Fluorescamine is added to each well of the reading plate (using a polypropylene tray to dispense Fluorescamine/acetone) and mixed immediately after every addition. The plate is read within 15 minutes after Fluorescamine addition with a Molecular Devices M2 fluorescence plate reader using the following settings: Excitation 380 nm, Emission 473 nm, cutoff 455 nm, 6 reads/well, PMT medium.

The concentration of GPA (μM) versus the emission at 473 nm and the concentration of collagenase (ng/ml) versus the emission at 473 nm are plotted. For each plot, a linear regression is fitted with no fixed parameters. For collagenase samples, the zero point data are excluded from the linear fit and the entire triplicate data set for each sample is used to generate the plot. The slopes for the tripeptide GPA standard and collagenase samples are determined.

Potency and Relative Potency Determination

The collagenase sample potency can by calculated as follows:

$$SRC\text{ Microplate Assay Units} = \big((\text{Slope of Collagenase Sample})/(\text{Slope of Tripeptide } GPA \times \text{incubation time})\big) \times 10^6$$

The potency of the collagenase test sample is determined from the slope of the tripeptide GPA standard and calculated by the curve-fitting program. Using the microplate method, different concentrations of substrate and different times may be used to calculate enzyme kinetics according to Michaelis-Menten.

Collagenase II Potency as Measured by GPA Assay (Cuvette)

The GPA assay is primarily used to measure the potency of collagenase II (a class II collagenase). The first step of the assay involves an enzymatic reaction involving the digestion of the substrate carbobenzoxy-glycyl-L-prolyl-glycyl-glycyl-prolyl-L-alanine (zGPGGPA) by a collagenase sample into two peptides: carbobenzoxy-glycyl-L-prolyl-glycine (zGPG) and glycyl-prolyl-L-alanine (GPA). The second step involves the subsequent measurement of liberated GPA with the fluorogenic derivative fluorescamine. The assay follows the methodology below, but a person of ordinary skill in the art will appreciate that certain modifications (e.g., dilution concentrations and times) may be made.

The general methodology is as follows. Leucine standards are prepared. A collagenase sample is obtained and solutions are prepared to be used in the first step for the enzymatic cleavage of zGPGGPA (hereafter "substrate") by collagenase. Following this step, the collagenase-treated samples (containing the liberated GPA) and leucine standards are treated at room temperature for a period of time with fluorescamine in order to fluorescently tag the free amino groups of the generated GPA and leucine molecules, respectively. The fluorescence emission of each solution at 480 nm is measured following excitation at 392 nm. The resulting slopes of the leucine and collagenase sample curves are then used to calculate potency units as follows:

$$\text{Potency}\left(f\text{-}GPA\ \text{units/mg}\right) = \left(M_{Sample}/M_{Leucine}\right) \times \left(DF/T\right)$$

where:

$M_{Sample}$=Slope of the collagenase sample potency curve $M_{Leucine}$=Slope of the leucine standard curve DF=Dilution Factor T=Reaction time Additional, non-limiting details regarding the GPA assay methodology are set forth below.

Buffers and Reagents

The following buffers and reagents are used:

1. f-Appel's Buffer, pH 7.2 (55 mM HEPES, 100 mM calcium acetate)
2. 1 mM Leucine Working Stock Solution
3. 200 mM Borate, pH 9.0
4. 0.5 mM Fluorescamine Solution in Acetone
5. 2 mg/mL zGPGGPA Substrate in f-Appel's Buffer Solution Preparation Solutions are prepared as follows:

f-Appel's Buffer: Dissolve 13.0 g HEPES and 17.6 g calcium acetate in approximately 800 mL of water. Adjust pH to 7.2 with sodium hydroxide and QS to 1 L with water. Store at 2-8 degrees C.

10 mM Leucine Stock Solution: Dissolve 65.5 mg of leucine in 50 mL of water. Leucine must be weighed directly into a 100 mL (or equivalent) glass beaker on the scale. Weigh out approximately 65 mg (target weight) of leucine into the beaker. Based on the weight of leucine, calculate the amount of water to add to the beaker using the equation below. Add the calculated volume of water to the beaker and mix thoroughly to ensure the leucine is fully dissolved. Dispense into 1 mL aliquots. Store at less than or equal to 20 degrees C.

$$V2(\text{mL}) = C2(\text{mg}) \times \frac{V1(50\ \text{mL})}{C1(65.5\ \text{mg})}$$

where:

C2=mass of leucine weighed (mg)

V1=50 (mL of water)

C1=65.5 (mg of leucine)

V2=volume of water needed to produce a 10 mM stock solution (mL)

1 mM Leucine Working Stock Solution: Thaw a vial of 10 mM Leucine Stock Solution and dilute to 1 mM by combining 150 μL with 1350 μL water. Mix well prior to use.

0.5 N HCl: Dilute HCl to 0.5 N with water and mix well. Store at room temperature. Alternatively, commercially available 0.5 N HCl may be used.

200 nM Borate, pH 9.0: Dissolve 2.4 g boric acid in approximately 150 mL water. Adjust the pH to 9.0 using sodium hydroxide. QS to 200 mL with water and mix well. Store at 2-8 degrees C.

0.5 mM Fluorescamine Solution: Mix 15 mg of fluorescamine with 100 mL acetone and swirl to dissolve. Store at 2-8 degrees C. protected from light.

Substrate Solution (2 mg/mL zGPGGPA): Prepare substrate at 2 mg/mL with f-Appel's buffer. Dissolve on a mechanical shaker/rotator, allowing sufficient time for complete dissolution (about 15 minutes).

Leucine Standard Curve

The leucine standard curve is prepared according to the following table.

TABLE 6

Preparation of the leucine standard curve.

| Standard | L1 | L2 | L3 | L4 | L5 | L6 |
|---|---|---|---|---|---|---|
| Leucine Conc. (μM) | 0 | 70 | 140 | 210 | 280 | 350 |
| Water (μL) | 500 | 430 | 360 | 290 | 220 | 150 |
| 0.5N HCl (μL) | 500 | 500 | 500 | 500 | 500 | 500 |
| 1 mM Leucine (μL) | 0 | 70 | 140 | 210 | 280 | 350 |

"L1" means Leucine standard sample 1,
"L2" means Leucine standard sample 2, etc.

100 μL of each Leucine Standard is then transferred into separate tubes for detection of fluorescamine.

Collagenase Sample Preparation

The collagenase sample is diluted to 0.01 mg/mL with f-Appel's Buffer in two stages and vortexed gently to mix. The following is an example dilution scheme:

$$1.\ 100\ \mu\text{L} \times 1.0\ \text{mg/mL} \rightarrow 1000\ \mu\text{L} = 0.1\ \text{mg/mL}$$

$$2.\ 100\ \mu\text{L} \times 0.1\ \text{mg/mL} \rightarrow 1000\ \mu\text{L} = 0.01\ \text{mg/mL}$$

Blank Preparations

Blanks are prepared by combining 45 μL of the diluted preparation with 500 μL of 0.5 N hydrochloric acid to inactivate the enzyme. 455 μL of zGPGGPA substrate solution is added and vortexed to mix thoroughly. 100 μL of each blank is transferred into separate tubes for detection of impurities that may react with fluorescamine.

Potency Curves

A set of potency curves are prepared for each collagenase sample as follows:

TABLE 7

| Tubes | 2 mg/mL Substrate Solution | f-Appel's Buffer (μL) |
|---|---|---|
| 1-2 | 1 | 45 |
| 3-4 | 1 | 30 |
| 5-6 | 1 | 15 |

The tubes containing substrate and buffer are warmed in a water bath at 25° C. for a minimum of 15 minutes. A second set of tubes is labeled and 50 μL of 0.5 N hydrochloric acid is added to each. The diluted collagenase sample preparations (0.01 mg/mL) is added to the tubes according to the below table for a 10-minute incubation, and the tubes are mixed and returned to the water bath. The incubation period is started upon addition of the first preparation to the pre-warmed substrate.

TABLE 8

| Sample Preparation | | |
|---|---|---|
| Preparation | Tubes | Sample (μL) |
| Potency Curve | 1-2 | 55 |
| Potency Curve | 3-4 | 70 |
| Potency Curve | 5-6 | 85 |

The preparations are removed from the water bath with 1-2 minutes remaining on the 10-minute incubation and vortexed gently to mix. Ten minutes after addition of the first preparation to the substrate, 50 μL is transferred from each tube into the tubes containing 50 μL of 0.5 N HCl. The preparations should be added directly to the acid to quench the digestion. Each tube is vortexed to mix well after quenching all preparations.

Detection

400 μL of 200 mM Borate Buffer and 500 μL of 0.5 mM Fluorescamine Solution is added to all detection tubes containing 100 μL of each preparation (blanks, collagenase sample potency curves, and leucine standards). The tubes are vortexed thoroughly to mix and are incubated at room temperature for a minimum of 10 minutes.

Fluorometer Setup

The fluorometer is set up with the following instrument parameters and the fluorescence of each preparation is read with 1 hour of derivatization.

TABLE 9

| Parameter | Setting |
|---|---|
| Excitation Wavelength | 392 nm |
| Emission Wavelength | 480 nm |
| Integration | 5.0 sec. |
| Slits (Ex & Em) | 5.0 nm (band pass) |
| Path Length | 3 mm |

Calculations

The concentration of each leucine standard (X-axis) is plotted against the fluorescence response at 480 nm (Y-axis). The slope (m), coefficient of determination ($R^2$), and mean fluorescence of each potency curve preparation is determined. Collagenase sample and leucine potency curves are calculated by plotting the concentration of each preparation (X-axis) against the mean fluorescent response at 480 nm (Y-axis). The slope (m) and coefficient of determination ($R^2$) for the resulting linear curves are determined.

Determine Potency of Collagenase Sample

Potency is determined using the following equation:

$$\text{Potency}\left(f\text{-}GPA\ \text{units/mg}\right) = \left(M_{Sample}/M_{Leucine}\right)\times\left(DF/T\right)$$

Where:

$M_{Sample}$=Slope of the collagenase sample potency curve $M_{Leucine}$=Slope of the leucine standard curve DF=Dilution Factor (1100 μL/50 μL=22)

T=Reaction time (10 minutes)

GPA Microplate Assay for the Determination of Collagenase II Activity in a Collagenase Sample This method is similar to the GPA assay above, except it is performed in a microplate. Like the assay above, the microplate assay measures the proteolytic activity of collagenase samples in the enzymatic cleavage of the substrate carbenzoxy-glycyl-L-prolyl-glycyl-glycyl-L-propyl-L-alanine (zGPGGPA) (hereafter, "substrate"). The assay follows the methodology below, but a person of ordinary skill in the art will appreciate that certain modifications (e.g., dilution concentrations and times) may be made.

Buffers and Reagents

The following buffers and reagents are used:

1. Peptide substrate (zGPGGPA) (Bachem M1260 or equivalent)
2. Tripeptide GPA (Bachem H3615 or equivalent)
3. Fluorescamine (Acros 191675000 or equivalent)
4. Purified Water (Milli-Q-Plus 18.2 M (2 system or equivalent)
5. 1 M HEPES buffer (Gibco 15630-080 or equivalent)
6. Surfact-Amps 20™ (10% Tween solution) (Pierce Cat. #28320 or equivalent)
7. 1 M Calcium Acetate ($Ca(C_2H_3O_2)_2$) (Emerald Biosciences Cat. #EBS-100-CAAC or equivalent)
8. Boric acid (Sigma B7660 or equivalent)
9. 2.5 N NaOH (J.T Baker 5666-02 or equivalent)
10. 0.5 N Hydrochloric Acid (VWR 101223-134 or equivalent)
11. Acetone (Sigma 270725 or equivalent)

Preparation of Solutions

Preparation of assay buffer (50 mM HEPES pH 7.1/0.05% Tween 20/5 mM ($Ca(C_2H_3O_2)_2$): An amount of 50 mL 1 M HEPES is pipetted into 800 mL DI water. 5 mL 1 M ($Ca(C_2H_3O_2)_2$) and 5 mL Surfact-Amps (10% Tween 20) are added. The pH is checked and adjusted to 7.1±0.05 if necessary. A sufficient quantity of water is added to adjust the volume to 1 L and the solution is filtered through a 0.22 micron filter. This assay buffer can be stored at room temperature for up to 3 months.

Preparation of 0.1 N NaOH: An amount of 2 mL of 2.5 N NaOH is added into 48 mL DI water. This solution can be stored at room temperature for up to 3 months.

Preparation of 4 mg/mL tripeptide GPA stock solution: An amount of 400 mg (±1 mg) of tripeptide GPA is dissolved into 10 mL 0.1 N NaOH and vortexed until totally dissolved. A sufficient quantity of assay buffer is added to make the volume 100 mL and the solution is dispensed into 0.5 mL aliquots and stored at −70° C. The 4 mg/mL tripeptide GPA stock can be stored at −70° C. for up to one year.

Preparation of 4 mg/mL (6.8 mM) peptide substrate zGPGGPA: An amount of 400 mg (+1 mg) of the peptide substrate zGPGGPA is dissolved into 10 mL 0.1 N NaOH and vortexed until totally dissolved. A sufficient quantity of assay buffer is added to make the volume 100 mL. This solution can be stored at 4° C. for up to 3 months.

Preparation of 120 mM Boric Acid pH 9.0: An amount of 7.4 g (±0.5 g) of the boric acid is dissolved into 800 mL DI water. The solution is titrated with NaOH to pH 9.0. A sufficient quantity of DI water is added to adjust the volume to 1 liter. This solution can be stored at room temperature for up to 3 months.

Preparation of 1 mM Fluorescamine in Acetone: An amount of 28±2 mg Fluorescamine is dissolved in 100 mL acetone. This solution needs to be freshly prepared and protected from light and moisture.

Preparation of Tripeptide GPA Standard and Serial Dilution

A 0.08 mg/mL (329 μM) tripeptide GPA standard is prepared by making a 50-fold dilution of the 4 mg/mL tripeptide GPA stock in assay buffer (for example, 20 μL 4 mg/mL tripeptide GPA in 980 μL assay buffer). In the assay plate, row A, 200 μL of 329 UM tripeptide GPA standard is pipetted into A1 and A7. An amount of 100 μL assay buffer is pipetted into A2-A6 and A8-A12.

For the tripeptide GPA standard serial dilution, an amount of 100 μL is transferred from A1 into A2, mixed, an amount of 100 L is transferred from A2 into A3, and repeated until A5. An amount of 100 μL is taken out from A5 so that its final volume is 100 μL. The A6 well contains buffer only.

For the second tripeptide GPA standard serial dilution, an amount of 100 μL is transferred from A7 into A8, mixed, an amount of 100 μL is transferred from A8 into A9, and repeated until well A11. An amount of 100 μL is taken out from All so that its final volume is 100 μL. The A12 well contains buffer only.

Preparation of Collagenase Samples

For collagenase samples (e.g., a lyophilized collagenase drug product), the sample is allowed to come to room temperature for at least 10 minutes and is reconstituted to form a 500 ng/mL stock solution. Different concentrations may be used. A test collagenase sample (T1A) is prepared from the stock solution by diluting with assay buffer. The procedure is repeated to prepare triplicate test samples (TIA, T1B, TIC).

Discussion

In this method, 50 μL of increasing concentrations of the collagenase test samples are mixed with 50 μL of excess substrate (2.0 mg/mL final concentration) in a 96-well plate. An amount of 50 μL of assay buffer is added to rows C-G in a U-bottomed, 96 well polypropylene reaction plate. 150 μL of collagenase samples are pipetted into row B. Then, a 1/1.5 serial dilution is performed using a multi-channel pipette, by transferring 100 μL of collagenase sample from row B into row C, mixing and repeating the process until row G is reached. An amount of 100 μL is removed and discarded from row G. The below table contains the final collagenase concentrations after adding 50 μL substrate to row B through row H.

The Blank is prepared in row H by pipetting 50 μL assay buffer to row H. This row contains no enzyme. Exemplary concentrations are shown in the table below.

Assay Target Concentrations After Substrate Addition

TABLE 10

| Row | Dilution | Collagenase (ng/ml) |
|---|---|---|
| A | N/A | N/A |
| B | Stock | 250 |
| C | 1/1.5 | 167 |
| D | 1/2.3 | 111 |
| E | 1/3.4 | 74 |
| F | 1/5.1 | 49 |
| G | 1/7.6 | 33 |
| H-Blank | N/A | 0 |

Collagenase Reaction

The zGPGGPA substrate is cleaved by class II collagenases into zGPG and GPA during a 15-minute incubation time at room temperature. The incubator and temperature probe are turned on to a temperature 22±1° C. prior to the addition of substrate to the plates. To column 1-12 in row B-H, 50 μL 4 mg/mL (6.8 mM) zGPGGPA substrate is added column by column, then mixed. The reaction start time begins after the substrate is added to the first column. The plate is covered and placed in the 22±1° C. incubator for a total reaction time of 15 ±1 minutes.

After incubation, the reaction is quenched by the addition of hydrochloric acid, and the amount of released GPA peptide is quantitated after reacting the free amino terminus of the peptide with the fluorogenic reagent, fluorescamine. To quench the reaction, 100 μL of 0.5 N HCl is added into each well from row A to row H, added column by column, and then mixed. Reaction time ends after the HCl is added to the first column.

Detection

An amount of 195 μL of 120 mM Borate pH 9.0 is added to each well of a Microplate Greiner polypropylene black reading plate. 30 μL of the quenched reaction mixture is transferred from the reaction plate into the corresponding wells of the reading plate and mixed well. Then, 75 μL of 1 mM Fluorescamine is added to each well of the reading plate (using a polypropylene tray to dispense Fluorescamine/acetone) and mixed immediately after every addition. The plate is read within 15 minutes after Fluorescamine addition with a Molecular Devices M2 fluorescence plate reader using the following settings: Excitation 380 nm, Emission 473 nm, cutoff 455 nm, 6 reads/well, PMT medium.

The concentration of GPA (μM) versus the emission at 473 nm and the concentration of collagenase (ng/mL) versus the emission at 473 nm are plotted. For each plot, a linear regression is fitted with no fixed parameters. For collagenase test samples, the zero point data are excluded from the linear fit and the entire triplicate data set for each sample is used to generate the plot. The slopes for the tripeptide GPA standard and collagenase samples are determined.

Potency Determination

The collagenase sample potency can be calculated as follows:

$$GPA \text{ Microplate Assay Units} = ((\text{Slope of Collagenase Sample}) / (\text{Slope of Tripeptide } GPA \times \text{incubation time})) \times 10^6.$$

The potency of the collagenase test sample is determined from the slope of the tripeptide GPA standard and calculated by the curve-fitting program. Using the microplate method, different concentrations of substrate and different times may be used to calculate enzyme kinetics according to Michaelis-Menten.

Collagenase Potency in BTC Unit Assay

The bovine tendon collagen (BTC) assay is based on the procedures of Mandl et al., *Arch. Biochem. Biophys.* 74:465-475 (1958), as modified by Keller and Mandl, *Arch. Biochem. Biophys.* 101:81-88 (1963). See also Rosen, *Arch. Biochem. Biophys.* 67:10-15 (1957). The BTC assay uses insoluble bovine tendon collagen as the substrate and measures the activity of both collagenase I and II. The BTC assay is colorimetric and utilizes ninhydrin to detect the peptides produced by collagenase I and II degradation of BTC. This reaction is also run at pH 7.2, but for 22 h at 37° C. in tris(hydroxymethyl)aminomethane (TRIS) buffer containing 10 mM divalent calcium ion. Since bovine tendon collagen is an insoluble substrate, it is important that it be finely divided. Trypsin is run as a control in order to account for the presence of denatured collagen or other protein impurities. The assay is run in the presence of calcium ions, which are required for collagenase activity. The number of peptides solubilized is determined by reacting the N-terminal amino group of the peptides with ninhydrin and measuring colorimetrically the amount of adjunct formed (Rosen 1957).

Reagents and Solutions

The following reagents and buffers are used:

1. Collagen Substrate (collagen)
2. Deionized (DI) Water (water)
3. Tris Assay Buffer
4. Trypsin Stock Solution
5. 0.5 M HCl
6. Leucine Standard Assay Solution (1 mM leucine)
7. Rosen Buffer
8. 3% Ninhydrin
9. 50% Isopropanol Incubation The reaction tubes are set up and labeled as follows: three tubes for the trypsin controls, six tubes for the Reference Solution and six tubes for each sample under test. 10±1 mg collagen is weighed out in the order indicated in the below table and the weighed collagen is placed into each reaction tube.

TABLE 11

| Order of Weighing | Reaction Tube # |
|---|---|
| 1 | 1 |
| 2 | 4 |
| 3 | 6 |
| 4 | 8 |
| 5 | 10 |
| 6 | 12 |
| 7 | 14 |
| 8 | 16 |
| 9 | 18 |
| 10 | 20 |
| 11 | 2 |
| 12 | 3 |
| 13 | 5 |
| 14 | 7 |
| 15 | 9 |
| 16 | 11 |
| 17 | 13 |
| 18 | 15 |
| 19 | 17 |
| 20 | 19 |
| 21 | 21 |

For samples under test, the amount of enzyme should contain an activity between 1.6 to 5.7 nmol leucine equivalent (leu eq)/min per reaction tube (ACT). Undissolved samples should first be dissolved in Tris assay buffer before they are used in the assay. The concentration (before adding to the reaction tubes) should be no less than 0.0065 mg/mL.

The reaction tubes are set up to have a matrix pattern as shown in the below table. The following table assumes 2 under test samples. If more or less samples are run, the number of reaction tubes are adjusted, but the pattern is retained. Constant volumes are listed in the table.

TABLE 12

| | The Matrix Pattern Reaction Tube # | | | | |
|---|---|---|---|---|---|
| Reaction Tube # | S1 Tris Buffer | S4 Trypsin | S3 Standard Solution | Samples*1 | Samples*2 |
| 1 | 1960 μL | 40 μL | | | |
| 2 | 1960 μL | 40 μL | | | |
| 3 | 1960 μL | 40 μL | | | |
| 4 | 1940 μL | | 60 μL | | |
| 5 | 1940 μL | | 60 μL | | |
| 6 | 1920 μL | | 80 μL | | |
| 7 | 1920 μL | | 80 μL | | |
| 8 | 1900 μL | | 100 μL | | |
| 9 | 1900 μL | | 100 μL | | |
| 10 | 1970 μL | | | 30 μL | |
| 11 | 1970 μL | | | 30 μL | |
| 12 | 1960 μL | | | 40 μL | |
| 13 | 1960 μL | | | 40 μL | |
| 14 | 1950 μL | | | 50 μL | |
| 15 | 1950 μL | | | 50 μL | |
| 16 | 1970 μL | | | | 30 μL |
| 17 | 1970 μL | | | | 30 μL |
| 18 | 1960 μL | | | | 40 μL |
| 19 | 1960 μL | | | | 40 μL |
| 20 | 1950 μL | | | | 50 μL |
| 21 | 1950 μL | | | | 50 μL |

*Suggested maximum number of samples is 3.

The reaction tubes are capped and the contents are mixed gently but thoroughly. The reaction tubes are placed in a 37° C. water bath and incubated for 22±0.5 hours.

Quenching and Filtration

A filtrate tube is labeled to correspond to each reaction tube incubated. A funnel containing a folded filter paper is placed onto each labeled filtrate tube. At the end of the incubation period, the reaction tubes are removed from the water bath. The actual time the incubation ends is recorded.

The reaction tubes are uncapped and the reaction is quenched by dispensing 2 mL 0.5 M HCl into each reaction tube. The contents of the tubes is mixed thoroughly and filtered into the appropriate filtrate tube.

The previous two steps need to be finished as quickly as possible because undigested collagen could be dissolved by HCl in a short time. The filtrate may be stored refrigerated in covered filtrate tubes for up to 95.5 hours before color development.

Color Development

Boiling tubes are set up and labeled as follows: six tubes for the water and the leucine controls (Step 1) and two tubes for each filtrate tub (Step 1). The following amounts of water and leucine standard assay solution are placed into the six leucine control tubes.

TABLE 13

| Tube # | 1 | 2 | 3 | 4 | 5 | 6 |
|---|---|---|---|---|---|---|
| Water (μL) | 1000 | 900 | 850 | 800 | 750 | 700 |
| Leu (μL) | 0 | 100 | 150 | 200 | 250 | 300 |
| Leu (nmol) | 0 | 100 | 150 | 200 | 250 | 300 |

0.8 mL of water is pipetted into each boiling tube (Step 2). 0.2 mL of filtrate is pipetted from each sample into the appropriately labeled boiling tubes. 0.5 mL of Rosen buffer is dispensed into each boiling tube. Under a containment hood, 0.5 mL of 3% ninhydrin is dispensed into each boiling tube. The contents of each tube is mixed thoroughly on a vortex mixer. The boiling tubes are placed in a boiling water bath in a fume hood and boiled for 15=1 minutes. At the end of the boiling period, the boiling tubes are removed from the water bath. Under a containment hood, 5.0 mL of 50% isopropanol is dispensed into each boiling tube and the contents are mixed thoroughly. The boiling tubes are allowed to reach ambient temperature (at least 10 minutes) before reading the absorbances.

Reading of Absorbances

The absorbances of the tubes are read while working under a containment hood. The spectrophotometer is turned on and allowed to warm up. The wavelength of the spectrophotometer is set to 570 nm and the spectrophotometer is zeroed against 50% isopropanol. The absorbances ($A_{570}$) of the water, leucine, trypsin controls, and the samples under test are read. The time that the first sample is read, in hours, is recorded. The readings as 1000× A570 and the time that the last sample is read, in hours, are recorded. All readings are to be done within a 1-hour interval.

Calculations Principles

The total reading time, in minutes, and the total time of incubation are calculated. The total reading time should be less than 60 minutes and the total time of incubation should be between 1290-1350 minutes. Using the linear least square method, the slope "b" and correlation coefficient "r" for leucine standards are calculated (x=nmol leucine vs y=$A_{570}$ reading). The unit for "b" value is $A_{570}$/nmol leucine. The "b" value is recorded to two decimal places. b value for leucine should be between 2.88-3.33. The average reading for the trypsin controls (T) is calculated. The average reading for the trypsin controls (T) should be 221-338. This average to the nearest whole number (Step A) is recorded. The average duplicated sample $A_{570}$ reading for each reaction tube is calculated. This number is recorded to the nearest whole number. The average trypsin (Step A) is subtracted from the average sample $A_{570}$ reading to get the net sample reading.

The activity (ACT) per tube, in nmol leu eq/min, is calculated as follows:

$$ACT\text{ (nmol leu eq/min)} = ((\text{Net sample reading})(20))/((b)(\text{Time in minutes}))$$

where 20 is the dilution factor for the amount of reaction mixture developed and "b" is the slope of the leucine standard curve. This number is recorded to one decimal point. The activity per tube of the samples under test should be 1.6-5.7 nmol leu eq/min.

The activity in BTC units is calculated as follows:

$$BTC\text{ units} = \text{activity in nmol leu eq/min} \times \text{collagen correction factor.}$$

The activity in BTC units/mL of the sample is calculated as follows:

$$BTC\text{ unit/mL} = (\text{Activity in } BTC\text{ units})/(\text{Sample volume used in mL})$$

The potency of the sample in BTC units/mm is calculated as follows:

$$BTC\text{ unit/mg} = (\text{Activity in } BTC\text{ units/mL})/(\text{Protein concentration in mg/mL})$$

Conversions

The conversion of BTC units to ABC units is:

$$ABC\text{ units} = BTC\text{ units} \times 1.09.$$

The conversion of ABC units to SRC units is:

$$SRC\text{ units} = ABC\text{ units} \times 6.3$$

The conversion of ABC units to mg is:

$$1\ ABC\text{ unit} = 0.000058\text{ mg of collagenase}$$

Other Assays

Assay methods utilizing labelled collagen have been reported by Gisslow et al., Anal. Biochem., 68:70-78 (1975); Robertson et al., Clinica Chimica Acta, 42:43-45 (1972); Sakamoto et al., A New Method for the Assay of Tissue Collagenase (36297) (1972); and the Worthington Biochemical Corp. Assay (www_worthington-biochem_com/CLS/assay) (accessed Jul. 3, 2019).

Example 2—Study EN3835-105

Study EN3835-105 was a Phase 1, multicenter, open-label, randomized, dose-ranging study to assess the safety, tolerability, and PK of EN3835 (XIAFLEX® (collagenase *Clostridium histolyticum*)) in the treatment of plantar fibromatosis. The effect of EN3835 on nodule size was also assessed. To be eligible for the initial treatment, subjects must have had plantar fibromatosis and only 1 palpable firm or hard nodule per foot or feet to be treated on clinical examination and measurable by ultrasound. During a 28-day Screening Period, the selected nodule(s) were examined and evaluated. This comprised collecting caliper measurements, palpating the nodule for consistency (firm or hard), and conducting an ultrasound during which measurements of the nodule were collected.

Twenty-four subjects were randomized into 3 treatment groups, each receiving a different concentration of EN3835. On the Initial Treatment Period Day 1, subjects were randomized in a 1:1:1 ratio to 1 of 3 EN3835 concentrations (Table 14). Subjects were admitted to an inpatient research unit for an overnight stay, during which intralesional EN3835 was administered and PK samples were collected.

Based on the largest diameter of width or length of the nodule collected on ultrasound, subjects received 1 or 2 intralesional injections of EN3835 per nodule (Table 14). During the Initial Treatment Period subjects with nodules of ≤1.5 cm received 1 injection of EN3835 per nodule. Subjects with nodules of >1.5 cm received 2 injections of EN3835 per nodule. After discharge from the inpatient unit, subjects were encouraged to resume normal daily activities including weight bearing and walking on the treated foot/feet.

TABLE 14

| EN3835 Treatment Concentrations for the Initial Treatment | | | | | | |
|---|---|---|---|---|---|---|
| Treatment Conc. | Conc. (mg/mL) | Volume/ Injection (mL) | mg/ Injection | Number of Injections/ Nodule | Total Volume (mL) | Total Dose Administered/ Nodule (mg) |
| 1 | 0.6 | 0.2 | 0.12 | 1 to 2 | 0.2 to 0.4 | 0.12 to 0.24 |
| 2 | 1.2 | 0.2 | 0.24 | 1 to 2 | 0.2 to 0.4 | 0.24 to 0.48 |
| 3 | 2.25 | 0.2 | 0.45 | 1 to 2 | 0.2 to 0.4 | 0.45 to 0.9 |

Subjects returned to the clinic for 4 follow-up visits, 1 week apart, on Days 8, 15, 22, and 29, and for an end of Initial Treatment Period visit on Day 57. An interim analysis was conducted after all subjects completed Day 57 of the Initial Treatment Period to confirm if the concentration and dose selected for the Retreatment Period and the Phase 2 study is the most effective.

Subjects were given the option to be retreated with EN3835. To be eligible for retreatment, subjects completing the Initial Treatment Period must have had a treated nodule that was still palpable (i.e., hard, firm, or soft) and measurable by caliper. Subjects must have met the Retreatment Criteria and have no Retreatment Exclusion Criteria. Subjects that did not meet criteria for retreatment completed the study on Initial Treatment Period Day 57.

On Retreatment Period Day 1, based on the maximum diameter of the nodule collected on caliper measurements, subjects received either 1 intralesional injection of EN3835 0.45 mg per nodule for nodules≤2 cm or 2 intralesional injections of EN3835 0.45 mg for nodules>2 cm (total dose EN3835 0.9 mg) as outpatients. Subjects were retreated with EN3835 at the highest concentration of EN3835, (Table 14, Treatment Concentration 3, 2.25 mg/mL) administered during the Initial Treatment Period.

After receiving EN3835, subjects were encouraged to resume normal daily activities including walking and bearing weight on the treated foot/feet. Subjects will return to the clinic for 2 follow-up visits, 2 weeks apart, on Days 15 and 29 of the Retreatment Period. On Retreatment Period Day 29, if the subject had a palpable nodule (i.e., hard, firm, or soft) measurable by caliper, met all of the inclusion criteria and none of the exclusion retreatment criteria, a third treatment of EN3835 may have been administered. All subjects were to return for an additional follow-up visit on Retreatment Period Day 43 and completed the study (EOS Visit) on Retreatment Period Day 57.

The maximum duration of study participation for subjects that finished the study at the end of the Initial Treatment Period was up to 85 days (Screening Period: Up to 28 days, Day 1 treatment visit, 1 additional day of clinical confinement, and a total duration of the follow up period of 55 days). The maximum duration of study participation for subjects completing the 85-day Initial Treatment Period and the 71-day Retreatment Period was up to 156 days. The Retreatment Period comprised a Retreatment Rescreening Period of up to 14 days, Retreatment on Day 1, and a Retreatment Follow-up Period of up to 56 days which included an option to receive a third dose of EN3835 on Day 29.

The duration of the study from first subject first visit, to the last subject last visit was dependent on the ability of the sites to identify and enroll eligible subjects.

The primary objective of the study was to assess the safety and tolerability of EN3835 in subjects with plantar fibromatosis. Secondary objectives included assessing: the change in nodule size after a single EN3835 treatment using 2 different methods of measurement; the change in nodule size as measured by calipers after retreatment with EN3835; patient-reported outcomes after a single EN3835 treatment; patient-reported outcomes with EN3835 after retreatment with EN3835; investigator assessment of improvement with a single EN3835 treatment; investigator assessment of improvement after retreatment with EN3835; the pharmacokinetics (PK) of EN3835 in subjects with plantar fibromatosis after a single treatment of EN3835; and the immunogenicity of EN3835 in subjects with plantar fibromatosis.

The primary endpoint of the study was to assess the safety of EN3835 by incidence, severity, and duration of treatment-emergent adverse events (TEAEs) throughout the study. Secondary endpoints included:

- Mean change from Baseline (Day 1) to the End of the Initial Treatment Period Visit (Day 57±5 days) in the size of the treated nodules by ultrasound.
- Mean change from Baseline (Day 1) to the end of the Initial Treatment Period Visit (Day 57±5 days) in the size of the treated nodules by calipers.
- Mean change from Baseline (Retreatment Period Day 1) to the EOS Visit (Retreatment Period Day 57±5 days) in the size of the treated nodules by calipers.
- Mean change from Baseline (Day 1) in the composite score on the Foot Function Index-Short Form-23 (FFI SF-23), on Initial Treatment Period Days 2, 8, 15, 22, 29, and 57, with higher scores indicating greater impairment, and on each of these subscales:
  - Foot Pain subscale (9 items). Each response ranges from 0 (“No Pain”) to 10 (“Worst Pain Imaginable”).
  - Difficulty subscale (9 items). Each response ranges from 0 (“No Difficulty”) to 10 (“So Difficult Unable”).
  - Disability subscale (5 items). Each response ranges from 0 (“None of the Time”) to 10 (“All of the Time”).
- For each treated nodule, the proportion of subjects reporting to be “Satisfied” (+1) and “Very Satisfied” (+2) on the Subject Treatment Satisfaction Scale, a 5 point scale ranging from −2 (“Very Dissatisfied”) to +2 (“Very Satisfied”) on Initial Treatment Period Days 8, 15, 22, 29, and 57.
- Mean change from Baseline (Day 1 of the Retreatment Period) in the composite score on the FFI-SF-23, on Retreatment Days 15, 29, 43 and 57, with higher scores indicating greater impairment, and on each of these subscales:
  - Foot Pain subscale (9 items). Each response ranges from 0 (“No Pain”) to 10 (“Worst Pain Imaginable”).

Difficulty subscale (9 items). Each response ranges from 0 ("No Difficulty") to 10 ("So Difficult Unable").

Disability subscale (5 items). Each response ranges from 0 ("None of the Time") to 10 ("All of the Time").

For each nodule, the proportion of subjects reporting to be "Satisfied" (+1) and "Very Satisfied" (+2) on the Subject Treatment Satisfaction Scale, a 5-point scale ranging from −2 ("Very Dissatisfied") to +2 ("Very Satisfied") on Retreatment Period Days 15, 29, 43 and 57.

For each treated nodule, the proportion of investigators reporting "Minimally Improved" (+1) "Much Improved" (+2) or "Very Much Improved" (+3) on the Investigator Assessment of Improvement with Treatment Scale, a 7-point scale ranging from −3 ("Very Much Worse") to +3 ("Very Much Improvement") on Initial Treatment Period Days 8, 15, 22, 29, and 57.

For each treated nodule, the proportion of investigators reporting "Minimally Improved" (+1) "Much Improved" (+2) or "Very Much Improved" (+3) on the Investigator Assessment of Improvement with Treatment Scale, a 7-point scale ranging from −3 ("Very Much Worse") to +3 ("Very Much Improvement") on Retreatment Period Days 15, 29, 43 and 57.

PK variables of the observed maximum drug concentration ($C_{max}$), time to maximum observed plasma concentration ($T_{max}$), time 0 to the time of the last measurable concentration ($T_{last}$). Area under the concentration-time curve from time 0 to $T_{last}$ ($AUC_{0-Tlast}$) based on samples collected prior to injection and at 10, 20, 30, 60 minutes, and 2, 4, 8, 12, and 24 hours following a single injection of EN3835 during the Initial Treatment Period.

Presence of anti-AUX-I and anti-AUX-II antibody titer levels at Screening and Day 57 of the Initial Treatment Period, and Day 57 of Retreatment Period.

Presence of anti-AUX-I and anti-AUX-II neutralizing antibodies at Screening, Day 57 of the Initial Treatment Period, and Day 57 of the Retreatment Period.

Initial Treatment Inclusion and Exclusion Criteria

In order to be eligible to participate in the study, at the Screening Visit or on Day 1, subjects must have:

1. Been an ambulatory male or female ≥18 years of age.
2. Had a diagnosis of plantar fibromatosis AND on clinical examination have only 1 palpable firm or hard nodule per foot or feet to be treated and measurable by ultrasound.
3. Agreed not to use orthotics or inserts designed to relieve symptoms of plantar fibromatosis during the study period.
4. Agreed not to use amphetamines, barbiturates, benzodiazepines, cocaine, methamphetamine, 3-4-methylenedioxymethamphetamine (Ecstasy), methadone, buprenorphine, opioids (e.g., codeine, heroin, hydrocodone, hydromorphone, morphine, oxycodone), phencyclidine, or cannabis during the study period.
5. If female, be of nonchildbearing potential or, if of childbearing potential, been nonpregnant, nonlactating and agree to use effective contraception.
6. Had a negative urine drug screen for all of the following substances: amphetamines, barbiturates, benzodiazepines, cocaine, methamphetamine, 3-4-methylenedioxymethamphetamine (Ecstasy), methadone, buprenorphine, opioids (e.g., codeine, heroin, hydrocodone, hydromorphone, morphine, oxycodone), phencyclidine, and cannabis.
7. Been willing and able to comply with all protocol required visits and assessments.

A subject was ineligible for study participation if, at the Screening Visit or on Day 1, the subject:

1. Received surgical or non-surgical treatment(s) (e.g., steroid injection, transdermal/intralesional verapamil, radiation therapy, extracorporeal shock wave therapy) on the foot or nodule(s) within 3 months before administration of EN3835.
2. Had the presence of or history of non-plantar fibromatosis-related nodules on the feet (e.g., neurofibroma, rhabdomyosarcoma, liposarcoma, neurilemmomas, rheumatoid nodules, desmoid tumors, or malignant soft tissue lesions of the foot or ankle).
3. Had a chronic or acute musculoskeletal, neurological, or neuromuscular disorder that affects the feet.
4. Had a complicated plantar nodule (e.g., encapsulating the nerves, tendons and/or vascular structures) as diagnosed by ultrasound that in investigator's opinion would make the subject unsuitable for EN3835 injection.
5. Had surgery on the foot/feet selected for treatment within 3 months before the Screening Visit.
6. Had a known systemic allergy to collagenase or any other excipient of EN3835.
7. Had received any collagenase treatment (e.g., Santyl® ointment, XIAFLEX/XIAPEX®, EN3835, or CCH) within 30 days prior to injection of EN3835 in the foot/feet selected for treatment.
8. Had a clinically significant abnormal ECG at Screening demonstrating QTc prolongation: QTc of ≥450 ms for males and ≥470 ms for females.
9. Had a clinically significant laboratory abnormality or any laboratory test results meeting the following criteria:
   a. alanine aminotransferase (ALT)≥3×upper limit of normal (ULN).
   b. total bilirubin (TBL)≥2×ULN (>35% direct bilirubin).
   c. aspartate aminotransferase (AST)≥3×ULN.
   d. international normalized ratio (INR)>1.5.
10. Was receiving or planned to receive anticoagulant or antiplatelet medication or has received anticoagulant or antiplatelet medication (except for ≤150 mg aspirin daily) within 7 days before injection of EN3835.
11. Had a known bleeding disorder.
12. Received an investigational drug within 30 days before injection of EN3835.
13. Was pregnant, plans to become pregnant, was breastfeeding, or was providing or planned to provide breast milk in any manner during the study.
14. Any other significant medical condition(s), which in the investigator's opinion would have made the subject unsuitable for enrollment in the study.
15. Had concurrent diseases that might interfere with the conduct of the study, confound the interpretation of the study results, or endanger the subject's well-being.

Retreatment Inclusion and Exclusion Criteria

In order to be eligible to receive EN3835 on Retreatment Day 1 and on Retreatment Day 29, subjects must have:

1. Been an ambulatory male or female ≥18 years of age.
2. Completed the Initial Treatment Period.
3. Have had a diagnosis of plantar fibromatosis AND on clinical examination have had only 1 palpable hard, firm or soft nodule per foot or feet to be treated that are measurable via caliper, and was/were treated during the Initial Treatment Period.

4. Agreed not to use orthotics or inserts designed to relieve symptoms of plantar fibromatosis during the study period.
5. If female, been of nonchildbearing potential or, if of childbearing potential, been nonpregnant, nonlactating and agreed to use effective contraception.

A subject was ineligible to receive retreatment on Retreatment Day 1 and/or Retreatment Day 29 of, if the subject:

1. Received surgical or non-surgical treatment(s) (e.g., steroid injection, transdermal/intralesional verapamil, radiation therapy, extracorporeal shock wave therapy) on the foot or nodule(s) within 3 months before administration of EN3835.
2. Had the presence of or history of non-plantar fibromatosis-related nodules on the feet (e.g., neurofibroma, rhabdomyosarcoma, liposarcoma, neurilemmomas, rheumatoid nodules, desmoid tumors, or malignant soft tissue lesions of the foot or ankle).
3. Had a chronic or acute musculoskeletal, neurological, or neuromuscular disorder that affects the feet.
4. Had surgery on the foot/feet selected for treatment within 3 months prior to first retreatment visit.
5. Had a known systemic allergy to collagenase or any other excipient of EN3835.
6. Had received any collagenase treatment (e.g., Santyl® ointment, XIAFLEX/XIAPEX®, EN3835, or CCH), with the exception of treatment in this study, within 30 days prior to injection of EN3835 in the foot/feet selected for treatment.
7. Had a clinically significant laboratory abnormality or any laboratory test results meeting the following criteria (applies to the first retreatment session only):

$$a.\ ALT \geq 3 \times ULN.$$

$$b.\ TBL \geq 2 \times ULN\ (>35\%\ \text{direct bilirubin}).$$

$$c.\ AST \geq 3 \times ULN.$$

$$d.\ INR > 1.5.$$

8. Had a known coagulation disorder and/or was taking any medication (e.g., anticoagulants or antiplatelet medications, except for ≤150 mg aspirin daily) that would increase the risk of bleeding within 7 days of injection of EN3835 and for the duration of the Retreatment Period.
9. Was pregnant, planned to become pregnant, was breastfeeding, or was providing or planned to provide breast milk in any manner during the study.
10. Any other significant medical condition(s), which in the investigator's opinion would have made the subject unsuitable for enrollment in the study.
11. Had concurrent diseases that might interfere with the conduct of the study, confound the interpretation of the study results, or endanger the subject's well-being.

Nodule Assessments

At the Initial Treatment Day 1 Visit, a graphic representation of the foot/feet and the location(s) of the nodule(s) to be treated was prepared. At select time points, the selected nodule was palpated, the consistency of the nodule was determined, and the nodule was classified. During the Initial Treatment Period, only hard or firm nodules were treated. During the Retreatment Period, nodules treated during the Initial Treatment Period, either hard, firm, or soft may have been retreated. At select time points, a handheld caliper was used to measure the length and width of the selected nodule, and nodule measurements were recorded. Data on perimeter measurements (including subcutaneous tissue thickness) was collected on ultrasound along with gross observations at each time of examination. For the initial Treatment Period, at select time points, an ultrasound of the selected foot or feet was conducted. The size (maximum diameter) of the nodule was determined based on the largest diameter of width or length measured on ultrasound. An ultrasound of the foot was not conducted in the Retreatment Period.

The nodules were classified as follows:

Hard (no give)—given a value of 4

Firm throughout (a little resistance)—given a value of 3

Moderately firm (some resistance)—given a value of 2

Soft (no resistance)—given a value of 1

Non-palpable—given a value of 0

"Hard," "Firm Throughout," "Moderately Firm," "Soft," or "Non-palpable." Only nodules presenting as hard or firm at Screening/Day 1 were treated during the Initial Treatment Period. During the Retreatment Period, nodules treated during the Initial Treatment Period, either hard, firm, or soft may have been retreated.

The nodular consistency improvement at Day 57 after treatment for each treatment group is presented for the subjects (at subject level) in the ITT Population for Initial Treatment Period and for the subjects in the Safety Population of the Retreatment Period for Retreatment Period. The nodular consistency improvement is defined as at least one level reduction on the scale of 0-4 from Baseline, i.e., Hard (4)→Firm Throughout (3), Firm Throughout (3)→Soft (1), etc. Similarly, the nodular consistency improvement at nodule level for each treatment group is also presented.

The nodule measurement (i.e. length and width) was recorded using handheld calipers. The change from Baseline (Day 1) in size of each treated nodule at EOS and other post baseline visits was analyzed at each treatment period. The size (i.e. length and width) of the nodule was determined by ultrasound procedure of the selected foot or feet. The change from Baseline (Day 1) in size of each treated nodule at EOS and other post baseline visits of the Initial Treatment Period were analyzed.

Subject and Investigator Reported Outcome Assessments

Foot Function Index-Short Form-23 (FFI-SF-23)—The FFI-SF-23 is a total foot function assessment instrument, which comprises 23 items used to assess foot pain, disability, and difficulty in subjects with ankle and foot disorders (as described in Budiman-Mak E, et al., A review of the foot function index and the foot function index-revised. *J Foot Ankle Res.* 2013; 6 (1): 5; Budiman-Mak E, et al., The Foot Function Index: a measure of foot pain and disability. *J Clin Epidemiol.* 1991; 44 (6): 561-570). The FFI-SF-23 was used in this study to assess the impact of nodules associated with plantar fibromatosis at Baseline (Day 1) and after treatment with EN3835. Higher scores indicate greater impairment. The FFI-SF-23 comprises 3 subscales:

Foot Pain subscale (9 items) with a total score of 90. The response to each of the following questions ranges from 0 ("No Pain") to 10 ("Worst Pain Imaginable"):

1. At its worst?
2. Before you get up in the morning?
3. When you walk barefoot?
4. When you stand barefoot?
5. When you walk wearing shoes?
6. When you stand wearing shoes?
7. When you walk wearing orthotics?
8. When you stand wearing orthotics?
9. At the end of the day?

Disability subscale, (5 items) with a total score of 50. The response to each of the following questions ranges from 0 ("None of the Time") to 10 ("All of the Time"):

1. Use a cane, crutches or walker indoors?
2. Use a cane, crutches or walker outdoors?
3. Stay indoors most of the day because of foot problems?
4. Stay in bed most of the day because of foot problems?
5. Limit your activities because of foot problems?

Difficulty subscale (9 items) with a total score of 90. The response to each of the following questions ranges from 0 ("No Difficulty") to 10 ("So Difficult and unable to do"):

1. Walking around the house
2. Walking outside on uneven ground
3. Walking four or more blocks
4. Climbing stairs
5. Descending stairs
6. Standing on tiptoes
7. Getting out of a chair
8. Climbing up or down curbs
9. Walking fast or running The subscale score (%) is calculated by adding the answered item scores and dividing by the sum of the maximum score of the items answered. The calculation is:

$$\text{Subscale score (\%)} = \frac{\text{Sum of answered item scores}}{\text{Sum of maximum score of answered items}} \times 100$$

The maximum total score of each subscale if all items answered is given as below:

Disability subscale (5 items) with a maximum total score of 50

Difficulty subscale (9 items) with a maximum total score of 90

Pain subscale (9 items) with a maximum total score of 90

The change from Baseline (Day 1) in each subscale score (%) and the individual item scores of each subscale will be analyzed on EOS and other post baseline visits at each treatment period. In addition, the change from Baseline (Day 1) in total subscale score for each subscale will be analyzed on EOS and other post baseline visits at each treatment period.

Total subscale score is defined as the sum of the scores of answered items in each subscale (i.e., Disability subscale, Difficulty subscale, and Pain subscale).

Composite score on FFI-SF-23 is defined as the weighted average of 3 subscale scores (%) (i.e., Disability subscale, Difficulty subscale, and Pain subscale) with number of answered items as weight. The calculation is:

$$\text{Composite score (\%)} = \frac{\sum_{i=1}^{s}[\text{Subscale score (\%)}(i) \times \text{Number of answered items in the subscale}(i)]}{\sum_{i=1}^{s}\text{Number of answered items in the subscale}(i)}$$

where i=1, 2, 3 (for each subscale score (%)).

The change from Baseline (Day 1) in composite score (%) on FFI-SF-23 will be analyzed on EOS and other post baseline visits at each treatment period. In addition, the change from Baseline (Day 1) in total score will be analyzed on EOS and other post baseline visits at each treatment period. Higher scores are indicative of greater impairment.

Total score is defined as the sum of all answered items of 23 questions.

Subject Satisfaction With Treatment Scale—At select time points, each subject will be asked to rate his/her satisfaction with treatment per treated nodule on a 5-point scale ranging from −2 ("Very Dissatisfied") to +2 ("Very Satisfied") as follows:

−2 Very Dissatisfied
−1 Quite Dissatisfied
0 Neither Satisfied nor Dissatisfied
+1 Quite Satisfied
+2 Very Satisfied A responder is defined as a subject with a response of "Quite Satisfied" or "Very Satisfied" in the Subject Satisfaction with treatment scale during evaluation of each treated nodule.

Investigator Assessment of Improvement—At select time points, the investigator will determine the degree of improvement per treated nodule on a 7-point scale ranging from −3 ("Very Much Worse") to +3 ("Very Much Improvement"):

−3 Very Much Worse
−2 Much Worse
−1 Minimally Worse
0 No Change
+1 Minimal Improvement
+2 Much Improvement
+3 Very Much Improvement A responder is defined as a subject with a response of "Minimal Improvement", "Much Improvement" or "Very Much Improvement" in the Investigator Assessment of Improvement Scale during evaluation of each treated nodule.

Populations for Analysis

The following populations are defined for the conduct of the analysis:

The Safety Population of the Initial Treatment Period will include all subjects who receive at least 1 dose of EN3835 during the Initial Treatment Period. All safety analyses in the Initial Treatment Period will be based on this population.

The Safety Population of the Retreatment Period will include all subjects who receive at least 1 dose of EN3835 during the Retreatment Period. All safety analyses during the Retreatment Period will be based on this population.

The Intent-to-Treat (ITT) Population of the Initial Treatment Period will include all randomized subjects who have at least 1 post-baseline nodule size assessment determined by any method specified in this protocol.

All analyses of changes in nodule size, investigator assessment of improvement, foot function assessment, and subject satisfaction assessment in the Initial Treatment Period will be based on the ITT Population.

All analyses of the changes in nodule size, investigator assessment of improvement, foot function assessment, and subject satisfaction assessments during the Retreatment Period will be based on the Safety Population of the Retreatment Period.

The PK Population will include all subjects in the Safety Population from the Initial Treatment Period with sufficient plasma concentration data to determine the PK parameters. All PK analyses will be based on the PK Population.

Adverse Events

Information on all serious adverse events (SAEs) and adverse events (AEs) will be collected from the time of signing the informed consent through the Initial Treatment Period Day 57/EOS Visit or Retreatment Period Day 57/EOS visit, if eligible. This will include any AEs that are ongoing at the time of completion/termination of the study. For subjects participating in the Retreatment Period, any ongoing AEs or any new AEs reported during the gap in time between the Initial Treatment Period and signing of the informed consent for the Retreatment Period will be retrospectively collected. For subjects who withdraw from the study early, SAEs and AEs will be collected for 28 days after the last study treatment. Treatment-related AEs were defined as those determined to be "probably related" or "possibly related" to study drug.

An AE is any unfavorable or unintended change in body structure (signs), body function (symptoms), laboratory result (e.g., chemistry, ECG, X-ray, etc.), or worsening of a preexisting condition associated temporally with the use of the study treatment whether or not considered related to the study treatment. AEs include:

- Changes in the general condition of the subject.
- Subjective symptoms offered by or elicited from the subject.
- Objective signs observed by the investigator or other study personnel.
- All concurrent diseases that occur after the start of the study, including any change in severity or frequency of preexisting disease.
- All clinically relevant laboratory abnormalities or physical findings that occur during the study.

A treatment-emergent adverse event (TEAE) is any condition that was not present prior to treatment with study treatment but appeared following treatment, was present at treatment initiation but worsened during treatment, or was present at treatment initiation but resolved and then reappeared while the individual was on treatment (regardless of the intensity of the AE when the treatment was initiated).

A SAE is defined as an AE that:

- Results in death
- Is immediately life-threatening (there is an immediate risk of death from the AE as it occurred; this does not include an AE that had it occurred in a more serious form may have caused death)
- Results in or prolongs an inpatient hospitalization (Note: a hospitalization for elective or preplanned surgery, procedure, or drug therapy does not constitute an SAE)
- Results in permanent or substantial disability (permanent or substantial disruption of one's ability to conduct normal life functions)
- Is a congenital anomaly/birth defect (in offspring of a subject using the study treatment regardless of time to diagnosis)
- Is considered an important medical event Important medical events are defined as events that, based upon appropriate medical judgment, may jeopardize the subject and may require medical or surgical intervention to prevent one of the other serious outcomes. Examples of important medical events include any cancer, allergic bronchospasm requiring intensive treatment in an emergency room or at home, blood dyscrasias or convulsions that do not result in inpatient hospitalization, or the development of drug dependency or drug abuse.

The degree of "relatedness" of the AE to EN3835 will be described using the following scale:

- Not related indicates that the AE is definitely not related to EN3835.
- Unlikely related indicates that there are other, more likely causes and EN3835 is not suspected as a cause.
- Possibly related indicates that a direct cause and effect relationship between EN3835 and the AE has not been demonstrated, but there is evidence to suggest there is a reasonable possibility that the event was caused by EN3835.
- Probably related indicates that there is evidence suggesting a direct cause and effect relationship between the AE and EN3835.

"Probably related" and "Possibly related" causality assessments will be considered as positive causality. "Not related" and "Unlikely related" causality assessments will be considered as negative causality.

The intensity (or severity) of AEs is characterized as mild, moderate, or severe:

- Mild AEs are usually transient, requiring no special treatment, and do not interfere with the subject's daily activities.
- Moderate AEs introduce a low level of inconvenience or concern to the subject and may interfere with daily activities, but are usually ameliorated by simple therapeutic measures.
- Severe AEs interrupt a subject's usual daily activity and typically require systemic drug therapy or other treatment.

Interim Analysis

An interim analysis was performed at the end of the Initial Treatment Period Day 57 to evaluate the treatment effect and to confirm the appropriate effective dose to use during Retreatment Period and the subsequent Phase 2 study. Study results for the primary and secondary endpoints defined for the Initial Treatment Period were analyzed and provided for the interim analysis.

Demographic and Baseline Characteristics 24 patients with plantar fibromatosis were enrolled, and 31 nodules were treated (Table 15). Overall, more than half (54.2%) of patients were male, with a mean age of 55.5 years.

TABLE 15

Demographic and Baseline Characteristics

| Parameter | CCH 0.6 mg/mL (n = 8) | CCH 1.2 mg/mL (n = 8) | CCH 2.25 mg/mL (n = 8) |
|---|---|---|---|
| Age, y, mean (SD) | 49.2 (7.4) | 63.6 (10.7) | 53.7 (11.8) |
| Sex, n (%) | | | |
| Male | 4 (50.0) | 3 (37.5) | 6 (75.0) |
| Female | 4 (50.0) | 5 (62.5) | 2 (25.0) |
| Race, n (%) | | | |
| White | 7 (87.5) | 8 (100) | 7 (87.5) |
| Black | 1 (12.5) | 0 | 1 (12.5) |
| BMI, kg/m$^2$, mean (SD) | 30.6 (5.1) | 32.0 (9.9) | 27.6 (4.7) |
| Nodules, n | 11 | 10 | 10 |

BMI = body mass index;
CCH = collagenase clostridium histolyticum;
SD = standard deviation.

Preliminary Results

The FFI-SF-23 score and nodule consistency and measurement were used as objective and subjective assessments for analyzing treatment response/improvement as described in the table below. Worsening in any one of these was considered poor treatment response.

TABLE 16

| Analysis criteria | | | |
|---|---|---|---|
| Nodule Consistency | Nodule Measurement | FFI-SF-23 Score | Conclusion |
| Reduced | Non-measurable/ Non-palpable | Reduced | Very Good treatment response |
| Reduced | Reduced | Reduced | Good treatment response |
| No change | No reduction | Reduced | Some treatment response |
| Reduced | No reduction | Reduced | Some treatment response |
| Reduced | Reduced | No change | Some treatment response |
| Reduced | No reduction | No change | No treatment response |
| No change | Reduced | No change | No treatment response |
| No change | No reduction | Reduced | No treatment response |
| No change | No reduction | No change | Poor treatment response |

Preliminary data on select subjects are provided in the Tables 17-29 and in FIG. 2-8. The preliminary data are summarized below:

Subjects Having a Nodule≤1.5 cm in Size and Treated with the Following Dose of Collagenase: 0.6 mg/mL, 0.12 mg, 1 Injection (0.2 mL) (Tables 17 and 18).

Although 0.12 mg showed some improvement in subjective assessments (FFI-SF-23, Subject satisfaction & Investigator assessment of improvement), no reduction was observed in the objective assessments (nodule consistency and measurement). Although almost 60-100% reduction was observed in FFI-SF-23 scores of the patients, lack of reduction in objective improvements suggests that the 0.12 mg dose does not show a treatment response on a PF nodule that was ≤1.5 cm.

Subjects Having a Nodule≤1.5 cm in Size and Treated with the Following Dose of Collagenase: 1.2 mg/mL, 0.24 mg, 1 Injection (0.2 mL) (Tables 19 and 20)

One patient showed some improvement in all subjective assessments (FFI-SF-23, Subject satisfaction & Investigator assessment of improvement) and quantitative assessments (nodule consistency), but no reduction in nodule measurement. This patient was classified as experiencing some treatment response.

The other patient worsened in all assessments, except the nodule consistency (some improvement). This patient was classified as experiencing a poor treatment response.

Some treatment response in one subject and a poor treatment response in another patient makes it inconclusive to determine if 0.24 mg dose shows a treatment response on a PF nodule that was ≤1.5 cm.

Subjects Having a Nodule≤1.5 cm in Size and Treated with the Following Dose of Collagenase: 2.25 mg/mL, 0.45 mg, 1 Injection (0.2 mL) (Tables 21 and 22)

This patient showed an improvement in all assessments (FFI-SF-23, Subject satisfaction, Investigator assessment of improvement & nodule consistency), but no reduction in nodule measurement. This patient was classified as experiencing some treatment response. Thus, some treatment response was observed with 0.45 mg dose for a PF nodule that was ≤1.5 cm.

Subjects Having a Nodule >1.5 cm in Size and Treated with the Following Dose of Collagenase: 0.6 mg/mL, 0.24 mg, 2 Injections (0.2 mL Each) (Tables 23 and 24)

This patient showed some improvement in Investigator assessment of improvement & nodule consistency but no change in the rest of the assessments (FFI-SF-23, Subject satisfaction, & nodule measurement) and no reduction in the nodule measurement. This patient was classified as experiencing no treatment response. Thus, no treatment response was observed with 0.24 mg dose for a PF nodule that was >1.5 cm.

Subjects Having a Nodule >1.5 cm in Size and Treated with the Following Dose of Collagenase: 1.2 mg/mL, 0.48 mg, 2 Injections (0.2 mL Each) (Tables 25 and 26)

This patient showed improvement in all assessments and was classified as experiencing a good treatment response. The improvement at Day 29 was better that the improvement at Day 57. Thus, a good treatment response was observed with 0.48 mg dose for a PF nodule that was >1.5 cm Subjects Having a Nodule >1.5 cm in Size and Treated with the Following Dose of Collagenase: 2.25 mg/mL, 0.9 mg, 2 Injections (0.2 mL Each) (Tables 27 and 28)

One patient showed an improvement in all assessments and was classified as experiencing a good treatment response. The other patient ended with a non-palpable lesion along with improvements in all other assessments, and was classified as experiencing a very good treatment response. Thus, a very good to good treatment response was observed with 0.9 mg dose for a PF nodule that was >1.5 cm.

Ultrasound findings for one patient included:

Loss of structure, disruption of fibrotic tissue, and loose contours;

Appreciable hypo-echogenic changes; and

Possible "capsule or outer layer" that remained

Overall Conclusions from Preliminary Results (Table 29)

The 2.25 mg/mL concentration at doses of 0.45 mg or 0.9 mg stands out with good treatment responses for nodules sizes of ≤1.5 cm or >1.5 cm respectively.

Although 1.2 mg/mL concentration at a dose of 0.24 mg for nodules size of ≤1.5 cm was inconclusive, a dose of 0.48 mg for nodules size >1.5 cm showed good response.

The 0.6 mg/mL concentration did not show much of a treatment response for nodules sizes of ≤1.5 cm or >1.5 cm.

From a dose perspective, doses of 0.45 mg or above (0.48 mg and 0.9 mg) could show at least some treatment response for different nodule sizes

TABLE 17

| Nodule ≤1.5 cm: 0.6 mg/mL, 0.12 mg, 1 injection (0.2 mL) - Preliminary Results | | | | | | | | | |
|---|---|---|---|---|---|---|---|---|---|
| | | Nodule | | FFI-SF-23 (230) | | | | | Investigator Assessment |
| | Nodule | Measurement | | Disability | Difficulty | | Total | Subject | of |
| Subject # | Consistency | Caliper | Ultrasound | (50) | (90) | Pain (90) | Score | Satisfaction | Improvement |
| 1802-4005 | No change-Firm Throughout at Day 1 to Day 57 | No reduction | No reduction | No change-0 throughout | No change-0 throughout | Reduced, Day 1-3, Day 15-1, Day 29-0 | Reduced, Day 1-3, Day 15-1, Day 29-0 | Improved, Very satisfied at Day 57 | Improved, Minimal improvement at Day 57 |

TABLE 17-continued

| Nodule ≤1.5 cm: 0.6 mg/mL, 0.12 mg, 1 injection (0.2 mL) - Preliminary Results | | | | | | | | | |
|---|---|---|---|---|---|---|---|---|---|
| | | Nodule Measurement | | FFI-SF-23 (230) | | | | | Investigator Assessment |
| Subject # | Nodule Consistency | Caliper | Ultrasound | Disability (50) | Difficulty (90) | Pain (90) | Total Score | Subject Satisfaction | of Improvement |
| 1802-4006 (Left foot) | Worsened-Firm Throughout at Day 1 to Hard at Day 57 | No reduction | No reduction | Reduced, Day 1-19, Day 8-12, Day 15-4, Day 22-5, Day 29-3 & Day 57-8 | Reduced, Day 1-70, Day 8-28, Day 15-21, Day 22-18, Day 29-22 & Day 57-28 | Reduced, Day 1-56, Day 8-44, Day 15-31, Day 22-37, Day 29-21 & Day 57-26 | Reduced, Day 1-145, Day 8-84, Day 15-56, Day 22-60, Day 29-46 & Day 57-62 | Improved, Quite satisfied at Day 57 | Improved, Minimal improvement at Day 57 |
| 1802-4006 (Right foot) | Worsened-Firm Throughout at Day 1 to Hard at Day 57 | No reduction | No reduction | | | | | | |

TABLE 18

| Nodule ≤ 1.5 cm: 0.6 mg/mL, 0.12 mg, 1 injection (0.2 mL) - Conclusion From Preliminary Results | | | | |
|---|---|---|---|---|
| Subject # | Nodule Consistency | Nodule Measurement | FFI-SF-23 Score | Conclusion |
| 1802-4005 | No change | No change | Reduced | No treatment response |
| 1802-4006 | Worsened | No change | Reduced | Poor treatment response |

TABLE 19

| Nodule ≤1.5 cm: 1.2 mg/mL, 0.24 mg, 1 injection (0.2 mL) - Preliminary Results | | | | | | | | | |
|---|---|---|---|---|---|---|---|---|---|
| | | Nodule Measurement | | FFI-SF-23 (230) | | | | | Investigator Assessment |
| Subject # | Nodule Consistency | Caliper | Ultrasound | Disability (50) | Difficulty (90) | Pain (90) | Total Score | Subject Satisfaction | of Improvement |
| 1806-4004 | Some reduction-Firm Throughout from Day 1 to Day 29, Soft at Day 57 | No reduction | No reduction | Reduced, Day 1-4, Day 8- 4, Day 15-3, Day 22-2, Day 29-1 & Day 57-1 | Reduced, Day 1-42, Day 8-46, Day 15-34, Day 22-32, Day 29-18 & Day 57-11 | Reduced, Day 1-43, Day 8-29, Day 15-13, Day 22-12, Day 29-5 & Day 57-13 | Reduced, Day 1-89, Day 8-79, Day 15-50, Day 22-46, Day 29-24 & Day 57-25 | Improved, Very satisfied at Day 57 | Improved, Minimal improvement at Day 57 |
| 1806-4009 | Some reduction-Hard at Day 1 to Firm Throughout ay Day 29 | No reduction | No reduction | Worsened, Day 1-8, Day 8-7, Day 15-14, Day 22-14 & Day 29-15 | Worsened, Day 1-46, Day 8-64, Day 15-68, Day 22-71 & Day 29-71 | Worsened, Day 1-46, Day 8-61, Day 15-54, Day 22-44 & Day 29-37 | Worsened, Day 1-100, Day 8-132, Day 15-136, Day 22-129 & Day 29-123 | No improvement, Neither satisfied nor dissatisfied at Day 29 | Worsened, Much worse at Day 8, 15 & Minimally worse at Day 29 |

TABLE 20

| Nodule ≤ 1.5 cm: 1.2 mg/mL, 0.24 mg, 1 injection (0.2 mL) - Conclusion From Preliminary Results | | | | |
|---|---|---|---|---|
| Subject # | Nodule Consistency | Nodule Measurement | FFI-SF-23 Score | Conclusion |
| 1806-4004 | Some reduction | No change | Reduced | Some treatment response |
| 1806-4009 | Some reduction | No change | Worsened | Poor treatment response |

TABLE 21

| Nodule ≤1.5 cm: 2.25 mg/mL, 0.45 mg, 1 injection (0.2 mL) - Preliminary Results | | | | | | | | | |
|---|---|---|---|---|---|---|---|---|---|
| | | | | FFI-SF-23 (230) | | | | | Investigator Assessment |
| | Nodule | Nodule Measurement | | Disability | Difficulty | | | Subject | of |
| Subject # | Consistency | Caliper | Ultrasound | (50) | (90) | Pain (90) | Total Score | Satisfaction | Improvement |
| 1806-4007 | Some reduction-Firm Throughout from Day 1 to Day 15, Soft at Day 22, 29 & 57 | No reduction | No reduction | No change-0 throughout | Reduced, Day 1-1, Day 22-1, Day 29-1 & Day 57-0 | Reduced, Day 1-3, Day 22-2, Day 29-2 & Day 57-0 | Reduced, Day 1-4, Day 22-3, Day 29-3 & Day 57-0 | Improved, Very satisfied at Day 29 | Improved, Minimal improvement at Day 29 |

TABLE 22

| Nodule ≤ 1.5 cm: 2.25 mg/mL, 0.45 mg, 1 injection (0.2 mL) - Conclusion From Preliminary Results | | | | |
|---|---|---|---|---|
| Subject # | Nodule Consistency | Nodule Measurement | FFI-SF-23 Score | Conclusion |
| 1806-4007 | Some reduction | No change | Reduced | Some treatment response |

TABLE 23

| Nodule >1.5 cm: 0.6 mg/mL, 0.24 mg, 2 injections (0.2 mL each) - Preliminary Results | | | | | | | | | |
|---|---|---|---|---|---|---|---|---|---|
| | | | | FFI-SF-23 (230) | | | | | Investigator Assessment |
| | Nodule | Nodule Measurement | | Disability | Difficulty | | | Subject | of |
| Subject # | Consistency | Caliper | Ultrasound | (50) | (90) | Pain (90) | Total Score | Satisfaction | Improvement |
| 1802-4002 (Left Foot) | Some reduction-Firm Throughout from Day 1 to Soft at Day 29 & 57 | No reduction | No reduction | No change-0 from Day 1 to Day 57 | No change-0 from Day 1 to Day 57 | No change, Day 1-19, Day 8-13, Day 8-13, Day 22-19, Day 29-17 & Day 57-18 | No change, Day 1-19, Day 8-13, Day 8-13, Day 22-19, Day 29-17 & Day 57-18 | No change, Neither satisfied nor dissatisfied at Day 57 | Improved, Much improved at Day 57 |
| 1802-4002 (Right Foot) | Some reduction-Firm Throughout from Day 1 to Soft from Day 15 | | | | | | | No change, Neither satisfied nor dissatisfied at Day 57 | Improved, Much improved at Day 57 |

TABLE 24

| Nodule > 1.5 cm: 0.6 mg/mL, 0.24 mg, 2 injections (0.2 mL each) - Conclusion From Preliminary Results | | | | |
|---|---|---|---|---|
| Subject # | Nodule Consistency | Nodule Measurement | FFI-SF-23 Score | Conclusion |
| 1802-4002 | Some reduction | No change | No change | No treatment response |

TABLE 25

Nodule >1.5 cm: 1.2 mg/mL, 0.48 mg, 2 injections (0.2 mL each) - Preliminary Results

| | | Nodule Measurement | | FFI-SF-23 (230) | | | | | |
|---|---|---|---|---|---|---|---|---|---|
| Subject # | Nodule Consistency | Caliper | Ultrasound | Disability (50) | Difficulty (90) | Pain (90) | Total Score | Subject Satisfaction | Investigator Assessment of Improvement |
| 1802-4001 | Reduced-Firm Throughout at Day 1 to Soft at Day 8 | Reduced, Day 1-1.24 × 1.48, Day 8-1.08 × 1.33, Day 15-1.03 × 1.07, Day 29-0.77 × 0.25 & Day 57-1.31 × 1.03 | No reduction | Reduced, Day 1-8, Day 8-5, Day 15-3, Day 22-0, Day 29-0 & Day 57-4 | Reduced, Day 1-65, Day 8-11, Day 15-11, Day 22-2, Day 29-3 & Day 57-2 | Reduced, Day 1-48, Day 8-13, Day 15-14, Day 22-6, Day 29-6 & Day 57-21 | Reduced, Day 1-121, Day 8-29, Day 15-28, Day 22-8, Day 29-9 & Day 57-27 | Improved, Very satisfied at Day 29; Neither satisfied nor dissatisfied at Day 57 | Improved, Very Much improvement at Day 29; Much improvement at Day 57 |

TABLE 26

Nodule > 1.5 cm: 1.2 mg/mL, 0.48 mg, 2 injections (0.2 mL each) - Conclusion From Preliminary Results

| Subject # | Nodule Consistency | Nodule Measurement | FFI-SF-23 Score | Conclusion |
|---|---|---|---|---|
| 1802-4001 | Reduced | Reduced | Reduced | Good treatment response |

TABLE 27

Nodule >1.5 cm: 2.25 mg/mL, 0.9 mg, 2 injections (0.2 mL each) - Preliminary Results

| | | Nodule Measurement | | FFI-SF-23 (230) | | | | | |
|---|---|---|---|---|---|---|---|---|---|
| Subject # | Nodule Consistency | Caliper | Ultrasound | Disability (50) | Difficulty (90) | Pain (90) | Total Score | Subject Satisfaction | Investigator Assessment of Improvement |
| 1806-4000 | Reduced-Firm Throughout at Day 1 to Soft at Day 8-57 | Non measurable, Day 1, 2.83 × 1.44, to Day 22, 29 & 57-Non Palpable | Some reduction, Day 1 L * W * D 3.41 * 1.58 * 0.91 TO Day 57 L * W * D 3.37 * 1.72 * 0.66 | Reduced, Day 1-0, Day 8-0, Day 15-0, Day 22-1, Day 29-0 & Day 57-0 | Reduced, Day 1-3, Day 8-0, Day 15-0, Day 22-0, Day 29-0 & Day 57-0 | Reduced, Day 1-6, Day 8-0, Day 15-0, Day 22-1, Day 29-0 & Day 57-1 | Reduced, Day 1-9, Day 8-0, Day 15-0, Day 22-2, Day 29-0 & Day 57-1 | Improved, Quite satisfied at Day 57 | Improved, Very Much improvement at Day 57 |
| 1802-4011 | Reduced-Hard at Day 1 to Moderately Firm at Day 15, 22 to Soft at Day 29 | Reduced, Day 1-2.53 × 2.39, Day 29-2.05 × 1.54 | Some reduction, Day 1 L * W * D 3.8 * 2.7 * 0.87 TO Day 22 L * W * D 3.67 * 2.99 * 0.89 | Reduced, Day 1-7, Day 8-5, Day 15-0, Day 22-0, & Day 29-0 | Reduced, Day 1-6, Day 8-4, Day 15-19, Day 22-3, & Day 29-3 | Reduced, Day 1-33, Day 8-44, Day 15-21, Day 22-15, & Day 29-14 | Reduced, Day 1-46, Day 8-53, Day 15-40, Day 22-18, & Day 29-17 | Improved, Very satisfied Day 57 | Improved, Very Much improvement at Day 57 |

TABLE 28

Nodule > 1.5 cm: 2.25 mg/mL, 0.9 mg, 2 injections (0.2 mL each) - Preliminary Analysis of Ultrasound Images (Subject 1806-4000)

| | Length (cm) | Width (cm) | Length (cm) | Width (cm) | Depth (cm) |
|---|---|---|---|---|---|
| Day 1 | 2.83 | 1.44 | 3.41 | 1.58 | 0.91 |
| Day 22 | Non-Palpable | Non-Palpable | 2.99 | 1.64 | 0.79 |
| Day 57 | Non-Palpable | Non-Palpable | 3.37 | 1.72 | 0.74 |

TABLE 29

| Nodule > 1.5 cm: 2.25 mg/mL, 0.9 mg, 2 injections (0.2 mL each), FFI-SF-23 Graph | | | | |
|---|---|---|---|---|
| Subject # | Nodule Consistency | Nodule Measurement | FFI-SF-23 Score | Conclusion |
| 1806-4000 | Reduced | Non-Palpable | Reduced | Very Good treatment response |
| 1802-4011 | Reduced | Reduced | Reduced | Good treatment response |

TABLE 30

| Overall Conclusions From Preliminary Results | | | | | |
|---|---|---|---|---|---|
| Treatment Concen-tration | Concen-tration (mg/mL) | Number of Injections/ Nodule Size | Total Volume (mL) | Total Dose Administered/ Nodule (mg) | Conclusions |
| 1 | 0.6 | 1/≤1.5 cm | 0.2 | 0.12 | Poor/No Treatment Response |
| | | 2/>1.5 cm | 0.4 | 0.24 | No Treatment Response |
| 2 | 1.2 | 1/≤1.5 cm | 0.2 | 0.24 | Some/Poor Treatment Response (inconclusive) |
| | | 2/>1.5 cm | 0.4 | 0.48 | Good Treatment Response |
| 3 | 2.25 | 1/≤1.5 cm | 0.2 | 0.45 | Some Treatment Response |
| | | 2/>1.5 cm | 0.4 | 0.9 | Very Good/Good Treatment Response |

Interim Efficacy Analysis

A prespecified interim efficacy analysis was conducted once all patients had completed Day 57.

Figure 9:
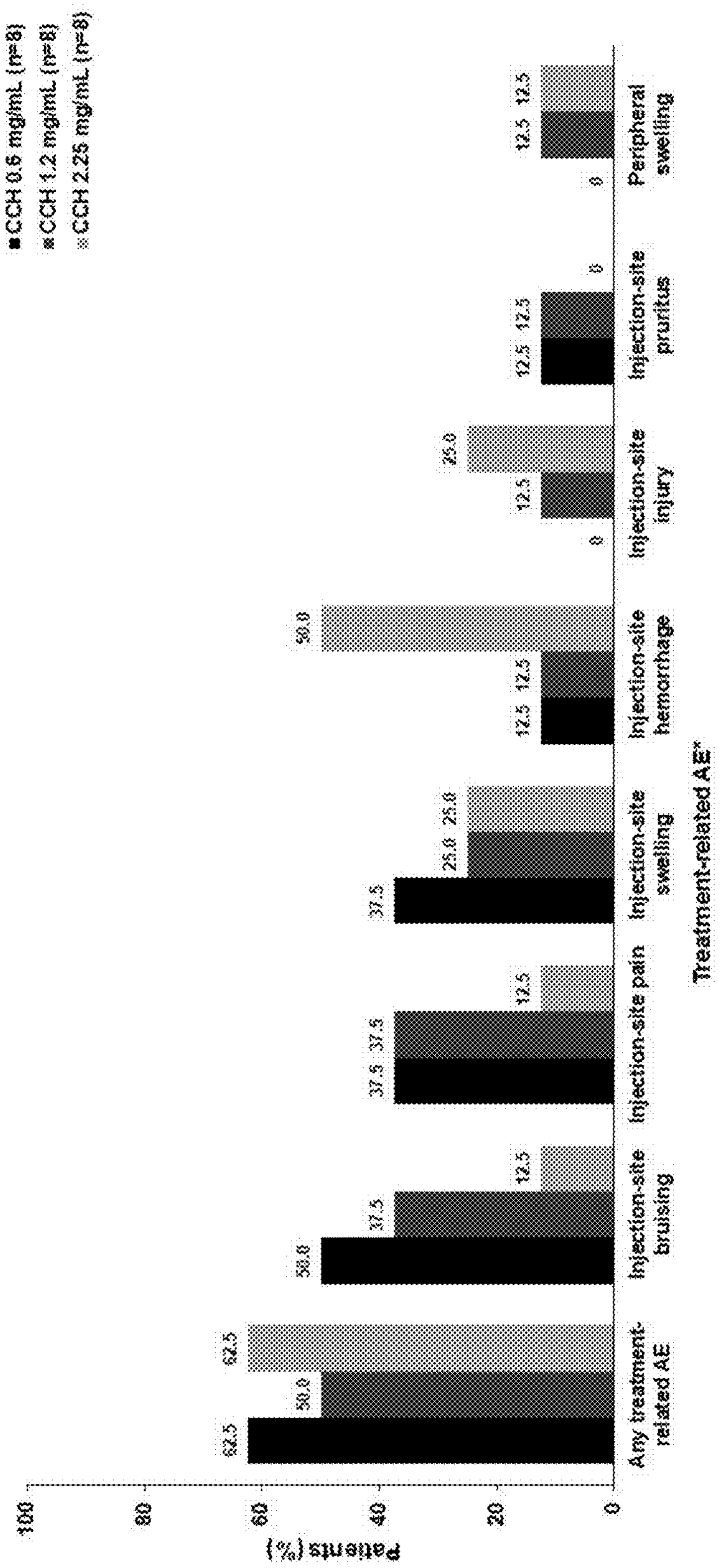
FIG. 9 illustrates the treatment-related adverse events (AEs) by group.

CCH treatment was generally well tolerated, with no discontinuations due to treatment-related AEs and no serious treatment related AEs reported. All treatment-related AEs were mild or moderate in intensity, and most (70.9%) resolved within 21 days. Overall, the most common treatment-related AEs were injection-site bruising, pain, and swelling (FIG. 9).

Figure 10:
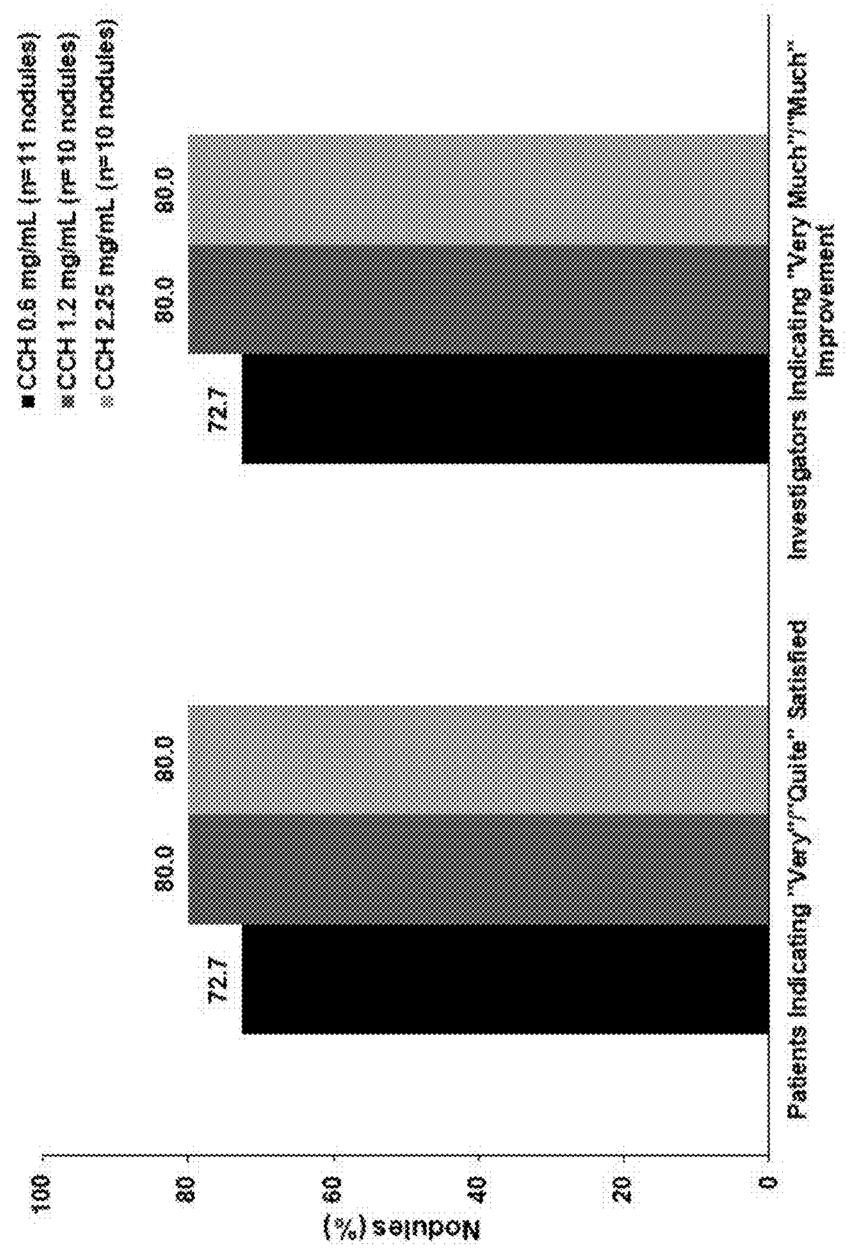
FIG. 10 illustrates exemplary patient satisfaction and investigator assessment of improvement with CCH treatment.

At Day 57, for the 31 nodules, most patients in each of the 3 CCH treatment groups indicated being "very satisfied" or "quite satisfied" with the first treatment of their nodule(s) (FIG. 10). Furthermore, most investigators reported "very much"/"much" improvement in the nodules in each of the 3 CCH treatment groups (FIG. 10).

Figure 11:
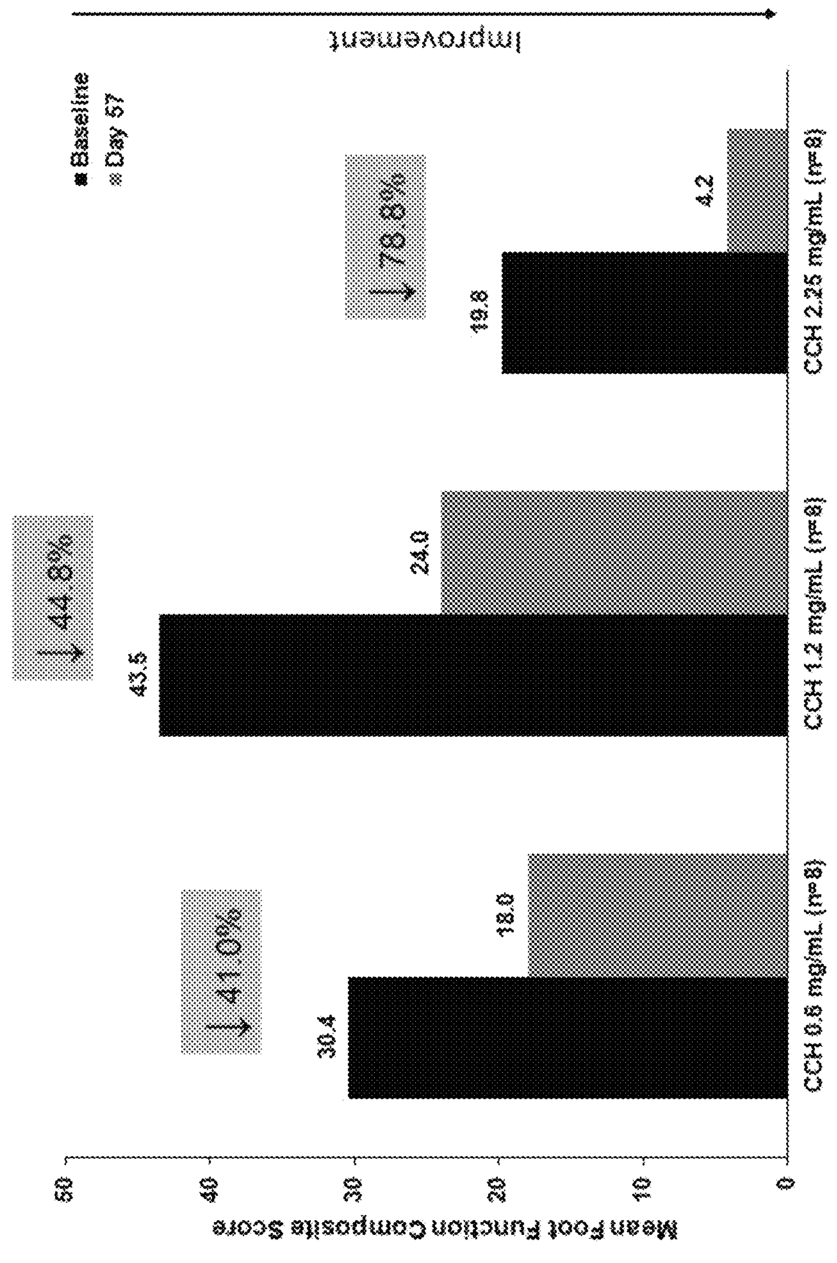
FIG. 11 illustrates the percentage improvement from baseline in FFI-SF-23 composite score at Day 57.

Improvement in FFI-SF-23 composite score and nodule consistency at Day 57 supported a CCH dose response. The CCH 2.25 mg/mL group had the highest percentage improvement from baseline in FFI-SF-23 composite score (78.8%; FIG. 11). The CCH 2.25 mg/mL and 1.2 mg/mL groups also had a high (90%) percentage improvement from baseline in softening of nodule consistency (>1 level), whereas the CCH 0.6 mg/mL group showed a 72.2% improvement.

Tables 31-40 below provide a summary of the observed results. A description of the various subjects follows the tables.

TABLE 31

| Foot Function Index (FFI-SF-23) Composite Scores (%)/Foot Function Index (FFI-SF-23) Total Score | | | | | | | | |
|---|---|---|---|---|---|---|---|---|
| | | | # of Injections (injection volume = | | Initial Tx Phase | | Retreatment Phase | |
| Subject | Dose | Conc. | 0.2 ml/injection) | Foot Function Index | Day 1 | Day 57 | Day 1 | Day 57 |
| 1804-4019 | 0.12 mg | 0.6 mg/ml | 1 | Composite Score (%) | 45.7 | 4.8 | — | — |
| 1804-4019 | 0.12 mg | 0.6 mg/ml | 1 | Total Score | 64.0 | 10.0 | — | — |
| 1806-4006 | 0.12 mg | 0.6 mg/ml | 1 | Composite Score (%) | 76.3 | 32.6 | — | — |
| 1806-4006 | 0.12 mg | 0.6 mg/ml | 1 | Total Score | 145.0 | 62.0 | — | — |
| 1806-4005 | 0.12 mg | 0.6 mg/ml | 1 | Composite Score (%) | 1.4 | 0.0 | 0.0 | 0.0 |
| 1806-4005 | 0.12 mg | 0.6 mg/ml | 1 | Total Score | 3.0 | 0.0 | 0.0 | 0.0 |
| 1806-4014 | 0.12 mg | 0.6 mg/ml | 1 | Composite Score (%) | 11.3 | 7.6 | 10.5 | 4.8 |

TABLE 31-continued

| Subject | Dose | Conc. | # of Injections (injection volume = 0.2 ml/injection) | Foot Function Index | Initial Tx Phase Day 1 | Initial Tx Phase Day 57 | Retreatment Phase Day 1 | Retreatment Phase Day 57 |
|---|---|---|---|---|---|---|---|---|
| Foot Function Index (FFI-SF-23) Composite Scores (%)/Foot Function Index (FFI-SF-23) Total Score | | | | | | | | |
| 1806-4014 | 0.12 mg | 0.6 mg/ml | 1 | Total Score | 18.0 | 16.0 | 22.0 | 10.0 |
| 1804-4023 | 0.24 mg | 1.2 mg/ml | 1 | Composite Score (%) | 66.8 | 47.1 | — | — |
| 1804-4023 | 0.24 mg | 1.2 mg/ml | 1 | Total Score | 127.0 | 99.0 | — | — |
| 1806-4009 | 0.24 mg | 1.2 mg/ml | 1 | Composite Score (%) | 47.6 | 50.0 | — | — |
| 1806-4009 | 0.24 mg | 1.2 mg/ml | 1 | Total Score | 100.0 | 105.0 | — | — |
| 1806-4015 | 0.24 mg | 1.2 mg/ml | 1 | Composite Score (%) | 7.6 | 0.0 | — | — |
| 1806-4015 | 0.24 mg | 1.2 mg/ml | 1 | Total Score | 16.0 | 0.0 | — | — |
| 1806-4004 | 0.24 mg | 1.2 mg/ml | 1 | Composite Score (%) | 42.4 | 11.9 | 30.5 | 13.3 |
| 1806-4004 | 0.24 mg | 1.2 mg/ml | 1 | Total Score | 89.0 | 25.0 | 64.0 | 28.0 |
| 1802-4002 | 0.24 mg | 0.6 mg/ml | 2 | Composite Score (%) | 8.3 | 10.6 | — | — |
| 1802-4002 | 0.24 mg | 0.6 mg/ml | 2 | Total Score | 19.0 | 18.0 | — | — |
| 1804-4024 | 0.24 mg | 0.6 mg/ml | 2 | Composite Score (%) | 85.7 | 72.8 | — | — |
| 1804-4024 | 0.24 mg | 0.6 mg/ml | 2 | Total Score | 180.0 | 131.0 | — | — |
| 1804-4028 | 0.24 mg | 0.6 mg/ml | 2 | Composite Score (%) | 2.0 | 6.3 | — | — |
| 1804-4028 | 0.24 mg | 0.6 mg/ml | 2 | Total Score | 4.0 | 12.0 | — | — |
| 1806-4016 | 0.24 mg | 0.6 mg/ml | 2 | Composite Score (%) | 12.9 | 9.1 | 6.2 | 12.4 |
| 1806-4016 | 0.24 mg | 0.6 mg/ml | 2 | Total Score | 27.0 | 19.0 | 13.0 | 26.0 |
| 1806-4007 | 0.45 mg | 2.25 mg/ml | 1 | Composite Score (%) | 2.0 | 0.0 | — | — |
| 1806-4007 | 0.45 mg | 2.25 mg/ml | 1 | Total Score | 4.0 | 0.0 | — | — |
| 1810-4027 | 0.45 mg | 2.25 mg/ml | 1 | Composite Score (%) | 32.2 | 0.5 | 4.8 | 8.1 |
| 1810-4027 | 0.45 mg | 2.25 mg/ml | 1 | Total Score | 74.0 | 1.0 | 10.0 | 17.0 |
| 1802-4001 | 0.48 mg | 1.2 mg/ml | 2 | Composite Score (%) | 57.6 | 22.5 | — | — |
| 1802-4001 | 0.48 mg | 1.2 mg/ml | 2 | Total Score | 121.0 | 27.0 | — | — |
| 1804-4012 | 0.48 mg | 1.2 mg/ml | 2 | Composite Score (%) | 46.4 | 0.6 | 9.0 | 8.4 |
| 1804-4012 | 0.48 mg | 1.2 mg/ml | 2 | Total Score | 51.0 | 1.0 | 17.0 | 16.0 |
| 1804-4025 | 0.48 mg | 1.2 mg/ml | 2 | Composite Score (%) | 17.9 | 1.1 | 11.1 | 1.1 |
| 1804-4025 | 0.48 mg | 1.2 mg/ml | 2 | Total Score | 34.0 | 2.0 | 21.0 | 2.0 |
| 1810-4021 | 0.48 mg | 1.2 mg/ml | 2 | Composite Score (%) | 61.7 | 59.1 | 35.0 | 26.7 |
| 1810-4021 | 0.48 mg | 1.2 mg/ml | 2 | Total Score | 142.0 | 124.0 | 63.0 | 56.0 |
| 1804-4018 | 0.9 mg | 2.25 mg/ml | 2 | Composite Score (%) | 29.5 | 5.2 | — | — |
| 1804-4018 | 0.9 mg | 2.25 mg/ml | 2 | Total Score | 56.0 | 11.0 | — | — |
| 1804-4026 | 0.9 mg | 2.25 mg/ml | 2 | Composite Score (%) | 24.4 | 0.0 | — | — |
| 1804-4026 | 0.9 mg | 2.25 mg/ml | 2 | Total Score | 44.0 | 0.0 | — | — |
| 1806-4000 | 0.9 mg | 2.25 mg/ml | 2 | Composite Score (%) | 3.9 | 0.5 | — | — |

TABLE 31-continued

Foot Function Index (FFI-SF-23) Composite Scores (%)/Foot Function Index (FFI-SF-23) Total Score

| Subject | Dose | Conc. | # of Injections (injection volume = 0.2 ml/injection) | Foot Function Index | Initial Tx Phase Day 1 | Initial Tx Phase Day 57 | Retreatment Phase Day 1 | Retreatment Phase Day 57 |
|---|---|---|---|---|---|---|---|---|
| 1806-4000 | 0.9 mg | 2.25 mg/ml | 2 | Total Score | 9.0 | 1.0 | — | — |
| 1802-4010 | 0.9 mg | 2.25 mg/ml | 2 | Composite Score (%) | 33.9 | 9.5 | 17.1 | 17.1 |
| 1802-4010 | 0.9 mg | 2.25 mg/ml | 2 | Total Score | 61.0 | 18.0 | 36.0 | 36.0 |
| 1802-4011 | 0.9 mg | 2.25 mg/ml | 2 | Composite Score (%) | 32.9 | 18.0 | 6.1 | 4.7 |
| 1802-4011 | 0.9 mg | 2.25 mg/ml | 2 | Total Score | 46.0 | 27.0 | 11.0 | 8.0 |
| 1804-4020 | 0.9 mg | 2.25 mg/ml | 2 | Composite Score (%) | 0.0 | 0.0 | 0.0 | 0.0 |
| 1804-4020 | 0.9 mg | 2.25 mg/ml | 2 | Total Score | 0.0 | 0.0 | 0.0 | 0.0 |

FFI-SF-23 has 23 items used to assess foot pain, disability, and difficulty. Response for each item ranges from 0 to 10. The higher score indicates more severe foot function. Composite score (%) = (Σ3(i = 1)[Subscale score (%)(i) *Number of answered items in the subscale(i)])/(Σ3(i = 1) Number of answered items in the subscale(i)).

TABLE 32

Foot Function Index (FFI-SF-23) Total Scores\Foot Function Index (FFI-SF-23) Total Subscale (Pain, Difficulty, and Disability) Scores

| Subject | Dose | Conc. | # of Inj | Foot Function Index | Initial Tx Phase Day 1 | Initial Tx Phase Day 57 | Retreatment Phase Day 1 | Retreatment Phase Day 57 |
|---|---|---|---|---|---|---|---|---|
| 1804-4019 | 0.12 mg | 0.6 mg/ml | 1 | Total Score | 64 | 10 | — | — |
| 1804-4019 | 0.12 mg | 0.6 mg/ml | 1 | Total Pain | 38 | 6 | — | — |
| 1804-4019 | 0.12 mg | 0.6 mg/ml | 1 | Total Difficulty | 26 | 3 | — | — |
| 1804-4019 | 0.12 mg | 0.6 mg/ml | 1 | Total Disability | — | 1 | — | — |
| 1806-4006 | 0.12 mg | 0.6 mg/ml | 1 | Total Score | 145 | 62 | — | — |
| 1806-4006 | 0.12 mg | 0.6 mg/ml | 1 | Total Pain | 56 | 26 | — | — |
| 1806-4006 | 0.12 mg | 0.6 mg/ml | 1 | Total Difficulty | 70 | 28 | — | — |
| 1806-4006 | 0.12 mg | 0.6 mg/ml | 1 | Total Disability | 19 | 8 | — | — |
| 1806-4005 | 0.12 mg | 0.6 mg/ml | 1 | Total Score | 3 | 0 | 0 | 0 |
| 1806-4005 | 0.12 mg | 0.6 mg/ml | 1 | Total Pain | 3 | 0 | 0 | 0 |
| 1806-4005 | 0.12 mg | 0.6 mg/ml | 1 | Total Difficulty | 0 | 0 | 0 | 0 |
| 1806-4005 | 0.12 mg | 0.6 mg/ml | 1 | Total Disability | 0 | 0 | 0 | 0 |
| 1806-4014 | 0.12 mg | 0.6 mg/ml | 1 | Total Score | 18 | 16 | 22 | 10 |
| 1806-4014 | 0.12 mg | 0.6 mg/ml | 1 | Total Pain | 18 | 9 | 22 | 10 |
| 1806-4014 | 0.12 mg | 0.6 mg/ml | 1 | Total Difficulty | 0 | 7 | 0 | 0 |
| 1806-4014 | 0.12 mg | 0.6 mg/ml | 1 | Total Disability | — | 0 | 0 | 0 |
| 1804-4023 | 0.24 mg | 1.2 mg/ml | 1 | Total Score | 127 | 99 | — | — |
| 1804-4023 | 0.24 mg | 1.2 mg/ml | 1 | Total Pain | 48 | 25 | — | — |
| 1804-4023 | 0.24 mg | 1.2 mg/ml | 1 | Total Difficulty | 59 | 65 | — | — |

TABLE 32-continued

| Foot Function Index (FFI-SF-23) Total Scores\Foot Function Index (FFI-SF-23) Total Subscale (Pain, Difficulty, and Disability) Scores | | | | | | | | |
|---|---|---|---|---|---|---|---|---|
| | | | # of | Foot | Initial Tx Phase | | Retreatment Phase | |
| Subject | Dose | Conc. | Inj | Function Index | Day 1 | Day 57 | Day 1 | Day 57 |
| 1804-4023 | 0.24 mg | 1.2 mg/ml | 1 | Total Disability | 20 | 9 | — | — |
| 1806-4009 | 0.24 mg | 1.2 mg/ml | 1 | Total Score | 100 | 105 | — | — |
| 1806-4009 | 0.24 mg | 1.2 mg/ml | 1 | Total Pain | 46 | 37 | — | — |
| 1806-4009 | 0.24 mg | 1.2 mg/ml | 1 | Total Difficulty | 46 | 64 | — | — |
| 1806-4009 | 0.24 mg | 1.2 mg/ml | 1 | Total Disability | 8 | 4 | — | — |
| 1806-4015 | 0.24 mg | 1.2 mg/ml | 1 | Total Score | 16 | 0 | — | — |
| 1806-4015 | 0.24 mg | 1.2 mg/ml | 1 | Total Pain | 6 | 0 | — | — |
| 1806-4015 | 0.24 mg | 1.2 mg/ml | 1 | Total Difficulty | 8 | 0 | — | — |
| 1806-4015 | 0.24 mg | 1.2 mg/ml | 1 | Total Disability | 2 | 0 | — | — |
| 1806-4004 | 0.24 mg | 1.2 mg/ml | 1 | Total Score | 89 | 25 | 64 | 28 |
| 1806-4004 | 0.24 mg | 1.2 mg/ml | 1 | Total Pain | 43 | 13 | 19 | 9 |
| 1806-4004 | 0.24 mg | 1.2 mg/ml | 1 | Total Difficulty | 42 | 11 | 39 | 17 |
| 1806-4004 | 0.24 mg | 1.2 mg/ml | 1 | Total Disability | 4 | 1 | 6 | 2 |
| 1802-4002 | 0.24 mg | 0.6 mg/ml | 2 | Total Score | 19 | 18 | — | — |
| 1802-4002 | 0.24 mg | 0.6 mg/ml | 2 | Total Pain | 19 | 18 | — | — |
| 1802-4002 | 0.24 mg | 0.6 mg/ml | 2 | Total Difficulty | 0 | 0 | — | — |
| 1802-4002 | 0.24 mg | 0.6 mg/ml | 2 | Total Disability | 0 | 0 | — | — |
| 1804-4024 | 0.24 mg | 0.6 mg/ml | 2 | Total Score | 180 | 131 | — | — |
| 1804-4024 | 0.24 mg | 0.6 mg/ml | 2 | Total Pain | 90 | 54 | — | — |
| 1804-4024 | 0.24 mg | 0.6 mg/ml | 2 | Total Difficulty | 81 | 53 | — | — |
| 1804-4024 | 0.24 mg | 0.6 mg/ml | 2 | Total Disability | 9 | 24 | — | — |
| 1804-4028 | 0.24 mg | 0.6 mg/ml | 2 | Total Score | 4 | 12 | — | — |
| 1804-4028 | 0.24 mg | 0.6 mg/ml | 2 | Total Pain | 3 | 7 | — | — |
| 1804-4028 | 0.24 mg | 0.6 mg/ml | 2 | Total Difficulty | 0 | 4 | — | — |
| 1804-4028 | 0.24 mg | 0.6 mg/ml | 2 | Total Disability | 1 | 1 | — | — |
| 1806-4016 | 0.24 mg | 0.6 mg/ml | 2 | Total Score | 27 | 19 | 13 | 26 |
| 1806-4016 | 0.24 mg | 0.6 mg/ml | 2 | Total Pain | 22 | 10 | 7 | 12 |
| 1806-4016 | 0.24 mg | 0.6 mg/ml | 2 | Total Difficulty | 5 | 9 | 6 | 14 |
| 1806-4016 | 0.24 mg | 0.6 mg/ml | 2 | Total Disability | 0 | 0 | 0 | 0 |
| 1806-4007 | 0.45 mg | 2.25 mg/ml | 1 | Total Score | 4 | 0 | — | — |
| 1806-4007 | 0.45 mg | 2.25 mg/ml | 1 | Total Pain | 3 | 0 | — | — |
| 1806-4007 | 0.45 mg | 2.25 mg/ml | 1 | Total Difficulty | 1 | 0 | — | — |
| 1806-4007 | 0.45 mg | 2.25 mg/ml | 1 | Total Disability | 0 | 0 | — | — |
| 1810-4027 | 0.45 mg | 2.25 mg/ml | 1 | Total Score | 74 | 1 | 10 | 17 |
| 1810-4027 | 0.45 mg | 2.25 mg/ml | 1 | Total Pain | 39 | 1 | 8 | 9 |
| 1810-4027 | 0.45 mg | 2.25 mg/ml | 1 | Total Difficulty | 32 | 0 | 2 | 7 |

TABLE 32-continued

Foot Function Index (FFI-SF-23) Total Scores\Foot Function Index (FFI-SF-23) Total Subscale (Pain, Difficulty, and Disability) Scores

| | | | # of | Foot | Initial Tx Phase | | Retreatment Phase | |
|---|---|---|---|---|---|---|---|---|
| Subject | Dose | Conc. | Inj | Function Index | Day 1 | Day 57 | Day 1 | Day 57 |
| 1810-4027 | 0.45 mg | 2.25 mg/ml | 1 | Total Disability | 3 | 0 | 0 | 1 |
| 1802-4001 | 0.48 mg | 1.2 mg/ml | 2 | Total Score | 121 | 27 | — | — |
| 1802-4001 | 0.48 mg | 1.2 mg/ml | 2 | Total Pain | 48 | 21 | — | — |
| 1802-4001 | 0.48 mg | 1.2 mg/ml | 2 | Total Difficulty | 65 | 2 | — | — |
| 1802-4001 | 0.48 mg | 1.2 mg/ml | 2 | Total Disability | 8 | 4 | — | — |
| 1804-4012 | 0.48 mg | 1.2 mg/ml | 2 | Total Score | 51 | 1 | 17 | 16 |
| 1804-4012 | 0.48 mg | 1.2 mg/ml | 2 | Total Pain | 42 | 1 | 8 | 7 |
| 1804-4012 | 0.48 mg | 1.2 mg/ml | 2 | Total Difficulty | 9 | 0 | 9 | 9 |
| 1804-4012 | 0.48 mg | 1.2 mg/ml | 2 | Total Disability | — | 0 | 0 | 0 |
| 1804-4025 | 0.48 mg | 1.2 mg/ml | 2 | Total Score | 34 | 2 | 21 | 2 |
| 1804-4025 | 0.48 mg | 1.2 mg/ml | 2 | Total Pain | 10 | 1 | 7 | 1 |
| 1804-4025 | 0.48 mg | 1.2 mg/ml | 2 | Total Difficulty | 24 | 1 | 14 | 0 |
| 1804-4025 | 0.48 mg | 1.2 mg/ml | 2 | Total Disability | 0 | 0 | 0 | 1 |
| 1810-4021 | 0.48 mg | 1.2 mg/ml | 2 | Total Score | 142 | 124 | 63 | 56 |
| 1810-4021 | 0.48 mg | 1.2 mg/ml | 2 | Total Pain | 73 | 58 | 29 | 20 |
| 1810-4021 | 0.48 mg | 1.2 mg/ml | 2 | Total Difficulty | 58 | 57 | 27 | 34 |
| 1810-4021 | 0.48 mg | 1.2 mg/ml | 2 | Total Disability | 11 | 9 | 7 | 2 |
| 1804-4018 | 0.9 mg | 2.25 mg/ml | 2 | Total Score | 56 | 11 | — | — |
| 1804-4018 | 0.9 mg | 2.25 mg/ml | 2 | Total Pain | 37 | 5 | — | — |
| 1804-4018 | 0.9 mg | 2.25 mg/ml | 2 | Total Difficulty | 14 | 3 | — | — |
| 1804-4018 | 0.9 mg | 2.25 mg/ml | 2 | Total Disability | 5 | 3 | — | — |
| 1804-4026 | 0.9 mg | 2.25 mg/ml | 2 | Total Score | 44 | 0 | — | — |
| 1804-4026 | 0.9 mg | 2.25 mg/ml | 2 | Total Pain | 37 | 0 | — | — |
| 1804-4026 | 0.9 mg | 2.25 mg/ml | 2 | Total Difficulty | 4 | 0 | — | — |
| 1804-4026 | 0.9 mg | 2.25 mg/ml | 2 | Total Disability | 3 | 0 | — | — |
| 1806-4000 | 0.9 mg | 2.25 mg/ml | 2 | Total Score | 9 | 1 | — | — |
| 1806-4000 | 0.9 mg | 2.25 mg/ml | 2 | Total Pain | 6 | 1 | — | — |
| 1806-4000 | 0.9 mg | 2.25 mg/ml | 2 | Total Difficulty | 3 | 0 | — | — |
| 1806-4000 | 0.9 mg | 2.25 mg/ml | 2 | Total Disability | 0 | 0 | — | — |
| 1802-4010 | 0.9 mg | 2.25 mg/ml | 2 | Total Score | 61 | 18 | 36 | 36 |
| 1802-4010 | 0.9 mg | 2.25 mg/ml | 2 | Total Pain | 22 | 7 | 15 | 13 |
| 1802-4010 | 0.9 mg | 2.25 mg/ml | 2 | Total Difficulty | 33 | 10 | 17 | 20 |
| 1802-4010 | 0.9 mg | 2.25 mg/ml | 2 | Total Disability | 6 | 1 | 4 | 3 |
| 1802-4011 | 0.9 mg | 2.25 mg/ml | 2 | Total Score | 46 | 27 | 11 | 8 |
| 1802-4011 | 0.9 mg | 2.25 mg/ml | 2 | Total Pain | 33 | 15 | 7 | 4 |
| 1802-4011 | 0.9 mg | 2.25 mg/ml | 2 | Total Difficulty | 6 | 12 | 4 | 3 |

TABLE 32-continued

| Foot Function Index (FFI-SF-23) Total Scores\Foot Function Index (FFI-SF-23) Total Subscale (Pain, Difficulty, and Disability) Scores | | | | | | | | |
|---|---|---|---|---|---|---|---|---|
| | | | | | Initial Tx Phase | | Retreatment Phase | |
| Subject | Dose | Conc. | # of Inj | Foot Function Index | Day 1 | Day 57 | Day 1 | Day 57 |
| 1802-4011 | 0.9 mg | 2.25 mg/ml | 2 | Total Disability | 7 | 0 | — | 1 |
| 1804-4020 | 0.9 mg | 2.25 mg/ml | 2 | Total Score | 0 | 0 | 0 | 0 |
| 1804-4020 | 0.9 mg | 2.25 mg/ml | 2 | Total Pain | 0 | 0 | 0 | 0 |
| 1804-4020 | 0.9 mg | 2.25 mg/ml | 2 | Total Difficulty | 0 | 0 | 0 | 0 |
| 1804-4020 | 0.9 mg | 2.25 mg/ml | 2 | Total Disability | — | 0 | 0 | 0 |

TABLE 33

| Nodular Consistency by Palpation | | | | | | | | |
|---|---|---|---|---|---|---|---|---|
| | | | | | Initial Tx Phase | | Retreatment Phase | |
| Subject | Dose | Conc. | # of Inj | Nodular Consistency (by Palpation) | Day 1 | Day 57 | Day 1 | Day 57 |
| 1804-4019 | 0.12 mg | 0.6 mg/ml | 1 | Nodular consistency of right foot | 3 | 1 | — | — |
| 1806-4006 | 0.12 mg | 0.6 mg/ml | 1 | Nodular consistency of left foot | 3 | 4 | — | — |
| 1806-4006 | 0.12 mg | 0.6 mg/ml | 1 | Nodular consistency of right foot | 3 | 4 | — | — |
| 1806-4005 | 0.12 mg | 0.6 mg/ml | 1 | Nodular consistency of left foot | 3 | 3 | 3 | 2 |
| 1806-4014 | 0.12 mg | 0.6 mg/ml | 1 | Nodular consistency of left foot | 4 | 1 | 3 | 3 |
| 1804-4023 | 0.24 mg | 1.2 mg/ml | 1 | Nodular consistency of left foot | 4 | 1 | — | — |
| 1804-4023 | 0.24 mg | 1.2 mg/ml | 1 | Nodular consistency of right foot | 4 | 2 | — | — |
| 1806-4009 | 0.24 mg | 1.2 mg/ml | 1 | Nodular consistency of right foot | 4 | 4 | — | — |
| 1806-4015 | 0.24 mg | 1.2 mg/ml | 1 | Nodular consistency of left foot | 4 | 1 | — | — |
| 1806-4004 | 0.24 mg | 1.2 mg/ml | 1 | Nodular consistency of right foot | 3 | 1 | 4 | 3 |
| 1802-4002 | 0.24 mg | 0.6 mg/ml | 2 | Nodular consistency of left foot | 3 | 1 | — | — |
| 1802-4002 | 0.24 mg | 0.6 mg/ml | 2 | Nodular consistency of right foot | 3 | 1 | — | — |
| 1804-4024 | 0.24 mg | 0.6 mg/ml | 2 | Nodular consistency of right foot | 4 | 1 | — | — |
| 1804-4028 | 0.24 mg | 0.6 mg/ml | 2 | Nodular consistency of left foot | 3 | 1 | — | — |
| 1806-4016 | 0.24 mg | 0.6 mg/ml | 2 | Nodular consistency of left foot | 4 | 3 | 4 | 3 |
| 1806-4016 | 0.24 mg | 0.6 mg/ml | 2 | Nodular consistency of right foot | 4 | 3 | 3 | 3 |

TABLE 33-continued

| Nodular Consistency by Palpation | | | | | | | | |
|---|---|---|---|---|---|---|---|---|
| | | | # of | Nodular Consistency | Initial Tx Phase | | Retreatment Phase | |
| Subject | Dose | Conc. | Inj | (by Palpation) | Day 1 | Day 57 | Day 1 | Day 57 |
| 1806-4007 | 0.45 mg | 2.25 mg/ml | 1 | Nodular consistency of right foot | 3 | 1 | — | — |
| 1810-4027 | 0.45 mg | 2.25 mg/ml | 1 | Nodular consistency of right foot | 3 | 1 | 1 | 1 |
| 1802-4001 | 0.48 mg | 1.2 mg/ml | 2 | Nodular consistency of left foot | 3 | 1 | — | — |
| 1804-4012 | 0.48 mg | 1.2 mg/ml | 2 | Nodular consistency of left foot | 4 | 1 | 2 | 1 |
| 1804-4025 | 0.48 mg | 1.2 mg/ml | 2 | Nodular consistency of left foot | 4 | 3 | 4 | 1 |
| 1804-4025 | 0.48 mg | 1.2 mg/ml | 2 | Nodular consistency of right foot | 4 | 3 | 4 | 1 |
| 1810-4021 | 0.48 mg | 1.2 mg/ml | 2 | Nodular consistency of right foot | 4 | 2 | 2 | 1 |
| 1804-4018 | 0.9 mg | 2.25 mg/ml | 2 | Nodular consistency of left foot | 3 | 2 | — | — |
| 1804-4026 | 0.9 mg | 2.25 mg/ml | 2 | Nodular consistency of right foot | 3 | 1 | — | — |
| 1806-4000 | 0.9 mg | 2.25 mg/ml | 2 | Nodular consistency of left foot | 3 | 0 | — | — |
| 1802-4010 | 0.9 mg | 2.25 mg/ml | 2 | Nodular consistency of left foot | 3 | 2 | 2 | 2 |
| 1802-4010 | 0.9 mg | 2.25 mg/ml | 2 | Nodular consistency of right foot | 3 | 2 | 2 | 1 |
| 1802-4011 | 0.9 mg | 2.25 mg/ml | 2 | Nodular consistency of right foot | 4 | 1 | 2 | 1 |
| 1804-4020 | 0.9 mg | 2.25 mg/ml | 2 | Nodular consistency of left foot | 3 | 2 | 2 | 1 |
| 1804-4020 | 0.9 mg | 2.25 mg/ml | 2 | Nodular consistency of right foot | 2 | 2 | 2 | 1 |

Nodular consistency was determined by palpation using the following scale: hard (4), firm throughout (3), moderately firm (2), soft (1) and non-palpable (0).

TABLE 34

| Nodular Size by Area of Treated Nodule | | | | | | | | |
|---|---|---|---|---|---|---|---|---|
| | | | # of | Nodular Size by Area of | Initial Tx Phase | | Retreatment Phase | |
| Subject | Dose | Conc. | Inj | Treated Nodule | Day 1 | Day 57 | Day 1 | Day 57 |
| 1804-4019 | 0.12 mg | 0.6 mg/ml | 1 | Caliper measured Area for right foot | 1.1 | 2.17 | — | — |
| 1804-4019 | 0.12 mg | 0.6 mg/ml | 1 | Ultrasound measured Area for right foot | 1.58 | 2.22 | — | — |
| 1806-4006 | 0.12 mg | 0.6 mg/ml | 1 | Caliper measured Area for left foot | 0.27 | 6.68 | — | — |
| 1806-4006 | 0.12 mg | 0.6 mg/ml | 1 | Caliper measured Area for right foot | 0.79 | 5.03 | — | — |
| 1806-4006 | 0.12 mg | 0.6 mg/ml | 1 | Ultrasound measured Area for left foot | 0.25 | 4.36 | — | — |
| 1806-4006 | 0.12 mg | 0.6 mg/ml | 1 | Ultrasound measured Area for right foot | 0.77 | 4.08 | — | — |

TABLE 34-continued

| Nodular Size by Area of Treated Nodule | | | | | | | | |
|---|---|---|---|---|---|---|---|---|
| | | | | | Initial Tx Phase | | Retreatment Phase | |
| Subject | Dose | Conc. | # of Inj | Nodular Size by Area of Treated Nodule | Day 1 | Day 57 | Day 1 | Day 57 |
| 1806-4005 | 0.12 mg | 0.6 mg/ml | 1 | Caliper measured Area for left foot | 1.21 | 1.47 | 3.11 | 2.67 |
| 1806-4005 | 0.12 mg | 0.6 mg/ml | 1 | Ultrasound measured Area for left foot | 1.07 | 1.02 | — | — |
| 1806-4014 | 0.12 mg | 0.6 mg/ml | 1 | Caliper measured Area for left foot | 0.71 | 0.71 | 3.3 | 4.67 |
| 1806-4014 | 0.12 mg | 0.6 mg/ml | 1 | Ultrasound measured Area for left foot | 1.03 | 3.89 | — | — |
| 1804-4023 | 0.24 mg | 1.2 mg/ml | 1 | Caliper measured Area for left foot | 1.41 | 0.95 | — | — |
| 1804-4023 | 0.24 mg | 1.2 mg/ml | 1 | Caliper measured Area for right foot | 3.47 | 1.06 | — | — |
| 1804-4023 | 0.24 mg | 1.2 mg/ml | 1 | Ultrasound measured Area for left foot | 1.72 | 2.63 | — | — |
| 1804-4023 | 0.24 mg | 1.2 mg/ml | 1 | Ultrasound measured Area for right foot | 1.85 | 3.41 | — | — |
| 1806-4009 | 0.24 mg | 1.2 mg/ml | 1 | Caliper measured Area for right foot | 1.02 | 5.97 | — | — |
| 1806-4009 | 0.24 mg | 1.2 mg/ml | 1 | Ultrasound measured Area for right foot | 0.53 | 8.27 | — | — |
| 1806-4015 | 0.24 mg | 1.2 mg/ml | 1 | Caliper measured Area for left foot | 0.82 | 0.38 | — | — |
| 1806-4015 | 0.24 mg | 1.2 mg/ml | 1 | Ultrasound measured Area for left foot | 0.82 | 0.61 | — | — |
| 1806-4004 | 0.24 mg | 1.2 mg/ml | 1 | Caliper measured Area for right foot | 0.55 | 6.44 | 2.97 | 6.93 |
| 1806-4004 | 0.24 mg | 1.2 mg/ml | 1 | Ultrasound measured Area for right foot | 1.45 | 4.94 | — | — |
| 1802-4002 | 0.24 mg | 0.6 mg/ml | 2 | Caliper measured Area for left foot | 10.41 | 10.95 | — | — |
| 1802-4002 | 0.24 mg | 0.6 mg/ml | 2 | Caliper measured Area for right foot | 11.91 | 9.74 | — | — |
| 1802-4002 | 0.24 mg | 0.6 mg/ml | 2 | Ultrasound measured Area for left foot | 10.55 | 8.21 | — | — |
| 1802-4002 | 0.24 mg | 0.6 mg/ml | 2 | Ultrasound measured Area for right foot | 10.35 | 9.53 | — | — |
| 1804-4024 | 0.24 mg | 0.6 mg/ml | 2 | Caliper measured Area for right foot | 3.52 | 0.63 | — | — |
| 1804-4024 | 0.24 mg | 0.6 mg/ml | 2 | Ultrasound measured Area for right foot | — | 3.91 | — | — |
| 1804-4028 | 0.24 mg | 0.6 mg/ml | 2 | Caliper measured Area for left foot | 2.64 | 3.06 | — | — |
| 1804-4028 | 0.24 mg | 0.6 mg/ml | 2 | Ultrasound measured Area for left foot | — | 3.58 | — | — |
| 1806-4016 | 0.24 mg | 0.6 mg/ml | 2 | Caliper measured Area for left foot | 1.98 | 1.43 | 1.65 | 3.2 |
| 1806-4016 | 0.24 mg | 0.6 mg/ml | 2 | Caliper measured Area for right foot | 1.74 | 2.98 | 3.3 | 6.68 |
| 1806-4016 | 0.24 mg | 0.6 mg/ml | 2 | Ultrasound measured Area for left foot | 3.08 | 1.83 | — | — |
| 1806-4016 | 0.24 mg | 0.6 mg/ml | 2 | Ultrasound measured Area for right foot | 1.14 | 4.82 | — | — |
| 1806-4007 | 0.45 mg | 2.25 mg/ml | 1 | Caliper measured Area for right foot | 1.41 | 1.76 | — | — |
| 1806-4007 | 0.45 mg | 2.25 mg/ml | 1 | Ultrasound measured Area for right foot | 1.21 | 5.84 | — | — |
| 1810-4027 | 0.45 mg | 2.25 mg/ml | 1 | Caliper measured Area for right foot | 1.12 | 0.22 | 2.54 | 4.87 |

TABLE 34-continued

| Nodular Size by Area of Treated Nodule | | | | | | | | |
|---|---|---|---|---|---|---|---|---|
| | | | | | Initial Tx Phase | | Retreatment Phase | |
| Subject | Dose | Conc. | # of Inj | Nodular Size by Area of Treated Nodule | Day 1 | Day 57 | Day 1 | Day 57 |
| 1810-4027 | 0.45 mg | 2.25 mg/ml | 1 | Ultrasound measured Area for right foot | 0.69 | 0.54 | — | — |
| 1802-4001 | 0.48 mg | 1.2 mg/ml | 2 | Caliper measured Area for left foot | 1.41 | 1.02 | — | — |
| 1802-4001 | 0.48 mg | 1.2 mg/ml | 2 | Ultrasound measured Area for left foot | 8.85 | 8.08 | — | — |
| 1804-4012 | 0.48 mg | 1.2 mg/ml | 2 | Caliper measured Area for left foot | 1.34 | 0.66 | 4.39 | 1.01 |
| 1804-4012 | 0.48 mg | 1.2 mg/ml | 2 | Ultrasound measured Area for left foot | 1.54 | 2.05 | — | — |
| 1804-4025 | 0.48 mg | 1.2 mg/ml | 2 | Caliper measured Area for left foot | 5.74 | 3.2 | 7.41 | 3.37 |
| 1804-4025 | 0.48 mg | 1.2 mg/ml | 2 | Caliper measured Area for right foot | 3.53 | 3.64 | 4.81 | 2.47 |
| 1804-4025 | 0.48 mg | 1.2 mg/ml | 2 | Ultrasound measured Area for left foot | 5.58 | 5.23 | — | — |
| 1804-4025 | 0.48 mg | 1.2 mg/ml | 2 | Ultrasound measured Area for right foot | 3.21 | 5.05 | — | — |
| 1810-4021 | 0.48 mg | 1.2 mg/ml | 2 | Caliper measured Area for right foot | 1.21 | 0.27 | 2.54 | 7.42 |
| 1810-4021 | 0.48 mg | 1.2 mg/ml | 2 | Ultrasound measured Area for right foot | 2.65 | 1.5 | — | — |
| 1804-4018 | 0.9 mg | 2.25 mg/ml | 2 | Caliper measured Area for left foot | 3.39 | 3.52 | — | — |
| 1804-4018 | 0.9 mg | 2.25 mg/ml | 2 | Ultrasound measured Area for left foot | 4.09 | 1.59 | — | — |
| 1804-4026 | 0.9 mg | 2.25 mg/ml | 2 | Caliper measured Area for right foot | 1.49 | 0.63 | — | — |
| 1804-4026 | 0.9 mg | 2.25 mg/ml | 2 | Ultrasound measured Area for right foot | 3.42 | 1.66 | — | — |
| 1806-4000 | 0.9 mg | 2.25 mg/ml | 2 | Caliper measured Area for left foot | 3.08 | Non-Measurable | — | — |
| 1806-4000 | 0.9 mg | 2.25 mg/ml | 2 | Ultrasound measured Area for left foot | 4.23 | 8.63 | — | — |
| 1802-4010 | 0.9 mg | 2.25 mg/ml | 2 | Caliper measured Area for left foot | 4.4 | 2.64 | 6.03 | 4.32 |
| 1802-4010 | 0.9 mg | 2.25 mg/ml | 2 | Caliper measured Area for right foot | 2.71 | 2.42 | 7.63 | 2.47 |
| 1802-4010 | 0.9 mg | 2.25 mg/ml | 2 | Ultrasound measured Area for left foot | 4.51 | 6.4 | — | — |
| 1802-4010 | 0.9 mg | 2.25 mg/ml | 2 | Ultrasound measured Area for right foot | 4.27 | 2.63 | — | — |
| 1802-4011 | 0.9 mg | 2.25 mg/ml | 2 | Caliper measured Area for right foot | 4.71 | 5.28 | 6.74 | 2.98 |
| 1802-4011 | 0.9 mg | 2.25 mg/ml | 2 | Ultrasound measured Area for right foot | 8.06 | 5.23 | — | — |
| 1804-4020 | 0.9 mg | 2.25 mg/ml | 2 | Caliper measured Area for left foot | 6.87 | 8.98 | 8.88 | 4.59 |
| 1804-4020 | 0.9 mg | 2.25 mg/ml | 2 | Caliper measured Area for right foot | 0.92 | 7.6 | 4.78 | 3.39 |
| 1804-4020 | 0.9 mg | 2.25 mg/ml | 2 | Ultrasound measured Area for left foot | 4.32 | 7.02 | — | — |
| 1804-4020 | 0.9 mg | 2.25 mg/ml | 2 | Ultrasound measured Area for right foot | 1.94 | 6.81 | — | — |

Area of the treated nodule was determined as (width * length * pi)/4.

Where pi = 22/7 and width and length of the treated nodule measured by the caliper or ultrasound method.

TABLE 35

| Subject | Dose | Foot | Initial Tx Phase: Nodular Consistency | Initial Tx Phase: Nodular Measurement | Initial Tx Phase: Foot Function Index (FFI-SF-23) | Retreatment Phase: Nodular Consistency | Retreatment Phase: Nodular Measurement | Retreatment Phase: Foot Function Index (FFI-SF-23) |
|---|---|---|---|---|---|---|---|---|
| 1804-4019 | 0.12 mg | Right | Reduction | No Reduction | Reduction | — | — | — |
| 1806-4006 | 0.12 mg | Left | No Reduction | No Reduction | Reduction | — | — | — |
| 1806-4006 | 0.12 mg | Right | No Reduction | No Reduction | Reduction | — | — | — |
| 1806-4005 | 0.12 mg | Left | No Change | No Reduction | Reduction | Reduction | Reduction | Baseline 0 |
| 1806-4014 | 0.12 mg | Left | Reduction | No Change | Reduction | No Change | No Reduction | Reduction |
| 1804-4023 | 0.24 mg | Left | Reduction | Reduction | Reduction | — | — | — |
| 1804-4023 | 0.24 mg | Right | Reduction | Reduction | Reduction | — | — | — |
| 1806-4009 | 0.24 mg | Right | No Change | No Reduction | No Reduction | — | — | — |
| 1806-4015 | 0.24 mg | Left | Reduction | Reduction | Reduction | — | — | — |
| 1806-4004 | 0.24 mg | Right | Reduction | No Reduction | Reduction | Reduction | No Reduction | Reduction |
| 1802-4002 | 0.24 mg | Left | Reduction | No Reduction | No Reduction | — | — | — |
| 1802-4002 | 0.24 mg | Right | Reduction | Reduction | No Reduction | — | — | — |
| 1804-4024 | 0.24 mg | Right | Reduction | Reduction | Reduction | — | — | — |
| 1804-4028 | 0.24 mg | Left | Reduction | No Reduction | No Reduction | — | — | — |
| 1806-4016 | 0.24 mg | Left | Reduction | Reduction | Reduction | Reduction | No Reduction | No Reduction |
| 1806-4016 | 0.24 mg | Right | Reduction | No Reduction | Reduction | No Change | No Reduction | No Reduction |
| 1806-4007 | 0.45 mg | Right | Reduction | No Reduction | Reduction | — | — | — |
| 1810-4027 | 0.45 mg | Right | Reduction | Reduction | Reduction | No Change | No Reduction | No Reduction |
| 1802-4001 | 0.48 mg | Left | Reduction | Reduction | Reduction | — | — | — |
| 1804-4012 | 0.48 mg | Left | Reduction | Reduction | Reduction | Reduction | Reduction | Reduction |
| 1804-4025 | 0.48 mg | Left | Reduction | Reduction | Reduction | Reduction | Reduction | Reduction |
| 1804-4025 | 0.48 mg | Right | Reduction | No Reduction | Reduction | Reduction | Reduction | Reduction |
| 1810-4021 | 0.48 mg | Right | Reduction | Reduction | Reduction | Reduction | No Reduction | Reduction |
| 1804-4018 | 0.9 mg | Left | Reduction | No Reduction | Reduction | — | — | — |
| 1804-4026 | 0.9 mg | Right | Reduction | Reduction | Reduction | — | — | — |
| 1806-4000 | 0.9 mg | Left | Reduction | Reduction | Reduction | — | — | — |
| 1802-4010 | 0.9 mg | Left | Reduction | Reduction | Reduction | No Change | Reduction | No Change |
| 1802-4010 | 0.9 mg | Right | Reduction | Reduction | Reduction | Reduction | Reduction | No Change |
| 1802-4011 | 0.9 mg | Right | Reduction | No Reduction | Reduction | Reduction | Reduction | Reduction |
| 1804-4020 | 0.9 mg | Left | Reduction | No Reduction | Baseline 0 | Reduction | Reduction | Baseline 0 |
| 1804-4020 | 0.9 mg | Right | No Change | No Reduction | Baseline 0 | Reduction | Reduction | Baseline 0 |

TABLE 36

Summary of 0.12 mg treatment

| | | | Initial Tx Phase | | | Retreatment Phase | | |
|---|---|---|---|---|---|---|---|---|
| Subject | Dose | Foot | Nodular Consistency | Nodular Measurement | Foot Function Index (FFI-SF-23) | Nodular Consistency | Nodular Measurement | Foot Function Index (FFI-SF-23) |
| 1804-4019 | 0.12 mg | Right | Reduction | No Reduction | Reduction | — | — | — |
| 1806-4006 | 0.12 mg | Left | No Reduction | No Reduction | Reduction | — | — | — |
| 1806-4006 | 0.12 mg | Right | No Reduction | No Reduction | Reduction | — | — | — |
| 1806-4005 | 0.12 mg | Left | No Change | No Reduction | Reduction | Reduction | Reduction | Baseline 0 |
| 1806-4014 | 0.12 mg | Left | Reduction | No Change | Reduction | No Change | No Reduction | Reduction |

TABLE 37

Summary of 0.24 mg treatment

| | | | Initial Tx Phase | | | Retreatment Phase | | |
|---|---|---|---|---|---|---|---|---|
| Subject | Dose | Foot | Nodular Consistency | Nodular Measurement | Foot Function Index (FFI-SF-23) | Nodular Consistency | Nodular Measurement | Foot Function Index (FFI-SF-23) |
| 1804-4023 | 0.24 mg | Left | Reduction | Reduction | Reduction | — | — | — |
| 1804-4023 | 0.24 mg | Right | Reduction | Reduction | Reduction | — | — | — |
| 1806-4009 | 0.24 mg | Right | No Change | No Reduction | No Reduction | — | — | — |
| 1806-4015 | 0.24 mg | Left | Reduction | Reduction | Reduction | — | — | — |
| 1806-4004 | 0.24 mg | Right | Reduction | No Reduction | Reduction | Reduction | No Reduction | Reduction |
| 1802-4002 | 0.24 mg | Left | Reduction | No Reduction | No Reduction | — | — | — |
| 1802-4002 | 0.24 mg | Right | Reduction | Reduction | No Reduction | — | — | — |
| 1804-4024 | 0.24 mg | Right | Reduction | Reduction | Reduction | — | — | — |
| 1804-4028 | 0.24 mg | Left | Reduction | No Reduction | No Reduction | — | — | — |
| 1806-4016 | 0.24 mg | Left | Reduction | Reduction | Reduction | Reduction | No Reduction | No Reduction |
| 1806-4016 | 0.24 mg | Right | Reduction | No Reduction | Reduction | No Change | No Reduction | No Reduction |

TABLE 38

Summary of 0.45 mg treatment

| | | | Initial Tx Phase | | | Retreatment Phase | | |
|---|---|---|---|---|---|---|---|---|
| Subject | Dose | Foot | Nodular Consistency | Nodular Measurement | Foot Function Index (FFI-SF-23) | Nodular Consistency | Nodular Measurement | Foot Function Index (FFI-SF-23) |
| 1806-4007 | 0.45 mg | Right | Reduction | No Reduction | Reduction | — | — | — |
| 1810-4027 | 0.45 mg | Right | Reduction | Reduction | Reduction | No Change | No Reduction | No Reduction |

TABLE 39

| Summary of 0.48 mg treatment | | | | | | | | |
|---|---|---|---|---|---|---|---|---|
| | | | Initial Tx Phase | | | Retreatment Phase | | |
| Subject | Dose | Foot | Nodular Consistency | Nodular Measurement | Foot Function Index (FFI-SF-23) | Nodular Consistency | Nodular Measurement | Foot Function Index (FFI-SF-23) |
| 1802-4001 | 0.48 mg | Left | Reduction | Reduction | Reduction | — | — | — |
| 1804-4012 | 0.48 mg | Left | Reduction | Reduction | Reduction | Reduction | Reduction | Reduction |
| 1804-4025 | 0.48 mg | Left | Reduction | Reduction | Reduction | Reduction | Reduction | Reduction |
| 1804-4025 | 0.48 mg | Right | Reduction | No Reduction | Reduction | Reduction | Reduction | Reduction |
| 1810-4021 | 0.48 mg | Right | Reduction | Reduction | Reduction | Reduction | No Reduction | Reduction |

TABLE 40

| Summary of 0.9 mg treatment | | | | | | | | |
|---|---|---|---|---|---|---|---|---|
| | | | Initial Tx Phase | | | Retreatment Phase | | |
| Subject | Dose | Foot | Nodular Consistency | Nodular Measurement | Foot Function Index (FFI-SF-23) | Nodular Consistency | Nodular Measurement | Foot Function Index (FFI-SF-23) |
| 1804-4018 | 0.9 mg | Left | Reduction | No Reduction | Reduction | — | — | — |
| 1804-4026 | 0.9 mg | Right | Reduction | Reduction | Reduction | — | — | — |
| 1806-4000 | 0.9 mg | Left | Reduction | Reduction | Reduction | — | — | — |
| 1802-4010 | 0.9 mg | Left | Reduction | Reduction | Reduction | No Change | Reduction | No Change |
| 1802-4010 | 0.9 mg | Right | Reduction | Reduction | Reduction | Reduction | Reduction | No Change |
| 1802-4011 | 0.9 mg | Right | Reduction | No Reduction | Reduction | Reduction | Reduction | Reduction |
| 1804-4020 | 0.9 mg | Left | Reduction | No Reduction | Baseline 0 | Reduction | Reduction | Baseline 0 |
| 1804-4020 | 0.9 mg | Right | No Change | No Reduction | Baseline 0 | Reduction | Reduction | Baseline 0 |

Dose 0.12 mg [0.6 mg/ml] (Single Injection)

Subject 1804-4019, a 40 year old, white male, with a history of diabetes, received a single injection in the right foot during the Initial Treatment Phase. Subject began with a FFI (FFI-SF-23) Composite Score (%) of 45.71% and a FFI (FFI-SF-23) Total Score of 64 (Pain 38, Difficulty 26, Disability N/A) with a nodule that was firm throughout on Day 1. After receiving the dose of 0.12 mg, the subject showed improvement in all the above measures at Day 57:

FFI (FFI-SF-23) Composite Score (%) of 4.76%

FFI (FFI-SF-23) Total Score of 10 (Pain 6, Difficulty 3, Disability 1)

Nodular Consistency: Soft

The subject reported being very satisfied (+2) with treatment and the investigator reported very much improvement (+3). Similar results seen at Day 29. Caliper and ultrasound measurements did not correlate with the above improvements and size reduction was not apparent. Subject opted not to enter the Retreatment Phase of the Study.

Subject 1806-4006, a 41 year old, white male, received a single injection in both feet during the Initial Treatment Phase. Subject began with a FFI (FFI-SF-23) Composite Score (%) of 76.32% and a FFI (FFI-SF-23) Total Score of 145 (Pain 56, Difficulty 70, Disability 19) with nodules that were both firm throughout on Day 1. After receiving a dose of 0.12 mg administered to each nodule the subject showed improvement on the FFI (FFI-SF-23) at Day 57:

FFI (FFI-SF-23) Composite Score (%) of 32.63%

FFI (FFI-SF-23) Total Score of 62 (Pain 26, Difficulty 28, Disability 8)

The subject reported being quite satisfied (+1) with treatment and the investigator reported minimal improvement (+1) for both feet. For both nodules, nodular consistency did not improve at Day 57 and an increase in caliper and ultrasound measurements was observed. Subject opted not to enter the Retreatment Phase of the Study.

Subject 1806-4005, a 62 year old, white female, received a single injection in the left foot during the Initial Treatment Phase. Subject began with a FFI (FFI-SF-23) Composite Score (%) of 1.43% and a FFI (FFI-SF-23) Total Score of 3 (Pain 3, Difficulty 0, Disability 0) with a nodule that was firm throughout on Day 1. After receiving the dose of 0.12 mg the subject had a FFI (FFI-SF-23) score of 0 at Day 57:

FFI (FFI-SF-23) Composite Score (%) of 0%

FFI (FFI-SF-23) Total Score of 0 (Pain 0, Difficulty 0, Disability 0)

The subject reported being very satisfied (+2) with treatment and the investigator reported minimal improvement (+1). Nodular consistency stayed the same. Caliper and ultrasound measurements did not demonstrate much change.

Subject opted to enter the Retreatment Phase of the Study. Due to the size of the nodule (after approximately 240 additional days after Initial Treatment), the subject received two injections administered into her nodule. Subject's FFI (FFI-SF-23) score was 0 and her nodule was still firm throughout on Day 1 of Retreatment Phase. At Day 29 the subject's nodule was deemed non-palpable and thus did not receive any additional treatment. However, at subsequent visits the nodule appeared to have recovered some size. At Day 57 of retreatment the nodule was deemed moderately firm and the investigator reported minimal improvement (+1). A reduction in caliper measured area was noted.

Subject 1806-4014, a 62 year old, white female, received a single injection in the left foot during the Initial Treatment Phase. Subject began with a FFI (FFI-SF-23) Composite Score (%) of 11.25% and a FFI (FFI-SF-23) Total Score of 18 (Pain 18, Difficulty 0, Disability 0) with a nodule that was hard on Day 1. After receiving the dose of 0.12 mg the subject had the following score at Day 57:

FFI (FFI-SF-23) Composite Score (%) of 7.62%

FFI (FFI-SF-23) Total Score of 16 (Pain 9, Difficulty 7, Disability N/A)

Nodular Consistency: Soft

While the subject reported being neither satisfied nor dissatisfied (0) with treatment, the investigator reported much improvement (+2). Caliper measurements stayed the same while ultrasound measurements should an increase in size.

Subject opted to enter the Retreatment Phase of the Study. After approximately 180 days since end of initial treatment, subject had a FFI (FFI-SF-23) Composite Score (%) of 10.48% and a FFI (FFI-SF-23) Total Score of 22 (Pain 22, Difficulty 0, Disability 0) with a nodule that was firm throughout on Day 1 of the Retreatment Phase. Due to the size of the nodule (after approximately 180 additional days after Initial Treatment), the subject received two injections administered into her nodule on both Day 1 and Day 29 of the Retreatment Phase. After receiving the dose of 0.9 mg the subject had the following scores at Day 57 of the Retreatment Phase:

FFI (FFI-SF-23) Composite Score (%) of 4.76%

FFI (FFI-SF-23) Total Score of 10 (Pain 10, Difficulty 0, Disability 0)

At Day 57 of retreatment, the nodule was deemed firm throughout and the investigator reported much improvement (+2). Subject continued to report being neither satisfied nor dissatisfied (0) with treatment. Caliper measurements did not demonstrate any reduction in size throughout the Retreatment Phase.

Overall Conclusion from the Dose 0.12 mg [0.6 mg/ml] (Single Injection)

The 2 subjects that received 0.12 mg (1 injections of 0.12 mg @ 0.6 mg/ml) and did not enter the retreatment phase saw:

- Decreases in their FFI (FFI-SF-23) Composite Scores, Total Scores, and Individual Subscale Scores.
- One subject had their nodule soften
- One subject was reported by investigators as having Very Much (+3) Improvement at Day 57. The other subject was reported as having minimal improvement.

The 2 subjects that received 0.12 mg (1 injections of 0.12 mg @ 0.6 mg/ml) and did enter the retreatment phase saw:

- Modest decreases in their FFI (FFI-SF-23) Composite Scores, Total Scores, and Individual Subscale Scores during the Initial Treatment Phase.
- One subject had their nodules soften throughout the Initial Treatment Phase
- Both nodules reported by investigators as having Much (+2) or Very Much (+3) Improvement at Day 57 of the Initial Treatment Phase
- Upon entering the retreatment phase (and receiving 0.9 mg per nodule at Day 1 and 29)
  - One of the two nodules continued to see softening
  - One nodule continued to be reported by investigators as having Much (+2) Improvement at Day 57 of the Retreatment Phase Dose 0.24 mg [1.2 mg/ml] (Single Injection)

Subject 1804-4023, a 60 year old, white Hispanic female, with a history of diabetes, received a single injection in both feet during the Initial Treatment Phase. Subject began with a FFI (FFI-SF-23) Composite Score (%) of 66.84% and a FFI (FFI-SF-23) Total Score of 127 (Pain 48, Difficulty 59, Disability 20) with nodules that were both hard on Day 1. After receiving the dose of 0.24 mg administered to both nodules the subject had the following scores at Day 57:

FFI (FFI-SF-23) Composite Score (%) of 47.14%

FFI (FFI-SF-23) Total Score of 99 (Pain 25, Difficulty 65, Disability 9)

Nodular Consistency: Left foot was soft and right foot was moderately firm

The subject reported being quite satisfied (+2) with treatment and the investigator reported very much improvement (+3) for both nodules. Caliper measurement showed reduction in size for both nodules. Subject opted not to enter the Retreatment Phase of the Study.

Subject 1806-4009, a 80 year old, white female, with a history of diabetes, received a single injection in the left foot during the Initial Treatment Phase. Subject began with a FFI (FFI-SF-23) Composite Score (%) of 47.62% and a FFI (FFI-SF-23) Total Score of 100 (Pain 46, Difficulty 46, Disability 8) with a nodule that was hard on Day 1. After receiving the dose of 0.24 mg the subject had the following scores at Day 57:

FFI (FFI-SF-23) Composite Score (%) of 50%

FFI (FFI-SF-23) Total Score of 105 (Pain 37, Difficulty 64, Disability 4)

Nodular Consistency: Hard

The subject reported being quite dissatisfied (−1) with treatment and the investigator reported very much worse (−3). Caliper and ultrasound measurements both demonstrated a significant increase in size. Subject opted not to enter the Retreatment Phase of the Study.

Subject 1806-4015, a 75 year old, white male, with a history of diabetes, received a single injection in the left foot during the Initial Treatment Phase. Subject began with a FFI (FFI-SF-23) Composite Score (%) of 7.62% and a FFI (FFI-SF-23) Total Score of 16 (Pain 6, Difficulty 8, Disability 2) with a nodule that was hard on Day 1. After receiving the dose of 0.24 mg the subject had the following scores at Day 57:

FFI (FFI-SF-23) Composite Score (%) of 0%

FFI (FFI-SF-23) Total Score of 0 (Pain 0, Difficulty 0, Disability 0)

Nodular Consistency: Soft

The subject reported being very satisfied (+2) with treatment and the investigator reported very much improvement (+3). Caliper and ultrasound measurements both demonstrated a reduction in size. Subject opted not to enter the Retreatment Phase of the Study.

Subject 1806-4004, a 65 year old, white female, with a history of diabetes, received a single injection in her right foot during the Initial Treatment Phase. Subject began with a FFI (FFI-SF-23) Composite Score (%) of 42.38% and a FFI (FFI-SF-23) Total Score of 89 (Pain 43, Difficulty 42, Disability 4) with a nodule that was moderately firm on Day 1. After receiving the dose of 0.24 mg the subject had the following scores at Day 57:

FFI (FFI-SF-23) Composite Score (%) of 11.9%

FFI (FFI-SF-23) Total Score of 25 (Pain 13, Difficulty 11, Disability 1)

Nodular Consistency: Soft

The subject reported being very satisfied (+2) with treatment. Investigator assessment of improvement was reported much worse (−2). Caliper and ultrasound measurement showed worsening in size.

Subject opted to enter the Retreatment Phase of the Study. After approximately 240 days since end of initial treatment, subject had a FFI (FFI-SF-23) Composite Score (%) of 30.48% and a FFI (FFI-SF-23) Total Score of 64 (Pain 19, Difficulty 39, Disability 6) with a nodule that was hard on Day 1 of the Retreatment Phase. After approximately 180 days, the nodule had reduced in size compared to Day 57 of the Initial Treatment phase. However, due to the remaining size of the nodule the subject received two injections administered into her nodule on both Day 1 and Day 29 of the Retreatment Phase. After receiving the dose of 0.9 mg the subject had the following scores at Day 57 of the Retreatment Phase:

FFI (FFI-SF-23) Composite Score (%) of 13.33%

FFI (FFI-SF-23) Total Score of 28 (Pain 9, Difficulty 17, Disability 2)

At Day 57 of retreatment, the nodule was deemed firm throughout and the investigator reported minimal improvement (+1). Subject reported being neither satisfied nor dissatisfied (0) with treatment.

Overall Conclusion from the Dose 0.24 mg [1.2 mg/ml] (Single Injection)

Of the four subjects that received 0.24 mg (1 injections of 0.24 mg @ 1.2 mg/ml) during initial treatment:

Three subjects saw decreases in their FFI (FFI-SF-23) Composite Scores, Total Scores, and Individual Subscale Scores. The other subject retained similar scores throughout the initial treatment phase.

Two subjects saw reduction in nodule size by caliper measurements at Day 57

Four of the five nodules had their nodular consistency soften at Day 57

Three of the five nodules were reported by investigators as having Very Much (+3) Improvement at Day 57

The subject that received 0.24 mg (1 injections of 0.24 mg @ 1.2 mg/ml) and did enter the retreatment phase saw during the retreatment phase:

Improvement in their FFI (FFI-SF-23) Composite Scores, Total Scores, and Individual Subscale Scores during the Retreatment Phase.

Did not see significant improvement in nodular consistency and was reported by the investigator as having minimal improvement (+1)

Dose 0.24 mg [0.6 mg/ml] (Two Injections)

Subject 1802-4002, a 48 year old, Hispanic white male, received two injections in both feet during the Initial Treatment Phase. Subject began with a FFI (FFI-SF-23) Composite Score (%) of 8.26% and a FFI (FFI-SF-23) Total Score of 19 (Pain 19, Difficulty 0, Disability 0) with a nodule that was firm throughout on Day 1. After receiving the dose of 0.24 mg administered to both of his nodules the subject had the following scores at Day 57:

FFI (FFI-SF-23) Composite Score (%) of 10.59%

FFI (FFI-SF-23) Total Score of 18 (Pain 18, Difficulty 0, Disability 0)

Nodular Consistency: Soft (both nodules)

The subject reported being neither satisfied nor dissatisfied (0) with treatment and the investigator reported much improvement (+2) for both nodules. Caliper measurements showed a reduction in nodule size for the nodule in the right foot. Caliper measurement did not show a change in nodule size for the nodule in the left foot. Subject opted not to enter the Retreatment Phase of the Study.

Subject 1804-4024, a 56 year old, black or African American female, received two injections in her right foot during the Initial Treatment Phase. Subject began with a FFI (FFI-SF-23) Composite Score (%) of 85.71% and a FFI (FFI-SF-23) Total Score of 180 (Pain 90, Difficulty 81, Disability 9) with a nodule that was hard on Day 1. After receiving the dose of 0.24 mg administered to her nodule the subject had the following scores at Day 57:

FFI (FFI-SF-23) Composite Score (%) of 72.78%

FFI (FFI-SF-23) Total Score of 131 (Pain 54, Difficulty 53, Disability 24)

Nodular Consistency: Soft

The subject reported being quite satisfied (+1) with treatment and the investigator reported very much improvement (+3). Caliper measurement showed reduction in size. Subject opted not to enter the Retreatment Phase of the Study.

Subject 1804-4028, a 45 year old, white female, received two injections in her left foot during the Initial Treatment Phase. Subject began with a FFI (FFI-SF-23) Composite Score (%) of 77.78% and a FFI (FFI-SF-23) Total Score of 140 (Pain 30, Difficulty 80, Disability 30) with a nodule that was firm throughout on Day 1. After receiving the dose of 0.24 mg administered to her nodule the subject had the following scores at Day 57:

FFI (FFI-SF-23) Composite Score (%) of 6.32%

FFI (FFI-SF-23) Total Score of 12 (Pain 7, Difficulty 4, Disability 1)

Nodular Consistency: Soft

The subject reported being quite satisfied (+1) with treatment and the investigator reported much improvement (+2). Caliper measurement did not show a change in nodule size. Subject opted not to enter the Retreatment Phase of the Study.

Subject 1806-4016, a 41 year old, white male, received two injections in both feet during the Initial Treatment Phase. Subject began with a FFI (FFI-SF-23) Composite Score (%) of 12.86% and a FFI (FFI-SF-23) Total Score of 27 (Pain 22, Difficulty 5, Disability 0) with a pair of nodules that were hard on Day 1. After receiving the dose of 0.24 mg administered to both of his nodules the subject had the following scores at Day 57:

FFI (FFI-SF-23) Composite Score (%) of 9.05%

FFI (FFI-SF-23) Total Score of 19 (Pain 10, Difficulty 9, Disability 0)

Nodular Consistency: Firm throughout (both nodules)

The subject reported being quite satisfied (+1) with treatment and the investigator reported much improvement (+2) for both nodules. Caliper and ultrasound measurement showed reduction in one nodule (left) and increase in the other nodule (right).

Subject opted to enter the Retreatment Phase of the Study. After approximately 160 days since end of initial treatment, subject had a FFI (FFI-SF-23) Composite Score (%) of 6.19% and a FFI (FFI-SF-23) Total Score of 13 (Pain 7, Difficulty 6, Disability 0) with one nodule that was hard (left) and the other nodule firm throughout (right) on Day 1 of the Retreatment Phase. The left nodule received a single injection (0.45 mg) and the right nodule received two injections (0.9 mg) due to their relative sizes on Day 1 of the Retreatment Phase. The nodules were both above the >2 cm threshold at Day 29 and thus received two injections (0.9 mg) during the second treatment visit. After each nodule receiving treatment on Day 1 and 29 the subject had the following scores at Day 57 of the Retreatment Phase:

FFI (FFI-SF-23) Composite Score (%) of 12.38%

FFI (FFI-SF-23) Total Score of 26 (Pain 12, Difficulty 14, Disability 0)

Nodular Consistency: Firm throughout (both nodules)

At Day 57 of retreatment, the subject reported being quite satisfied (+1) with treatment in both nodules and the investigator reported minimal worsening (−1).

Overall Conclusion from the Dose 0.24 mg [0.6 mg/ml] (Two Injections)

The 3 subjects that received 0.24 mg (2 injections of 0.12 mg @ 0.6 mg/ml) and did not enter the retreatment phase:

- One subject saw significant decreases in their FFI (FFI-SF-23) Composite Scores, Total Scores, and Individual Subscale Scores. The other two retained similar scores throughout the initial treatment phase.
- One subject saw reduction in nodule size by caliper measurements at Day 57
- The four nodules had their nodules soften at Day 57
- Were reported by investigators as having Much (+2) or Very Much (+3) Improvement at Day 57

The subject that received 0.24 mg (2 injections of 0.12 mg @ 0.6 mg/ml) and did enter the retreatment phase:

- Some improvement in their FFI (FFI-SF-23) Composite Scores, Total Scores, and Individual Subscale Scores during the Initial Treatment Phase.
- Had some softening reported for both nodules throughout the Initial Treatment Phase
- Had both nodules reported as Much (+2) Improvement at Day 57 of the Initial Treatment Phase
- Upon entering the retreatment phase (Left nodule receiving 0.45 mg at Day 1 and 29 and right nodule receiving 0.9 mg at Day 1 and 29)
  - Did not see improvement on FFI (FFI-SF-23) scores or size as measured by calipers
  - Had some softening reported for both nodules throughout the Retreatment Phase Dose 0.45 mg [2.25 mg/ml] (Single Injection)

Subject 1806-4007, a 40 year old, white male, received a single injection in the right foot during the Initial Treatment Phase. Subject began with a FFI (FFI-SF-23) Composite Score (%) of 4.5% and a FFI (FFI-SF-23) Total Score of 4 (Pain 3, Difficulty 1, Disability 0) with a nodule that was firm throughout on Day 1. After receiving the dose of 0.45 mg the subject showed improvement in all the above measures at Day 57:

- FFI (FFI-SF-23) Composite Score (%) of 0%
- FFI (FFI-SF-23) Total Score of 0 (Pain 0, Difficulty 0, Disability 0)
- Nodular Consistency: Soft The subject reported being quite satisfied (+1) with treatment and the investigator reported no change (0). Caliper and ultrasound measurements did not correlate with the above improvements and size reduction was not apparent. Subject opted not to enter the Retreatment Phase of the Study.

Subject 1810-4027, a 68 year old, white male, received a single injection in the right foot during the Initial Treatment Phase. Subject began with a FFI (FFI-SF-23) Composite Score (%) of 32.17% and a FFI (FFI-SF-23) Total Score of 74 (Pain 39, Difficulty 32, Disability 3) with a nodule that was firm throughout on Day 1. After receiving the dose of 0.45 mg the subject showed improvement in all the above measures at Day 57:

- FFI (FFI-SF-23) Composite Score (%) of 0.48%
- FFI (FFI-SF-23) Total Score of 1 (Pain 1, Difficulty 0, Disability 0)
- Nodular Consistency: Soft The subject reported being very satisfied (+2) with treatment and the investigator reported much improvement (+2). Caliper measurements showed size reduction and ultrasound measurements showed some small size reduction.

Subject opted to enter the Retreatment Phase of the Study. After approximately 115 days since end of initial treatment, subject had a FFI (FFI-SF-23) Composite Score (%) of 4.76% and a FFI (FFI-SF-23) Total Score of 10 (Pain 8, Difficulty 2, Disability 0) with a nodule that was soft on Day 1 of the Retreatment Phase. On Day 1 the subject received 1 injection (0.45 mg) while on Day 29 Visit the subject received 2 injections (0.9 mg). After receiving the respective doses at both visits, the subject had the following scores at Day 57 of the Retreatment Phase:

- FFI (FFI-SF-23) Composite Score (%) of 8.1%
- FFI (FFI-SF-23) Total Score of 17 (Pain 9, Difficulty 7, Disability 1)
- Nodular Consistency remained soft At Day 57 of retreatment, the investigator reported much improvement (+2). Subject reported being neither satisfied nor dissatisfied (0) with treatment. Caliper measurements demonstrated increase in size during the Retreatment Phase.

Overall Conclusion from the Dose 0.45 mg [2.25 mg/ml] (Single Injection)

Both subjects that received 0.45 mg (1 injections of 0.45 mg @ 2.25 mg/ml) saw during the initial treatment phase:

- Decreases in the FFI (FFI-SF-23) Composite Scores, Total Scores, and Individual Subscale Scores to 0 or 1 Total Score.
- Had their nodule soften to Soft at Day 57
- One nodule was reported by the investigator as having Much (+2) Improvement at Day 57
- One nodule saw size reduction using both size assessments (caliper and ultrasound)

The subjects that received retreatment received 0.45 mg per nodule at Day 1 and 0.9 mg per nodule at Day 29. The subject maintained the improvements seen for nodular consistency and was reported by the investigator as having Much (+2) Improvement at Day 57 of the retreatment phase. FFI (FFI-SF-23) scores were still improved when comparing Day 57 of the retreatment phase with Day 1 baseline of the study.

Dose 0.48 mg [1.2 mg/ml] (Two Injections)

Subject 1802-4001, a 50 year old, Hispanic white female, received two injections in her left foot during the Initial Treatment Phase. Subject began with a FFI (FFI-SF-23) Composite Score (%) of 57.62% and a FFI (FFI-SF-23) Total Score of 121 (Pain 48, Difficulty 65, Disability 8) with a nodule that was firm throughout on Day 1. After receiving the dose of 0.48 mg the subject had the following scores at Day 57:

- FFI (FFI-SF-23) Composite Score (%) of 22.5%
- FFI (FFI-SF-23) Total Score of 27 (Pain 21, Difficulty 2, Disability 4)
- Nodular Consistency: Soft The subject reported being neither satisfied nor dissatisfied (0) with treatment and the investigator reported much improvement (+2). Caliper and ultrasound measurements showed a reduction in nodule size. Subject opted not to enter the Retreatment Phase of the Study.

Subject 1804-4012, a 67 year old, white male, with a history of diabetes, received two injections in his left foot during the Initial Treatment Phase. Subject began with a FFI (FFI-SF-23) Composite Score (%) of 46.36% and a FFI (FFI-SF-23) Total Score of 51 (Pain 42, Difficulty 9, Disability N/A) with a nodule that was hard on Day 1. After receiving the dose of 0.48 mg the subject showed improvement in all the above measures at Day 57:

- FFI (FFI-SF-23) Composite Score (%) of 0.56%
- FFI (FFI-SF-23) Total Score of 1 (Pain 1, Difficulty 0, Disability 0)
- Nodular Consistency: Soft The subject reported being very satisfied (+2) with treatment and the investigator reported very much improvement (+3). Caliper measurements showed size reduction.

Subject opted to enter the Retreatment Phase of the Study. After approximately 190 days since end of initial treatment, subject had a FFI (FFI-SF-23) Composite Score (%) of 8.95% and a FFI (FFI-SF-23) Total Score of 17 (Pain 8, Difficulty 9, Disability 0) with a nodule that was moderately firm and larger on Day 1 of the Retreatment Phase. Subject received 2 injections (0.9 mg) on Day 1 and Day 29 each. After receiving the respective doses at both visits, the subject had the following scores at Day 57 of the Retreatment Phase:

FFI (FFI-SF-23) Composite Score (%) of 8.42%

FFI (FFI-SF-23) Total Score of 16 (Pain 7, Difficulty 9, Disability 0)

Nodular Consistency: Soft

At Day 57 of retreatment, the subject reported being very satisfied (+2) and the investigator reported very much improvement (+3). Caliper measurements demonstrated decrease in size during the Retreatment Phase.

Subject 1804-4025, a 55 year old, white female, received two injections in both foot during the Initial Treatment Phase. Subject began with a FFI (FFI-SF-23) Composite Score (%) of 17.89% and a FFI (FFI-SF-23) Total Score of 34 (Pain 10, Difficulty 24, Disability 0) with nodular consistency that was hard for both nodules on Day 1. After receiving the dose of 0.48 mg the subject showed improvement in all the above measures at Day 57:

FFI (FFI-SF-23) Composite Score (%) of 1.05%

FFI (FFI-SF-23) Total Score of 2 (Pain 1, Difficulty 1, Disability 0)

The subject reported being quite satisfied (+1) with treatment and the investigator reported much improvement (+2). Both nodules were firm throughout. Caliper measurements showed size reduction in one of the two nodules. Other size measurements did not reflect any significant change in nodule size.

Subject opted to enter the Retreatment Phase of the Study. After approximately 100 days since end of initial treatment, subject had a FFI (FFI-SF-23) Composite Score (%) of 11.05% and a FFI (FFI-SF-23) Total Score of 21 (Pain 7, Difficulty 14, Disability 0) with nodular consistency that was hard for both nodules on Day 1 of the Retreatment Phase. Both nodules appeared to be larger. Subject received 2 injections (0.9 mg) on Day 1 and Day 29 each. After receiving the respective doses at both visits, the subject had the following scores at Day 57 of the Retreatment Phase:

FFI (FFI-SF-23) Composite Score (%) of 1.05%

FFI (FFI-SF-23) Total Score of 2 (Pain 1, Difficulty 0, Disability 1)

Nodular Consistency: Soft

At Day 57 of retreatment, the subject reported being quite satisfied (+1) and the investigator reported very much improvement (+3). Caliper measurements demonstrated a reduction in size during the Retreatment Phase.

Subject 1810-4021, a 53 year old, white male, with a history of diabetes, received two injections in his right foot during the Initial Treatment Phase. Subject began with a FFI (FFI-SF-23) Composite Score (%) of 61.74% and a FFI (FFI-SF-23) Total Score of 142 (Pain 73, Difficulty 58, Disability 11) with a nodule that was hard on Day 1. After receiving the dose of 0.48 mg the subject showed modest improvement in all the above measures at Day 57:

FFI (FFI-SF-23) Composite Score (%) of 59.05%

FFI (FFI-SF-23) Total Score of 124 (Pain 58, Difficulty 57, Disability 9)

Nodular Consistency: Moderately Firm

The subject reported being very satisfied (+2) with treatment and the investigator reported much improvement (+2). Caliper measurements showed size reduction and ultrasound measurements showed size reduction.

Subject opted to enter the Retreatment Phase of the Study. After approximately 150 days since end of initial treatment, subject had a FFI (FFI-SF-23) Composite Score (%) of 35% and a FFI (FFI-SF-23) Total Score of 63 (Pain 29, Difficulty 27, Disability 7) with a nodule that was moderately firm on Day 1 of the Retreatment Phase. Due to size, on Day 1 the subject received 1 injection (0.45 mg) while on Day 29 Visit the subject received 2 injections (0.9 mg). After receiving the respective doses at both visits, the subject had the following scores at Day 57 of the Retreatment Phase:

FFI (FFI-SF-23) Composite Score (%) of 26.67%

FFI (FFI-SF-23) Total Score of 56 (Pain 20, Difficulty 34, Disability 2)

Nodular Consistency: Soft

At Day 57 of retreatment, the subject reported being quite satisfied (+1) and the investigator reported minimal improvement (+1). Caliper measurements demonstrated increase in size during the Retreatment Phase.

Overall Conclusion from the Dose 0.48 mg [1.2 mg/ml] (Two Injections)

One subject received 0.48 mg (2 injections of 0.24 mg @ 1.2 mg/ml) and did not enter the retreatment phase:

- Decreases in the FFI (FFI-SF-23) Composite Scores, Total Scores, and Individual Subscale Scores.
- Had their nodule soften to Soft at Day 57
- Was reported by the investigator as having Much (+2) Improvement at Day 57

The three subjects that received 0.48 mg (2 injections of 0.45 mg @ 2.25 mg/ml) and did enter the retreatment phase:

- Two subjects saw significant decreases in their FFI (FFI-SF-23) Composite Scores, Total Scores, and Individual Subscale Scores during the Initial Treatment Phase.
- Had their nodules soften throughout the Initial Treatment Phase
- The four nodules reported by investigators as having Much (+2) or Very Much (+3) Improvement at Day 57 of the Initial Treatment Phase
- Upon entering the retreatment phase (Two receiving 0.9 mg per nodule at Day 1 and 29 and one receiving 0.45 mg per nodule at Day 1 and receiving 0.9 mg per nodule at Day 29)
  - Four nodules continued to see softening
  - Three of the four nodules saw reduction in nodule size by caliper measurements over the course of the retreatment period.
  - Three of the four nodules were reported by investigators as having Much (+2) or Very Much (+3) Improvement at Day 57 of the Retreatment Phase Dose 0.9 mg [2.25 mg/ml] (Two Injections)

Subject 1804-4018, a 40 year old, white male, received two injections in the left foot during the Initial Treatment Phase. Subject began with a FFI (FFI-SF-23) Composite Score (%) of 29.47% and a FFI (FFI-SF-23) Total Score of 56 (Pain 37, Difficulty 14, Disability 5) with a nodule that was firm throughout on Day 1. After receiving the dose of 0.9 mg the subject showed improvement in all the above measures at Day 57:

FFI (FFI-SF-23) Composite Score (%) of 5.24%

FFI (FFI-SF-23) Total Score of 11 (Pain 5, Difficulty 3, Disability 3)

Nodular Consistency: Moderately Firm

The subject reported being quite satisfied (+1) with treatment and the investigator reported much improvement (+2). Ultrasound demonstrated size reduction. Caliper measurements didn't demonstrate any significant change in size. Subject opted not to enter the Retreatment Phase of the Study.

Subject 1804-4026, a 49 year old, white female, received two injections in the right foot during the Initial Treatment Phase. Subject began with a FFI (FFI-SF-23) Composite Score (%) of 24.4% and a FFI (FFI-SF-23) Total Score of 44 (Pain 37, Difficulty 4, Disability 3) with a nodule that was firm throughout on Day 1. After receiving the dose of 0.9 mg the subject showed improvement in all the above measures at Day 57:

FFI (FFI-SF-23) Composite Score (%) of 0%

FFI (FFI-SF-23) Total Score of 0 (Pain 0, Difficulty 0, Disability 0)

Nodular Consistency: Soft

The subject reported being very satisfied (+2) with treatment and the investigator reported very much improvement (+3). Ultrasound and caliper measurements demonstrated size reduction. Subject opted not to enter the Retreatment Phase of the Study.

Subject 1806-4000, a 69 year old, black or African American male, received two injections in the left foot during the Initial Treatment Phase. Subject began with a FFI (FFI-SF-23) Composite Score (%) of 3.91% and a FFI (FFI-SF-23) Total Score of 9 (Pain 6, Difficulty 3, Disability 0) with a nodule that was firm throughout on Day 1. After receiving the dose of 0.9 mg the subject showed improvement in all the above measures at Day 57:

FFI (FFI-SF-23) Composite Score (%) of 0.48%

FFI (FFI-SF-23) Total Score of 1 (Pain 1, Difficulty 0, Disability 0)

Nodular Consistency: Non-Palpable

The subject reported being quite satisfied (+1) with treatment and the investigator reported very much improvement (+3). Caliper measurements were not obtainable at End of Study due to a non-palpable and non-measurable nodule. Ultrasound did not demonstrate any size reduction. Subject opted not to enter the Retreatment Phase of the Study.

Subject 1802-4010, a 45 year old, white male, received two injections in both feet during the Initial Treatment Phase. Subject began with a FFI (FFI-SF-23) Composite Score (%) of 33.89% and a FFI (FFI-SF-23) Total Score of 61 (Pain 22, Difficulty 33, Disability 6) with both nodules being firm throughout on Day 1. After receiving the dose of 0.9 mg the subject showed improvement in all the above measures at Day 57:

FFI (FFI-SF-23) Composite Score (%) of 9.47%

FFI (FFI-SF-23) Total Score of 18 (Pain 7, Difficulty 10, Disability 1)

Nodular Consistency: Moderately Firm

The subject reported being quite satisfied (+1) with treatment of the right nodule and reporting no satisfaction or dissatisfaction (+0) with treatment of the left nodule. The investigator reported very much improvement (+3) for the treatment of the right nodule and much improvement (+2) for the treatment of the left nodule. Ultrasound and caliper measurements demonstrated size reduction on all measurements except for the left nodule on ultrasound.

Subject opted to enter the Retreatment Phase of the Study. After approximately 180 days since end of initial treatment, subject had a FFI (FFI-SF-23) Composite Score (%) of 17.14% and a FFI (FFI-SF-23) Total Score of 36 (Pain 15, Difficulty 17, Disability 4) with nodular consistency that was moderately firm for both nodules on Day 1 of the Retreatment Phase. Both nodules appeared to be larger. Subject received 2 injections (0.9 mg) on Day 1 and Day 29 each. After receiving the respective doses at both visits the subject had the following scores at Day 57 of the Retreatment Phase:

FFI (FFI-SF-23) Composite Score (%) of 17.14%

FFI (FFI-SF-23) Total Score of 36 (Pain 13, Difficulty 20, Disability 3)

Nodular Consistency: Soft for right nodule, moderately firm for left nodule

At Day 57 of retreatment, the subject reported being quite satisfied (+1) with treatment of the right nodule and reporting no satisfaction or dissatisfaction (+0) with treatment of the left nodule. The investigator reported much improvement (+2) for both nodules. Caliper measurements demonstrated a reduction in size for both nodules during the Retreatment Phase.

Subject 1802-4011, a 57 year old, white Hispanic female, with a history of diabetes, received two injections in the right foot during the Initial Treatment Phase. Subject began with a FFI (FFI-SF-23) Composite Score (%) of 32.86% and a FFI (FFI-SF-23) Total Score of 46 (Pain 33, Difficulty 6, Disability 7) with a nodule that was hard on Day 1. After receiving the dose of 0.9 mg the subject showed improvement in all the above measures at Day 57:

FFI (FFI-SF-23) Composite Score (%) of 18%

FFI (FFI-SF-23) Total Score of 27 (Pain 15, Difficulty 12, Disability 0)

Nodular Consistency: Soft

The subject reported being very satisfied (+2) with treatment and the investigator reported very much improvement (+3). Ultrasound demonstrated size reduction while caliper measurements remained similar.

Subject opted to enter the Retreatment Phase of the Study: After approximately 180 days since end of initial treatment, subject had a FFI (FFI-SF-23) Composite Score (%) of 6.11% and a FFI (FFI-SF-23) Total Score of 11 (Pain 7, Difficulty 4, Disability N/A) with a nodule that was moderately firm and larger on Day 1 of the Retreatment Phase. Subject received 2 injections (0.9 mg) on Day 1 and Day 29 each. After receiving the respective doses at both visits, the subject had the following scores at Day 57 of the Retreatment Phase:

FFI (FFI-SF-23) Composite Score (%) of 4.71%

FFI (FFI-SF-23) Total Score of 8 (Pain 4, Difficulty 3, Disability 1)

Nodular Consistency: Soft

At Day 57 of retreatment, the subject reported being very satisfied (+2) and the investigator reported much improvement (+2). Caliper measurements demonstrated decrease in size during the Retreatment Phase.

Subject 1804-4020, a 61 year old, white male, received two injections in both feet during the Initial Treatment Phase. Subject began with a FFI (FFI-SF-23) Composite Score (%) of 0% and a FFI (FFI-SF-23) Total Score of 0 (Pain 0, Difficulty 0, Disability N/A) with the left nodule being firm throughout and the right nodule being moderately firm on Day 1. After receiving the dose of 0.9 mg the subject showed the following at Day 57:

FFI (FFI-SF-23) Composite Score (%) of 0%

FFI (FFI-SF-23) Total Score of 0 (Pain 0, Difficulty 0, Disability 0)

Nodular Consistency: Moderately Firm for both nodules

The subject reported being quite satisfied (+1) with treatment of the right nodule and reporting no satisfaction or dissatisfaction (+0) with treatment of the left nodule. The investigator reported much improvement (+2) for the treatment of the right nodule and minimal improvement (+1) for the treatment of the left nodule. Ultrasound and caliper measurements demonstrated no size reduction on all measurements.

Subject opted to enter the Retreatment Phase of the Study. After approximately 165 days since end of initial treatment, subject had a FFI (FFI-SF-23) Composite Score (%) of 0% and a FFI (FFI-SF-23) Total Score of 0 (Pain 0, Difficulty 0, Disability 0) with nodular consistency that was moderately firm for both nodules on Day 1 of the Retreatment Phase. Subject received 2 injections (0.9 mg) on Day 1 and Day 29 each. After receiving the respective doses at both visits, the subject had the following scores at Day 57 of the Retreatment Phase:

- FFI (FFI-SF-23) Composite Score (%) of 0%
- FFI (FFI-SF-23) Total Score of 0 (Pain 0, Difficulty 0, Disability 0)
- Nodular Consistency: Soft for both nodules At Day 57 of retreatment, the subject reported being very satisfied (+2) with treatment for both nodules. The investigator reported very much improvement (+3) for both nodules. Caliper measurements demonstrated a reduction in size during the Retreatment Phase.

Overall Conclusion from the Dose 0.9 mg [2.25 mg/ml] (Two Injections)

The three subjects that received 0.9 mg (2 injections of 0.45 mg @ 2.25 mg/ml) and did not enter the retreatment phase:

- Decreases in their FFI (FFI-SF-23) Composite Scores, Total Scores, and Individual FFI (FFI-SF-23) Subscale Scores.
- Reduction in nodule size in one or both measures (calipers/ultrasound)
- Had their nodules soften with one subject having a non-palpable nodule at Day 57
- Were reported by investigators as having Much (+2) or Very Much (+3) Improvement at Day 57

The three subjects that received 0.9 mg (2 injections of 0.45 mg @ 2.25 mg/ml) and did enter the retreatment phase:

- The 2 subjects that had non-zero FFI (FFI-SF-23) scores on Day 1 saw decreases in their FFI (FFI-SF-23) Composite Scores, Total Scores, and Individual Subscale Scores during the Initial Treatment Phase.
- Had their nodules soften throughout the Initial Treatment Phase
- Four of the five nodules reported by investigators as having Much (+2) or Very Much (+3) Improvement at Day 57 of the Initial Treatment Phase
- Upon entering the retreatment phase (and receiving 0.9 mg per nodule at Day 1 and 29)
  - Four out of the five nodules continued to see softening
  - The five nodules saw reduction in nodule size by caliper measurements over the course of the retreatment period.
  - The five nodules were reported by investigators as having Much (+2) or Very Much (+3) Improvement at Day 57 of the Retreatment Phase.

Conclusions

The results support the safety, tolerability, and efficacy of CCH for the treatment of plantar fibromatosis.

Example 3—Study EN3835-222

A phase 2, double-blind, randomized, placebo-controlled study is being conducted to assess the efficacy, safety, and tolerability of EN3835 vs placebo in the treatment of plantar fibromatosis. Subjects will receive a maximum dose of up to 1.8 mg per treatment for up to 2 treatments based on the configuration of their nodules. For subjects with bilateral PF, no more than 2 injections (0.9 mg) per foot will be administered. For subjects with unilateral PF, no more than 3 injections (1.35 mg) will be administered in the single foot. Multiple nodules may be treated on the same foot. Efficacy and safety data will be collected throughout the study.

Overall Design

Figure 12:
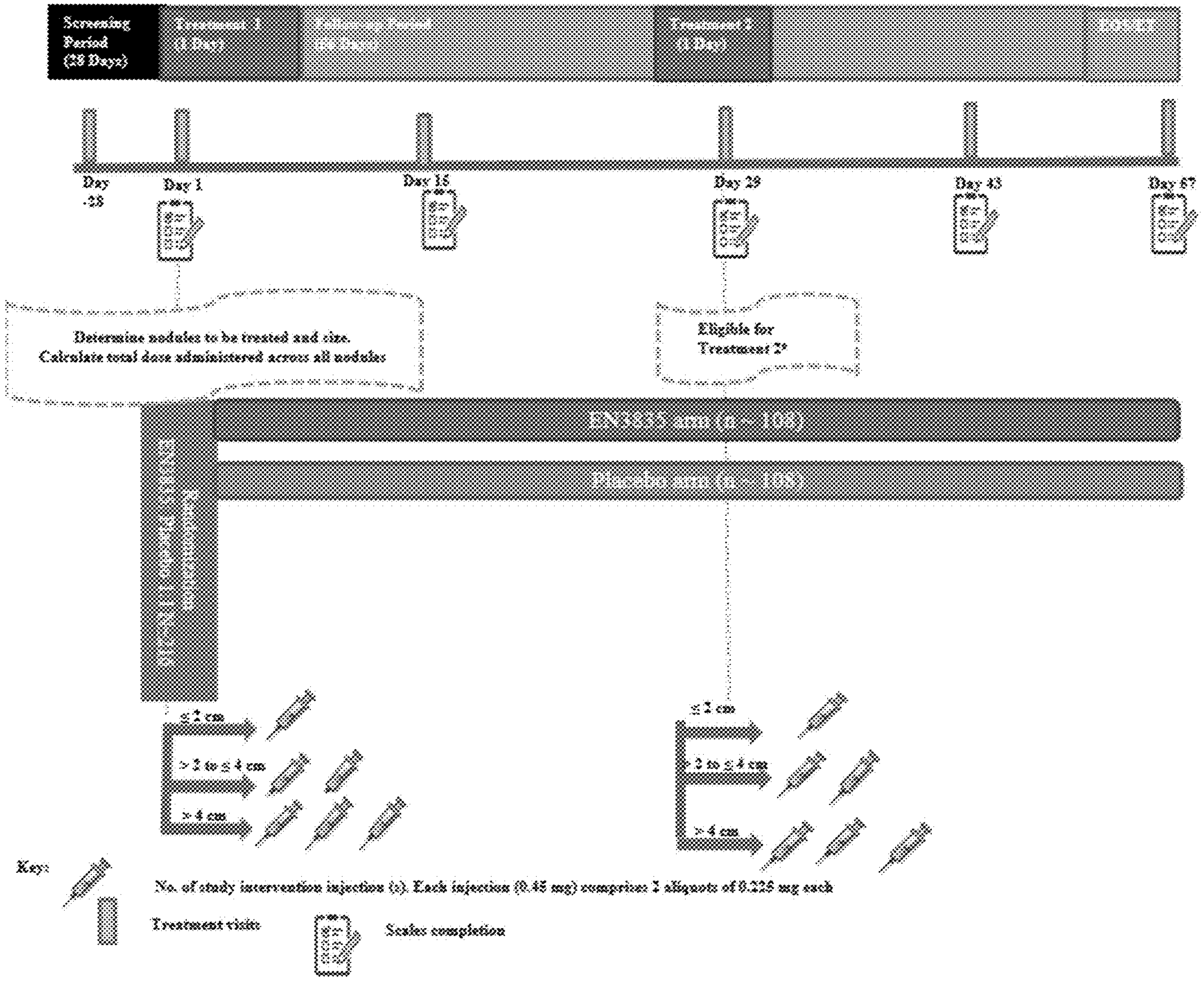
FIG. 12 illustrates the "study schema" for Study 222. [a]Based on the Day 29 examination of the nodule(s) and review of inclusion/exclusion criteria. The total number of EN3835 injections across all nodules present shall not exceed 3 injections (1.35 mg) in a single foot when treating subjects with unilateral plantar fibromatosis. When treating subjects with bilateral plantar fibromatosis, the total number of EN3835 injections across all nodules present shall not exceed 4 injections (1.8 mg) in total with each foot receiving a maximum dose of 0.9 mg.

Subjects will be screened to randomize approximately 216 subjects into 2 groups, an EN3835 group (n~108) and a placebo group (n~108) in a 1:1 ratio. Study intervention (Table 41) will be administered intralesionally to all nodules present based on the size of each nodule at the doses described in the dosage table (Table 42). Nodules will be measured using calipers and the largest width or length will be used to determine the number of injections to be administered in each nodule. The total number of EN3835 injections across all nodules present shall not exceed 3 injections (1.35 mg) in a single foot when treating subjects with unilateral plantar fibromatosis. When treating subjects with bilateral plantar fibromatosis, the total number of EN3835 injections across all nodules present shall not exceed 4 injections (1.8 mg) in total with each foot receiving a maximum dose of 0.9 mg. All nodules present on each foot on Day 1 must be treated. After receiving study intervention, subjects will be encouraged to resume normal daily activities including weight bearing and walking on the treated foot/feet. Subjects should be encouraged to wear supportive footwear (such as sneakers or tennis shoes) when on their feet during the study. Subjects must agree to not initiate or change the use of orthotics or inserts designed to relieve symptoms of plantar fibromatosis during the study period. All subjects will return to the clinic for 4 follow-up visits, 2 weeks apart, on Days 15, 29, 43, and 57. The study schema for Study 222 is depicted in FIG. 12.

TABLE 41

Study Intervention Administration

| Treatment | Study Intervention | |
|---|---|---|
| Concentrations | EN3835 | Placebo |
| Product Name | EN3835 (0.9 mg of collagenase clostridium histolyticum with 0.5 mg of hydrochloric acid, 18.5 mg of sucrose and 1.1 mg of tromethamine) plus diluent | Placebo (0.5 mg of hydrochloric acid, 18.5 mg of sucrose and 1.1 mg of tromethamine) plus diluent |
| Type | Biologic | NA |
| Dose Formulation | Injectable liquid | Injectable liquid |

TABLE 41-continued

| Study Intervention Administration | | |
|---|---|---|
| Treatment | Study Intervention | |
| Concentrations | EN3835 | Placebo |
| Unit Dose Strengths | 2.25 mg/mL | NA |
| Dose Amount and Frequency [a] | 0.45 mg administered as 1 injection<br>0.9 mg administered as 2 injections<br>1.35 mg administered as 3 injections | Volume matched placebo administered as 1 injection, 2 injections, or 3 injections per nodule depending on nodule size |
| Route of Administration | Intralesional injection | Intralesional injection |
| Sourcing | Provided centrally by the sponsor | Provided centrally by the sponsor |
| Packaging and Labeling | Product will be provided in vials. Each vial will be labeled per country requirement. | Product will be provided in vials. Each vial will be labeled per country requirement. |

[a] Each injection (0.45 mg) of EN3835will be administered as 2 aliquots of 0.225 mg each.
Study intervention will be injected intralesionally directly into the nodule using a 27-gauge, 0.5 inch needle.

TABLE 42

| Dose of Study Intervention per Nodule | | | |
|---|---|---|---|
| Palpable Nodule Size | Injections | Total Volume (mL) | Where Study Intervention is EN3835, Total Dose EN3835 Administered/Nodule (mg) |
| Up to 2 cm | 1 | 0.2 | 0.45 |
| >2 cm to ≤4 cm | 2 | 0.4 | 0.9 |
| >4 cm | 3 | 0.6 | 1.35 |

The size of each nodule will be determined by caliper and the largest width or length will be used to determine the number of injections/aliquots to be administered.
Each injection of EN3835 (0.45 mg) is administered as 2 aliquots of 0.225 mg each.
The maximum dose EN3835 at 1 treatment visit not to exceed 1.8 mg in total (with maximum of 0.9 mg/per foot) when treating bilateral PF. When treating unilateral PF, the maximum dose EN3835 at 1 treatment should not exceed 1.35 mg in the affected foot. All nodules present on each foot on Day 1 must be treated.

At the Day 29 visit, if the subject has any previously treated palpable (i.e., hard, firm or soft) nodules measurable by caliper, the nodules are deemed appropriate for treatment by the investigator, and the inclusion/exclusion criteria are met, a second dose of the study intervention may be administered.

For all subjects, the efficacy of the study intervention will be assessed on the FFI-PF-May 2021, the Subject Satisfaction with Treatment Scale, the PGIC PF Overall and individual PGIC subscales of pain, difficulty, and activity limitation, the Pain Intensity NRS, the PGIS PF Overall, and the individual PGIS subscales of pain, difficulty, and activity limitation, and the Clinician Global Impression of Change Scale. Safety will be assessed by evaluating the incidence and duration of TEAEs, AESIs, SAEs, and changes in vital signs and clinical laboratory values.

All subjects will complete the study on EOS (Day 57) Visit, regardless of whether they receive 1 or 2 treatments during the study. At the EOS visit, immunogenicity samples will be collected, safety will be assessed, and nodules will be measured. The maximum duration of participation is up to 85 days (Screening Period: 28 days, Treatment Periods: 1 or 2 days, and a total Follow-up Period of 56 days).

Selection of Nodules

During the Screening Visit, the nodules on the affected foot/feet will be examined and evaluated, by conducting caliper measurements, measuring nodule hardness using a durometer, palpating the nodule for consistency, and assessing the FFI-PF-May 2021. Only hard or firm fibrous nodules that are palpable on clinical examination and measurable on calipers are eligible for treatment on Day 1. All nodules present on each foot on Day 1 must be treated. Study intervention will be administered intralesionally to nodules present meeting eligibility criteria based on the size of each nodule at the doses described in Table 42.

Based on the largest diameter of width or length of the nodule determined by calipers, subjects will receive 1 to 3 injections of study intervention per foot. Subjects with nodules of ≤2 cm will receive 1 intralesional injection of study intervention per nodule. Subjects with nodules of >2 cm to ≤4 cm will receive 2 intralesional injections of study intervention per nodule. Subjects with nodules of >4 cm will receive 3 intralesional injections of study intervention per nodule. Hard, firm, or soft fibrous nodules treated on Day 1, measurable by calipers and palpable on clinical examination are eligible for a second treatment on Day 29.

Injection Technique

Nodules Up to 2 cm in Size

Figure 13A:
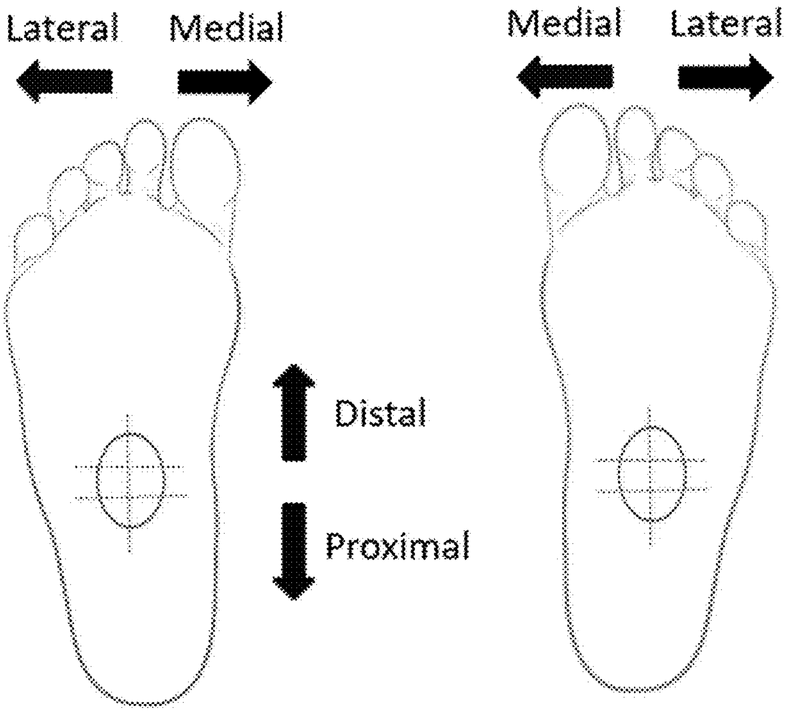
FIG. 13A, FIG. 13B, FIG. 13C, FIG. 13D, FIG. 13E, and FIG. 13F illustrate exemplary injection techniques for nodules of various sizes based upon the length or width of the nodule, as described in the Examples.

Nodule's Largest Diameter is Length—Study intervention will be administered as follows when the largest diameter of the nodule is length:

1. One (1) administration syringe will be prepared.
2. The subject's affected foot will be secured, having the ankle angled at 90 degrees and the hallux dorsiflexed to isolate the nodule to be treated.
3. Study Intervention will be distributed as evenly throughout the nodule as possible and each administration syringe will be injected as two (2) aliquots of 0.1 ml each. The nodule will be divided into imaginary approximate thirds along the largest diameter of length and then into imaginary halves along the diameter of width as shown in FIG. 13A.
4. The needle will be inserted directly into the nodule (perpendicular to the base of the foot) so that the needle tip is in one of the two intersections created by the lines established in step 3, using caution to keep the needle within the nodule. Care will be taken to avoid having the needle tip pass completely through the nodule to help minimize the potential for injection of EN3835 into tissues other than the nodule. If insertion of the needle into the plantar fascia is suspected or paresthesia is noted by the subject, the needle will be withdrawn and repositioned into the nodule. Prior to injection, the syringe will be aspirated to make sure it is not in any vascular structure. If there are signs of blood coming inside the syringe, a new injection site will be selected. If there was negative aspiration, continue with step 5.

5. If the needle is in the proper location, there will be some resistance noted during the injection procedure. After confirming that the needle is correctly placed in the nodule, an aliquot of 0.1 ml of study intervention will be injected ensuring the study intervention is maintained completely within the nodule.
6. For the second aliquot of 0.1 ml of study intervention, steps 4-5 are repeated ensuring that the injection is administered in the other intersection created by the lines established in step 3 that wasn't previously injected.
7. The subject's treated foot will be wrapped with an appropriate dressing (such as a self-adherent compression bandage) to cover the treated area.

Figure 13B:
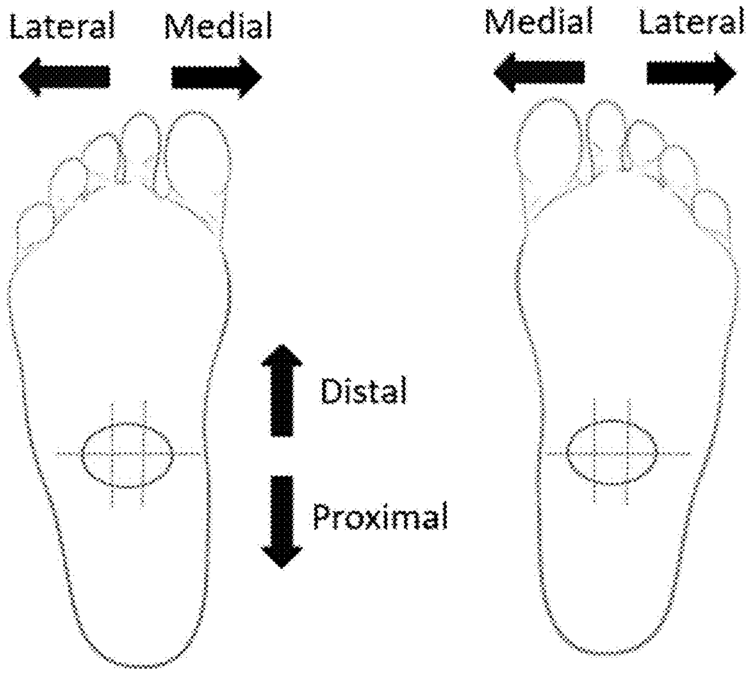

Study intervention will be administered as follows when the largest diameter of the nodule is width:

1. One (1) administration syringe will be prepared.
2. The subject's affected foot will be secured, having the ankle angled at 90 degrees and the hallux dorsiflexed to isolate the nodule to be treated.
3. Study intervention will be distributed as evenly throughout the nodule as possible and each administration syringe will be injected as two (2) aliquots of 0.1 ml each. The nodule will be divided into imaginary approximate thirds along the largest diameter of width and then into imaginary halves along the diameter of length as shown in FIG. 13B.
4. The needle will be inserted directly into the nodule (perpendicular to the base of the foot) so that the needle tip is in one of the two intersections created by the lines established in step 3, using caution to keep the needle within the nodule. Care will be taken to avoid having the needle tip pass completely through the nodule to help minimize the potential for injection of EN3835 into tissues other than the nodule. If insertion of the needle into the plantar fascia is suspected or paresthesia is noted by the subject's, the needle will be withdrawn and repositioned. Prior to injection, the syringe will be aspirated to make sure it is not in any vascular structure. If there are signs of blood coming inside the syringe, a new injection site will be selected. If there was negative aspiration, continue with step 5.
5. If the needle is in the proper location, there will be some resistance noted during the injection procedure. After confirming that the needle is correctly placed in the nodule, an aliquot of 0.1 ml of study intervention will be injected ensuring the study intervention is maintained completely within the nodule.
6. For the second aliquot of 0.1 ml of study intervention, steps 4-5 will be repeated ensuring that the injection is administered in the other intersection created by the lines established in step 3 that wasn't previously injected.
7. The subject's treated foot will be wrapped with an appropriate dressing (such as a self-adherent compression bandage) to cover the treated area.

Nodules between > 2 cm to < or = 4 cm in Size

Figure 13C:
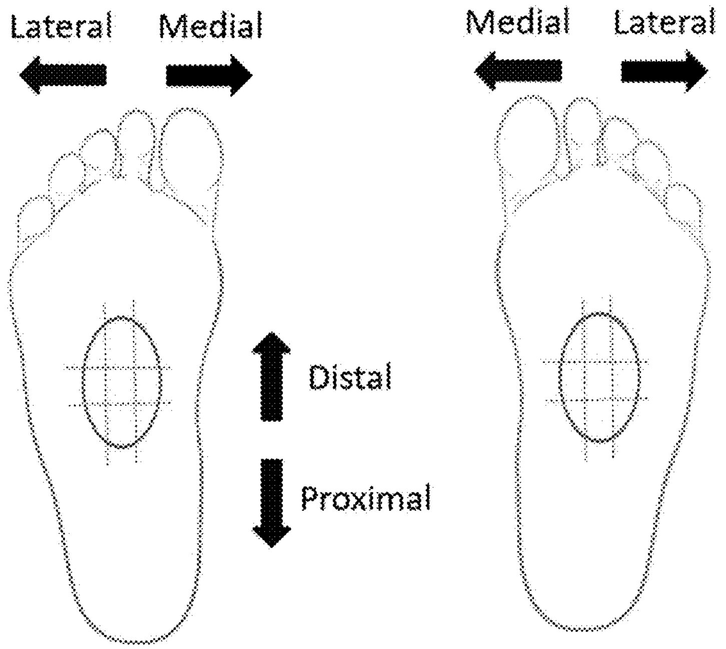

Study intervention will be administered as follows when the largest diameter of the nodule is length:

1. Two (2) administration syringes will be prepared.
2. The subject's affected foot will be secured, having the ankle angled at 90 degrees and the hallux dorsiflexed to isolate the nodule to be treated.
3. Study intervention will be distributed as evenly throughout the nodule as possible and each administration syringe will be injected as two (2) aliquots of 0.1 ml each. The nodule will be divided into imaginary approximate thirds along the largest diameter of length and then into imaginary thirds along the diameter of width as shown in FIG. 13C.
4. The needle will be inserted directly into the nodule (perpendicular to the base of the foot) so that the needle tip is in one of the two distal intersections created by the lines established in step 3, using caution to keep the needle within the nodule. Care should be taken to avoid having the needle tip pass completely through the nodule to help minimize the potential for injection of EN3835 into tissues other than the nodule. If insertion of the needle into the plantar fascia is suspected or paresthesia is noted by the subject, the needle will be withdrawn and reposition into the nodule. Prior to injection, the syringe will be aspirated to make sure it is not in any vascular structure. If there are signs of blood coming inside the syringe, a new injection site will be selected. If there was negative aspiration, continue with step 5.
5. If the needle is in the proper location, there will be some resistance noted during the injection procedure. After confirming that the needle is correctly placed in the nodule, an aliquot of 0.1 ml of study intervention will be injected ensuring the study intervention is maintained completely within the nodule.
6. For the second aliquot of 0.1 ml of study intervention, steps 4-5 will be repeated ensuring that the injection is administered in the other distal intersection created by the lines established in step 3 that wasn't previously injected.
7. For the remaining two proximal intersections created by the lines established in step 3, steps 4-6 will be repeated using the second administration syringe ensuring that each remaining injection site receives an aliquot of 0.1 ml.
8. The subject's treated foot will be wrapped with an appropriate dressing (such as a self-adherent compression bandage) to cover the treated area.

Figure 13D:
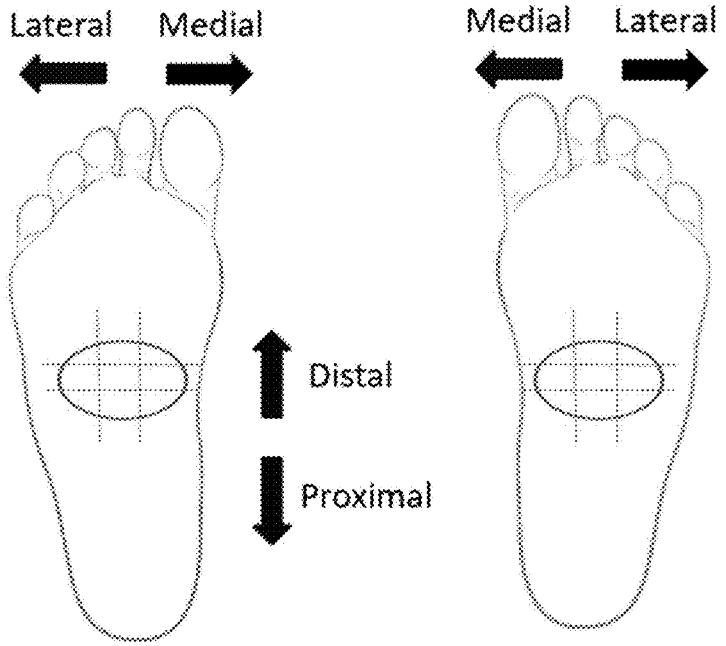

Study intervention will be administered as follows when the largest diameter of the nodule is width:

1. Two (2) administration syringes will be prepared.
2. The subject's affected foot will be secured, having the ankle angled at 90 degrees and the hallux dorsiflexed to isolate the nodule to be treated.
3. Study intervention will be distributed as evenly throughout the nodule as possible and each administration syringe will be injected as two (2) aliquots of 0.1 ml each. The nodule will be divided into imaginary approximate thirds along the largest diameter of width and then into imaginary thirds along the diameter of length as shown in FIG. 13D.
4. The needle will be inserted directly into the nodule (perpendicular to the base of the foot) so that the needle tip is in one of the two lateral intersections created by the lines established in step 3, using caution to keep the needle within the nodule. Care will be taken to avoid having the needle tip pass completely through the nodule to help minimize the potential for injection of EN3835 into tissues other than the nodule. If insertion of the needle into the plantar fascia is suspected or paresthesia is noted by the subject, the needle will be withdrawn and repositioned. Prior to injection, the syringe will be aspirated to make sure it's not in any vascular structure. If there are signs of blood coming inside the syringe, a new injection site will be selected. If there was negative aspiration, continue with step 5.

5. If the needle is in the proper location, there will be some resistance noted during the injection procedure. After confirming that the needle is correctly placed in the nodule, an aliquot of 0.1 ml of study intervention will be injected ensuring the study intervention is maintained completely within the nodule.
6. For the second aliquot of 0.1 ml of study intervention, steps 4-5 will be repeated ensuring that the injection is administered in the other lateral intersection created by the lines established in step 3 that wasn't previously injected.
7. For the remaining two medial intersections created by the lines established in step 3, steps 4-6 will be repeated using the second administration syringe ensuring that each remaining injection site receives an aliquot of 0.1 ml.
8. The subject's treated foot will be wrapped with an appropriate dressing (such as a self-adherent compression bandage) to cover the treated area.

Nodules > 4 cm in Size

Figure 13E:
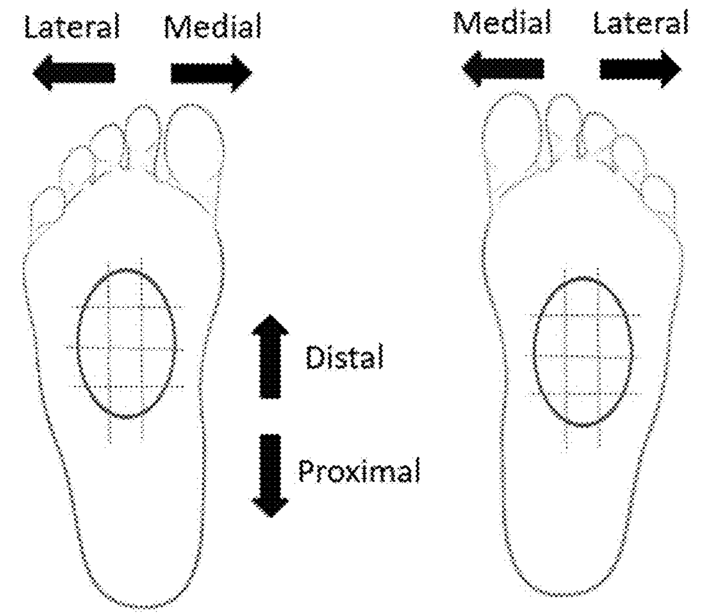

Study intervention will be administered as follows when the largest diameter of the nodule is length:

1. Three (3) administration syringes will be prepared.
2. The subject's affected foot will be secured, having the ankle angled at 90 degrees and the hallux dorsiflexed to isolate the nodule to be treated.
3. Study intervention will be distributed as evenly throughout the nodule as possible and each administration syringe will be injected as two (2) aliquots of 0.1 ml each. The nodule will be divided into imaginary approximate fourths along the largest diameter of length and then into imaginary thirds along the diameter of width as shown in FIG. 13E.
4. The needle will be inserted directly into the nodule (perpendicular to the base of the foot) so that the needle tip is in one of the two distal intersections created by the lines established in step 3, using caution to keep the needle within the nodule. Care will be taken to avoid having the needle tip pass completely through the nodule to help minimize the potential for injection of EN3835 into tissues other than the nodule. If insertion of the needle into the plantar fascia is suspected or paresthesia is noted by the subject, the needle will be withdrawn and repositioned. Prior to injection, the syringe will be aspirated to make sure it's not in any vascular structure. If there are signs of blood coming inside the syringe, a new injection site will be selected. If there was negative aspiration, continue with step 5.
5. If the needle is in the proper location, there will be some resistance noted during the injection procedure. After confirming that the needle is correctly placed in the nodule, an aliquot of 0.1 ml of study intervention will be injected ensuring the study intervention is maintained completely within the nodule.
6. For the second aliquot of 0.1 ml of study intervention, steps 4-5 will be repeated ensuring that the injection is administered in the other distal intersection created by the lines established in step 3 that wasn't previously injected.
7. For the central two intersections created by the lines established in step 3, steps 4-6 will be repeated using the second administration syringe ensuring that each injection site receives an aliquot of 0.1 ml.
8. For the proximal two intersections created by the lines established in step 3, steps 4-6 will be repeated using the third administration syringe ensuring that each remaining injection site receives an aliquot of 0.1 ml.
9. The subject's treated foot will be wrapped with an appropriate dressing (such as a self-adherent compression bandage) to cover the treated area.

Figure 13F:
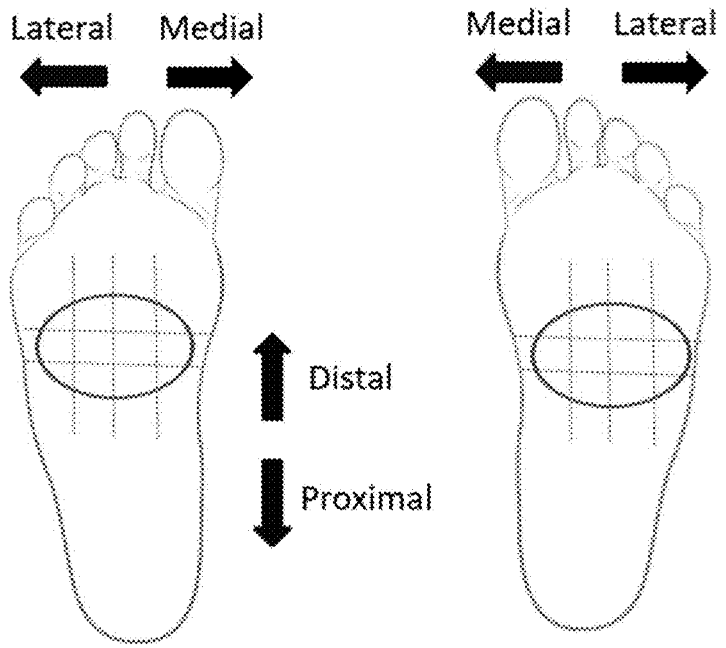
Figure 14:
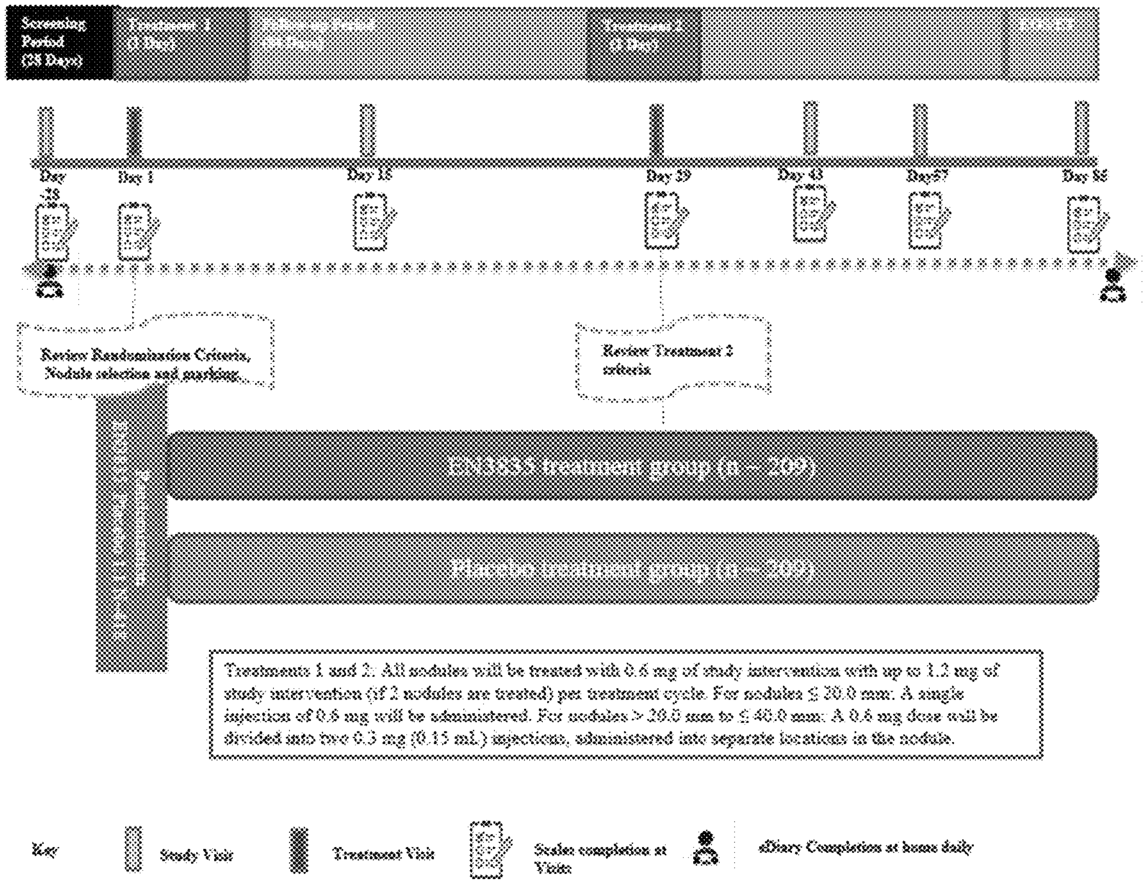
FIG. 14 illustrates the study design for the Phase 3 "STRIDE" study as disclosed herein.

Study intervention will be administered as follows when the largest diameter of the nodule is width:

1. Three (3) administration syringes will be prepared.
2. The subject's affected foot will be secured, having the ankle angled at 90 degrees and the hallux dorsiflexed to isolate the nodule to be treated.
3. Study intervention will be distributed as evenly throughout the nodule as possible and each administration syringe will be injected as two (2) aliquots of 0.1 ml each. The nodule will be divided into imaginary approximate fourths along the largest diameter of width and then into imaginary thirds along the diameter of length as shown in FIG. 13F.
4. The needle will be inserted directly into the nodule (perpendicular to the base of the foot) so that the needle tip is in one of the two lateral intersections created by the lines established in step 3, using caution to keep the needle within the nodule. Care will be taken to avoid having the needle tip pass completely through the nodule to help minimize the potential for injection of EN3835 into tissues other than the nodule. If insertion of the needle into the plantar fascia is suspected or paresthesia is noted by the subject, the needle will be withdrawn and repositioned. Prior to injection, the syringe will be aspirated to make sure it's not in any vascular structure. If there are signs of blood coming inside the syringe, a new injection site will be selected. If there was negative aspiration, continue with step 5.
5. If the needle is in the proper location, there will be some resistance noted during the injection procedure. After confirming that the needle is correctly placed in the nodule, an aliquot of 0.1 ml of study intervention will be injected ensuring the study intervention is maintained completely within the nodule.
6. For the second aliquot of 0.1 ml of study intervention, steps 4-5 will be repeated ensuring that the injection is administered in the other lateral intersection created by the lines established in step 3 that wasn't previously injected.
7. For the central two intersections created by the lines established in step 3, steps 4-6 will be repeated using the second administration syringe ensuring that each injection site receives an aliquot of 0.1 ml.
8. For the medial two intersections created by the lines established in step 3, steps 4-6 will be repeated using the third administration syringe ensuring that each remaining injection site receives an aliquot of 0.1 ml.
9. The subject's treated foot will be wrapped with an appropriate dressing (such as a self-adherent compression bandage) to cover the treated area.

Objectives and Endpoints

The objectives and endpoints are provided below:

TABLE 43

| Objective | Endpoint |
|---|---|
| Primary | |
| To assess the improvement with EN3835 vs placebo in the Foot Function Index FFI-PF-May 2021 pain subscale. | The difference between EN3835 and placebo in the mean change from Baseline (Day 1) to Day 57 on the foot pain subscale (total score on 9 items) of the FFI-PF-May 2021 ranging from 0 ("None") to 4 ("Extreme"). |
| Secondary | |
| To assess the improvement with EN3835 vs placebo in the FFI-PF-May 2021 pain subscale over time. | The mean change from Baseline (Day 1) to Days 15, 29, 43, and 57 on the pain subscale of the FFI-PF-May 2021 (total score on 9 items), ranging from 0 ("None") to 4 ("Extreme") with EN3835 vs placebo. |
| To assess the overall improvement in the combined score of the FFI-PF-May 2021 pain and difficulty subscales with EN3835 vs placebo. | The difference between EN3835 and placebo in the mean change from Baseline (Day 1) to Day 57 on the total score of the FFI-PF-May 2021 pain and difficulty subscales (combined).<br>The mean change from Baseline (Day 1) to Days 15, 29, 43, and 57 on the total score of the pain and difficulty subscales of the FFI-PF-May 2021 with EN3835 vs placebo. |
| To assess investigator assessment of improvement with EN3835 treatment vs placebo. | The difference in the proportion of EN3835-treated subjects and those receiving only placebo reporting "Minimally Improved" (+1) "Much Improved" (+2) or "Very Much Improved" (+3) on the Clinician Global Impression of Change Scale, a 7-point scale ranging from −3 ("Very Much Worse") to +3 ("Very Much Improvement") on Days 15, 29, 43, and 57. |
| To assess the change in nodule hardness after administration of EN3835 vs placebo. | The difference between EN3835 and placebo in the mean change from Baseline (Day 1) to Day 57 in the nodular hardness of the treated nodules by durometer measurements.<br>The mean change from Baseline (Day 1) to Days 15, 29, 43, and 57 in the nodular hardness of the treated nodules by durometer measurements with EN3835 vs placebo. |
| Safety | |
| To assess the safety and tolerability of EN3835 in subjects with plantar fibromatosis. | Safety of EN3835 as assessed by incidence, severity and duration of treatment-emergent adverse events (TEAEs), adverse events of special interest (AESIs), and serious adverse events (SAEs).<br>The change from baseline in vital signs and clinical laboratory values at each visit where these parameters are measured. |
| To assess the immunogenicity of EN3835 in subjects with plantar fibromatosis. | Presence of anti-AUX-I and anti-AUX-II antibody titer levels in EN3835 treated-subjects at Day 1 and Day 57.<br>Presence of neutralizing antibodies to AUX-I and AUX-II in EN3835 treated-subjects at Day 1 and Day 57. |
| Exploratory | |
| To assess the overall improvement in the FFI-PF-May 2021 total score with EN3835 vs placebo. | The difference between EN3835 and placebo in the mean change from Baseline (Day 1) to Day 57 on the FFI-PF-May 2021 total score of 21 items with the score of each item ranging from 0 to 4, with 4 indicating higher severity.<br>The mean change from Baseline (Day 1) to Days 15, 29, 43, and 57 on the FFI-PF-May 2021 total score with EN3835 vs placebo. |
| To assess the overall improvement in severity of plantar fibromatosis on the Patient Global Impression of Severity (PGIS) PF Overall scale. | The difference between EN3835 and placebo at Day 57 on the PGIS PF Overall score.<br>The difference between EN3835 and placebo Days 15, 29, 43, and 57 on the PGIS PF Overall score with EN3835 vs placebo. |

TABLE 43-continued

| Objective | Endpoint |
| --- | --- |
| To assess the overall improvement in the severity of foot pain with EN3835 vs placebo in the PGIS foot pain subscale. | The difference between EN3835 and placebo at Day 57 on the foot pain subscale of the PGIS.<br>The difference between EN3835 and placebo at Days 15, 29, 43, and 57 on the PGIS foot pain subscale, ranging from 0 (“None”) to 4 (“Severe”) with EN3835 vs placebo. |
| To assess the overall improvement in the severity of difficulty with EN3835 vs placebo in the PGIS difficulty subscale. | The difference between EN3835 and placebo at Day 57 on the difficulty subscale of the PGIS.<br>The difference between EN3835 and placebo at Days 15, 29, 43, and 57 on the PGIS difficulty subscale, ranging from 0 (“None”) to 4 (“Severe”) with EN3835 vs placebo. |
| To assess the overall improvement in the severity of difficulty with EN3835 vs placebo in the PGIS activity limitation subscale. | The difference between EN3835 and placebo at Day 57 on the activity limitation subscale of the PGIS.<br>The difference between EN3835 and placebo at Days 15, 29, 43, and 57 on the PGIS activity limitation subscale, ranging from 0 (“None”) to 4 (“Severe”) with EN3835 vs placebo. |
| To assess the Patient Global Impression of Change (PGIC) PF Overall with EN3835 treatment vs placebo. | The difference in the proportion of subjects treated with EN3835 or placebo reporting Minimal Improvement (+1), Much Improvement (+2), and Very Much Improvement (+3) on the PGIC scale, a 7-point scale ranging from −3 (“Very Much Worse”) to +3 (“Very Much Improvement”) on Days 15, 29, 43, and 57. |
| To assess the change in the overall severity of foot pain on the Foot Pain Subscale of the PGIC. | The difference in the proportion of subjects treated with EN3835 or placebo reporting Minimal Improvement (+1), Much Improvement (+2), and Very Much Improvement (+3) on the foot pain subscale of the PGIC scale, a 7 point scale ranging from −3 (“Very Much Worse”) to +3 (“Very Much Improvement”) on Days 15, 29, 43, and 57. |
| To assess the change in the overall severity of difficulty on the Difficulty Subscale of the PGIC. | The difference in the proportion of subjects treated with EN3835 or placebo reporting Minimal Improvement (+1), Much Improvement (+2), and Very Much Improvement (+3) on the difficulty subscale of the PGIC scale, a 7 point scale ranging from −3 (“Very Much Worse”) to +3 (“Very Much Improvement”) on Days 15, 29, 43, and 57. |
| To assess the change in the overall severity of activity limitation on the Activity Limitation Subscale of the PGIC. | The difference in the proportion of subjects treated with EN3835 or placebo reporting Minimal Improvement (+1), Much Improvement (+2), and Very Much Improvement (+3) on the activity limitation subscale of the PGIC scale, a 7 point scale ranging from −3 (“Very Much Worse”) to +3 (“Very Much Improvement”) on Days 15, 29, 43, and 57. |
| To assess the overall improvement in foot pain with EN3835 vs placebo on the Pain Intensity Numerical Rating Scale (NRS). | The difference between EN3835 and placebo in the mean change from Baseline (Day 1) to Day 57 on the Pain Intensity NRS.<br>The mean change from Baseline (Day 1) to Days 15, 29, 43, and 57 on the Pain Intensity NRS, ranging from 0 (“None”) to 10 (“Worst Pain Imaginable”) with EN3835 vs placebo. |
| To assess subject satisfaction with EN3835 treatment vs placebo. | The difference in the proportion of subjects treated with EN3835 or placebo reporting to be “Satisfied” (+1) and “Very Satisfied” (+2) on the Subject Satisfaction With Treatment Scale, a 5-point scale ranging from −2 (“Very Dissatisfied”) to +2 (“Very Satisfied”) on Days 15, 29, 43, and 57. |
| To assess the improvement with EN3835 vs placebo in the FFI-PF-May 2021 activity limitation subscale in subjects on the activity limitation subscale at baseline. | The difference between EN3835 and placebo in the mean change from Baseline (Day 1) to Day 57 on the activity limitation subscale (total score on 3 items) of the FFI-PF-May 2021, ranging from 0 (“Never”) to 4 (“Always”). |

TABLE 43-continued

| Objective | Endpoint |
|---|---|
| | The mean change from Baseline (Day 1) to Days 15, 29, 43, and 57 on the activity limitation subscale (total score on 3 items) of the FFI-PF-May 2021, ranging from 0 ("Never") to 4 ("Always") with EN3835 vs placebo. |
| To assess the improvement with EN3835 vs placebo in the FFI-PF-May 2021 difficulty subscale in subjects on the difficulty subscale at baseline. | The difference between EN3835 and placebo in the mean change from Baseline (Day 1) to Day 57 on the difficulty subscale (total score on 9 items) of the FFI-PF-May 2021, ranging from 0 ("No Difficulty") to 4 ("A Lot of Difficulty"). |
| | The mean change from Baseline (Day 1) to Days 15, 29, 43, and 57 on the difficulty subscale (total score on 9 items) of the FFI-PF-May 2021, ranging from 0 ("No Difficulty") to 4 ("A Lot of Difficulty") with EN3835 vs placebo. |
| To assess the change in nodule size after administration of EN3835 vs placebo. | The difference between EN3835 and placebo in the mean change from Baseline (Day 1) to Day 57 in the size of the treated nodules by caliper measurements. |
| | The mean change from Baseline (Day 1) to Days 15, 29, 43, and 57 in nodule size with EN3835 vs placebo. |
| To assess the change in nodule consistency (by palpation) after administration of EN3835 vs placebo. | The difference between EN3835 and placebo in the change in consistency from Baseline (Day 1) to Day 57 as determined by the number of subjects with a soft or non-palpable consistency at Day 57. |
| | The change from Baseline (Day 1) to Days 15, 29, 43, and 57 in nodule consistency with EN3835 vs placebo. |

Inclusion and Exclusion Criteria

To be eligible to participate in the study, the subject must meet the following criteria:

Age and Sex:

1. Be an ambulatory male or female ≥18 years of age.

Disease Characteristics:

2. Has a diagnosis of plantar fibromatosis AND have at least 1 hard or firm, palpable fibrous nodule on clinical examination and measurable by caliper.
3. Has a score of at least 50% on the pain subscale of the FFI-PF-May 2021 (maximum score of 28 [without orthotics] or 36 [with orthotics] as applicable).
4. Requires ≤4 injections (1.8 mg maximum total dose) per treatment visit.
   a. For subjects with bilateral plantar fibromatosis, has a nodule configuration requiring ≤2 injections per foot (0.9 mg maximum dose per foot) based on the total count and size of all plantar nodules present.
   b. For subjects with unilateral plantar fibromatosis, has a nodule configuration requiring ≤3 injections (1.35 mg maximum dose per foot), based on the total count and size of plantar nodules.
5. Has no significant medical history or examination findings related to the subject's plantar nodule(s), which would make the subject unsuitable for study intervention administration.
6. To Receive Treatment Visit 2 only: The subject may receive additional treatment if the subject has a palpable (e.g., hard, firm, or soft) previously treated nodule on clinical examination and measurable by caliper.

Type of Subject:

7. Agree not to use opioids (e.g., codeine, heroin, hydrocodone, hydromorphone, morphine, oxycodone) during the study period and has not used opioids 2 weeks before the Screening Visit.
8. Agree to not initiate or change use of orthotics or inserts designed to relieve symptoms of plantar fibromatosis during the study period.
9. If female, be of non-childbearing potential; or, if of childbearing potential, be nonpregnant, non-lactating and agree to use effective contraception for the duration of the study and for 28 days after any active treatment period.

A subject is ineligible for study participation if the subject meets any of the following criteria:

Medical Conditions:

1. Has the presence of non-plantar fibromatosis-related nodules on the foot/feet (e.g., neurofibroma, rhabdomyosarcoma, liposarcoma, neurilemmomas, rheumatoid nodules, desmoid tumors, or malignant soft tissue lesions of the foot or ankle).
2. Has any musculoskeletal, neuromuscular, neurosensory, other neurological or related disorder that affects the subject's use of his or her feet and/or would impair his/her completion of study assessments as determined by the investigator.
3. Has a known systemic allergy to collagenase or any other excipient of EN3835.
4. Has a known bleeding disorder which would make the subject unsuitable for enrollment in the study.
5. Has a clinically significant laboratory abnormality or any laboratory test results meeting any of the following criteria:
   a. alanine aminotransferase (ALT)≥3×upper limit of normal (ULN)
   b. total bilirubin (TBL)≥2×ULN (>35% direct bilirubin)
   c. aspartate aminotransferase (AST)≥3×ULN
   d. international normalized ratio (INR)>1.5

6. Has concurrent diseases that might interfere with the conduct of the study, confound the interpretation of the study results, or endanger the subject's well-being or any significant hematological, endocrine, cardiovascular, respiratory, renal, hepatic, or gastrointestinal disease.
7. Any other significant medical condition(s), which in the investigator's opinion would make the subject unsuitable for enrollment in the study.
8. Is pregnant or plans to become pregnant, or is breast-feeding, or is providing or plans to provide breast milk in any manner during the study.

Prior/Concomitant Therapy:

9. Received surgical or non-surgical treatment(s) (e.g., steroid injection, transdermal/intralesional verapamil, radiation therapy, extracorporeal shock wave therapy) on the foot or nodule(s) to be treated within 3 months before administration of study intervention.
10. Has received any collagenase treatment (e.g., Santyl® ointment, XIAFLEX®/XIAPEX® EN3835, or CCH) within 30 days prior to Day 1.
11. Is currently receiving, has received (within 7 days of the first treatment of study intervention), or plans to receive any anticoagulant or antiplatelet medication (except for ≤150 mg aspirin daily) that would increase the risk of bleeding during the study.

Prior/Concurrent Clinical Study Experience:

12. Participation in other studies involving an investigational drug within 30 days before treatment with study intervention and/or during study participation.

Efficacy Assessments

Nodule Assessments

Anatomical Representation of Nodule Location—At Screening, Days 1, 29, and 57 Visits, a graphic representation of the foot/feet will be completed and the location(s) of the nodule(s) treated.

Consistency of the Selected Nodule—At select time points, the selected nodule will be palpated, the consistency of the nodule will be determined, and the nodule will be classified as follows:

Hard (no give)—given a value of 4;

Firm throughout (a little resistance)—given a value of 3;

Moderately firm (some resistance)—given a value of 2;

Soft (no resistance)—given a value of 1;

Non-palpable—given a value of 0.

For the first treatment, only hard or firm nodules will be treated. For the second treatment, previously treated nodules (Day 1) that are either hard, firm, or soft are eligible for retreatment.

Caliper Measurements of the Selected Module—At select time points, a surgical marker will be used to outline the circumference of the selected nodule. After the nodule has been marked, a handheld caliper will be used to measure the length and width of the selected nodule, and nodule measurements will be recorded. Gross observations will be solicited from the investigator at each time of examination.

Durometer Measurements—A durometer will be used to measure changes in nodules during the study. At select time points, a Type OO Shore Durometer will be used to measure the hardness of each of the selected nodule, on a scale ranging from 0 to 100, and the nodule hardness measurements will be recorded.

Patient-Reported Outcome Assessments

The order of scale completion by the subject is as follows: FFI-PF-May 2021, PGIS Foot Pain Subscale, PGIC Foot Pain Subscale, PGIS Difficulty Subscale, PGIC Difficulty Subscale, PGIS Activity Limitation Subscale, PGIC Activity Limitation Subscale, PGIS-PF Overall, PGIC PF Overall, Pain Intensity NRS, and Subject Satisfaction with Treatment Scale. Foot Function Index The Foot Function Index (FFI) scale for use in Study EN3835-105 was adapted from the Foot Function Index-Short Form-23 (FFI-SF-23) for use in plantar fibromatosis. The FFI-SF-23 is a total foot function assessment instrument (as described in Budiman-Mak et. al., 1991; Budiman-Mak et. al., 2013) comprising 23 items used to assess foot pain, disability, and difficulty in subjects with ankle and foot disorders.

Concept elicitation and cognitive interviews were conducted with subjects with plantar fibromatosis (n=19) using the FFI-SF-23 to confirm content validity and to confirm that the measure was understandable and relevant in this population. The feedback from the interviews, in combination with FDA feedback resulted in minor revisions to the instrument, which produced a 21-item version, the FFI-PF-May 2021, which will be used in this study. This pain subscale of the FFI-PF-May 2021 will be used in this study in the assessment of the primary endpoint. Additional cognitive interviews (n=7) were conducted, focused specifically on the changes present in the FFI-PF-May 2021, to confirm content validity and comprehension of the FFI-PF-May 2021. Based on the second round of cognitive interviews, subjects felt that the FFI-PF-May 2021 applied to them and did not recommend changes to the items or response options, therefore no additional changes were made to the FFI-PF-May 2021.

At select time points, each subject will be asked to complete the FFI-PF-May 2021, which assesses the impact of foot pathology on 3 domains of pain, difficulty, and activity limitation. The subject will complete the scale prior to evaluation by the investigator.

The activity limitation subscale of the FFI-PF-May 2021 consists of the following 3 items and measures limitations in activities because of the subject's feet in the past week, such as staying off one foot or both feet:

1. Stay indoors most of the day because of foot problems?
2. Stay off one or both of my feet most of the day because of foot problems?
3. Limit your activities because of your foot problems?

The activity limitation subscale of the FFI-PF-May 2021 is scored on a 5-point verbal rating scale as follows:

0—Never
1—Rarely
2—Sometimes
3—Often
4—Always

The difficulty subscale of the FFI-PF-May 2021 consists of 9 items and measures difficulty performing various functional activities because of the subject's feet in the past week, such as difficulty climbing stairs:

1. Walking around the house?
2. Walking outside on uneven ground?
3. Walking four or more blocks?
4. Climbing stairs?
5. Descending stairs?
6. Standing on tiptoes?
7. Getting out of a chair?
8. Climbing up or down curbs?
9. Walking or running fast?

The difficulty subscale of the FFI-PF-May 2021 is scored on a 5-point verbal rating scale as follows:

0—No difficulty
1—A little difficulty
2—Some difficulty

3—Much difficulty

4—A lot of difficulty

The pain subscale of the FFI-PF-May 2021 consists of 9 items and measures the severity of foot pain during the past week in different situations, such as walking barefoot versus walking with shoes:

1. At its worst?
2. Before you get up in the morning?
3. When you walk barefoot?
4. When you stand barefoot?
5. When you walk wearing shoes?
6. When you stand wearing shoes?
7. When you walk wearing orthotics? (or do not wear orthotics)
8. When you stand wearing orthotics? (or do not wear orthotics)
9. At the end of the day?

For the pain subscale of the FFI-PF-May 2021, if the subject marks "does not wear orthotics" items pertaining to orthotics are not scored and are not included in the total score. The pain subscale of the FFI-PF-May 2021 is scored on a 5-point verbal rating scale as follows:

0—None

1—Mild

2—Moderate

3—Severe

4—Extreme

Patient Global Impression of Severity (PGIS)

A single global item PGIS scale will be used for overall severity of plantar fibromatosis. Additional PGIS subscales will measure the overall severity of foot pain, difficulty, and activity limitation.

Overall—At select time points, each subject will be asked to describe the severity of plantar fibromatosis in the past week on a 5 point scale ranging from 0 ("None") to 4 ("Severe"):

0 None

1 Minimal

2 Mild

3 Moderate

4 Severe

Foot Pain—At select time points, each subject will be asked to describe the overall severity of foot pain in the past week on the same 5 point scale ranging from 0 ("None") to 4 ("Severe").

Difficulty—At select time points, each subject will be asked to describe the overall difficulty had with their foot or feet doing physical activities (e.g., walking, running, going up and down stairs and curbs) in the past week on the same 5 point scale ranging from 0 ("None") to 4 ("Severe").

Activity limitation—At the specified time points, each subject will be asked to describe the overall limitations in the daily activities experienced in the past week on the same 5 point scale ranging from 0 ("None") to 4 ("Severe").

Patient Global Impression of Change (PGIC)

A single global item PGIC scale will be used for overall impression of change in plantar fibromatosis. Additional PGIC subscales will measure the overall impression of change in the severity of foot pain, difficulty with the foot/feet, and activity limitation due to the feet.

Overall—At select time points, each subject will be asked to describe the change in the overall severity of plantar fibromatosis in the past week on a 7-point scale, ranging from −3 ("Very Much Worse") to +3 ("Very Much Improvement") as follows:

−3 Very Much Worse

−2 Much Worse

−1 Minimally Worse

0 No Change

+1 Minimal Improvement

+2 Much Improvement

+3 Very Much Improvement

Foot Pain Subscale—At select time points, each subject will be asked to describe the change in the overall severity of foot pain experienced in the past week on the same 7-point scale, ranging from −3 ("Very Much Worse") to +3 ("Very Much Improvement").

Difficulty Subscale—At select time points, each subject will be asked to describe the change in the overall difficulty with the foot or feet doing physical activities (e.g., walking, running, going up and down stairs and curbs) in the past week on the same 7-point scale, ranging from −3 ("Very Much Worse") to +3 ("Very Much Improvement").

Activity Limitation Subscale—At select time points, each subject will be asked to describe the change in the overall limitations in the daily activities experienced in the past week on the same 7-point scale, ranging from −3 ("Very Much Worse") to +3 ("Very Much Improvement").

Pain Intensity Numerical Rating Scale (NRS)

A single item NRS will be used to capture the intensity for foot pain related to plantar fibromatosis.

At select time points, each subject will be asked to describe the worst severity of foot pain in the past week, ranging from 0 (No Pain) to 10 (Worst Pain Imaginable).

Subject Satisfaction with Treatment Scale

At select time points, each subject will be asked to rate his/her satisfaction with treatment of their nodule(s) per treated foot on a 5-point scale ranging from −2 ("Very Dissatisfied") to +2 ("Very Satisfied") as follows:

−2 Very Dissatisfied

−1 Quite Dissatisfied

0 Neither Satisfied nor Dissatisfied

+1 Quite Satisfied

+2 Very Satisfied

Investigator Assessments

Clinician Global Impression of Scale Change

At select time points, the investigator will determine the degree of improvement with treatment per each foot on a 7-point scale ranging from −3 ("Very Much Worse") to +3 ("Very Much Improvement") as follows:

−3 Very Much Worse

−2 Much Worse

−1 Minimally Worse

0 No Change

+1 Minimal Improvement

+2 Much Improvement

+3 Very Much Improvement

Statistical Considerations and Methods

Populations for Analysis

For the purposes of analysis, the following populations are defined:

The Safety Population will include all subjects who receive at least 1 injection of EN3835 or placebo. All safety and immunogenicity analyses will be based on the Safety Population.

The Intent-to-Treat (ITT) Population will include all randomized subjects. Treatment group assignment will be based on the randomized treatment. The ITT population will be used for analysis of the primary and secondary endpoints.

The Full Analysis Set (FAS) Population will include all ITT subjects who receive at least 1 injection of EN3835 or Placebo and have at least 1 post injection FFI-PF-May 2021 pain subscale measures. Treatment group assignment will be based on the randomized treatment. This population will be used for analysis of the primary and secondary endpoints.

The modified Intent-to-Treat (mITT) Population will include all ITT subjects who receive at least 1 injection of EN3835 or Placebo and have both baseline and at least one post injection FFI-PF-May 2021 pain subscale measures. The treatment group assignment will be based on the randomized treatment. This population will be used for analysis of the primary, secondary and exploratory endpoints.

Efficacy Analysis

The ITT population will be the primary population for the efficacy analysis. Efficacy analyses will also be performed for the FAS and mITT populations as supportive analyses. For the data collected at nodule level, the analyses will be performed at subject level and nodule level. The data interpretation will be based on subject level results. The nodule level results will be supportive.

Primary Analysis

Primary Estimand—The primary estimand is defined as follows. In subjects with plantar fibromatosis, what is the difference in mean change from baseline (Day 1) to Day 57 in foot pain score (as measured with the FFI-PF-May 2021 pain subscale) between EN3835 and placebo after 57 days of randomization, regardless of discontinuation of study intervention?

The primary estimand will be based the data at Baseline and Day 57 after randomization. Therefore subjects who withdraw from the study will be encouraged to complete the remaining study visits and evaluations and provide any additional follow-up information as required by the study. In cases where the subjects do not have FFI-PF-May 2021 pain subscale score at Day 57 due to early study discontinuation, the missing values will be imputed before the analysis using a multiple imputation washout model.

After imputation, the changes from Baseline to Day 57 will be analyzed using an ANCOVA model with treatment group as fixed effect, FFI-PF-May 2021 pain subscale at baseline, the nodule size and the number of nodules as covariates. The summary measure, least squares (LS) mean estimate for treatment difference between EN3835 and placebo and their corresponding 95% confidence intervals (CIs) will be reported.

A sensitivity analysis will be performed based all observed data up to Day 57 after randomization. The changes from Baseline will be analyzed using a mixed effect model for repeated measures (MMRM). This MMRM model will include treatment group, study visit, treatment by visit interaction as fixed effects, and the covariates of the baseline score, nodule size and the number of nodules. The repeated measure is the subject visits. The dependent variable will be the change from the Baseline at each visit. The summary measure, LS mean estimate for treatment difference at Day 57 between EN3835 and placebo and their corresponding 95% CIs will be reported.

Another sensitivity analysis using MMRM with imputation of missing values for withdrawn subjects. The missing values will be imputed using a control-based pattern mixture model. The MMRM model used will be the same as previously described.

The FFI-PF-May 2021 pain subscales, and their changes from Baseline will be summarized by study visit (if applicable) and treatment group using appropriate descriptive statistics.

Secondary and Exploratory Analyses

All secondary and exploratory endpoints will be summarized by study visit (if applicable) and treatment group using appropriate descriptive statistics.

Key Secondary Endpoint 1 has been defined as: The difference of mean change from baseline to Day 57 for FFI-PF-May 2021 Pain and Difficulty combined score between EN3835 and placebo.

Key Secondary Estimand 1: In subjects with plantar fibromatosis, what is the difference in mean change from baseline to Day 57 in foot pain and difficulty combined score (as measured with combined score of the FFI-PF-May 2021 pain subscale and the FFI-PF-May 2021 difficulty subscale) between EN3835 and Placebo after 57 days of randomization, regardless of discontinuation of study intervention?

This estimand will be based on the data at Baseline and Day 57 after randomization. Therefore subjects who withdraw from the study will be encouraged to complete the remaining study visits and evaluations and provide any additional follow-up information as required by the study. In case where the subjects do not have FFI-PF-May 2021 pain/Difficulty subscales at Day 57 due to early study discontinuation, the missing values will be imputed before the analysis using a multiple imputation washout model. The imputation and the analysis methods are similar to the primary estimand. The summary measure, LS mean estimate for treatment difference between EN3835 and placebo and the corresponding 95% CIs will be reported.

Sensitivity analyses used for primary analysis will also be performed for the change from Baseline in FFI-PF-May 2021 Pain/Difficulty Subscale combined score.

Key Secondary Endpoint 2: The Difference in the Proportion of Subjects Treated with EN3835 or Placebo Reporting to be "Satisfied" (+1) and "Very Satisfied" (+2) on the Subject Satisfaction with Treatment Scale at Day 57

Key Secondary Estimand 2: In subjects with plantar fibromatosis, what is the difference in the proportion of subjects with an improvement (as measured with subjects reporting to be "Satisfied" (+1) and "Very Satisfied" (+2) on the Subject Satisfaction With Treatment Scale) between EN3835 and Placebo at Day 57 after randomization, regardless of study withdrawal?

The proportions (response rates) will be compared between treatment groups using the Cochran-Mantel-Haenszel method. All subjects who withdrew early from the study will be considered as non-responders. The responder is defined as a subject who reports a score to be "Satisfied" (+1) and "Very Satisfied" (+2) on the Subject Satisfaction with Treatment Scale at Day 57

Key Secondary Endpoint 3: The Difference of Mean Changes from Baseline to Day 57 for Hardness Measurements Between EN3835 and Placebo.

Key Secondary Estimand 3: In subjects with plantar fibromatosis, what is the difference in mean change from baseline to Day 57 in hardness measurements (as measured by durometer) between EN3835 and placebo after 57 days of randomization, regardless of discontinuation of study treatment?

This estimand will be based the data at Baseline and Day 57 after randomization. The imputation and the analysis methods are similar to the primary estimand. The summary measure, LS mean estimates for treatment difference between EN3835 and placebo, and the corresponding 95% CIs will be reported.

The other secondary endpoints, including the mean changes from Baseline (Day 1) to study visits (Days 15, 29, 43 and 57) for FFI-PF-May 2021-Pain and -Difficulty combined score, FFI-PF-May 2021-pain subscale, FFI-PF-May 2021-difficulty subscale, and FFI-PF-May 2021-activity limitation subscale, FFI-PF-May 2021-total score, Pain intensity NRS, nodule size, and hardness measurement will be analyzed using the MMRM method based on observed data and imputed data using control based PMM model. The LS mean estimates for the treatment difference at each visit and their corresponding 95% CIs will be reported.

The PGIS (overall, pain, difficulty, and activity limitation subscales) scores at each study visit (Days 15, 29, 43, and 57) will be compared between treatment groups using a rank based analysis. The Hodges-Lehmann estimator and its 95% CIs will be provided to represent the median difference/location shift between the treatment groups.

In addition, response rates for the PGIC for PF overall and each individual subscale, subject satisfaction with treatments, Clinician Global Impression of Change Scale, and nodule consistency will be compared between treatment groups using the Cochran-Mantel-Haenszel method.

Safety Analyses

All subjects who receive at least 1 injection of study intervention will be included in the safety analyses. Subjects will be included in the safety analyses based on the actual treatment received.

Adverse Events

Adverse event (AE) analysis by treatment group will include the incidence of AEs, AEs resulting in drug discontinuation, AEs leading to study withdrawal, SAEs, and AESIs. Summaries of AEs will be provided including the number and percentage of subjects who experienced at least 1 AE. These summaries will be presented by system organ class (SOC) and preferred term (PT). The occurrence of AEs will also be tabulated by severity. SAEs and AEs resulting in study withdrawal will be summarized separately by treatment group.

Multiplicity Adjustment

The significance tests for key secondary endpoints will be conducted in sequential order to preserve the overall type-I error rate <0.05 according to the following order 1) Key secondary endpoint 1
2) Key secondary endpoint 2
3) Key secondary endpoint 3

Testing of the first key secondary endpoint will be conducted if the results of the primary endpoint are statistically significant. Testing of these key secondary endpoints will be conducted in a hierarchical manner until p value >0.05.

No multiplicity adjustment will be made on other secondary endpoints and exploratory endpoints. The nominal p-values will be reported for those endpoints.

Handling of Missing Data

Before the primary efficacy analysis, the missing values due to subject withdrawal from the study will be imputed using a multiple imputation washout model. The washout model will be performed on actual values, i.e., FFI-PF-May 2021 pain subscale. The changes from baseline will be calculated after the imputation.

In addition, sensitivity analyses using MMRM without multiple imputation and a control-based pattern mixture model (PMM) will be performed on the primary and key secondary efficacy endpoints (if applicable) to assess the impact of missing values.

No imputation will be performed for all non-specified secondary and exploratory endpoints. The analyses for those endpoints will be based on observed data.

Adverse Events and Serious Adverse Events

An adverse event (AE) is any unfavorable or unintended change in body structure (signs), body function (symptoms), laboratory result (e.g., chemistry, ECG, X-ray, etc.), or worsening of a preexisting condition associated temporally with the use of the study intervention whether or not considered related to the study intervention. Any medical condition or laboratory abnormality already present at screening or baseline should be reported as medical history. If the medical condition present at baseline changes in severity or seriousness at any time during the study, it should be reported as an AE. AEs include:

- Changes in the general condition of the subject.
- Subjective symptoms offered by or elicited from the subject.
- Objective signs observed by the investigator or other study personnel.
- All concurrent diseases and/or medical occurrences that occur after the start of the study, including any change in severity or frequency of pre-existing disease.
- All clinically relevant laboratory abnormalities or physical findings that occur during the study.

A treatment-emergent adverse event (TEAE) is any condition that was not present prior to treatment with study intervention but appeared following treatment, was present at treatment initiation but worsened during treatment, or was present at treatment initiation but resolved and then reappeared while the individual was on treatment (regardless of the intensity of the AE when the treatment was initiated).

A serious adverse event (SAE) is defined as an AE that:

- Results in death
- Is immediately life-threatening (there is an immediate risk of death from the AE as it occurred; this does not include an AE that had it occurred in a more serious form may have caused death)
- Results in or prolongs an inpatient hospitalization
- Results in permanent or substantial disability (permanent or substantial disruption of one's ability to conduct normal life functions)
- Is a congenital anomaly/birth defect (in offspring of a subject who received study intervention regardless of time to diagnosis)
- Is considered an important medical event Important medical events are defined as events that, based upon appropriate medical judgment, may jeopardize the subject and may require medical or surgical intervention to prevent one of the other serious outcomes. Examples of important medical events include any cancer, allergic bronchospasm requiring intensive treatment in an emergency room or at home, blood dyscrasias or convulsions that do not result in inpatient hospitalization, or the development of drug dependency or drug abuse.

Relationship to Study Intervention

The degree of "relatedness" of the AE to study intervention must be described using the following scale:

- Not related indicates that the AE is definitely not related to study intervention.
- Unlikely related indicates that there are other, more likely causes and study intervention is not suspected as a cause.
- Possibly related indicates that a direct cause and effect relationship between study intervention and the AE has not been demonstrated, but there is evidence to suggest there is a reasonable possibility that the event was caused by study intervention
- Probably related indicates that there is evidence suggesting a direct cause and effect relationship between the AE and EN3835.

Intensity Assessment

The intensity (or severity) of AEs is characterized as Grades 1 to 5 according to the Common Terminology Criteria for Adverse Events (CTCAE) Version 5.0. For the AEs not directly referenced in CTCAE, such events will be assessed using the below categories as a guide:

Grade 1 Mild; asymptomatic or mild symptoms; clinical or diagnostic observations only; intervention not indicated.

Grade 2 Moderate; Minimal, local, or noninvasive intervention indicated; limiting age-appropriate instrumental activities of daily living (ADL) (Instrumental ADL refer to preparing meals, shopping for groceries or clothes, using the telephone, managing money, etc.).

Grade 3 Severe or medically significant but not immediately life-threatening; hospitalization or prolongation of hospitalization indicated; disabling; limiting self-care activities of daily living (Self-care ADL refer to bathing, dressing and undressing, feeding self, using the toilet, taking medications, and not bedridden).

Grade 4 Life-threatening consequences; urgent intervention indicated

Grade 5 Death related to AE.

Results

Although the Study was originally designed to enroll subjects having at least 1 hard or firm palpable fibrous nodule, 35 subjects having at least 1 "moderately firm" palpable fibrous nodule were included in the Study as shown in Table 44.

TABLE 44

Nodular consistency

| | Statistic | EN3835 (N = 88) | Placebo (N = 88) | Overall (N = 176) |
|---|---|---|---|---|
| Nodular Consistency | | | | |
| Hard | n (%) | 37 (42.0) | 42 (47.7) | 79 (44.9) |
| Moderately Firm | n (%) | 18 (20.5) | 17 (19.3) | 35 (19.9) |
| Firm Throughout | n (%) | 32 (36.4) | 28 (31.8) | 60 (34.1) |
| Soft | n (%) | 0 (0.0) | 0 (0.0) | 0 (0.0) |
| Non-palpable | n (%) | 0 (0.0) | 0 (0.0) | 0 (0.0) |
| Missing | n (%) | 1 (1.1) | 1 (1.1) | 2 (1.1) |

Efficacy Evaluation

Efficacy Results and Tabulations of Individual Participant Data

Analysis of Efficacy

The analysis of efficacy in this study included changes from Baseline and differences between the EN3835 and placebo treatment groups in the FFI Composite score and the FFI subscales (Pain, Difficulty, and Activity Limitation), the PGIS Overall Scale and the PGIS Subscales (Foot Pain, Difficulty, and Activity Limitation), PGIC Overall and the PGIC Subscales (Foot Pain, Difficulty, and Activity Limitation), Pain Intensity NRS, Participant Satisfaction with Treatment, change in nodule size and change in nodule consistency.

Primary Endpoint

The primary endpoint in this study was the difference between EN3835 and placebo in the mean change from Baseline (Day 1) to Day 57 on the Foot Pain Subscale (total score on 9 items) of the FFI ranging from 0 ("None") to 4 ("Extreme"). At Baseline (Day 1), the mean (SD) scores on the FFI Total Pain Subscale were similar between the EN3835 and placebo treatment groups. At Day 57, while the mean Total Foot Pain Subscale score decreased (improved) in the EN3835 (LSM [SE], −9.844 [0.91]) and in the placebo treatment groups (LSM [SE], −8.417 [0.89]), the difference was not significant (LSM difference, −1.427; 95% CI, −3.985 to 1.131; p=0.274).

TABLE 45

ANCOVA Estimates of Mean Change from Baseline to EOS (Day 57) on FFI Total Pain Subscale Score by Treatment Group (ITT Population)

| Visit | LSM Change from Baseline (SE) [a] EN3835 | LSM Change from Baseline (SE) [a] Placebo | Estimated LSM Treatment Difference between EN3835-Placebo [b] Difference (LCL, UCL) | p value [b] |
|---|---|---|---|---|
| Day 57 | −9.844 (0.91) | −8.417 (0.89) | −1.427 (−3.985, 1.131) | 0.274 |

[a] ANCOVA was performed to estimate the LSM change from Baseline in the Foot Pain Subscale for EN3835 and placebo treatment

[b] The treatment effect and 95% CI for comparing EN3835 with placebo was estimated using ANCOVA with treatment group as fixed effect, FFI Pain Subscale at Baseline, the maximum of nodule length/nodule width and the total number of treated nodules as covariates.

Note:

ANCOVA was performed on imputed data using multiple washout model.

The results of a sensitivity analysis based on the observed data (not imputed) in the ITT Population using the MMRM was consistent with the primary analysis (p=0.154). The results of supportive analyses in the mITT and FAS Populations were also non-significant at Day 57 (p=0.252).

Secondary Endpoints

Key Secondary Endpoint 1: Mean Change from Baseline to Day 57 on FFI Total Combined (Pain and Difficulty) Score At Baseline (Day 1) the mean (SD) scores on the FFI Total Combined (Pain and Difficulty) Subscales were similar between the EN3835 and placebo treatment groups. At Day 57, while the mean FFI Combined Pain and Difficulty Subscale scores decreased (improved) from Baseline in the EN3835 (LSM [SE] −19.145 [1.893]) and placebo treatment groups (LSM [SE] −16.530 [1.858]), the difference was not significant (LSM difference, −2.615; 95% CI, −7.927 to 2.698; p=0.335).

TABLE 46

ANCOVA Estimates of Change from Baseline to Day 57 on FFI Total Combined (Pain and Difficulty) Score by Treatment Group (ITT Population)

| Visit | LSM Change from Baseline (SE)[a] EN3835 | LSM Change from Baseline (SE)[a] Placebo | Estimated LSM Treatment Difference between EN3835-Placebo[b] Difference (LCL, UCL) | p value[b] |
|---|---|---|---|---|
| Day 57 | −19.145 (1.893) | −16.530 (1.858) | −2.615 (−7.927, 2.698) | 0.335 |

[a]ANCOVA was performed to estimate the LSM change from Baseline in the FFI pain and Difficulty (Combined) Subscale for EN3835 and placebo treatment.

[b]The treatment effect comparing EN3835 with placebo and 95% CI were estimated using ANCOVA with treatment group as fixed effect, FFI Pain and Difficulty (Combined) Subscale at Baseline, the maximum of nodule length/nodule width and the total number of treated nodules as covariates as covariates using the SAS Mixed procedure.

The results of a sensitivity analysis based on observed data (not imputed) using an MMRM in the ITT Population at Day 57 were consistent with the primary analysis (p=0.204). The results of supportive analyses in the FAS and mITT Populations were also non-significant (p=0.307).

Key Secondary Endpoint 2: Comparison of CGIC Scale Scores by Visit and Treatment Group The second key secondary endpoint was the difference in the proportion of EN3835-treated participants and those receiving only placebo reporting "Minimally Improved" (+1) "Much Improved" (+2) or "Very Much Improved" (+3) on the CGIC Scale, a 7-point scale ranging from −3 ("Very Much Worse") to +3 ("Very Much Improvement") on Days 15, 29, 43, and 57. A responder (by foot/feet) was defined as a participant with a response of "Minimal Improvement", "Much Improvement" or "Very Much Improvement" on the CGIC Scale.

CGIC was assessed for each treated foot. Given that CGIC was assessed for each treated foot, if a participant was treated for both feet, then the assessment was combined at a participant level using worst case approach. If a response was 'Minimal Improvement' recorded in one foot and 'Very Much Improvement' in another foot, then the response was considered 'Minimal Improvement.'

On a participant-level, there was significantly higher proportion of responders on the CGIC Scale on Day 57 in the EN3835 treatment group (61 of 88 participants; 69.3%; 95% CI 59.0 to 78.0) than in the placebo treatment group (48 of 88 participants; 54.5%; 95% CI 44.2 to 64.5) (p=0.044). CGIC scores on a foot level by treated foot and a participant level by treated foot are presented herein.

TABLE 47

Summary and Statistical Comparison of CGIC Scale at Day 57 and by Treatment Group on a Participant Level (ITT Population)

| Improvement Scale Ratings | Statistics | EN3835 (N = 88) | Placebo (N = 88) |
|---|---|---|---|
| Participant Level: Overall | | | |
| Day 57 | N | 81 | 83 |
| −3 (Very Much Worse) | n (%) | 1 (1.2) | 1 (1.2) |
| −2 (Much Worse) | n (%) | 0 (0.0) | 1 (1.2) |
| −1 (Minimally Worse) | n (%) | 4 (4.9) | 4 (4.8) |
| 0 (No Change) | n (%) | 15 (18.5) | 29 (34.9) |
| +1 (Minimal Improvement) | n (%) | 15 (18.5) | 16 (19.3) |
| +2 (Much Improvement) | n (%) | 27 (33.3) | 21 (25.3) |
| +3 (Very Much Improvement) | n (%) | 19 (23.5) | 11 (13.3) |
| | Mean (SD) | 1.5 (1.29) | 1.0 (1.28) |
| Responders [a] | n (%) | 61 (69.3) | 48 (54.5) |
| 95% CI [b] | (LCL, UCL) | (59.0, 78.0) | (44.2, 64.5) |
| Risk Difference (EN3835-Placebo) [c] | N | 14.8 | |
| 95% CI | (LCL, UCL) | (0.6, 29.0) | |
| p value (CMH test for General association) [d] | | | 0.044 |

[a] The responder (by foot/feet) was defined as a participant with a response of "Minimal Improvement", "Much Improvement" or "Very Much Improvement" in the CGIC Scale. All participants who withdrew early from the study are considered as non-responders. If participant was treated for both feet, then the assessment can be combined at the participant level using worst case approach, if one foot response recorded as 'Minimal Improvement' and 'Very Much Improvement' in another foot, then response was considered as 'Minimal Improvement'.

[b] Based on Wilson score method

[c] The risk difference is the difference in proportion of responders between EN3835 and Placebo.

[d] The p value derived from CMH test of general association.

Note:

Percentages are based on the number of participants treated at each treatment group and current visit.

CGIC Scale Rating scores by participant are presented herein.

To assess the impact of missing data, a TPA was conducted using a CMH by imputing missing values in a portion of participants as responders in the EN3835 and placebo treatment groups. Multiple combinations using a wide range for the shift parameters were applied in the TPA, and the tipping points were identified.

Supportive analyses in the FAS and mITT and Populations on a participant-level and on a foot-level were supportive of the primary analysis.

Key Secondary Endpoint 3: Change from Baseline to Day 57 in the Nodular Hardness The third key secondary endpoint was the difference of mean changes from Baseline to Day 57 for nodular hardness measurements between EN3835 and placebo. Nodule hardness was collected at nodule level, The average of all hardness measurements for nodules treated were used for data analyses and participant level data. At Baseline (Day 1), durometer measurements of nodular hardness were similar between the EN3835 and placebo treatment groups.

There was a significant difference in the improvement (decreases) in mean nodular hardness from Baseline to Day 57 between the EN3835 (LSM [SE] −13.537 [1.76]) and the placebo treatment groups (LSM [SE]) −7.660 [1.75]), favoring EN3835 treatment (LSM difference, −5.877; 95% CI, −10.847 to −0.908; p=0.020).

TABLE 48

ANCOVA Estimates of Mean Change from Baseline to Day 57 in the Nodular Hardness (Participant Level) by Treatment Group (ITT Population)

| Visit | LSM Change from Baseline (SE)[a] EN3835 | LSM Change from Baseline (SE)[a] Placebo | Estimated LSM Treatment Difference of EN3835-Placebo[b] Difference (LCL, UCL) | p value[b] |
|---|---|---|---|---|
| Day 57 | −13.537 (1.76) | −7.660 (1.75) | −5.877 (−10.847, −0.908) | 0.020 |

[a]ANCOVA was performed to estimate the LSM change from Baseline in the nodular hardness for EN3835 and placebo treatment.

[b]The treatment effect and 95% CI comparing EN3835 with placebo was estimated using ANCOVA with treatment group as fixed effect, average nodular hardness at Baseline, the maximum of nodule length/nodule width and the total number of treated nodules as covariates.

The results of a sensitivity analysis based on the observed data (not imputed) in the ITT Population using the MMRM was consistent with the primary analysis. There were significant differences in the mean nodule hardness at Day 57 favoring EN3835 treatment on a participant level (p=0.009) and a nodule level (p=0.001).

To assess the impact of missing data, a TPA was conducted using a CMH with a delta adjustment. Multiple combinations using a wide range for the shift parameters were applied in the TPA, but the tipping point was not identified within the ranges given that too few participants withdrew from the study.

Supportive analyses using an ANCOVA in the mITT and FAS Populations, showed that mean nodular hardness decreased (improved) from Baseline in the EN3835 (LSM [SE]) −13.588 [1.78]) and in the placebo groups (LSM [SE] −7.700 [1.75]). The difference between treatment groups at Day 57 was significant, favoring the EN3835 treatment group (LSM difference, −5.888; 95% CI, −10.921 to −0.856; p=0.022).

Other Secondary Endpoints

Change from Baseline on FFI Total Pain Subscale Score

Figure 17:
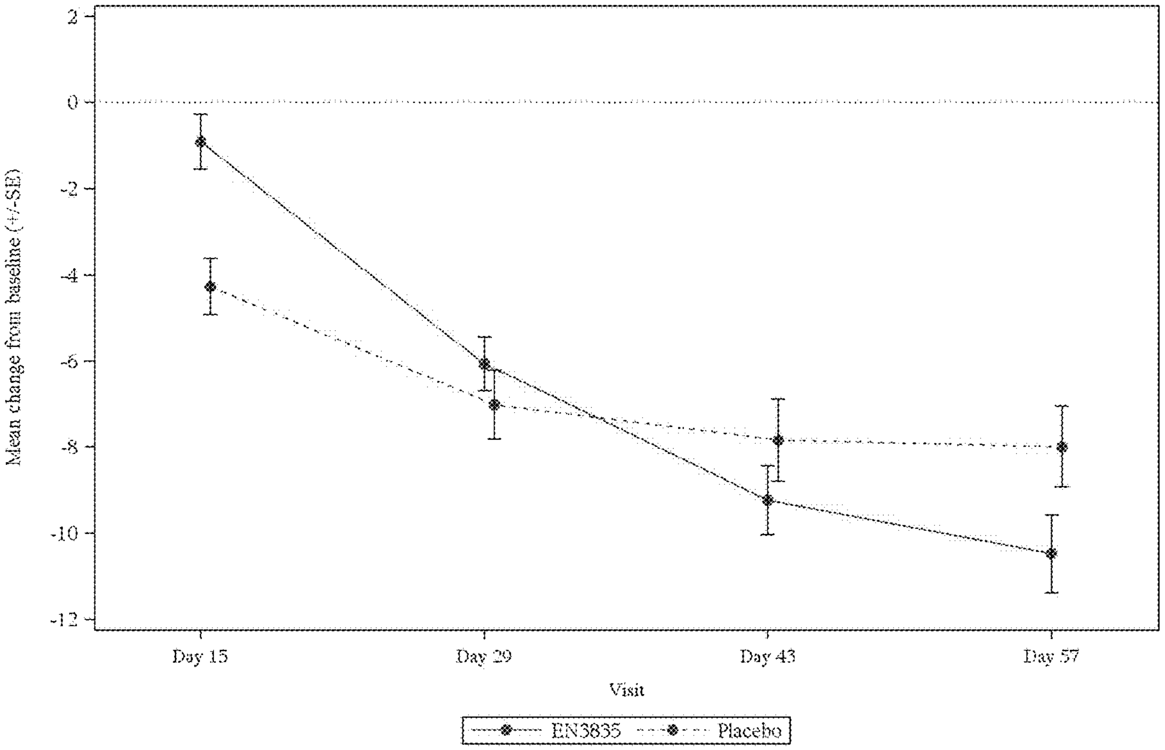
FIG. 17 illustrates the mean change from baseline on Total FFI Pain Subscale Score Based on observed data by visit and treatment group (ITT Population).

Overall, on Days 29, 43 and 57, the Total Pain Subscale score decreased (improved) in the EN3835 and the placebo treatment groups (FIG. 17). Changes from Baseline in the FFI Total Pain Subscale score for participants treated in their left foot only/or right foot only or both feet are presented herein.

TABLE 49

Mean Change from Baseline to EOS (Day 57) on FFI Total Pain Subscale Score Overall by Treatment Group (ITT Population)

| | | EN3835 (N = 88) | | Placebo (N = 88) | | Overall (N = 176) | |
|---|---|---|---|---|---|---|---|
| Overall Visit | Statistic | Observed Value | Change from Baseline[a] | Observed Value | Change from Baseline[a] | Observed Value | Change from Baseline[a] |
| Baseline[a] | n | 87 | | 87 | | 174 | |
| | Mean | 25.30 | | 24.84 | | 25.07 | |
| | SD | 5.199 | | 5.401 | | 5.291 | |
| | Median | 25.00 | | 24.40 | | 24.70 | |
| | Min | 15.0 | | 9.0 | | 9.0 | |
| | Max | 36.0 | | 36.0 | | 36.0 | |
| Day 15 | n | 84 | 84 | 82 | 82 | 166 | 166 |
| | Mean | 24.54 | −0.91 | 20.64 | −4.26 | 22.61 | −2.56 |
| | SD | 6.723 | 5.783 | 8.013 | 5.939 | 7.621 | 6.079 |
| | Median | 23.55 | −1.30 | 20.60 | −2.60 | 22.50 | −2.50 |
| | Min | 10.0 | −13.1 | 2.0 | −23.0 | 2.0 | −23.0 |
| | Max | 36.0 | 15.4 | 36.0 | 6.4 | 36.0 | 15.4 |
| Day 29 | n | 83 | 83 | 79 | 79 | 162 | 162 |
| | Mean | 19.40 | −6.07 | 18.00 | −7.02 | 18.72 | −6.53 |
| | SD | 7.935 | 5.791 | 8.106 | 7.161 | 8.025 | 6.492 |
| | Median | 19.30 | −5.20 | 18.00 | −6.40 | 18.00 | −5.60 |
| | Min | 3.9 | −20.5 | 0.0 | −33.0 | 0.0 | −33.0 |
| | Max | 36.0 | 3.9 | 36.0 | 7.7 | 36.0 | 7.7 |
| Day 43 | n | 77 | 77 | 81 | 81 | 158 | 158 |
| | Mean | 16.20 | −9.23 | 17.09 | −7.84 | 16.66 | −8.52 |
| | SD | 8.479 | 7.036 | 8.557 | 8.556 | 8.503 | 7.859 |
| | Median | 15.40 | −9.00 | 18.00 | −6.00 | 16.85 | −7.50 |
| | Min | 0.0 | −27.0 | 0.0 | −32.0 | 0.0 | −32.0 |
| | Max | 36.0 | 4.9 | 36.0 | 9.0 | 36.0 | 9.0 |
| Day 57/EOS/ET | n | 82 | 82 | 83 | 83 | 165 | 165 |
| | Mean | 15.01 | −10.47 | 16.80 | −7.99 | 15.91 | −9.22 |
| | SD | 9.132 | 8.160 | 8.661 | 8.551 | 8.916 | 8.426 |
| | Median | 14.05 | −9.30 | 18.00 | −6.40 | 16.70 | −9.00 |
| | Min | 0.0 | −27.0 | 0.0 | −30.0 | 0.0 | −30.0 |
| | Max | 36.0 | 3.9 | 36.0 | 10.3 | 36.0 | 10.3 |

[a]Baseline was defined as the last non-missing assessment prior to the study intervention injection on Day 1.

Note:

The Total Pain Subscale score is the sum of the scores of answered items normalized by a multiplying factor of 9/7 for participants who didn't wear orthotics.

Change from Baseline on FFI Total Pain Subscale Score Percent

Overall, on Days 29, 43 and 57, the Total Pain Subscale score percent decreased (improved) in the EN3835 and the placebo treatment groups. Changes from Baseline on the FFI Total Pain Subscale score percent in participants treated in their left foot only, or right foot only or both feet are presented herein.

A sensitivity analysis based on observed data (not imputed) was conducted using an MMRM in the mITT Population. The differences between treatment groups, favoring EN3835 treatment in the change from Baseline on the FFI Total Pain Subscale score were not significant.

TABLE 50

Observed and Mean Change from Baseline on FFI Pain Subscale Score (%) by Visit and Treatment Group (ITT Population)

| | | EN3835 (N = 88) | | Placebo (N = 88) | | Overall (N = 176) | |
|---|---|---|---|---|---|---|---|
| Treated Foot Visit | Statistic | Observed Value | Change from Baseline[a] | Observed Value | Change from Baseline[a] | Observed Value | Change from Baseline[a] |
| Overall | | | | | | | |
| Day 29 | n | 83 | 83 | 79 | 79 | 162 | 162 |
| | Mean | 53.899 | −16.853 | 50.003 | −19.491 | 51.999 | −18.139 |
| | SD | 22.0429 | 16.0865 | 22.5173 | 19.8926 | 22.2919 | 18.0349 |
| | Median | 53.610 | −14.440 | 50.000 | −17.780 | 50.000 | −15.555 |
| | Min | 10.83 | −56.95 | 0.00 | −91.67 | 0.00 | −91.67 |
| | Max | 100.00 | 10.83 | 100.00 | 21.39 | 100.00 | 21.39 |
| Day 43 | n | 77 | 77 | 81 | 81 | 158 | 158 |
| | Mean | 45.010 | −25.642 | 47.462 | −21.780 | 46.267 | −23.662 |
| | SD | 23.5525 | 19.5458 | 23.7680 | 23.7677 | 23.6198 | 21.8297 |

TABLE 50-continued

Observed and Mean Change from Baseline on FFI Pain Subscale Score (%) by Visit and Treatment Group (ITT Population)

| Treated Foot Visit | Statistic | EN3835 (N = 88) Observed Value | EN3835 (N = 88) Change from Baseline[a] | Placebo (N = 88) Observed Value | Placebo (N = 88) Change from Baseline[a] | Overall (N = 176) Observed Value | Overall (N = 176) Change from Baseline[a] |
|---|---|---|---|---|---|---|---|
| | Median | 42.780 | −25.000 | 50.000 | −16.670 | 46.805 | −20.835 |
| | Min | 0.00 | −75.00 | 0.00 | −88.89 | 0.00 | −88.89 |
| | Max | 100.00 | 13.61 | 100.00 | 25.00 | 100.00 | 25.00 |
| Day 57/EOS/ET | n | 82 | 82 | 83 | 83 | 165 | 165 |
| | Mean | 41.704 | −29.085 | 46.656 | −22.206 | 44.195 | −25.625 |
| | SD | 25.3678 | 22.6669 | 24.0589 | 23.7542 | 24.7674 | 23.4050 |
| | Median | 39.030 | −25.830 | 50.000 | −17.780 | 46.390 | −25.000 |
| | Min | 0.00 | −75.00 | 0.00 | −83.34 | 0.00 | −83.34 |
| | Max | 100.00 | 10.83 | 100.00 | 28.61 | 100.00 | 28.61 |

[a]Baseline was defined as the last non-missing assessment prior to the study intervention injection on Day 1.
Note:
Subscale score = (sum of answered item scores/sum of maximum score of answered items) * 100.

Change from Baseline in Individual Item Scores on the FFI

The change from Baseline in the individual item scores on the FFI by left foot only or right foot only, both feet and overall, in the ITT Population are presented herein.

FFI individual item scores, Total Subscale scores, Subscale scores (%), FFI Total Composite scores, FFI Composite scores (%), FFI Total Combined (Pain and Difficulty) scores and the FFI Combined scores (%) are presented by participant herein.

Figure 15:
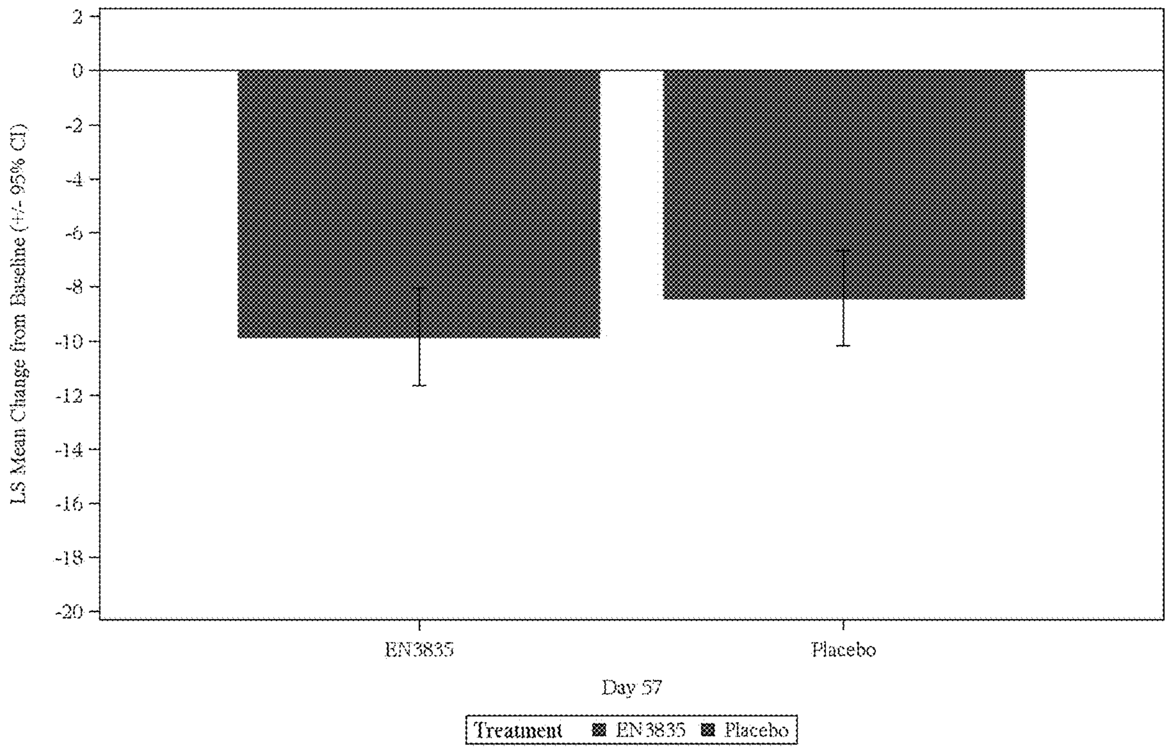
FIG. 15 illustrates the mean change from baseline to Day 57 on FFI Total Pain Subscale Score based on ANCOVA (Washout) by treatment group (ITT Population). The Total Pain Subscale score is the sum of the scores of answered items normalized by a multiplying factor of 9/7 for participants who didn't wear orthotics.
Figure 16:
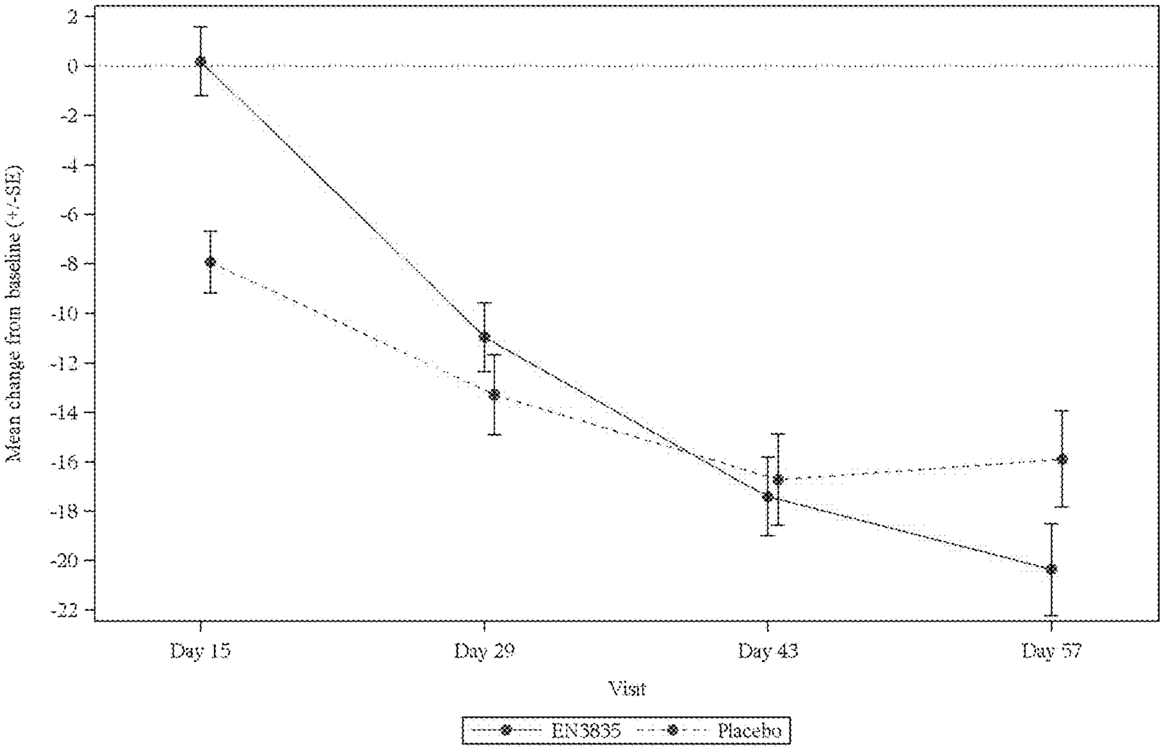
FIG. 16 illustrates the mean change from baseline on FFI Total Combined (Pain and Difficulty) Score based on observed data by visit and treatment group (ITT Population).

Change from Baseline to Each Visit on the FFI Total Combined (Pain and Difficulty) Score At Baseline (Day 1) the mean (SD) FFI Total Combined (Pain and Difficulty) Subscales scores were similar between the EN3835 and placebo treatment groups. The FFI Total Combined (Pain and Difficulty) scores decreased (improved) in both the EN3835 and placebo treatment groups during the study (FIG. 15). The mean (SD) change from Baseline to Day 57 was −20.361 (16.7527) in the EN3835 treatment group and −15.886 (17.6938) in the placebo treatment group. Change from Baseline on the FFI Total Combined (Pain and Difficulty) scores for participants treated in the left foot or right foot only or both feet are presented herein.

TABLE 51

Overall Observed and Change from Baseline on the FFI Total Combined (Pain and Difficulty) Score by Visit and by Treatment Group (ITT Population)

| Treated Foot Visit | Statistic | EN3835 (N = 88) Observed Value | EN3835 (N = 88) Change from Baseline[a] | Placebo (N = 88) Observed Value | Placebo (N = 88) Change from Baseline[a] | Overall (N = 176) Observed Value | Overall (N = 176) Change from Baseline[a] |
|---|---|---|---|---|---|---|---|
| Overall | | | | | | | |
| Baseline[a] | n | 87 | | 87 | | 174 | |
| | Mean | 50.036 | | 49.646 | | 49.841 | |
| | SD | 11.5532 | | 11.3135 | | 11.4025 | |
| | Median | 49.400 | | 50.700 | | 50.300 | |
| | Min | 24.00 | | 17.00 | | 17.00 | |
| | Max | 72.00 | | 72.00 | | 72.00 | |
| Day 15 | n | 84 | 84 | 82 | 82 | 166 | 166 |
| | Mean | 50.481 | 0.187 | 41.749 | −7.928 | 46.167 | −3.822 |
| | SD | 13.6232 | 12.6304 | 16.5927 | 11.3181 | 15.7382 | 12.6369 |
| | Median | 52.250 | −0.450 | 43.250 | −5.000 | 46.000 | −3.150 |
| | Min | 22.10 | −28.00 | 3.00 | −43.00 | 3.00 | −43.00 |
| | Max | 72.00 | 30.10 | 72.00 | 14.30 | 72.00 | 30.10 |
| Day 29 | n | 83 | 83 | 79 | 79 | 162 | 162 |
| | Mean | 39.464 | −10.959 | 36.482 | −13.282 | 38.010 | −12.092 |
| | SD | 17.0008 | 12.5837 | 17.0285 | 14.4256 | 17.0272 | 13.5212 |
| | Median | 42.000 | −10.000 | 37.000 | −10.000 | 38.650 | −10.000 |
| | Min | 5.90 | −38.50 | 2.00 | −66.00 | 2.00 | −66.00 |
| | Max | 72.00 | 10.50 | 71.00 | 13.30 | 72.00 | 13.30 |
| Day 43 | n | 77 | 77 | 81 | 81 | 158 | 158 |
| | Mean | 33.022 | −17.400 | 33.198 | −16.717 | 33.112 | −17.050 |
| | SD | 17.8108 | 14.0100 | 17.7929 | 16.6544 | 17.7451 | 15.3775 |
| | Median | 29.400 | −16.900 | 33.300 | −13.000 | 31.500 | −14.850 |
| | Min | 0.00 | −53.00 | 0.00 | −65.00 | 0.00 | −65.00 |
| | Max | 72.00 | 15.90 | 72.00 | 14.30 | 72.00 | 15.90 |

TABLE 51-continued

Overall Observed and Change from Baseline on the FFI Total Combined (Pain and Difficulty) Score by Visit and by Treatment Group (ITT Population)

| | | EN3835 (N = 88) | | Placebo (N = 88) | | Overall (N = 176) | |
|---|---|---|---|---|---|---|---|
| Treated Foot Visit | Statistic | Observed Value | Change from Baseline[a] | Observed Value | Change from Baseline[a] | Observed Value | Change from Baseline[a] |
| Day 57/EOS/ET | n | 82 | 82 | 83 | 83 | 165 | 165 |
| | Mean | 30.209 | −20.361 | 33.688 | −15.886 | 31.959 | −18.110 |
| | SD | 19.2486 | 16.7527 | 18.4716 | 17.6938 | 18.8849 | 17.3259 |
| | Median | 28.200 | −17.500 | 34.700 | −12.000 | 32.000 | −15.400 |
| | Min | 0.00 | −57.00 | 0.00 | −65.00 | 0.00 | −65.00 |
| | Max | 72.00 | 11.80 | 72.00 | 12.90 | 72.00 | 12.90 |

[a]Baseline was defined as the last non-missing assessment prior to the study intervention injection on Day 1.
Note:
Total Combined score is defined as the sum of both Total Pain (normalized) and Total Difficulty Subscale scores.

A sensitivity analysis based on observed data (not imputed) was conducted using an MMRM in the mITT Population. The LSM treatment difference between EN3835 and placebo treatment groups for the change from Baseline to Days 15, 29, 43, and 57 on the FFI Total Combined (Pain and Difficulty), favoring EN3835 treatment, was not significant at any timepoint.

Supportive analyses in the FAS and mITT Populations were consistent with the primary analysis.

Change from Baseline to Each Visit on the FFI Total Activity Limitation Subscale Score At Baseline (Day 1) the mean (SD) scores on the FFI Total Activity Limitation Subscale were similar between the EN3835 and placebo treatment groups. Decreases (improvements) in the Activity Limitation Subscale score were similar between the EN3835 and placebo treatment groups. Changes from Baseline in participants treated in the left or right foot only both feet are presented herein.

TABLE 52

Observed and Change from Baseline on the FFI Total Activity Limitation Subscale Score by Visit and Treatment Group (mITT Population)

| | | EN3835 (N = 85) | | Placebo (N = 87) | | Overall (N = 172) | |
|---|---|---|---|---|---|---|---|
| Treated Foot Visit | Statistic | Observed Value | Change from Baseline | Observed Value | Change from Baseline | Observed Value | Change from Baseline |
| Overall | | | | | | | |
| Baseline[a] | n | 85 | | 87 | | 172 | |
| | Mean | 8.5 | | 8.1 | | 8.3 | |
| | SD | 2.08 | | 2.17 | | 2.13 | |
| | Median | 9.0 | | 9.0 | | 9.0 | |
| | Min | 4 | | 2 | | 2 | |
| | Max | 12 | | 12 | | 12 | |
| Day 15 | n | 84 | 84 | 82 | 82 | 166 | 166 |
| | Mean | 8.6 | 0.2 | 6.9 | −1.3 | 7.8 | −0.5 |
| | SD | 2.56 | 2.29 | 2.94 | 2.40 | 2.88 | 2.45 |
| | Median | 9.0 | 0.0 | 7.0 | −1.0 | 8.0 | 0.0 |
| | Min | 0 | −5 | 0 | −9 | 0 | −9 |
| | Max | 12 | 8 | 12 | 5 | 12 | 8 |
| Day 29 | n | 83 | 83 | 79 | 79 | 162 | 162 |
| | Mean | 6.6 | −1.9 | 6.0 | −2.1 | 6.3 | −2.0 |
| | SD | 3.24 | 2.34 | 2.84 | 2.77 | 3.06 | 2.55 |
| | Median | 7.0 | −2.0 | 6.0 | −1.0 | 6.0 | −2.0 |
| | Min | 0 | −8 | 0 | −11 | 0 | −11 |
| | Max | 12 | 5 | 11 | 3 | 12 | 5 |
| Day 43 | n | 77 | 77 | 81 | 81 | 158 | 158 |
| | Mean | 5.6 | −2.8 | 5.5 | −2.7 | 5.5 | −2.8 |
| | SD | 3.20 | 2.41 | 3.09 | 2.92 | 3.14 | 2.67 |
| | Median | 5.0 | −3.0 | 6.0 | −2.0 | 6.0 | −3.0 |
| | Min | 0 | −7 | 0 | −10 | 0 | −10 |
| | Max | 12 | 4 | 12 | 3 | 12 | 4 |
| Day 57/EOS/ET | N | 82 | 82 | 83 | 83 | 165 | 165 |
| | Mean | 5.1 | −3.3 | 5.6 | −2.5 | 5.4 | −2.9 |
| | SD | 3.32 | 3.05 | 3.23 | 3.35 | 3.27 | 3.22 |

TABLE 52-continued

Observed and Change from Baseline on the FFI Total Activity Limitation Subscale Score by Visit and Treatment Group (mITT Population)

| | | EN3835 (N = 85) | | Placebo (N = 87) | | Overall (N = 172) | |
|---|---|---|---|---|---|---|---|
| Treated Foot Visit | Statistic | Observed Value | Change from Baseline | Observed Value | Change from Baseline | Observed Value | Change from Baseline |
| | Median | 5.0 | −3.0 | 6.0 | −2.0 | 6.0 | −3.0 |
| | Min | 0 | −9 | 0 | −10 | 0 | −10 |
| | Max | 12 | 5 | 12 | 10 | 12 | 10 |

[a]Baseline was defined as the last non-missing assessment prior to the study intervention injection on Day 1.

Note:

Total Activity Limitation Subscale score is the sum of the scores of answered items of activity limitation score.

A sensitivity analysis based on observed data (not imputed) was conducted using an MMRM in the mITT Population. The difference between EN3835 and placebo treatment groups for the change from Baseline in the FFI Total Activity Subscale score, favoring EN3835 treatment was not significant at any visit.

Change from Baseline to Each Visit on the FFI Total Difficulty Subscale Score

At Baseline (Day 1) the mean (SD) scores on the FFI Total Difficulty Limitation Subscale were similar between the EN3835 and placebo treatment groups. Decreases (improvements) in the FFI Total Difficulty Subscale score were similar between the EN3835 and placebo treatment groups. Changes from Baseline in the Total Difficulty score in participants treated in the left or right foot only and in both feet are presented herein.

TABLE 53

Observed and Mean Change from Baseline on the FFI Total Difficulty Subscale Score by Visit and Treatment Group (mITT Population)

| | | EN3835 (N = 85) | | Placebo (N = 87) | | Overall (N = 172) | |
|---|---|---|---|---|---|---|---|
| Treated Foot Visit | Statistic | Observed Value | Change from Baseline | Observed Value | Change from Baseline | Observed Value | Change from Baseline |
| | | Overall | | | | | |
| Baseline[a] | n | 85 | | 87 | | 172 | |
| | Mean | 24.9 | | 24.8 | | 24.8 | |
| | SD | 6.88 | | 6.74 | | 6.79 | |
| | Median | 25.0 | | 26.0 | | 25.0 | |
| | Min | 6 | | 8 | | 6 | |
| | Max | 36 | | 36 | | 36 | |
| Day 15 | N | 84 | 84 | 82 | 82 | 166 | 166 |
| | Mean | 25.9 | 1.1 | 21.1 | −3.7 | 23.6 | −1.3 |
| | SD | 7.49 | 7.92 | 9.09 | 6.36 | 8.64 | 7.56 |
| | Median | 27.0 | 1.0 | 22.5 | −2.5 | 24.5 | 0.0 |
| | Min | 8 | −18 | 1 | −20 | 1 | −20 |
| | Max | 36 | 27 | 36 | 13 | 36 | 27 |
| Day 29 | n | 83 | 83 | 79 | 79 | 162 | 162 |
| | Mean | 20.1 | −4.9 | 18.5 | −6.3 | 19.3 | −5.6 |
| | SD | 9.46 | 7.41 | 9.35 | 7.94 | 9.41 | 7.68 |
| | Median | 21.0 | −3.0 | 19.0 | −4.0 | 20.0 | −4.0 |
| | Min | 2 | −22 | 0 | −33 | 0 | −33 |
| | Max | 36 | 13 | 35 | 12 | 36 | 13 |
| Day 43 | n | 77 | 77 | 81 | 81 | 158 | 158 |
| | Mean | 16.8 | −8.2 | 16.1 | −8.9 | 16.5 | −8.5 |
| | SD | 9.77 | 7.65 | 9.72 | 8.80 | 9.72 | 8.24 |
| | Median | 16.0 | −7.0 | 16.0 | −7.0 | 16.0 | −7.0 |
| | Min | 0 | −26 | 0 | −33 | 0 | −33 |
| | Max | 36 | 11 | 36 | 13 | 36 | 13 |

TABLE 53-continued

Observed and Mean Change from Baseline on the FFI Total Difficulty Subscale Score by Visit and Treatment Group (mITT Population)

| Treated Foot Visit | Statistic | EN3835 (N = 85) Observed Value | EN3835 (N = 85) Change from Baseline | Placebo (N = 87) Observed Value | Placebo (N = 87) Change from Baseline | Overall (N = 172) Observed Value | Overall (N = 172) Change from Baseline |
|---|---|---|---|---|---|---|---|
| Day 57/EOS/ET | n | 82 | 82 | 83 | 83 | 165 | 165 |
| | Mean | 15.2 | −9.9 | 16.9 | −7.9 | 16.0 | −8.9 |
| | SD | 10.44 | 9.13 | 10.17 | 9.65 | 10.30 | 9.42 |
| | Median | 14.0 | −9.0 | 17.0 | −5.0 | 16.0 | −7.0 |
| | Min | 0 | −30 | 0 | −35 | 0 | −35 |
| | Max | 36 | 8 | 36 | 9 | 36 | 9 |

[a]Baseline was defined as the last non-missing assessment prior to the study intervention injection on Day 1.
Note:
The Total Difficulty Subscale score is the sum of the scores of answered items of difficulty.

A sensitivity analysis based on observed data (not imputed) was conducted using MMRM in the mITT Population. The LSM treatment difference between EN3835 and placebo treatment groups for the change from Baseline in the FFI Total Difficulty Subscale score, favoring EN3835 treatment was not significant at any visit.

Change from Baseline to Each Visit in Nodule Hardness

At Baseline (Day 1) the mean (SD) measurements of nodular hardness by foot and by participant were similar between the EN3835 and placebo treatment groups. On Days 15, 29, 43, and 57, improvements in nodular hardness occurred to a greater extent in the EN3835 treatment group than the placebo treatment group. Improvements on a foot level and a nodular level by left foot, right foot, and both feet are presented herein.

TABLE 54

Overall Observed and Mean Change from Baseline in the Nodular Hardness by Visit and Treatment Group on a Participant Level (ITT Population)

| Participant Level: Overall | Statistic | EN3835 (N = 88) Observed Value | EN3835 (N = 88) Change from Baseline | Placebo (N = 88) Observed Value | Placebo (N = 88) Change from Baseline | Overall (N = 176) Observed Value | Overall (N = 176) Change from Baseline |
|---|---|---|---|---|---|---|---|
| Baseline[a] | n | 87 | | 87 | | 174 | |
| | Mean | 46.585 | | 42.493 | | 44.539 | |
| | SD | 16.0885 | | 16.0813 | | 16.1691 | |
| | Median | 44.250 | | 40.500 | | 42.190 | |
| | Min | 9.50 | | 5.25 | | 5.25 | |
| | Max | 80.50 | | 76.25 | | 80.50 | |
| | | 87 | | 87 | | 174 | |
| Day 15 | n | 86 | 86 | 84 | 84 | 170 | 170 |
| | Mean | 37.304 | −9.371 | 38.491 | −4.243 | 37.891 | −6.837 |
| | SD | 17.3239 | 18.3033 | 17.6933 | 10.8187 | 17.4657 | 15.2509 |
| | Median | 36.750 | −5.750 | 37.625 | −2.625 | 37.250 | −3.625 |
| | Min | 0.00 | −71.63 | 0.00 | −42.63 | 0.00 | −71.63 |
| | Max | 74.75 | 22.25 | 77.81 | 21.92 | 77.81 | 22.25 |
| Day 29 | n | 84 | 84 | 82 | 82 | 166 | 166 |
| | Mean | 37.033 | −9.882 | 39.486 | −2.967 | 38.245 | −6.466 |
| | SD | 17.3746 | 19.1495 | 19.4848 | 10.8320 | 18.4321 | 15.9401 |
| | Median | 36.565 | −6.210 | 38.875 | −1.250 | 37.000 | −3.155 |
| | Min | 0.00 | −80.50 | 0.00 | −42.63 | 0.00 | −80.50 |
| | Max | 78.13 | 22.25 | 78.25 | 26.75 | 78.25 | 26.75 |
| Day 43 | n | 78 | 78 | 80 | 80 | 158 | 158 |
| | Mean | 33.116 | −13.038 | 37.889 | −4.550 | 35.533 | −8.740 |
| | SD | 18.8738 | 18.5024 | 19.0498 | 12.5181 | 19.0536 | 16.2749 |
| | Median | 34.220 | −9.415 | 34.915 | −3.625 | 34.750 | −5.375 |
| | Min | 0.00 | −80.50 | 0.00 | −46.50 | 0.00 | −80.50 |
| | Max | 84.50 | 19.50 | 76.50 | 26.75 | 84.50 | 26.75 |

TABLE 54-continued

Overall Observed and Mean Change from Baseline in the Nodular Hardness by Visit and Treatment Group on a Participant Level (ITT Population)

| | | EN3835 (N = 88) | | Placebo (N = 88) | | Overall (N = 176) | |
|---|---|---|---|---|---|---|---|
| Participant Level: Overall | Statistic | Observed Value | Change from Baseline | Observed Value | Change from Baseline | Observed Value | Change from Baseline |
| Day 57/EOS/ET | n | 83 | 83 | 83 | 83 | 166 | 166 |
| | Mean | 31.016 | −15.419 | 36.229 | −6.135 | 33.622 | −10.777 |
| | SD | 18.4071 | 20.1556 | 19.2595 | 13.1801 | 18.9621 | 17.6042 |
| | Median | 34.500 | −9.630 | 35.000 | −3.000 | 34.815 | −7.000 |
| | Min | 0.00 | −80.50 | 0.00 | −50.50 | 0.00 | −80.50 |
| | Max | 77.00 | 9.38 | 77.56 | 13.67 | 77.56 | 13.67 |

[a]Baseline was defined as the last non-missing assessment prior to the study intervention injection on Day 1.

The observed and change from Baseline in the nodular hardness by nodule size, visit and treatment group is presented herein. The observed changes were consistent with the MMRM model estimates.

A sensitivity analysis based on observed data (not imputed) was conducted using MMRM in the mITT Population. On a participant level, there was a significant difference between the EN3835 and placebo treatment groups, favoring EN3835 treatment on Days 43 and 57. On a nodular level, there was a significant difference between EN3835 and placebo treatment groups for the change from Baseline in nodular hardness at all time points.

TABLE 55

MMRM Estimate (Observed Data) of Change from Baseline in the Nodular Hardness by Visit and Treatment Group (mITT Population)

| | | LSM Change from Baseline (SE)[a] | | Estimated LSM Treatment Difference of EN3835-Placebo[b] | |
|---|---|---|---|---|---|
| Analysis | Visit | EN3835 | Placebo | Difference (LCL, UCL) | p value [b] |
| Participant Level | Day 15 | −8.228 (1.56) | −5.347 (1.56) | −2.881 (−7.329, 1.568) | 0.203 |
| | Day 29 | −8.350 (1.64) | −3.960 (1.65) | −4.390 (−9.087, 0.306) | 0.067 |
| | Day 43 | −12.204 (1.71) | −5.515 (1.70) | −6.689 (−11.541, −1.838) | 0.007 |
| | Day 57 | −13.948 (1.76) | −7.357 (1.76) | −6.591 (−11.585, −1.598) | 0.010 |
| Nodule Level | Day 15 | −7.735 (1.23) | −4.001 (1.09) | −3.735 (−7.033, −0.437) | 0.027 |
| | Day 29 | −8.073 (1.38) | −3.173 (1.21) | −4.900 (−8.568, −1.232) | 0.009 |
| | Day 43 | −10.368 (1.37) | −5.573 (1.21) | −4.795 (−8.454, −1.137) | 0.010 |
| | Day 57 | −12.800 (1.50) | −6.345 (1.31) | −6.454 (−10.425, −2.484) | 0.002 |

[a]The LSM change from Baseline to Days 15, 29, 43 and 57 in the nodular hardness for EN3835 and placebo treatment was obtained from the fitted MMRM model.
[b]The treatment effect and 95% CI comparing EN3835 with placebo was also estimated using MMRM.

Note:

MMRM was performed on observed data. The MMRM model included as a dependent variable the change from the Baseline to each visit (ie, change from Baseline score to Days 15, 29, 43, 57), fixed effect as treatment group, treatment by visit interaction, covariates such as the baseline average nodular hardness at Day 1, maximum of nodule length/nodule width and the total number of nodules and repeated measures is the study visit. An unstructured covariance matrix is used to model the covariance of within-participants values. MMRM was performed on observed data.

Participant Level: The MMRM model included as a dependent variable the change from Baseline to each visit (ie, change from Baseline score to Days 15, 29, 43, and 57), fixed effect as treatment group and visit, treatment by visit interaction, covariates such as the baseline average nodular hardness at Day 1, maximum of nodule length/nodule width and the total number of treated nodules and repeated measures was the study visit. An unstructured covariance matrix was used to model the covariance of within-participant values.

Nodule Level: The MMRM model included as a dependent variable the change from Baseline to each visit (ie, change from Baseline score to Days 15, 29, 43, and 57), fixed effect as treatment group and visit, treatment by visit interaction, covariates such as the baseline average nodular hardness at Day 1, maximum of nodule length/nodule width and the total number of treated nodules and repeated measures was the study visit and nodule identifier. An unstructured covariance matrix was used to model the covariance of within participant values.

Exploratory Endpoints

Change in the FFI Total Composite Score by Visit and by Treatment Group

The FFI Total Composite score was defined as the sum of all total subscale scores (Activity Limitation, Difficulty, and Pain Subscales [normalized]). At Baseline, FFI Total Composite scores were similar between the EN3835 and placebo treatment groups. Decreases (improvements) in the mean FFI Total Composite score on Days 29, 43, and 57 were similar between treatment groups. Changes from Baseline in the FFI Total Composite score in participants treated in the left or right foot only and in both feet are presented herein.

TABLE 56

Observed and Change from Baseline on the FFI Total Composite Score by Visit and Treatment Group (mITT Population)

| Overall Visit | Statistic | EN3835 (N = 85) Observed Value | EN3835 (N = 85) Change from Baseline | Placebo (N = 87) Observed Value | Placebo (N = 87) Change from Baseline | Overall (N = 172) Observed Value | Overall (N = 172) Change from Baseline |
|---|---|---|---|---|---|---|---|
| Baseline[a] | n | 85 | | 87 | | 172 | |
| | Mean | 58.76 | | 57.75 | | 58.25 | |
| | SD | 13.207 | | 12.928 | | 13.038 | |
| | Median | 58.10 | | 60.00 | | 59.20 | |
| | Min | 30.0 | | 19.0 | | 19.0 | |
| | Max | 84.0 | | 84.0 | | 84.0 | |
| Day 15 | n | 84 | 84 | 82 | 82 | 166 | 166 |
| | Mean | 59.10 | 0.35 | 48.61 | −9.17 | 53.92 | −4.35 |
| | SD | 15.790 | 14.367 | 18.997 | 13.092 | 18.172 | 14.518 |
| | Median | 60.85 | 0.40 | 50.80 | −6.15 | 54.75 | −3.50 |
| | Min | 26.1 | −31.0 | 3.0 | −52.0 | 3.0 | −52.0 |
| | Max | 84.0 | 35.0 | 82.7 | 14.3 | 84.0 | 35.0 |
| Day 29 | n | 83 | 83 | 79 | 79 | 162 | 162 |
| | Mean | 46.07 | −12.87 | 42.49 | −15.36 | 44.32 | −14.09 |
| | SD | 19.957 | 14.503 | 19.376 | 16.593 | 19.696 | 15.558 |
| | Median | 49.00 | −11.60 | 44.00 | −11.40 | 45.95 | −11.50 |
| | Min | 5.9 | −45.5 | 2.0 | −77.0 | 2.0 | −77.0 |
| | Max | 81.0 | 12.5 | 77.0 | 16.3 | 81.0 | 16.3 |
| Day 43 | n | 77 | 77 | 81 | 81 | 158 | 158 |
| | Mean | 38.61 | −20.24 | 38.68 | −19.40 | 38.64 | −19.81 |
| | SD | 20.703 | 15.931 | 20.454 | 19.161 | 20.510 | 17.610 |
| | Median | 34.30 | −20.70 | 38.00 | −14.70 | 37.05 | −17.35 |
| | Min | 0.0 | −59.0 | 0.0 | −75.0 | 0.0 | −75.0 |
| | Max | 81.7 | 19.9 | 80.0 | 17.3 | 81.7 | 19.9 |
| Day 57/EOS/ET | n | 82 | 82 | 83 | 83 | 165 | 165 |
| | Mean | 35.35 | −23.67 | 39.29 | −18.36 | 37.33 | −20.99 |
| | SD | 22.252 | 19.344 | 21.313 | 20.561 | 21.808 | 20.082 |
| | Median | 32.50 | −21.00 | 40.70 | −13.40 | 38.00 | −17.70 |
| | Min | 0.0 | −66.0 | 0.0 | −75.0 | 0.0 | −75.0 |
| | Max | 82.0 | 14.8 | 84.0 | 22.9 | 84.0 | 22.9 |

[a]Baseline was defined as the last non-missing assessment prior to the study intervention injection on Day 1.

Note:

Total Composite score was defined as the sum of all total subscale scores (Activity Limitation Subscale, Difficulty Subscale, and Pain Subscale [normalized]).

An analysis based on observed data (not imputed) was conducted using the MMRM in the mITT Population. The difference in the FFI Total Composite score between EN3835 and placebo treatment groups was not significant in favor of EN3835 treatment.

Change in the PGIS PF Overall Score by Visit and by Treatment Group

At Baseline (Day 1), the distribution of moderate and severe PGIS PF Overall scores were similar in the EN3835 and placebo treatment groups. Over time, while there were decreases (improvements) in the severity of plantar fibromatosis on the PGIS PF Overall score in both the EN3835 and placebo treatment groups, the median differences in the PGIS PF overall score between treatment groups were not significant in favor of EN3835 treatment. PGIS PF Overall scores in participants treated in the left or right foot only and in both feet are presented in herein. PGIS scores by participant are presented herein.

Change in the PGIS Foot Pain Subscale Scores by Visit and by Treatment Group

At Baseline (Day 1), the mean (SD) PGIS Foot Pain Subscales scores in the EN3835 and in the placebo treatment groups were similar. While the PGIS Foot Pain Subscale scores decreased (improved) in both the EN3835 and placebo treatment groups, with few participants reporting moderate or severe pain at the end of the study, these differences were not significant in favor of EN3835 treatment. PGIS PF Foot Pain Subscale scores in participants treated in the left or right foot only and in both feet are presented herein.

Change in the PGIS Difficulty Subscale Scores by Visit and by Treatment Group

At Baseline (Day 1), the mean (SD) PGIS Difficulty Subscales scores in the EN3835 and in the placebo treatment groups were similar. While the PGIS Difficulty Subscale scores improved throughout the study for both the EN3835 and placebo treatment groups, with few participants reporting moderate or severe difficulty, these differences were not significant in favor of EN3835 treatment. PGIS PF Foot Pain Subscale scores in participants treated in the left or right foot only and in both feet are presented herein.

Change in the PGIS Activity Limitation Subscale Scores by Visit and by Treatment Group At Baseline (Day 1), the mean (SD) PGIS Activity Limitation Subscales scores in the EN3835 and in the placebo treatment groups were similar. While the PGIS Activity Limitation Subscale scores decreased (improved) throughout the study for both the EN383 and placebo treatment groups, these differences were not significant in favor of EN3835 treatment. PGIS Activity Limitation Subscale scores in participants treated in the left or right foot only and in both feet are presented herein.

Comparison of the PGIC Scores by Visit and by Treatment Group

There were no significant differences between the EN3835 and placebo treatment groups in the PGIC PF Overall score and the overall PGIC Foot Pain Subscale, PGIC Activity Subscale and the PGIC Difficulty Subscale scores in favor of EN3835 treatment.

The PGIC scores by participant are presented herein.

Change in the Pain Intensity NRS Scores by Visit and Treatment Group

At Baseline, Pain Intensity NRS scores were similar between the EN3835 and placebo treatment groups. While an improvement in pain was observed in both the EN3835 and placebo treatment groups on the Pain Intensity NRS Scale during the study, these differences were not statistically significant.

TABLE 57

Observed and Mean Change from Baseline by Visit and Treatment Group on the Pain Intensity NRS by Visit and Treatment Group (mITT Population)

| | | EN3835 (N = 85) | | Placebo (N = 87) | | Overall (N = 172) | |
|---|---|---|---|---|---|---|---|
| Overall | Statistic | Observed Value | Change from Baseline | Observed Value | Change from Baseline | Observed Value | Change from Baseline |
| Baseline[a] | n | 85 | | 87 | | 172 | |
| | Mean | 8.0 | | 7.9 | | 7.9 | |
| | SD | 1.34 | | 1.30 | | 1.32 | |
| | Median | 8.0 | | 8.0 | | 8.0 | |
| | Min | 5 | | 4 | | 4 | |
| | Max | 10 | | 10 | | 10 | |
| Day 15 | n | 83 | 83 | 82 | 82 | 165 | 165 |
| | Mean | 7.8 | −0.1 | 6.4 | −1.6 | 7.1 | −0.8 |
| | SD | 1.96 | 1.90 | 2.06 | 1.90 | 2.14 | 2.04 |
| | Median | 8.0 | 0.0 | 7.0 | −1.0 | 8.0 | −1.0 |
| | Min | 2 | −5 | 1 | −7 | 1 | −7 |
| | Max | 10 | 4 | 10 | 2 | 10 | 4 |
| Day 29 | n | 83 | 83 | 80 | 80 | 163 | 163 |
| | Mean | 6.0 | −2.0 | 5.6 | −2.3 | 5.8 | −2.2 |
| | SD | 2.33 | 2.12 | 2.49 | 2.26 | 2.41 | 2.19 |
| | Median | 6.0 | −2.0 | 6.0 | −2.0 | 6.0 | −2.0 |
| | Min | 1 | −7 | 0 | −9 | 0 | −9 |
| | Max | 10 | 2 | 10 | 1 | 10 | 2 |
| Day 43 | n | 78 | 78 | 81 | 81 | 159 | 159 |
| | Mean | 5.1 | −2.9 | 5.4 | −2.6 | 5.2 | −2.8 |
| | SD | 2.68 | 2.51 | 2.74 | 2.51 | 2.71 | 2.51 |
| | Median | 5.0 | −2.5 | 6.0 | −2.0 | 6.0 | −2.0 |
| | Min | 0 | −8 | 0 | −8 | 0 | −8 |
| | Max | 10 | 2 | 10 | 2 | 10 | 2 |
| Day 57/EOS/ET | n | 82 | 82 | 83 | 83 | 165 | 165 |
| | Mean | 4.9 | −3.1 | 5.3 | −2.6 | 5.1 | −2.9 |
| | SD | 2.95 | 2.84 | 2.76 | 2.59 | 2.86 | 2.72 |
| | Median | 5.0 | −2.5 | 6.0 | −2.0 | 5.0 | −2.0 |
| | Min | 0 | −9 | 0 | −9 | 0 | −9 |
| | Max | 10 | 2 | 10 | 3 | 10 | 3 |

[a]Baseline was defined as the last non-missing assessment prior to the study intervention injection on Day 1.

TABLE 58

MMRM Estimates (Observed Data) of the Mean Change from Baseline on Pain Intensity Numerical Rating Scale by Visit and Treatment Group (mITT Population)

| | LS Means Change from Baseline (SE) [a] | | Estimated LS Means of Treatment Difference between EN3835-Placebo [b] | p |
|---|---|---|---|---|
| Visit | EN3835 | Placebo | Difference (LCL, UCL) | value |
| Day 15 | −0.027 (0.21) | −1.613 (0.21) | 1.586 (0.998, 2.174) | <0.001 |
| Day 29 | −1.926 (0.24) | −2.351 (0.24) | 0.425 (−0.263, 1.113) | 0.225 |

TABLE 58-continued

MMRM Estimates (Observed Data) of the Mean Change from Baseline on Pain Intensity Numerical Rating Scale by Visit and Treatment Group (mITT Population)

| | LS Means Change from Baseline (SE) [a] | | Estimated LS Means of Treatment Difference between EN3835-Placebo [b] | p |
|---|---|---|---|---|
| Visit | EN3835 | Placebo | Difference (LCL, UCL) | value |
| Day 43 | −2.741 (0.28) | −2.618 (0.28) | −0.122 (−0.914, 0.669) | 0.760 |
| Day 57 | −2.907 (0.30) | −2.677 (0.30) | −0.230 (−1.067, 0.606) | 0.588 |

[a] The LSM change from Baseline to Days 15, 29, 43 and 57 on the Pain Intensity NRS for EN3835 and placebo treatment was obtained from the fitted MMRM model.

[b] The treatment effect and 95% CI comparing EN3835 with placebo was also estimated using MMRM.

TABLE 58-continued

MMRM Estimates (Observed Data) of the Mean Change from Baseline on Pain Intensity Numerical Rating Scale by Visit and Treatment Group (mITT Population)

| Visit | LS Means Change from Baseline (SE) [a] | | Estimated LS Means of Treatment Difference between EN3835-Placebo [b] | p |
|---|---|---|---|---|
| | EN3835 | Placebo | Difference (LCL, UCL) | value |

Note:
MMRM was performed on observed data. The MMRM model included dependent variable as the change from Baseline to each visit (ie, change from Baseline score to Days 15, 29, 43, and 57), fixed effect as treatment group and visit, treatment by visit interaction, covariates such as the baseline Pain Intensity NRS at Day 1, maximum of nodule length/nodule width and the total number of treated nodules and repeated measures is the study visit. An unstructured covariance matrix is used to model the covariance of within-participant values.

Comparison in the Subject Satisfaction with Treatment Scale Scores by Visit and Treatment Group On Day 57, 43 (50.6%) participants in the EN3835 treatment group and 36 (41.4%) participants in the placebo treatment group were responders on the Subject Satisfaction with Treatment Scale. There were no significant differences in the proportion of responders at any visit.

The Subject Satisfaction with Treatment Scale ratings are presented by participant herein.

Change in Nodule Size by Visit and by Treatment Group

There was no significant difference in the change in nodule size from Baseline (Day 1) between treatment groups at any time point, when assessed on a nodular-level or a participant-level. Nodule sizes by participant as measured by handheld calipers are presented herein. Nodule hardness as measured by a durometer is presented herein.

Change in Nodule Consistency

A responder in nodule consistency had a 1-level reduction in nodule consistency from Baseline. Participants with "Hard", "Firm Throughout", and "Moderately Firm" nodules were enrolled in the study, while those with "Soft" nodules were excluded. There was a significantly higher proportion of participants that were responders in the EN3835 treatment group as compared to the placebo treatment at all timepoints. At Day 57, there was a significantly higher proportion of responders (64; 75.3%) in the EN3835 treatment group than in the placebo treatment group (46; 52.9%) (risk difference, 22.4%; 95% CI, 8.5-36.4; p=0.002).

TABLE 59

Summary and Statistical Comparison of Overall Nodular Consistency by Participant and by Visit and Treatment Group using the CMH Test (mITT Population)

| Participant Level: Overall Improvement Scale Ratings | Statistics | EN3835 (N = 85) | Placebo (N = 87) |
|---|---|---|---|
| Baseline [a] | n | 85 | 87 |
| Hard | n (%) | 37 (43.5) | 42 (48.3) |
| Firm Throughout | n (%) | 31 (36.5) | 28 (32.2) |
| Moderately Firm | n (%) | 17 (20.0) | 17 (19.5) |
| Soft | n (%) | 0 (0.0) | 0 (0.0) |
| Non-Palpable | n (%) | 0 (0.0) | 0 (0.0) |
| | Mean (SD) | 3.2 (0.77) | 3.3 (0.78) |
| Day 57 | n | 82 | 83 |
| Hard | n (%) | 4 (4.9) | 16 (19.3) |
| Firm Throughout | n (%) | 9 (11.0) | 26 (31.3) |
| Moderately Firm | n (%) | 33 (40.2) | 25 (30.1) |
| Soft | n (%) | 26 (31.7) | 10 (12.0) |
| Non-Palpable | n (%) | 10 (12.2) | 6 (7.2) |
| | Mean (SD) | 1.6 (1.00) | 2.4 (1.15) |

TABLE 59-continued

Summary and Statistical Comparison of Overall Nodular Consistency by Participant and by Visit and Treatment Group using the CMH Test (mITT Population)

| Participant Level: Overall Improvement Scale Ratings | Statistics | EN3835 (N = 85) | Placebo (N = 87) |
|---|---|---|---|
| Responders [b] | n (%) | 64 (75.3) | 46 (52.9) |
| 95% CI [c] | (LCL, UCL) | (65.2, 83.2) | (42.5, 63.0) |
| Risk Difference (EN3835-Placebo)[d] | % | 22.4 | |
| 95% CI | (LCL, UCL) | (8.5, 36.4) | |
| p value (CMH test for General association)[e] | | 0.002 | |

[a] Baseline was defined as the last non-missing measurement prior to the first injection of study intervention at Day 1.
[b] A responder was defined as at least 1-level reduction in nodule consistency from Baseline for any nodule at follow-up visits.
[c] Based on Wilson Score method.
[d] The risk difference was the difference in proportion of responders between EN3835 and Placebo.
[e] The p value derived from CMH test of general association.

Nodule consistency by participant is presented herein.

Adjustments for Covariates

For all the continuous endpoints, the adjustments for covariates were accounted for in the ANCOVA and MMRM analyses. For analyses of CGIC, PGIC, Subject Satisfaction with Treatment Scale, and nodule consistency, there were no adjustments for covariates.

Multiple Comparisons/Multiplicity

Multiplicity arising from testing of secondary endpoints was addressed by using a fixed sequence hierarchical testing procedure. A step-down testing procedure was applied where inference for an endpoint in the predefined hierarchy was dependent on statistical significance having been achieved for the previous endpoints in the hierarchy.

The hierarchy of endpoints was defined as follows:

Primary endpoint: Mean change from Baseline to EOS in Total Foot Pain Subscale score Key secondary endpoint 1: Mean change from Baseline to EOS in FFI Total Combined (Pain and Difficulty) score Key secondary endpoint 2: Proportion of participants with an improvement on the CGIC Key secondary endpoint 3: Mean change from Baseline to EOS in nodular hardness measurements All the tests were performed at the 0.05 level of significance following the prespecified order. The testing of the first key secondary endpoint was to be conducted if the result of the primary endpoint was statistically significant and testing of the second key secondary endpoint was to be conducted if the result of the first key secondary endpoint was statistically significant and so on.

The other secondary endpoints and exploratory endpoints did not fall under this hierarchical approach since no multiplicity adjustment was made for these endpoints and only nominal p values were reported.

Use of an "Efficacy Subset" of Participants

The mITT and FAS Populations were used for the efficacy analyses to ensure that the efficacy analyses most closely reflected the scientific model underlying the study design. In this study, the mITT and FAS Populations were identical. These populations are subsets of the ITT Population and are supportive.

Results in participants with unilateral or bilateral plantar fibromatosis with "Hard", "Firm Throughout", and "Moderately Firm" nodules showed that after 1 or 2 treatments of EN3835 or placebo, there was a significant improvement in the nodular hardness and nodular consistency; nodules softened to a greater extent in the EN3835-treated participants than in placebo-treated participants (there were statistically significant improvements in nodule hardness (LSM difference, −5.877; P=0.020) and consistency (22.4% more responders; P=0.002) between the CCH group and placebo, favoring CCH treatment.). (Table 45). There was a significantly higher proportion of responders on the Clinician Global Impression of Change (CGIC) Scale on Day 57 in the EN3835 treatment group than in the placebo treatment group (the CGIC showed there were 14.8% more responders in the CCH group vs placebo (P=0.044)). The mean FFI-Total subscale Pain score trended toward improvement in both groups; however, the difference was not statistically significant (least squares mean [LSM] difference, −1.427; P=0.274). While remaining endpoints trended in favor of EN3835, these differences were not statistically significant. (Foot Function Index [FFI]-PF Total Foot Pain Subscale, FFI Composite, FFI Total Combined (Pain and Difficulty) Subscale, FFI Total Activity Limitation Subscale, Pain Intensity Numeric Rating Scale [NRS] and Patient Global Impression of Change [PGIC]). Top treatment-related or -emergent adverse events (AEs) were injection site pain, bruising, and swelling. There were no deaths, serious AEs, or study withdrawals in the CCH treatment group.

Refined Population

Further analyses were conducted in an efficacy subset of the FAS Population. This subset excluded participants with "Moderately Firm" nodules and participants with a Pain Intensity NRS score of 10 at Baseline.

In this study, nodules were characterized as "Non-palpable", "Soft", "Moderately Firm", "Firm Throughout" and "Hard". Data was examined with consideration of exclusion of "Moderately Firm" nodules. These softer nodules may have less collagen content and therefore EN3835 may not be as effective in these nodules.

Participants with a Pain Intensity NRS of 10 were excluded as these participants may have extreme psychological distress or such severe pain that they would not be appropriate for study inclusion and evaluation.

Importantly, the Refined Population comprised more than two-thirds (126 of 172; 73.3%) of the participants included in the FAS Population. There were numerically more participants in the placebo treatment group (65 of 87; 74.7%) meeting criteria for inclusion in this population than in the EN3835 treatment group (61 of 85; 71.8%).

A summary of the analyses of the endpoints at Day 57 in the FAS and Refined Populations are presented herein.

TABLE 60

Summary of the Efficacy Analyses at Day 57 in the FAS and Refined Populations

| Endpoints | FAS Population N = 172 | Refined Population N = 126 |
|---|---|---|
| FFI Foot Pain Subscale [c] | 0.252 | 0.014[a] |
| FFI Combined Pain and Difficulty Subscale [e] | 0.307[c] | 0.020 [a] |
| CGIC[d] | 0.037 | 0.025 [a] |
| Nodule Hardness-Participant level [c] | 0.022 [a] | 0.002[b] |
| Pain Intensity NRS | 0.588 | 0.099 |
| Nodule Consistency [e] - Nodular level | 0.002[b] | <0.001 [b] |
| PGIC-PF Overall [d] | 0.095 | 0.023[b] |
| FFI Total Composite Score [e] | 0.203 | 0.023 [a] |
| FFI Difficulty Subscale [e] | 0.311 | 0.042 [a] |
| FFI Activity Limitation Subscale [e] | 0.343 | 0.059 |
| PGIS PF Overall | 0.178[f] | 0.064[e] |
| Subject Satisfaction with Treatment [d] | 0.227 | 0.056 |

[a] p values < 0.05;
[b] p value < 0.01;
[c] ANCOVA;
[d] CMH;
[e] MMRM;
[f] Rank Sum Test Demographic Characteristics—Subset The demographic characteristics in the FAS and the Refined Populations were similar. More than half of all participants were female (82 participants; 65.1%), white (106 participants; 84.1%) and not Hispanic or Latino (106 participants; 84.1%). Most participants were overweight (median [range] BMI: 28.440 [6.39-50.43] kg/m2). The median (range) age of participants overall was 56.5 years old (range: 19 to 82 years old). No relevant differences in demographic characteristics between treatment groups were observed.

More participants in the subset population (73 of 126; 57.9%) had unilateral plantar fibromatosis than bilateral plantar fibromatosis (53 of 126; 42.1%). The treatment groups remained somewhat imbalanced with respect to distribution and sizes of the nodules. There were more participants with bilateral plantar fibromatosis in the placebo treatment group (34 participants; 52.3%) than the EN3835 treatment group (16 participants; 26.2%).

Overall, 2 (1.6%) participants overall had nodules >4 cm, one participant in each treatment group. Like the FAS, the distribution of small and medium size nodules in the subgroup was also dissimilar among the treatment groups. More participants in the EN3835 treatment group had the smallest size nodules (up to 2 cm; 36 participants; 59%) than the placebo treatment group (28 participants; 43.1%). There were more mid-size nodules (>2 cm to ≤4 cm) in the placebo treatment group (36 participants; 55.4%) than in the EN3835 treatment group (24 participants; 39.3%).

At Baseline, overall, the mean (SD) FFI Total Composite scores, FFI Total Pain Subscale scores, Pain Intensity NRS scores, FFI Total Activity scores FFI Difficulty Subscale score, PGIS Activity and Difficulty Subscale scores were similar between treatment groups.

At Baseline, almost all participants in the EN3835 and placebo treatment groups reported moderate or severe PF on the PF Overall score of the PGIS.

Primary Endpoint—Subset

In the Refined Population, there was a significant difference from Baseline to Day 57 between the LSM [SE] decrease (improvement) in the mean Total Foot Pain Subscale score in the EN3835 (−11.057 [1.03]) and placebo treatment groups (−7.451 [0.99]), favoring EN3835 treatment (LSM difference, −3.516; 95% CI, −6.312 to −0.720; p=0.014).

TABLE 61

ANCOVA (Washout) Estimates of the Mean Change from Baseline to Day 57 on FFI Total Pain Subscale Score by Treatment Group (Refined Population)

| | LSM Change from Baseline (SE) [a] | | Estimated LSM Treatment Difference of EN3835-Placebo[b] | p |
|---|---|---|---|---|
| Visit | EN3835 | Placebo | Difference (LCL, UCL) | value[b] |
| Day 57 | −11.057 (1.03) | −7.541 (0.99) | −3.516 (−6.312, −0.720) | 0.014 |

[a] ANCOVA was performed to estimate the LSM change from Baseline in the Foot Pain Subscale for EN3835 and placebo treatment

[b]The treatment effect and 95% CI for comparing EN3835 with placebo was estimated using ANCOVA with treatment group as fixed effect, FFI Pain Subscale at Baseline.

Note:

ANCOVA was performed on imputed data using multiple washout model.

Secondary Endpoints

Secondary Endpoint 1: Mean Change from Baseline to Day 57 on FFI Total Combined (Pain and Difficulty) Score—Subset In the Refined Population, there was a significant difference between treatment groups in the mean change from Baseline to Day 57 on the FFI Total Combined (Pain and Difficulty) Subscale score, favoring EN3835 treatment (LSM difference, −6.889; 95%, CI −12.674 to −1.104; p=0.02).

TABLE 62

ANCOVA (Washout) Estimated of the Mean Change from Baseline to Day 57 on FFI Total Combined (Pain and Difficulty) Score by Treatment Group (Refined Population)

| | LSM Change from Baseline (SE)[a] | | Estimated LSM Treatment Difference of EN3835-Placebo[b] Difference (LCL, | p |
|---|---|---|---|---|
| Visit | EN3835 | Placebo | UCL) | value[b] |
| Day 57 | −21.415 (2.13) | −14.526 (2.05) | −6.889 (−12.674, −1.104) | 0.020 |

[a]ANCOVA was performed to estimate the LSM change from Baseline in the FFI pain and Difficulty (Combined) Subscale for EN3835 and placebo treatment.

[b]The treatment effect comparing EN3835 with placebo and 95% CI were estimated using ANCOVA with treatment group as fixed effect, FFI Pain and Difficulty (Combined) Subscale at Baseline.

Secondary Endpoint 2: Comparison of CGIC Scale Scores by Visit and by Treatment Group In the Refined Population, at Day 57, there was significantly higher proportion of responders on the CGIC Scale in the EN3835 treatment group (43 of 57 participants; 75.4%; 95% CI, 62.9-84.8) than in the placebo treatment group (34 of 61 participants; 55.7%; 95% CI, 43.3-67.5) (p=0.025). Changes in the CGIC on foot level and on a participant level by treated foot are presented herein.

TABLE 63

Analysis of Results of the CGIC Scale at Day 57 using the CMH Test (Refined Population)

| | Statistics | EN3835 (N = 61) | Placebo (N = 65) |
|---|---|---|---|
| Participant Level: Overall | | | |
| Day 57 | N | 57 | 61 |
| −3 (Very Much Worse) | n (%) | 1 (1.8) | 0 (0.0) |
| −2 (Much Worse) | n (%) | 0 (0.0) | 1 (1.6) |
| −1 (Minimally Worse) | n (%) | 4 (7.0) | 4 (6.6) |
| 0 (No Change) | n (%) | 9 (15.8) | 22 (36.1) |
| +1 (Minimal Improvement) | n (%) | 11 (19.3) | 9 (14.8) |

TABLE 63-continued

Analysis of Results of the CGIC Scale at Day 57 using the CMH Test (Refined Population)

| | Statistics | EN3835 (N = 61) | Placebo (N = 65) |
|---|---|---|---|
| +2 (Much Improvement) | n (%) | 20 (35.1) | 18 (29.5) |
| +3 (Very Much Improvement) | n (%) | 12 (21.1) | 7 (11.5) |
| | Mean (SD) | 1.4 (1.33) | 1.0 (1.24) |
| Responders | n (%) | 43 (75.4) | 34 (55.7) |
| 95% CI [b] | (LCL, UCL) | (62.9, 84.8) | (43.3, 67.5) |
| Risk Difference (EN3835-Placebo) [c] | N | 19.7 | |
| 95% CI | (LCL, UCL) | (3.0, 36.4) | |
| p value (CMH test for General association) [d] | | | 0.025 |

[a] The responder (by foot/feet) was defined as a participant with a response of "Minimal Improvement", "Much Improvement" or "Very Much Improvement" in the CGIC Scale. All participants who withdrew early from the study are considered as non-responders. If participant was treated for both feet, then the assessment can be combined at the participant level using worst case approach, if one foot response recorded as 'Minimal Improvement' and 'Very Much Improvement' in another foot, then response was considered as 'Minimal Improvement'.

[b] Based on Wilson score method

[c] Stratum adjusted risk difference was the difference in proportion of responders between EN3835 and Placebo.

[d] The p value derived from CMH test of general association.

Note:

Percentages are based on the number of participants treated at each treatment group and current visit.

The results of the analyses of the CGIC Scale scores by visit in the Refined Population are supportive and are presented herein.

Secondary Endpoint 3: Change from Baseline to Day 57 in the Nodular Hardness In the Refined Population, there was a significant difference in the improvement (decreases) in mean nodular hardness from Baseline to Day 57 between treatment groups, favoring EN3835 treatment (LSM difference, −8.975; 95% CI, −14.730 to −3.220; p=0.002).

TABLE 64

ANCOVA (Washout) Estimate of Mean Change from Baseline to Day 57 in the Nodular Hardness (Participant Level) by Treatment Group (Refined Population)

| | LSM Change from Baseline (SE)[a] | | Estimated LSM Treatment Difference of EN3835-Placebo [b] Difference | p |
|---|---|---|---|---|
| Visit | EN3835 | Placebo | (LCL, UCL) | value[b] |
| Day 57 | −16.221 (2.09) | −7.246 (2.04) | −8.975 (−14.730, −3.220) | 0.002 |

[a]ANCOVA was performed to estimate the LSM change from Baseline in the nodular hardness for EN3835 and placebo treatment.

[b]The treatment effect and 95% CI comparing EN3835 with placebo was estimated using ANCOVA with treatment group as fixed effect, average nodular hardness at Baseline.

Analysis of Other Secondary Endpoints in the Refined Population

Change from Baseline on FFI Total Pain Subscale Score

Overall, on Days 15,29, 43, and 57, the Total Pain Subscale score decreased (improved) in the EN3835 and the placebo treatment groups. Changes from Baseline in the FFI Total Pain Subscale score for participants treated in their left foot only, or right foot only or both feet are presented herein.

TABLE 65

Overall Mean Change from Baseline by Visit to EOS (Day 57) on the FFI Total Pain Subscale Score by Treatment Group (Refined Population)

| | | EN3835 (N = 61) | | Placebo (N = 65) | | Overall (N = 126) | |
|---|---|---|---|---|---|---|---|
| Visit | Statistic | Observed Value | Change from Baseline[a] | Observed Value | Change from Baseline[a] | Observed Value | Change from Baseline[a] |
| Overall | | | | | | | |
| Baseline[a] | n | 61 | | 65 | | 126 | |
| | Mean | 24.75 | | 24.35 | | 24.54 | |
| | SD | 4.781 | | 4.839 | | 4.796 | |
| | Median | 24.40 | | 24.40 | | 24.40 | |
| | Min | 16.7 | | 14.1 | | 14.1 | |
| | Max | 36.0 | | 34.7 | | 36.0 | |
| Day 15 | n | 60 | 60 | 60 | 60 | 120 | 120 |
| | Mean | 23.58 | −1.18 | 20.28 | −4.10 | 21.93 | −2.64 |
| | SD | 6.661 | 5.954 | 7.429 | 5.374 | 7.219 | 5.835 |
| | Median | 23.10 | −1.80 | 19.30 | −2.60 | 21.90 | −2.60 |
| | Min | 10.0 | −13.1 | 5.0 | −18.0 | 5.0 | −18.0 |
| | Max | 36.0 | 15.4 | 34.7 | 6.1 | 36.0 | 15.4 |
| Day 29 | n | 60 | 60 | 57 | 57 | 117 | 117 |
| | Mean | 17.85 | −6.87 | 17.44 | −7.08 | 17.65 | −6.97 |
| | SD | 7.092 | 5.903 | 7.494 | 6.886 | 7.262 | 6.374 |
| | Median | 18.00 | −6.20 | 16.70 | −6.00 | 18.00 | −6.00 |
| | Min | 3.9 | −20.5 | 0.0 | −33.0 | 0.0 | −33.0 |
| | Max | 32.1 | 3.9 | 32.0 | 3.0 | 32.1 | 3.9 |
| Day 43 | n | 55 | 55 | 60 | 60 | 115 | 115 |
| | Mean | 14.67 | −9.97 | 16.49 | −7.82 | 15.62 | −8.85 |
| | SD | 7.612 | 7.112 | 7.992 | 7.879 | 7.832 | 7.567 |
| | Median | 13.00 | −10.00 | 17.50 | −6.00 | 15.40 | −7.70 |
| | Min | 0.0 | −24.4 | 0.0 | −32.0 | 0.0 | −32.0 |
| | Max | 32.1 | 4.9 | 32.1 | 9.0 | 32.1 | 9.0 |
| Day 57/EOS/ET | n | 59 | 59 | 62 | 62 | 121 | 121 |
| | Mean | 13.58 | −11.24 | 16.79 | −7.42 | 15.22 | −9.29 |
| | SD | 8.527 | 8.256 | 8.105 | 8.128 | 8.434 | 8.379 |
| | Median | 12.00 | −10.30 | 18.00 | −6.20 | 16.70 | −9.00 |
| | Min | 0.0 | −27.0 | 0.0 | −30.0 | 0.0 | −30.0 |
| | Max | 33.4 | 3.9 | 34.0 | 10.3 | 34.0 | 10.3 |

[a]Baseline was defined as the last non-missing assessment prior to the study intervention injection on Day 1.

Note:

Total Pain Subscale score was the sum of the scores of answered items normalized by a multiplying factor of 9/7 for participants who didn't wear orthotics.

In the Refined Population, the difference between EN3835 and placebo treatment groups in the change from Baseline on the FFI Total Pain Subscale score based on an MMRM was significant in favor of EN3835 on Day 57 (LSM difference, −3.664; 95% CI, −6.532 to −0.796; p=0.013).

TABLE 66

MMRM Estimates (Observed Data) of the Mean Change from Baseline on the FFI Total Pain Subscale Score by Visit and Treatment Group (Refined Population)

| | LSM Change from Baseline [a] (SE) | | Estimated LSM Treatment Difference of EN3835-Placebo[b] | p |
|---|---|---|---|---|
| Visit | EN3835 | Placebo | (LCL, UCL) | value[b] |
| Day 15 | −1.132 (0.74) | −4.056 (0.73) | 2.925 (0.867, 4.982) | 0.006 |
| Day 29 | −6.810 (0.83) | −6.839 (0.84) | 0.029 (−2.305, 2.364) | 0.980 |
| Day 43 | −9.639 (0.96) | −7.705 (0.93) | −1.934 (−4.588, 0.720) | 0.152 |
| Day 57 | −11.107 (1.04) | −7.443 (1.01) | −3.664 (−6.532, −0.796) | 0.013 |

[a] The LSM change from Baseline to Days 15, 29, 43, and 57 in the Foot Pain Subscale for EN3835 and placebo treatment was obtained from the fitted MMRM model.

[b]The treatment effect and 95% CI comparing EN3835 with placebo was also estimated using MMRM.

TABLE 66-continued

MMRM Estimates (Observed Data) of the Mean Change from Baseline on the FFI Total Pain Subscale Score by Visit and Treatment Group (Refined Population)

| | LSM Change from Baseline [a] (SE) | | Estimated LSM Treatment Difference of EN3835-Placebo[b] | p |
|---|---|---|---|---|
| Visit | EN3835 | Placebo | (LCL, UCL) | value[b] |

Note:

MMRM was performed on observed data. The MMRM model included dependent variable as the change from the Baseline to each visit (ie, change from Baseline score to Days 15, 29, 43, and 57), fixed effect as treatment group, treatment by visit interaction, covariates such as the Baseline Foot Pain Subscale at Day 1, maximum of Nodule length/Nodule width and the total, number of nodules and the repeated measure was the study visit. An unstructured covariance matrix was used to model the covariance of within-participants values.

Change from Baseline to Each Visit on the FFI Total Combined (Pain and Difficulty) Score The FFI Total Combined (Pain and Difficulty) score decreased (improved) in both the EN3835 and placebo treatment groups during the study. The mean (SD) change from Baseline to Day 57 was −21.719 (16.9844) in the EN3835 treatment group and −14.519 (16.5685) in the placebo treatment group. Changes from Baseline on the FFI Total Combined (Pain and Difficulty) score for participants treated in the left foot or right foot only or both feet are presented herein.

TABLE 67

Overall Observed and Change from Baseline on the FFI Total Combined (Pain and Difficulty) Score by Visit and by Treatment Group (Refined Population)

| | | EN3835 (N = 61) | | Placebo (N = 65) | | Overall (N = 126) | |
|---|---|---|---|---|---|---|---|
| Visit | Statistic | Observed Value | Change from Baseline[a] | Observed Value | Observed from Baseline[a] | Change Value | Observed from Baseline[a] |
| Overall | | | | | | | |
| Baseline[a] | n | 61 | | 65 | | 126 | |
| | Mean | 48.716 | | 48.520 | | 48.615 | |
| | SD | 10.8847 | | 10.4757 | | 10.6333 | |
| | Median | 48.300 | | 49.400 | | 49.100 | |
| | Min | 24.00 | | 23.10 | | 23.10 | |
| | Max | 72.00 | | 69.70 | | 72.00 | |
| Day 15 | n | 60 | 60 | 60 | 60 | 120 | 120 |
| | Mean | 48.668 | −0.010 | 41.050 | −7.418 | 44.859 | −3.714 |
| | SD | 13.3040 | 12.8693 | 15.6985 | 9.9308 | 14.9857 | 12.0352 |
| | Median | 49.750 | −0.600 | 43.050 | −5.000 | 45.750 | −3.150 |
| | Min | 22.10 | −27.10 | 8.10 | −33.00 | 8.10 | −33.00 |
| | Max | 72.00 | 30.10 | 70.70 | 6.70 | 72.00 | 30.10 |
| Day 29 | n | 60 | 60 | 57 | 57 | 117 | 117 |
| | Mean | 36.213 | −12.448 | 35.530 | −12.996 | 35.880 | −12.715 |
| | SD | 15.4111 | 12.6666 | 16.2738 | 13.9466 | 15.7724 | 13.2507 |
| | Median | 37.300 | −11.500 | 37.000 | −9.600 | 37.000 | −10.300 |
| | Min | 5.90 | −38.50 | 2.00 | −66.00 | 2.00 | −66.00 |
| | Max | 66.10 | 10.50 | 67.00 | 6.00 | 67.00 | 10.50 |
| Day 43 | n | 55 | 55 | 60 | 60 | 115 | 115 |
| | Mean | 29.960 | −18.702 | 31.957 | −16.588 | 31.002 | −17.599 |
| | SD | 15.7583 | 14.0138 | 16.6350 | 14.9229 | 16.1817 | 14.4708 |
| | Median | 28.700 | −17.300 | 31.550 | −13.250 | 29.400 | −15.400 |
| | Min | 0.00 | −48.40 | 0.00 | −65.00 | 0.00 | −65.00 |
| | Max | 66.10 | 15.90 | 63.00 | 8.00 | 66.10 | 15.90 |
| Day 57/EOS/ET | n | 59 | 59 | 62 | 62 | 121 | 121 |
| | Mean | 27.344 | −21.719 | 33.773 | −14.519 | 30.638 | −18.030 |
| | SD | 17.9546 | 16.9844 | 17.6012 | 16.5685 | 17.9918 | 17.0889 |
| | Median | 24.000 | −22.300 | 34.850 | −11.150 | 32.000 | −16.000 |
| | Min | 0.00 | −55.00 | 0.00 | −65.00 | 0.00 | −65.00 |
| | Max | 68.40 | 11.80 | 67.00 | 12.90 | 68.40 | 12.90 |

[a]Baseline was defined as the last non-missing assessment prior to the study intervention injection on Day 1.
Note:
Total Combined score was defined as the sum of both Total Pain (normalized) and Total Difficulty Subscale scores.

In the Refined Population, the difference between the EN3835 and placebo treatment groups on the FFI Total Combined (Pain and Difficulty) score was significant favoring EN3835 treatment on Day 57 only (LSM difference, −6.962; 95% CI, −12.873 to −1.051; p=0.021).

TABLE 68

MMRM Estimate (Observed Data) of the Change from Baseline on the FFI Total Combined (Pain and Difficulty) Score by Visit and Treatment Group (Refined Population)

| | LSM Change from Baseline [a] (SE) | | Estimated LSM Treatment Difference of EN3835-Placebo [b] Difference | p |
|---|---|---|---|---|
| Visit | EN3835 | Placebo | (LCL, UCL) | value [b] |
| Day 15 | −0.026 (1.48) | −7.269 (1.47) | 7.243 (3.109, 11.376) | <0.001 |
| Day 29 | −12.387 (1.72) | −12.646 (1.73) | 0.260 (−4.572, 5.091) | 0.915 |
| Day 43 | −17.932 (1.88) | −16.167 (1.82) | −1.764 (−6.953, 3.424) | 0.502 |

TABLE 68-continued

MMRM Estimate (Observed Data) of the Change from Baseline on the FFI Total Combined (Pain and Difficulty) Score by Visit and Treatment Group (Refined Population)

| | LSM Change from Baseline [a] (SE) | | Estimated LSM Treatment Difference of EN3835-Placebo [b] Difference | p |
|---|---|---|---|---|
| Visit | EN3835 | Placebo | (LCL, UCL) | value [b] |
| Day 57 | −21.387 (2.14) | −14.424 (2.09) | −6.962 (−12.873, −1.051) | 0.021 |

[a] The LSM change from Baseline to Days 15, 29, 43, and 57 in the Foot Pain Subscale for EN3835 and placebo treatment was obtained from the fitted MMRM model.
[b] The treatment effect and 95% CI comparing EN3835 with placebo was also estimated using MMRM.
Note:
MMRM was performed on observed data. The MMRM model included dependent variable as the change from the Baseline to each visit (ie, change from Baseline score to Days 15, 29, and 57), fixed effect as treatment group, treatment by visit interaction, covariates such as the Baseline Foot Pain Subscale at Day 1, maximum of nodule length/nodule width and the total number of nodules and repeated measures was the study visit. An unstructured covariance matrix was used to model the covariance of within-participant's values.

Comparison Between Treatment Groups in the Change from Baseline to Each Visit on the FFI Total Activity Limitation Subscale Score In the Refined Population, there was no significant difference between EN3835 and placebo treatment groups in the mean change from Baseline in the FFI Total Activity Subscale score however there was a trend towards improvement at Day 57 favoring EN3835 treatment.

TABLE 69

MMRM Estimate (Observed Data) of Change from Baseline on the FFI Total Activity Limitation Subscale Score by Visit Treatment Group (Refined Population)

| | LSM Change from Baseline [a] (SE) | | Estimated LSM Treatment Difference of EN3835-Placebo[b] | p |
|---|---|---|---|---|
| Visit | EN3835 | Placebo | Difference (LCL, UCL) | value[b] |
| Day 15 | 0.009 (0.28) | −1.126 (0.28) | 1.135 (0.355, 1.915) | 0.005 |
| Day 29 | −2.120 (0.33) | −1.956 (0.33) | −0.164 (−1.094, 0.766) | 0.728 |
| Day 43 | −2.882 (0.36) | −2.432 (0.35) | −0.451 (−1.436, 0.535) | 0.367 |
| Day 57 | −3.437 (0.42) | −2.324 (0.41) | −1.113 (−2.269, 0.043) | 0.059 |

[a] The LSM change from Baseline to Days 15, 29, 43 and 57 on the FFI Total Activity Limitation Subscale score for EN3835 and placebo treatment was obtained from the fitted MMRM model.

[b]The treatment effect and 95% CI comparing EN3835 with placebo was also estimated using MMRM.

Note:

MMRM was performed on observed data. The MMRM model included dependent variable as the change from Baseline to each visit (ie, change from Baseline score to Days 15, 29, 43 and 57), fixed effect as treatment group and visit, treatment by visit interaction, covariates such as the Baseline FFI Total Activity Limitation Subscale score at Day 1, and the repeated measure is the study visit. An unstructured covariance matrix is used to model the covariance of within-participant values. Total Activity Limitation Subscale score is the sum of the scores of answered items of activity limitation score.

Comparison Between Treatment Groups in the Change from Baseline to Each Visit on the FFI Total Difficulty Subscale Score In the Refined Population, the difference between EN3835 and placebo treatment groups for the change from Baseline in the FFI Total Difficulty Subscale score was significant at Day 57 (LSM difference, −3.310; 95% CI, −6.490 to −0.129; p=0.042).

TABLE 70

MMRM Estimate (Observed Data) of Change from Baseline on the FFI Total Difficulty Subscale Score by Visit and Treatment Group (Refined Population)

| | LSM Change from Baseline [a] (SE) | | Estimated LSM Treatment Difference of EN3835-Placebo [b] | p |
|---|---|---|---|---|
| Visit | EN3835 | Placebo | Difference (LCL, UCL) | value[b] |
| Day 15 | 1.092 (0.87) | −3.200 (0.87) | 4.292 (1.859, 6.724) | <0.001 |
| Day 29 | −5.582 (0.96) | −5.824 (0.97) | 0.242 (−2.457, 2.942) | 0.859 |
| Day 43 | −8.312 (0.99) | −8.465 (0.96) | 0.152 (−2.582, 2.887) | 0.912 |
| Day 57 | −10.295 (1.15) | −6.985 (1.12) | −3.310 (−6.490, −0.129) | 0.042 |

[a] The LSM change from Baseline to Days 15, 29, 43, and 57 on the FFI Total Difficulty Subscale score for EN3835 and placebo treatment is obtained from the fitted MMRM model.

[b] The treatment effect and 95% CI comparing EN3835 with placebo is also estimated using MMRM.

Note:

MMRM was performed on observed data. The MMRM model included dependent variable as the change from Baseline to each visit (i.e., change from Baseline score to Days 15, 29, 43 and 57), fixed effect as treatment group and visit, treatment by visit interaction, covariates such as the Baseline FFI Total Difficulty Subscale score at Day 1, and the repeated measure was the study visit. An unstructured covariance matrix was used to model the covariance of within-participant values. The Total Difficulty Subscale score is the sum of the scores of answered items of difficulty score.

Change from Baseline to Each Visit in Nodule Hardness

In the Refined Population, on Days 15, 29, 43, and 57, improvements in nodular hardness occurred to a greater extent in the EN3835 treatment group than the placebo treatment group. Improvements on a foot level and a nodular level by left foot, right foot, and both feet are presented herein.

TABLE 71

Overall Observed and Mean Change from Baseline in the Nodular Hardness by Visit and Treatment Group on a Participant Level (Refined Population)

| | | EN3835 (N = 61) | | Placebo (N = 65) | | Overall (N = 126) | |
|---|---|---|---|---|---|---|---|
| Participant Level: Overall | Statistic | Observed Value | Change from Baseline | Observed Value | Change from Baseline | Observed Value | Change from Baseline |
| Baseline[a] | N | 61 | | 65 | | 126 | |
| | Mean | 48.199 | | 44.040 | | 46.054 | |
| | SD | 16.3919 | | 15.3308 | | 15.9269 | |
| | Median | 45.250 | | 40.500 | | 44.250 | |
| | Min | 9.50 | | 16.00 | | 9.50 | |
| | Max | 80.50 | | 76.25 | | 80.50 | |
| Day 15 | N | 61 | 61 | 62 | 62 | 123 | 123 |
| | Mean | 36.380 | −11.820 | 40.561 | −3.881 | 38.487 | −7.818 |
| | SD | 17.4342 | 19.8761 | 16.5036 | 10.6540 | 17.0316 | 16.3379 |
| | Median | 35.000 | −6.120 | 39.875 | −1.500 | 38.130 | −4.370 |
| | Min | 0.00 | −71.63 | 8.50 | −38.75 | 0.00 | −71.63 |
| | Max | 72.00 | 22.25 | 72.75 | 21.92 | 72.75 | 22.25 |
| Day 29 | N | 60 | 60 | 60 | 60 | 120 | 120 |
| | Mean | 37.286 | −11.108 | 41.885 | −2.230 | 39.586 | −6.669 |
| | SD | 19.1444 | 21.5113 | 18.3925 | 10.3030 | 18.8352 | 17.3759 |
| | Median | 37.000 | −6.460 | 43.000 | −1.375 | 38.875 | −3.155 |
| | Min | 0.00 | −80.50 | 0.00 | −41.00 | 0.00 | −80.50 |
| | Max | 78.13 | 22.25 | 76.50 | 26.75 | 78.13 | 26.75 |
| Day 43 | N | 55 | 55 | 59 | 59 | 114 | 114 |
| | Mean | 32.419 | −15.366 | 39.703 | −4.553 | 36.189 | −9.770 |
| | SD | 19.2098 | 19.6976 | 18.6225 | 12.0003 | 19.1759 | 16.9936 |
| | Median | 34.190 | −10.250 | 40.250 | −2.580 | 34.915 | −5.500 |

TABLE 71-continued

Overall Observed and Mean Change from Baseline in the Nodular Hardness by Visit and Treatment Group on a Participant Level (Refined Population)

| | | EN3835 (N = 61) | | Placebo (N = 65) | | Overall (N = 126) | |
|---|---|---|---|---|---|---|---|
| Participant Level: Overall | Statistic | Observed Value | Change from Baseline | Observed Value | Change from Baseline | Observed Value | Change from Baseline |
| | Min | 0.00 | −80.50 | 0.00 | −46.50 | 0.00 | −80.50 |
| | Max | 84.50 | 19.50 | 76.50 | 20.00 | 84.50 | 20.00 |
| Day 57/EOS/ET | N | 59 | 59 | 61 | 61 | 120 | 120 |
| | Mean | 30.798 | −17.302 | 37.478 | −6.488 | 34.194 | −11.805 |
| | SD | 18.8800 | 20.4508 | 19.0903 | 13.8087 | 19.2023 | 18.1510 |
| | Median | 34.500 | −11.750 | 36.750 | −3.420 | 34.815 | −7.685 |
| | Min | 0.00 | −80.50 | 0.00 | −50.50 | 0.00 | −80.50 |
| | Max | 77.00 | 9.00 | 76.25 | 13.67 | 77.00 | 13.67 |

[a]Baseline was defined as the last non-missing assessment prior to the study intervention injection on Day 1.

In the Refined Population, on a participant level there was a significant difference in the change in nodular hardness from Baseline to Days 15, 29, 43, and 57 between the EN3835 and placebo treatment groups. Nodule level changes were supportive and significant at all time points (p<0.001).

TABLE 72

MMRM Estimate (Observed Data) of Change from Baseline in the Nodular Hardness by Visit and Treatment Group (Refined Population)

| | | LSM Change from Baseline (SE) [a] | | Estimated LSM Treatment Difference of EN3835-Placebo[b] Difference (LCL, | p |
|---|---|---|---|---|---|
| Analysis | Visit | EN3835 | Placebo | UCL) | value[b] |
| Participant Level | Day 15 | −10.995 (1.85) | −4.611 (1.82) | −6.384 (−11.536, −1.232) | 0.016 |
| | Day 29 | −10.180 (2.03) | −2.763 (2.01) | −7.417 (−13.081, −1.753) | 0.011 |
| | Day 43 | −14.854 (2.05) | −5.020 (2.01) | −9.834 (−15.523, −4.145) | <0.001 |
| | Day 57 | −16.113 (2.10) | −7.352 (2.06) | −8.760 (−14.608, −2.913) | 0.004 |

[a] The LSM change from Baseline to Days 15,/29, 43 and 57 in the nodular hardness for EN3835 and placebo treatment was obtained from the fitted MMRM model.

[b]The treatment effect and 95% CI comparing EN383/5 with placebo was also estimated using MMRM.

Note:

MMRM was performed on observed data. The MMRM model included dependent variable as the change from the Baseline to each visit (ie, change from Baseline score to Days 15, 29, 43, 57), fixed effect as treatment group, treatment by visit interaction, covariates such as the Baseline average nodular hardness at Day 1-and the repeated measure was the study visit. An unstructured covariance matrix was used to model the covariance of within-participants values.

Participant Level: The MMRM model included dependent variable as the change from Baseline to each visit (ie, change from Baseline score to Days 15, 29, 43, and 57), fixed effect as treatment group and visit, treatment by visit interaction, covariates such as the baseline average nodular hardness at Day 1, maximum of nodule length/nodule width and the total number of treated nodules and repeated measures is the study visit. An unstructured covariance matrix is used to model the covariance of within-participant values.

Nodule Level: The MMRM model included dependent variable as the change from Baseline to each visit (ie, change from Baseline score to Days 15, 29, 43, and 7), fixed effect as treatment group and visit, treatment by visit interaction, covariates such as the baseline average nodular hardness at Day 1, maximum of nodule length/nodule width and the total number of treated nodules and repeated measures was the study visit and nodule identifier. An unstructured covariance matrix was used to model the covariance of within-participant values.

Analysis of Exploratory Endpoints in the Refined Population

Comparison Between Treatment Groups in the Changes from Baseline in the FFI Total Composite Score by Visit In the Refined Population, the difference in the FFI Total Composite score between EN3835 and placebo treatment groups was significant, favoring the EN3835 treatment group on Day 57 (LSM difference, −8.089; 95% CI, −15.029 to −1.148; p=0.023).

TABLE 73

MMRM Estimates (Observed Data) of the Mean Change from Baseline on the FFI Total Composite Score by Visit and by Treatment Group (Refined Population)

| | LSM Change from Baseline (SE)[a] | | Estimated LSM Treatment Difference between EN3835-Placebo[b] | p |
|---|---|---|---|---|
| Visit | EN3835 | Placebo | Difference (LCL, UCL) | value[b] |
| Day 15 | −0.019 (1.69) | −8.377 (1.68) | 8.358 (3.635, 13.082) | <0.001 |
| Day 29 | −14.511 (1.99) | −14.590 (1.99) | 0.079 (−5.498, 5.656) | 0.978 |
| Day 43 | −20.833 (2.19) | −18.562 (2.12) | −2.270 (−8.301, 3.760) | 0.457 |
| Day 57 | −24.812 (2.51) | −16.724 (2.45) | −8.089 (−15.029, −1.148) | 0.023 |

[a]The LSM change from Baseline to Days 15, 29, 43, and 57 on the FFI Total Composite score for EN3835 and placebo treatment was obtained from the fitted MMRM model.

[b]The treatment effect and 95% CI comparing EN3835 with placebo was also estimated using MMRM.

Note:

MMRM was performed on observed data.

The MMRM model included dependent variable as the change from Baseline to each visit (ie, change from Baseline score to Days 15, 29, 43 and 57), fixed effect as treatment group and visit, treatment by visit interaction, covariates such as the Baseline FFI Total Composite score at Day 1, and the repeated measure was the study visit. An unstructured covariance matrix was used to model the covariance of within-participant values.

Comparison Between Treatment Groups in the Changes in the PGIS PF Overall Score by Visit In the Refined Population, the differences between treatment groups in the change from Baseline in the PGIS PF Overall scores were significant, favoring EN3835 treatment on the Day 43 Visit (LSM difference, −0.397; 95% CI, −0.786 to −0.007; p=0.046).

TABLE 74

MMRM Estimates (Observed Data) of the Mean Change from Baseline on the PGIS PF Overall Score by Visit and by Treatment Group (Refined Population)

| Visit | LSM Change from Baseline (SE)[a] EN3835 | Placebo | Estimated LSM Treatment Difference between EN3835-Placebo[b] Difference (LCL, UCL) | p value[b] |
|---|---|---|---|---|
| Day 15 | −0.319 (0.11) | −0.781 (0.11) | 0.463 (0.155, 0.771) | 0.004 |
| Day 29 | −0.973 (0.13) | −0.885 (0.13) | −0.087 (−0.459, 0.285) | 0.643 |
| Day 43 | −1.408 (0.14) | −1.011 (0.14) | −0.397 (−0.786, −0.007) | 0.046 |
| Day 57 | −1.496 (0.15) | −1.099 (0.15) | −0.397 (−0.817, 0.023) | 0.064 |

[a]The LSM change from Baseline to Days 15, 29, 43 and 57 on the PGIS PF Overall score for EN3835 and placebo treatment was obtained from the fitted MMRM mode.
[b]The treatment effect and 95% CI comparing EN3835 with placebo was also estimated using MMRM.
Note:
MMRM was performed on observed data.
The MMRM model included dependent variable as the change from Baseline to each visit (ie change from Baseline score to Days 15, 29, 43 and 57), fixed effect as treatment group and visit, treatment by visit interaction, covariate as the Baseline PGIS PF Overall score at Day 1 and repeated measures was the study visit. An unstructured covariance matrix was used to model the covariance of within-participant values.

Comparison Between Treatment Groups in the Changes in the PGIS Foot Pain Subscale Scores by Visit In the Refined Population, the differences between treatment groups in the change from Baseline in the PGIS Foot Pain Subscale scores were significant, favoring EN3835 treatment on the Day 57 Visit (LSM difference, −0.455; 95% CI, −0.870 to −0.041; p=0.032).

TABLE 75

MMRM Estimates (Observed Data) of the Mean Change from Baseline on the PGIS Foot Pain Subscale by Visit and Treatment Group (Refined Population)

| Visit | LSM Change from Baseline (SE)[a] EN3835 | Placebo | Estimated LSM Treatment Difference between EN3835-Placebo[b] Difference (LCL, UCL) | p value[b] |
|---|---|---|---|---|
| Day 15 | −0.091 (0.10) | −0.592 (0.10) | 0.501 (0.229, 0.772) | <0.001 |
| Day 29 | −0.703 (0.12) | −0.762 (0.12) | 0.059 (−0.284, 0.403) | 0.733 |
| Day 43 | −1.223 (0.14) | −1.033 (0.14) | −0.190 (−0.583, 0.203) | 0.341 |
| Day 57 | −1.442 (0.15) | −0.986 (0.15) | −0.455 (−0.870, −0.041) | 0.032 |

[a]The LSM change from Baseline to Days 15, 29, 43 and 57 on the PGIS PF Overall score for EN3835 and placebo treatment was obtained from the fitted MMRM model.
[b]The treatment effect and 95% CI comparing EN3835 with placebo was also estimated using MMRM.
Note:
MMRM was performed on observed data.
The MMRM model included dependent variable as the change from Baseline to each visit (ie change from Baseline score to Days 15, 29, 43 and 57), fixed effect as treatment group and visit, treatment by visit interaction, covariate as the Baseline PGIS PF Overall score at Day 1 and repeated measures was the study visit. An unstructured covariance matrix was used to model the covariance of within-participant values.

Comparison Between Treatment Groups in the Changes in the PGIS Difficulty and Activity Limitation Subscale Scores by Visit In the Refined Population, there were no significant difference between treatment groups in the change from Baseline in the PGIS Difficulty and Activity Limitation Subscale scores favoring EN3835 treatment.

Comparison Between Treatment Groups in the Changes from Baseline in the CGIC Scores by Visit In the Refined Population, there was a significantly higher proportion of responders in the EN3835 treatment group on the Days 29 (EN3835: 46 of 58 participants; 79.3% vs placebo: 36 of 60; 60%; p=0.023) and 57 Visits (EN3835: 43 of 57 participants; 75.4% vs placebo: 34 of 61; 55.7%; p=0.025). The proportion of responders on a foot level are presented herein.

TABLE 76

Statistical Analysis of CGIC Scale Scores by Treatment Group and by Visit (Refined Population)

| Level: Participant Visit Improvement Scale Ratings | Statistics | EN3835 (N = 61) | Placebo (N = 65) |
|---|---|---|---|
| Day 15 | N | 59 | 61 |
| −3 (Very Much Worse) | n (%) | 2 (3.4) | 0 (0.0) |
| −2 (Much Worse) | n (%) | 2 (3.4) | 2 (3.3) |
| −1 (Minimally Worse) | n (%) | 6 (10.2) | 3 (4.9) |
| 0 (No Change) | n (%) | 11 (18.6) | 17 (27.9) |
| +1 (Minimal Improvement) | n (%) | 22 (37.3) | 25 (41.0) |
| +2 (Much Improvement) | n (%) | 14 (23.7) | 13 (21.3) |
| +3 (Very Much Improvement) | n (%) | 2 (3.4) | 1 (1.6) |
| | Mean (SD) | 0.7 (1.32) | 0.8 (1.01) |
| Responders[a] | n (%) | 38 (64.4) | 39 (63.9) |
| 95% CI[b] | (LCL, UCL) | (51.7, 75.4) | (51.4, 74.8) |
| Risk Difference (EN3835 - Placebo)[c] | % | 0.5 | |
| 95% CI | (LCL, UCL) | (−16.7, 17.6) | |
| p value (CMH test for General association)[d] | | | 0.957 |
| Day 29 | n | 58 | 60 |
| −3 (Very Much Worse) | n (%) | 0 (0.0) | 0 (0.0) |
| −2 (Much Worse) | n (%) | 0 (0.0) | 0 (0.0) |
| −1 (Minimally Worse) | n (%) | 6 (10.3) | 3 (5.0) |
| 0 (No Change) | n (%) | 6 (10.3) | 21 (35.0) |
| +1 (Minimal Improvement) | n (%) | 20 (34.5) | 19 (31.7) |
| +2 (Much Improvement) | n (%) | 21 (36.2) | 14 (23.3) |
| +3 (Very Much Improvement) | n (%) | 5 (8.6) | 3 (5.0) |
| | Mean (SD) | 1.2 (1.09) | 0.9 (0.99) |
| Responders[a] | n (%) | 46 (79.3) | 36 (60.0) |
| 95% CI[b] | (LCL, UCL) | (67.2, 87.7) | (47.4, 71.4) |
| Risk Difference (EN3835 - Placebo)[c] | % | 19.3 | |
| 95% CI | (LCL, UCL) | (3.1, 35.5) | |
| p value (CMH test for General association)[d] | | | 0.023 |

TABLE 77

Statistical Analysis of CGIC Scale Scores by Treatment Group and by Visit (Refined Population) (Continued)

| Level: Participant Visit Improvement Scale Ratings | Statistics | EN3835 (N = 61) | Placebo (N = 65) |
|---|---|---|---|
| Day 43 | n | 54 | 59 |
| −3 (Very Much Worse) | n (%) | 0 (0.0) | 0 (0.0) |
| −2 (Much Worse) | n (%) | 1 (1.9) | 0 (0.0) |
| −1 (Minimally Worse) | n (%) | 2 (3.7) | 3 (5.1) |
| 0 (No Change) | n (%) | 7 (13.0) | 17 (28.8) |
| +1 (Minimal Improvement) | n (%) | 18 (33.3) | 15 (25.4) |
| +2 (Much Improvement) | n (%) | 15 (27.8) | 19 (32.2) |
| +3 (Very Much Improvement) | n (%) | 11 (20.4) | 5 (8.5) |
| | Mean (SD) | 1.4 (1.18) | 1.1 (1.08) |
| Responders[a] | n (%) | 44 (81.5) | 39 (66.1) |
| 95% CI[b] | (LCL, UCL) | (69.2, 89.6) | (53.4, 76.9) |
| Risk Difference (EN3835 - Placebo)[c] | % | 15.4 | |
| 95% CI | (LCL, UCL) | (−0.5, 31.3) | |
| p value (CMH test for General association)[d] | | | 0.066 |
| Day 57 | n | 57 | 61 |
| −3 (Very Much Worse) | n (%) | 1 (1.8) | 0 (0.0) |
| −2 (Much Worse) | n (%) | 0 (0.0) | 1 (1.6) |
| −1 (Minimally Worse) | n (%) | 4 (7.0) | 4 (6.6) |
| 0 (No Change) | n (%) | 9 (15.8) | 22 (36.1) |
| +1 (Minimal Improvement) | n (%) | 11 (19.3) | 9 (14.8) |

TABLE 77-continued

Statistical Analysis of CGIC Scale Scores by Treatment Group and by Visit (Refined Population) (Continued)

| Level: Participant Visit Improvement Scale Ratings | Statistics | EN3835 (N = 61) | Placebo (N = 65) |
|---|---|---|---|
| +2 (Much Improvement) | n (%) | 20 (35.1) | 18 (29.5) |
| +3 (Very Much Improvement) | n (%) | 12 (21.1) | 7 (11.5) |
| | Mean (SD) | 1.4 (1.33) | 1.0 (1.24) |
| Responders[a] | n (%) | 43 (75.4) | 34 (55.7) |
| 95% CI[b] | (LCL, UCL) | (62.9, 84.8) | (43.3, 67.5) |
| Risk Difference (EN3835 - Placebo)[c] | % | 19.7 | |
| 95% CI | (LCL, UCL) | (3.0, 36.4) | |
| p value (CMH test for General association)[d] | | | 0.025 |

[a]The responder (by foot/feet) is defined as a participant with a response of "Minimal Improvement", "Much Improvement" or "Very Much Improvement" in the CGIC Scale. If participant is treated for both feet, then the assessment can be combined at participant level using worst case approach, if one foot response recorded as 'Minimal Improvement' and 'Very Much Improvement' in another foot, then response is considered as 'Minimal Improvement'.
[b]Based on Wilson Score method.
[c]The risk difference is the difference in proportion of responders between EN3835 and Placebo.
[d]The p value derived from CMH test of general association.

Comparison Between Treatment Groups in the Changes from Baseline in the PGIC PF Overall Scores In the Refined Population, the difference between treatment groups in the change in the PGIC PF Overall Scale scores from Baseline to Day 57 was significant, favoring EN38385 treatment (risk difference, 20.7; 95% CI, 3.3-38.1; p=0.023). Changes in the PGIC Overall scores on a foot level are presented herein.

TABLE 78

Analysis Results of PGIC PF Overall Scale at Day 57 by Treatment Group (Refined Population)

| Treated Foot Visit Improvement Scale Ratings | Statistic | EN3835 (N = 61) | Placebo (N = 65) |
|---|---|---|---|
| Overall | | | |
| Day 57 | n | 59 | 62 |
| −3 (Very Much Worse) | n (%) | 1 (1.7) | 2 (3.2) |
| −2 (Much Worse) | n (%) | 2 (3.4) | 5 (8.1) |
| −1 (Minimally Worse) | n (%) | 3 (5.1) | 10 (16.1) |
| 0 (No Change) | n (%) | 17 (28.8) | 20 (32.3) |
| +1 (Minimal Improvement) | n (%) | 12 (20.3) | 12 (19.4) |
| +2 (Much Improvement) | n (%) | 15 (25.4) | 7 (11.3) |
| +3 (Very Much Improvement) | n (%) | 9 (15.3) | 6 (9.7) |
| | Mean (SD) | 1.0 (1.40) | 0.3 (1.50) |
| Responders[a] | n (%) | 36 (61.0) | 25 (40.3) |
| 95% CI[b] | (LCL, UCL) | (48.3, 72.4) | (29.0, 52.7) |
| Risk Difference (EN3835 - Placebo)[c] | % | 20.7 | |
| 95% CI | (LCL, UCL) | (3.3, 38.1) | |
| p value (CMH test for General association)[d] | | | 0.023 |

[a]A responder is defined as a participant with a response of "Minimal Improvement", "Much Improvement" or "Very Much Improvement" in the PGIC-PF Overall score.
[b]Based on the Wilson Score method.
[c]The risk difference is the difference in proportion of responders between EN3835 and Placebo.
[d]The p value is derived from CMH test of general association.

Comparison Between Treatment Groups in the Changes from Baseline in the PGIC Foot Pain Subscale Scores In the Refined Population, the difference between treatment groups in the change in the PGIC PF Foot Pain Subscale scores from Baseline to Day 57 was significant, favoring EN38385 treatment (risk difference, 20.9; 95% CI, 3.6-38.2, p=0.021). Changes in the PGIC Foot Pain Subscale scores on a foot level are presented herein.

TABLE 79

Analysis Results of PGIC PF Overall Scale at Day 57 by Treatment Group (Refined Population)

| Treated Foot Visit Improvement Scale Ratings | Statistic | EN3835 (N = 61) | Placebo (N = 65) |
|---|---|---|---|
| Overall | | | |
| Day 57 | n | 59 | 62 |
| −3 (Very Much Worse) | n (%) | 0 (0.0) | 3 (4.8) |
| −2 (Much Worse) | n (%) | 4 (6.8) | 5 (8.1) |
| −1 (Minimally Worse) | n (%) | 1 (1.7) | 9 (14.5) |
| 0 (No Change) | n (%) | 15 (25.4) | 17 (27.4) |
| +1 (Minimal Improvement) | n (%) | 8 (13.6) | 16 (25.8) |
| +2 (Much Improvement) | n (%) | 20 (33.9) | 7 (11.3) |
| +3 (Very Much Improvement) | n (%) | 11 (18.6) | 5 (8.1) |
| | Mean (SD) | 1.2 (1.42) | 0.3 (1.52) |
| Responders[a] | n (%) | 39 (66.1) | 28 (45.2) |
| 95% CI[b] | (LCL, UCL) | (53.4, 76.9) | (33.4, 57.5) |
| Risk Difference (EN3835 - Placebo)[c] | % | | 20.9 |
| 95% CI | (LCL, UCL) | (3.6, 38.2) | (3.6, 38.2) |
| p value (CMH test for General association)[d] | | | 0.021 |

[a]A responder is defined as a participant with a response of "Minimal Improvement", "Much Improvement" or "Very Much Improvement" in the Foot Pain Subscale score.
[b]Based on the Wilson Score method.
[c]The risk difference is the difference in proportion of responders between EN3835 and Placebo.
[d]The p value is derived from CMH test of general association.

Comparison Between Treatment Groups in the Changes from Baseline in the PGIC PF Difficulty and Activity Limitation Subscale Scores In the Refined Population, the differences between treatment groups in the change in the PGIC PF Difficulty (risk difference, 17.6; 95% CI, 0.1-35.0; p=0.054) and Activity Limitation Subscale scores from Baseline to Day 57 (risk difference, 17.5; 95% CI, −0.1 to 35.0; p=0.056) were not significant. Changes in these subscales scores on a foot level are presented herein.

Comparison Between Treatment Groups in the Changes from Baseline in the Pain Intensity NRS Scores by Visit In the Refined Population, the change from Baseline to Day 57 in the Pain Intensity NRS numerically improved in both treatment groups, but there were no significant differences amongst the treatment groups (LSM difference, −0.829; 95% CI, −1.817 to 0.159; p=0.099).

Comparison in the Subject Satisfaction with Treatment Scale Scores by Visit and Treatment Group In the Refined Population, at Day 57, there were 33 (56.9%) responders in the EN3835 treatment group, and 24 (39.3%) responders in the placebo treatment group on the Subject Satisfaction with Treatment Scale. While the difference in the proportion of responders was not significant, a clinically relevant treatment difference was observed (p=0.056).

Change in Nodule Size by Visit and by Treatment Group

In the Refined Population, there was no significant difference in the change in nodule size from Baseline between treatment groups at any visit, when assessed on a nodular level or a participant level.

Change in Nodular Consistency

In the Refined Population, on a participant-level, there was a significant difference between treatment groups in the change in nodular consistency from Baseline to Day 57 (risk difference, 25.8; 95% CI, 11.1-40.5; p=0.001). Changes in nodular consistency from Baseline to Days 15, 29, 43, and 57 were also significant on a nodular level (p<0.001).

Examination of Subgroups

Subgroup analyses were conducted for the primary endpoint, secondary endpoints, and frequency of TEAEs were performed for the following subgroups:

Number of injections (1 vs 2 vs 3 vs 4) at Day 1

Baseline FFI Total Pain Subscale score: Group 1 vs Group 2 a. Group 1: subscale score ≤20 for participants without orthotics or subscale score ≤26 for participants with orthotics b. Group 2: subscale score >21 for participants without orthotics or subscale score ≥27 for participants with orthotics.

FFI Total Pain Subscale Score

A subgroup analysis of the primary endpoint showed that there were no significant differences between EN3835 and placebo in the mean change from Baseline to Day 57 on the FFI Total Pain Subscale score when analyzed by the count of injections (1, 2, 3, and 4) and by the Total Pain Subscale score at Baseline in Groups 1 and 2.

FFI Total Combined (Pain and Difficulty) Score

A subgroup analysis of first key secondary endpoint, showed that there were no significant differences between EN3835 and placebo treatment groups in the mean change from Baseline to Day 57 by the FFI Total Combined (Pain and Difficulty) score when analyzed by the count of injections (1, 3, and 4) and by the Baseline Total Pain Subscale score in Groups 1 and 2. There was a significant difference amongst the treatment groups in this score, favoring EN3835 treatment when 2 injections were given (−9.464; 95% CI, −18.703 to −0.225; p=0.045).

Clinical Global Impression of Change

A subgroup analysis of the key second secondary endpoint, using the CMH test, showed that there was a significant difference between the proportion of EN3835-treated participants and placebo-treated participants that were responders at Day 57 on the CGIC Scale in the following subgroups:

Two injections in the left foot: risk difference, 48.2%; 95% CI, 20.2-76.3; p=0.003

Two injections in the left foot only: risk difference, 54.6%; 95% CI, 20.1-89.1; p=0.009.

Two injections in the left foot only or right foot only: risk difference, 40.9%; 95% CI, 14.2-67.7; p=0.006

Two injections on a participant level overall: risk difference, 37.1%; 95% CI, 13.4-60.9; p=0.004.

Total Pain Subscale Score in Group 2 for the left or right foot only: 29.7%; 95% CI, 2.1-57.4; p=0.039

Nodular Hardness by Durometer Measurements

A subgroup analysis of the third secondary endpoint, showed that there was a significant difference between treatment groups, favoring EN3835 treatment in the mean change from Baseline (Day 1) to the Day 57 in the nodular hardness of the treated nodules in the subgroup of participants that received 2 injections (LSM difference, −11.950; 95% CI, −20.729 to −3.171; p=0.008) and in Group 1 participants (−6.491; 95% CI, −12.953 to −0.028; p=0.049).

By-Participant Displays

There were no by-participant displays of individual response to study intervention except as presented in the data listings.

Efficacy Conclusions

The primary endpoint of this study was the change from Baseline to Day 57 in the FFI Total Pain Subscale. There was no significant difference between treatment groups in the decreases in the mean Total Foot Pain Subscale score at Day 57.

There was significantly higher proportion of responders on the CGIC Scale on Day 57 in the EN3835 treatment group (61 of 88 participants; 69.3%; 95% CI, 59.0-78.0) than in the placebo treatment group (48 of 88 participants; 54.5%; 95% CI, 44.2-64.5) (p=0.044).

There was a significant difference in the improvement from Baseline in mean nodular hardness on Day 57 favoring EN3835 treatment (LSM difference, −5.877; 95% CI, −10.847 to −0.908; p=0.020).

Changes from Baseline in the FFI Composite score, FFI Total Pain Subscale score, Total Pain Subscale score percent, FFI Total Combined (Pain and Difficulty) Subscale score, and the FFI Total Activity Limitation Subscale score, were similar between treatment groups.

In EN3835-treated participants, nodules softened to a greater extent than in placebo treated participants.

There was a significantly higher proportion of participants whose nodule responded (nodule consistency became at least 1-level softer) in the EN3835 treatment group than the placebo treatment at all timepoints. At Day 57, there was a significantly higher proportion of responders (64; 75.3%) in the EN3835 treatment group than in the placebo treatment group (46; 52.9%) (risk difference, 22.4%; 95% CI, 8.5-36.4; p=0.002).

Improvements in the severity of plantar fibromatosis on the PGIS PF Overall score, PGIS Foot Pain Subscale score, PGIS Difficulty, and PGIS Activity Limitation score were similar between the EN3835 and placebo treatment groups on Days 15, 29, 43, and 57, with no significant differences favoring EN3835 treatment.

Participants in both treatment groups reported changes in the PGIC PF Overall Scale, the overall PGIC Foot Pain, Activity Limitation and Difficulty Subscales, however, there were no significant differences between scores favoring EN3835 treatment.

Participants in both treatment groups reported improvements on the Pain Intensity NRS Scale, however, there were no significant differences between scores favoring EN3835 treatment.

There was no significant difference between treatment groups in the change in nodule size from Baseline at any visit.

Efficacy Conclusions in the Refined Population

Ad-hoc analyses were conducted in the Refined Population (n=126). This population comprised participants in the FAS Population with nodules that were "Hard" and "Firm Throughout" (excluding "Moderately Firm") and a Pain Intensity NRS score ≤9 (excluding participants with a Pain Intensity NRS score=10 at Baseline).

In this Refined Population:

There was a significant difference from Baseline to Day 57 in the mean Total Foot Pain Subscale score between the EN3835 (LSM [SE], −11.057 [1.03]) and placebo treatment groups (−7.451 [0.99]), favoring EN3835 treatment (LSM difference, −3.516; 95% CI, −6.312 to −0.720; p=0.014).

There was a significant difference between treatment groups in the mean change from Baseline to Day 57 on the FFI Total Combined (Pain and Difficulty) Subscale score, favoring EN3835 treatment (LSM difference, −6.889; 95% CI, −12.674 to −1.104, p=0.02).

There was a significantly higher proportion of responders on the CGIC Scale on Day 57 in the EN3835 treatment group (43 of 57 participants; 75.4%; 95% CI, 62.9-84.8) compared to the placebo treatment group (34 of 61 participants (55.7%; 95% CI, 43.3-67.5) (p=0.025).

There was a significant difference in the improvement (decreases) in mean nodular hardness from Baseline to Day 57 between treatment groups, favoring EN3835 treatment (LSM difference, −8.975; 95% CI, −14.730 to −3.220; p=0.002).

There was no significant difference between EN3835 and placebo treatment groups for the mean change from Baseline in the FFI Total Activity Limitation Subscale.

There was a significant difference between EN3835 and placebo treatment groups for the change from Baseline in the FFI Total Difficulty Subscale score favoring EN3835 treatment at the Day 57 Visit (LSM difference, −3.310; 95% CI, −6.490 to −0.129; p=0.042).

There was a significant difference between EN3835 and placebo treatment groups, favoring EN3835 treatment on a participant-level and a nodular-level, in the change from Baseline to Days 15, 29, 43, and 57 in nodular hardness.

There was a significant difference between treatment groups, favoring EN3835 treatment, on a participant-level and on a nodular-level in the change in nodular consistency from Baseline to Days 15, 29, 43, and 57.

There was a significant difference between the EN3835 and placebo treatment groups in the change from Baseline on the FFI Total Composite score, favoring the EN3835 treatment group on Day 57 only (LSM difference, −8.089; 95% CI, −15.029 to −1.148, p=0.023).

There was a significant difference between the EN3835 and placebo treatment groups in the change from Baseline in the PGIS PF Overall scores favoring EN3835 treatment at the Day 43 Visit (LSM difference, −0.397; 95% CI, −0.786 to −0.007; p=0.046).

There was a significant difference between the EN3835 and placebo treatment groups in the change from Baseline in the PGIS Foot Pain Subscale scores favoring EN3835 treatment at the Day 57 Visit (LSM difference, −0.455; 95% CI, −0.870 to −0.041; p=0.032).

There was no significant difference between the EN3835 and placebo treatment groups in the change from Baseline in the PGIS Difficulty or Activity Subscale scores favoring EN3835 treatment.

There was a significant difference between treatment groups in the change in the PGIC PF Overall Scale scores from Baseline to Day 57, favoring EN3835 treatment (risk difference, 20.7; 95% CI, 3.3-38.1; p=0.023).

There was a significant difference between treatment groups in the change in the PGIC PF Foot Pain Subscale scores from Baseline to Day 57, favoring EN3835 treatment (risk difference, 20.9; 95% CI, 3.6-38.2; p=0.021).

There were no significant differences between treatment groups in the change in the PGIC PF Difficulty (risk difference, 17.6; 95% CI, 0.1-35.0, p=0.054) and Activity Limitation Subscale scores from Baseline to Day 57 (risk difference, 17.5; 95% CI, −0.1 to 35.0; p=0.056).

Participants in both treatment groups reported improvements on the Pain Intensity NRS Scale scores, however, there was no significant difference between treatment groups in the change from Baseline to Day 57 in the Pain Intensity NRS scores (LSM difference, −0.829; 95% CI, −1.817 to 0.159; p=0.099).

At Day 57, there were 33 (56.9%) responders in the EN3835 treatment group, and 24 (39.3%) responders in the placebo treatment group on the Subject Satisfaction with Treatment Scale. While the difference in the proportion of responders was not significant, a clinically relevant treatment difference was observed (p=0.056).

There was no significant difference in the change in nodule size from Baseline between treatment groups at any time point, when assessed on a nodular-level or a participant-level.

In summary, these ad hoc analyses support the treatment effect of EN3835 in an appropriately refined patient population.

When exploratory analyses were conducted in a refined subgroup of participants that excluded participants with "Moderately Firm" nodules (which was consistent with Study EN3835-105; Table 80) and a participants with "moderately firm" nodules and Pain Intensity NRS score of 10 (Table 80), there was a significant improvement from Baseline in the EN3835 treatment group in the FFI Pain Subscale score, FFI Total Combined (Pain and Difficulty) Subscale score, the FFI Difficulty Subscale score, and FFI Total score. Significant improvements of EN3835 vs placebo were demonstrated in CGIC scale scores and improvements in nodular hardness and consistency.

TABLE 80

Results as p-values

| Endpoints | Full Analysis Set Population N = 172 | FAS Subset A (Exclude Firmness = Moderately Firm) N = 138 | FAS Subset B (Exclude NRS = 10) N = 152 | Refined Population (Exclude NRS = 10 and Firmness = Moderately Firm) N = 126 |
|---|---|---|---|---|
| FFI Foot Pain Subscale | 0.252*** | 0.026** | 0.038** | 0.014** |
| FFI Combined Pain and Difficulty Subscale | 0.307*** | 0.048** | 0.043** | 0.020** |
| CGIC | 0.037* | 0.009* | 0.024** | 0.025** |
| Nodule Hardness-Participant level | 0.022* | 0.004* | 0.002* | 0.002* |
| Pain Intensity NRS | 0.588*** | 0.160*** | 0.198*** | 0.099*** |
| Nodule Consistency - Nodular level | 0.002** | <0.001* | <0.001* | <0.001* |
| PGIC-PF Overall | 0.095*** | 0.031** | 0.081*** | 0.023** |
| FFI Total Composite Score | 0.203*** | 0.050** | 0.053*** | 0.023** |
| FFI Difficulty Subscale | 0.311*** | 0.107*** | 0.082*** | 0.042** |
| FFI Activity Limitation Subscale | 0.343*** | 0.082*** | 0.089*** | 0.059*** |
| PGIS PF Overall | 0.178*** | 0.100*** | 0.148*** | 0.064*** |
| Subject Satisfaction with Treatment | 0.227*** | 0.046** | 0.216*** | 0.056*** |

*P < 0.01;
**P < 0.05;
***P > 0.05

Characterization of Patients with Plantar Fibromatosis: Examining Baseline Characteristics From Study 222

While PFI is reportedly more common among middle-aged Caucasian men, the phase 1 study suggests that race/ethnicity, sex, and other demographics may not completely align with previous reports: 46% (11/24) of participants were female, and 8% were Black/African American (AA). Here, baseline demographic/clinical characteristics of a larger number of patients from Study 222 were characterized.

Methods

Adults with PFI scoring ≥50% on the Foot Function Index (FFI)-Pain subscale with ≥1 "moderately firm" to "hard"

nodule requiring ≤4 intralesional injections per visit were eligible. Clinical/demographic characteristics, nodule features, orthotics use, and foot function (pain, activity, and difficulty) via the FFI-overall scale and a Patient Global Impression of PFI-related Severity (PGIS-PF overall) measure were collected.

Results 176 patients enrolled in the study. More than half were female (67.6%, n=119) and White (79.5%; n=140). The median (range) age was 56 (19-82) years, and 19% (n=33) were Black/AA. Most had unilateral PFI (60.8%; n=107), did not use orthotics (72.2%; n=127), and had nodules≤4 cm (98%; n=172) with a median (range) of nodular hardness (by durometer, scored 0-100) of 42.19 (5.25-80.50). The mean (SD) score on the FFI-Pain subscale was 25.07 (5.29), with PGIS-PF overall score reported as "moderate" by 49.4% (n=87) and "severe" by 47.7% (n=84) of patients.

Example 4—A Phase 3, Double-Blind, Randomized, Placebo-Controlled Study to Assess the Efficacy, Safety, and Tolerability of EN3835 vs Placebo in the Treatment of Plantar Fibromatosis (PFI) (Also Known as Ledderhose Disease) (STRIDE)

Study Design

This is a Phase 3, double-blind, placebo-controlled, study of the efficacy, safety, and tolerability study of EN3835 vs placebo in the treatment of plantar fibromatosis (also known as "Ledderhose disease"). Participants will be screened to randomize approximately 418 participants into 2 groups, an EN3835 group (n~209) and a placebo group (n~209) in a 1:1 ratio. Participants with unilateral plantar fibromatosis, with up to 2 nodules in the foot to be treated, will be enrolled in the study.

Nodules must be "Hard" or "Firm Throughout" on Screening and Day 1. Nodules will be measured on Days 1 and 29 using calipers. The size of the nodules using the largest width or length and the configuration of the nodules will be used to determine eligibility. Participants are permitted to receive up to a maximum of 2 treatment cycles (Day 1 and Day 29). The total number of study intervention injections across all nodules present shall not exceed 2 injections with a dose of 0.6 mg per nodule and a maximum total dose of 1.2 mg in the treated foot per treatment cycle. Rescue analgesic medication will be provided for the treatment of breakthrough pain due to plantar fibromatosis. Participants will be counseled to take rescue medications only to treat breakthrough pain due to plantar fibromatosis. Should rescue analgesic medication be required, the Pain Intensity NRS score should be documented before each dose of rescue medication. At approximately the same time every day, between 6:00 PM and 10:00 PM local time, participants will record the ADP score on the Pain Intensity NRS. The dose, frequency, amount, and timing of the rescue analgesic medication taken will be documented every time rescue medication is taken. At the Day 29 Visit, a second treatment cycle of the study intervention may be administered if Treatment 2 Criteria are met.

After receiving each treatment of study intervention, participants will be encouraged to resume normal daily activities, including walking, and bearing weight on the treated foot. All participants will return to the clinic for 5 follow-up visits on Days 15, 29, 43, 57, and 85.

For all participants, at the appropriate time points, the efficacy of the study intervention will be assessed on the Pain Intensity NRS, the FFI Scale, the PGIS subscales of foot pain, difficulty, activity limitation and the PGIS PF Overall, the PGIC subscales of foot pain, difficulty, activity limitation and the PGIC PF Overall, the Subject Satisfaction with Treatment Scale, the CGIC Scale, rescue medication use, nodular consistency (firmness) via palpation and nodular hardness via durometer. Safety will be assessed by evaluating the incidence, severity, and duration of TEAEs, AESIs, SAEs, changes in vital signs, and clinical laboratory values.

All participants will complete the study on the End of Study (EOS; Day 85) Visit, regardless of whether they receive 1 or 2 treatment cycles during the study. At the EOS visit, the treated nodules and safety will be assessed. The maximum duration of participation is up to 113 days (Screening Period: 28 days, Treatment Periods: up to 2 days, and a total Follow-up Period of 84 days). The duration of the study from first participant, first visit to last participant, last visit will be dependent on the ability of the sites to identify and enroll eligible participants.

After completing this study, participants will have the option to enroll in an observational Phase 3 extension study.

TABLE 81

| Objectives/Endpoints | |
|---|---|
| Objectives | Endpoints |
| Primary | |
| To assess the overall improvement in the intensity of foot pain with EN3835 vs placebo on the Pain Intensity Numeric Rating Scale (NRS). | The mean change from Baseline to Week 12 in the weekly mean of the average daily (24-hour) pain (ADP) score as measured on the Pain Intensity NRS, ranging from 0 ("No Pain") to 10 ("Worst Pain Imaginable") for EN3835 vs placebo. |
| Key Secondary | |
| To assess the improvement on the Foot Function Index (FFI)[a] Difficulty Subscale with EN3835 vs placebo. | The mean change from Baseline to Day 85 in the FFI Difficulty Subscale score (total score on 9 items) of the FFI, ranging from 0 ("No Difficulty") to 4 ("A Lot of Difficulty") for EN3835 vs placebo. |
| To assess the improvement on the FFI Activity Limitation Subscale with EN3835 vs placebo. | The mean change from Baseline to Day 85 on the FFI Activity Limitation Subscale score (total score on 3 items) ranging from 0 ("Never") to 4 ("Always") for EN3835 vs placebo. |

TABLE 81-continued

| Objectives/Endpoints | |
|---|---|
| Objectives | Endpoints |
| Secondary | |
| To assess the overall improvement in the intensity of foot pain on the Pain Intensity NRS with EN3835 vs placebo. | The mean change from Baseline to Weeks 2, 4, 6, 8, and 12 in the weekly mean of the ADP score as measured on the Pain Intensity NRS, ranging from 0 ("No Pain") to 10 ("Worst Pain Imaginable") for EN3835 vs placebo.<br>The proportion of participants treated with EN3835 vs placebo with ≥30% decrease from Baseline to Week 12 in the weekly mean of the ADP score as measured on the Pain Intensity NRS.<br>The proportion of participants treated with EN3835 vs placebo with ≥50% decrease from Baseline to Week 12 in the weekly mean of the ADP score as measured on the Pain Intensity NRS. |
| To assess the improvement on the FFI Pain Subscale with EN3835 vs placebo. | The mean change from Baseline to Days 15, 29, 43, 57, and 85 on the FFI Pain Subscale score (total score on 9 items), ranging from 0 ("None") to 4 ("Extreme") for EN3835 vs placebo. |
| To assess the improvement on the FFI Difficulty Subscale with EN3835 vs placebo. | The mean change from Baseline to Days 15, 29, 43, 57, and 85 in the FFI Difficulty Subscale score (total score on 9 items) of the FFI, ranging from 0 ("No Difficulty") to 4 ("A Lot of Difficulty") for EN3835 vs placebo. |
| To assess the improvement on the FFI Activity Limitation Subscale with EN3835 vs placebo. | The mean change from Baseline to Days 15, 29, 43, 57, and 85 on the FFI Activity Limitation Subscale score (total score on 3 items) ranging from 0 ("Never") to 4 ("Always") for EN3835 vs placebo. |
| To assess the overall improvement in the FFI Total score with EN3835 vs placebo. | The mean change from Baseline on Days 15, 29, 43, 57, and 85 on the FFI Total score for EN3835 vs placebo. The FFI Total score ranges from 0 to 84, with a higher score indicating worse pain, difficulty, and activity limitation. |
| To assess the overall improvement in severity of plantar fibromatosis on the Patient Global Impression of Severity (PGIS) PF Overall scale with EN3835 vs placebo. | The mean change from Baseline to Days 15, 29, 43, 57, and 85 on the PGIS PF Overall score, a 5-point scale, ranging from 0 ("None") to 4 ("Severe") with EN3835 vs placebo. |
| To assess the overall improvement in the severity of foot pain on the PGIS Foot Pain Subscale with EN3835 vs placebo. | The mean change from Baseline to Days 15, 29, 43, 57, and 85 on the PGIS Foot Pain Subscale, a 5-point scale, ranging from 0 ("None") to 4 ("Severe") with EN3835 vs placebo. |
| To assess the overall improvement in the severity of difficulty on the PGIS Difficulty Subscale with EN3835 vs placebo. | The mean change from Baseline to Days 15, 29, 43, 57, and 85 on the PGIS Difficulty Subscale, a 5-point scale, ranging from 0 ("None") to 4 ("Severe") with EN3835 vs placebo. |
| To assess the overall improvement in the severity of activity limitation on the PGIS Activity Limitation Subscale with EN3835 vs placebo. | The mean change from Baseline to Days 15, 29, 43, 57, and 85 on the PGIS Activity Limitation Subscale, a 5-point scale, ranging from 0 ("None") to 4 ("Severe") with EN3835 vs placebo. |
| To assess the overall change in severity of plantar fibromatosis on the Patient Global Impression of Change (PGIC) PF Overall with EN3835 vs placebo. | The proportion of participants treated with EN3835 or placebo reporting "Minimal Improvement" (+1), "Much Improvement" (+2), and "Very Much Improvement" (+3) on the PGIC Overall scale, a 7-point scale ranging from −3 ("Very Much Worse") to +3 ("Very Much Improvement") on Days 15, 29, 43, 57, and 85. |
| To assess the overall change in the severity of foot pain on the PGIC Foot Pain Subscale with EN3835 vs placebo. | The proportion of participants treated with EN3835 or placebo reporting "Minimal Improvement" (+1), "Much Improvement" (+2), and "Very Much Improvement" (+3) on the foot PGIC Foot Pain Subscale, a 7-point scale ranging from −3 ("Very Much Worse") to +3 ("Very Much Improvement") on Days 15, 29, 43, 57, and 85. |
| To assess the overall change in the severity of difficulty on the PGIC Difficulty Subscale with EN3835 vs placebo | The proportion of participants treated with EN3835 or placebo reporting "Minimal Improvement" (+1), "Much Improvement" (+2), and "Very Much Improvement" (+3) on the PGIC Difficulty Subscale, a 7-point scale ranging from −3 ("Very Much Worse") to +3 ("Very Much Improvement") on Days 15, 29, 43, 57, and 85. |

TABLE 81-continued

| Objectives/Endpoints | |
|---|---|
| Objectives | Endpoints |
| To assess the overall change in the severity of activity limitation on the PGIC Activity Limitation Subscale with EN3835 vs placebo | The proportion of participants treated with EN3835 or placebo reporting "Minimal Improvement" (+1), "Much Improvement" (+2), and "Very Much Improvement" (+3) on the PGIC Activity Limitation Subscale, a 7-point scale ranging from −3 ("Very Much Worse") to +3 ("Very Much Improvement") on Days 15, 29, 43, 57, and 85. |
| To assess rescue analgesic medication use with EN3835 vs placebo. | Proportion of participants treated with EN3835 vs placebo that used rescue analgesic medication during the study. The amount (mg) of rescue analgesic medication used by participants treated with EN3835 vs placebo during the study. |
| To assess investigator assessment of improvement on the CGIC Scale with EN3835 vs placebo. | The proportion of participants treated with EN3835 vs placebo for whom the investigator reported "Minimal Improvement" (+1), "Much Improvement" (+2), or "Very Much Improvement" (+3) on the CGIC Scale score, a 7-point scale ranging from −3 ("Very Much Worse") to +3 ("Very Much Improvement") on Days 15, 29, 43, 57, and 85. |
| To assess participant satisfaction with EN3835 vs placebo. | The proportion of participants treated with EN3835 vs placebo reporting to be "Quite Satisfied" (+1) and "Very Satisfied" (+2) on the Subject Satisfaction with Treatment Scale, a 5-point scale ranging from −2 ("Very Dissatisfied") to +2 ("Very Satisfied") on Days 15, 29, 43, 57, and 85. |
| To assess the change in nodule consistency (firmness) after administration of EN3835 vs placebo. | The mean change from Baseline to Days 15, 29, 43, 57, and 85 in nodule consistency (firmness) of the treated nodules as measured by palpation in participants for EN3835 vs placebo. |
| To assess the change in nodule hardness after administration of EN3835 vs placebo. | The mean change from Baseline to Days 15, 29, 43 57, and 85 in the nodular hardness of the treated nodules by durometer measurements for EN3835 vs placebo. |
| Safety | |
| To assess the safety and tolerability of EN3835 vs placebo in participants with plantar fibromatosis. | Proportion of participants reporting treatment-emergent adverse events (TEAE), adverse events of special interest (AESIs), and serious adverse events (SAEs) by incidence, severity, and duration. The change from Baseline in vital signs at Days 15, 29, 43, 57, and 85. The change from Baseline in clinical laboratory values at Day 85/EOS. |

[a]For use in this study, the Foot Function Index has been adapted for plantar fibromatosis (FFI-PF-May 2021) and will hereafter be referred to as the FFI.

Participant Inclusion Criteria

To be eligible to participate in the study, at the Screening Visit, the participant must:

1. Be an ambulatory male or female ≥18 years of age.
2. Have a diagnosis of plantar fibromatosis AND at least 1 "Hard" or "Firm Throughout", palpable fibrous nodule on clinical examination and measurable by caliper.
3. Have unilateral plantar fibromatosis with ≤2 nodules in the foot to be treated.
4. Have current foot pain due to plantar fibromatosis.
5. Be willing and able to comply with all protocol required visits, procedures, and assessments.
6. Be able to read and understand the patient reported assessments and is adequately informed and understand the nature and risks of the study.
7. Agree not to use opioids (e.g., codeine, heroin, hydrocodone, hydromorphone, morphine, oxycodone) during the study period and has not used opioids 30 days before the Screening Visit.
8. Agree not to use drugs (e.g., marijuana, cocaine) and/or use of prescription drugs for the purposes of inducing psychoactive effects during the study and has not used these products in the 30 days prior to the Screening Visit.
9. Agree to not use prohibited medication, and not use any medication to treat plantar fibromatosis pain throughout the study, except as permitted per the protocol.
10. If female, be of non-childbearing potential or, if of childbearing potential, be nonpregnant, non-lactating and agree to use effective contraception for the duration of the study and for 28 days after any active treatment period.
11. Be capable of providing consent, are adequately informed, and understand the nature and risks of the study.

Participant Exclusion Criteria

A participant is ineligible for study participation if the participant meets any of the following criteria:

1. Has the presence of non-plantar fibromatosis-related nodules on the affected foot (e.g., neurofibroma, rhabdomyosarcoma, liposarcoma, neurilemmomas, rheumatoid nodules, desmoid tumors, or malignant soft tissue lesions of the foot or ankle).

2. Has any musculoskeletal, neuromuscular, neurosensory, other neurological or related disorder that affects the participant's use of his or her foot and/or would impair his/her completion of study assessments as determined by the investigator.
3. Has any significant medical history or examination findings related to the participant's plantar nodule(s), which in the investigator's opinion, would make the participant unsuitable for study intervention administration or required assessments and evaluations.
4. Has any nodule >40.0 mm.
5. Has a known systemic allergy to collagenase or any excipient of EN3835 or placebo.
6. History of intolerance or hypersensitivity to acetaminophen/paracetamol or any of its excipients or existence of a medical condition for which the use of acetaminophen is contraindicated (refer to product labeling).
7. Has a known bleeding disorder which would make the participant unsuitable for enrollment in the study.
8. Has a clinically significant laboratory abnormality or any laboratory test results meeting any of the following criteria:
   - alanine aminotransferase (ALT)≥3×upper limit of normal (ULN)
   - total bilirubin (TBL)≥2×ULN (>35% direct bilirubin)
   - aspartate aminotransferase (AST)≥3×ULN
   - international normalized ratio (INR)>1.5
9. Has concurrent diseases that might interfere with the conduct of the study, confound the interpretation of the study results, endanger the participant's well-being (e.g., evidence or history of malignancy other than excised basal-cell carcinoma), or any significant hematological, endocrine, cardiovascular, respiratory, renal, hepatic, or gastrointestinal disease. If there is a history of such disease but the condition has been stable (defined as not requiring significant change in therapy or hospitalization for worsening disease) for more than 1 year and is judged by the investigator not to interfere with participation in the study, the participant may be included, with the documented approval of the medical monitor.
10. Any other significant medical condition(s), which in the investigator's opinion would make the participant unsuitable for enrollment in the study.
11. Is pregnant or plans to become pregnant.
12. Is breastfeeding or is providing or plans to provide breast milk in any manner during the study.
13. Has received any surgical or non-surgical treatment(s) (e.g., steroid injection, transdermal/intralesional verapamil, radiation therapy, extracorporeal shock wave therapy) on the foot or nodule(s) to be treated within 3 months before administration of study intervention.
14. Has received any collagenase treatment (e.g., Santyl® ointment, XIAFLEX®, EN3835, or CCH) within 30 days prior to Day 1.
15. Is currently receiving, has received (within 7 days of the first treatment of study intervention), or plans to receive any anticoagulant or antiplatelet medication (except for ≤150 mg aspirin daily) that would increase the risk of bleeding during the study.
16. Participation in other studies involving an investigational drug within 30 days before treatment with study intervention and/or concurrent study participation.
17. Has previously participated in clinical studies of EN3835 in plantar fibromatosis or plantar fasciitis.

Randomization Inclusion Criteria

To be eligible to participate in the study, on Day 1, participants should have no clinically significant changes that impact previously established eligibility and meet the following criteria:

1. Demonstrate compliance with documenting Pain Intensity NRS scores. Compliance is defined as documenting ≥11 days within the last 14 days of the Screening Period.
2. Have an ADP score on the Pain Intensity NRS of ≥5 and <10 on ≥5 daily pain entries during the 7 days prior to randomization and treatment (Day 1).
3. Have a weekly mean ADP score on the Pain Intensity NRS of ≥5 during the 7 days prior to randomization and treatment (Day 1).
4. Women of childbearing potential must have a negative urine pregnancy test.

Randomization Exclusion Criteria

A participant is ineligible for study participation on Day 1, if the participant has clinically significant changes that impact previously established eligibility and meets the following criterion:

5. Any significant medical conditions, which in the investigator's opinion would preclude receiving treatment with study intervention.

Participant Inclusion Criteria—Treatment 2

To be eligible to receive the second treatment cycle, on Day 29, the participant must meet the following criteria:

6. Has a previously treated nodule(s) that remains palpable (e.g., "Hard", "Firm Throughout", "Moderately Firm", or "Soft") on clinical examination.
7. Has a weekly mean ADP score on the Pain Intensity NRS of >1 during the 7 days prior to Day 29.
8. Women of childbearing potential must have a negative urine pregnancy test.

Participant Exclusion Criteria—Treatment 2

On Day 29, the participant must not have:

9. Any significant medical conditions, which in the investigator's opinion would preclude receiving a second treatment cycle of study intervention.

Selection of Nodules

During the Screening and Day 1 Visits, the investigator will examine and evaluate the nodules on the affected foot by measuring the nodule using calipers, measuring nodule hardness using a durometer, and palpating the nodule for consistency (firmness). Only "Hard" and "Firm Throughout", fibrous nodules that are palpable on clinical examination and measurable on calipers are eligible for treatment on Day 1. All "Hard" and "Firm Throughout" nodules present on the treated foot on Day 1 must be treated. If all nodules on the treated foot are not "Hard" or "Firm Throughout" on Screening and Day 1, the participant will not be eligible for study inclusion. Study intervention will be administered intralesionally to nodules present meeting eligibility criteria at the doses described below.

Topical anesthetics (e.g., cream, ointment, gel, spray) may be administered before intralesional injection of study intervention provided it does not interfere with proper identification of the nodule or with administration of the study intervention.

TABLE 82

| Study Intervention - EN3835 or Placebo Administration | | |
|---|---|---|
| Treatment Concentrations | EN3835 | Placebo |
| Product Name | EN3835 (0.9 mg of collagenase clostridium histolyticum with 0.5 mg of hydrochloric acid, 18.5 mg of sucrose and 1.1 mg of tromethamine) plus diluent | Placebo (0.5 mg of hydrochloric acid, 18.5 mg of sucrose and 1.1 mg of tromethamine) plus diluent |
| Type | Biologic | NA |
| Dose Formulation | Injectable liquid | Injectable liquid |
| Unit Dose Concentration | 2.0 mg/mL | NA |
| Dose Amount and Frequency | 0.6 mg (0.3 mL)<br>Nodules ≤20.0 mm: A single injection of 0.6 mg (0.3 mL).<br>Nodules >20.0 mm to ≤40.0 mm: Dose divided into 2 injections delivered as 2 aliquots of 0.3 mg (0.15 mL), administered into separate locations in the nodule (total 0.6 mg)<br>Up to 2 treatment cycles can be administered:<br>Maximum dose per treatment cycle: 1.2 mg<br>Maximum dose in the study: 2.4 mg | Volume-matched placebo administered as 1 injection or 2 injections (delivered as 2 aliquots) depending on nodule size |
| Route of Administration | Intralesional injection | Intralesional injection |
| Sourcing | Provided centrally by the sponsor | Provided centrally by the sponsor |
| Packaging and Labeling | Product will be provided in vials. Each vial will be labeled per country requirement. | Product will be provided in vials. Each vial will be labeled per country requirement. |

All nodules will be treated with 0.6 mg of study intervention with up to 1.2 mg of study intervention (if 2 nodules are treated) per treatment cycle. The method of administration of study intervention per nodule is based on nodule size and is presented below. Based on the largest diameter of width or length of the nodule, measured using calipers, participants will receive 1 or 2 injections of study intervention in the treated foot on Days 1 and 29. For nodules ≤20.0 mm: a single injection of 0.6 mg will be administered. For nodules >20.0 mm to ≤40.0 mm: a 0.6-mg dose will be divided into 2 injections delivered as 2 aliquots of 0.3 mg (0.15 mL), administered into separate locations in the nodule.

TABLE 83

| Method of Administration of Study Intervention per Nodule | | | | | | |
|---|---|---|---|---|---|---|
| Palpable Nodule Size[a] | # of Kits | # of Syringes for Injection[b] | Number of Injections | Volume (mL) Administered per Injection | Total Volume (mL)[c] | Total Dose Administered/ Nodule (mg) |
| ≤20.0 mm | 1 | 1 | 1 | 0.3 | 0.3 | 0.6 |
| >20.0 mm to ≤40.0 mm[d] | 1 | 1 | 2[c] | 0.15 | 0.3 | 0.6 |

[a]Size of each nodule will be determined by caliper and the largest width or length will be used to determine number of injections to be administered.
[b]Each injection delivers a single aliquot.
[c]The total injectable volume (0.3 mL) of study intervention should be withdrawn into the dosing syringe at once, regardless of nodule size and number of injections needed per nodule.
[d]For nodules >20.0 mm to ≤40.0 mm, the total dose of study intervention (0.6 mg) should be administered as 2 injections delivered as 2 aliquots of 0.3 mg (0.15 mL per injection) into separate locations in the nodule.

For participants with nodules of ≤20.0 mm, the volume of an entire syringe (0.3 mL) will be administered into the nodule at a single location. In participants with larger nodules (>20.0 mm to ≤40.0 mm), the volume of the syringe will be divided and administered equally as 2 separate injections delivered as 2 aliquots (0.15 mL per injection) into separate locations in the nodule.

On Day 29, nodules previously treated on Day 1 that remain palpable (e.g., "Hard", "Firm Throughout", "Moderately Firm", or "Soft"), are painful, and meet Treatment 2 eligibility criteria, may receive an additional treatment cycle of study intervention. Nodules should be measured on Day 29, to determine the number of injections to be administered.

Study intervention will be injected intralesionally directly into the nodule using a 25-gauge, 1-inch needle.

On Day 1, eligible participants will be provided with acetaminophen/paracetamol as rescue analgesic medication for breakthrough pain due to plantar fibromatosis. Acetaminophen/paracetamol caplets/tablets/capsules will be issued by the sponsor in its approved marketed product (carton, bottle, documents) labeled for clinical use. Participants will be counseled to take up to 2×500-mg caplets/tablets/capsules of acetaminophen (paracetamol) every 6 hours as needed for breakthrough plantar fibromatosis pain. Participants will be counseled not to exceed 3000 mg (6 caplets/tablets/capsules) in a 24-hour period unless directed by the investigator. Further, participants will be instructed to take rescue medications only to treat breakthrough pain due to plantar fibromatosis. Should rescue analgesic medication be required, the Pain Intensity NRS score should be documented every time a dose of rescue medication is taken. Additionally, at approximately the same time every day, between 6:00 PM and 10:00 PM local time, participants will record the ADP score on the Pain Intensity NRS. The dose, frequency, amount, and timing of the rescue analgesic medication taken will be documented every time it is taken.

Efficacy Assessments

During this study, efficacy will be assessed by the investigator via the CGIC Scale, nodule consistency (firmness), and nodular hardness (durometer). Efficacy will be assessed by the participant through the following PRO assessments, including, Pain Intensity NRS, FFI, PGIC Foot Pain, and Subject Satisfaction with Treatment Scale. Rescue medication use will also be assessed. A general description of each of these assessments follows.

Participants will complete the scales prior to evaluation by the investigator. The Pain Intensity NRS will be completed at home at a standard time daily and every time a rescue analgesic medication is taken and at a standard time daily, throughout the study. The order of scale completion by the participant at the study visits is as follows:

1. Foot Function Index
2. PGIS Foot Pain Subscale
3. PGIS Difficulty Subscale
4. PGIS Activity Limitation Subscale
5. PGIS PF Overall
6. PGIC Foot Pain Subscale
7. PGIC Difficulty Subscale
8. PGIC Activity Limitation Subscale
9. PGIC PF Overall
10. Subject Satisfaction with Treatment Scale Patient-Reported Outcome Assessments The Pain Intensity NRS will be completed daily at home. The scales will be completed by participants during study visits in the following order: Pain Intensity NRS, the FFI Scale, the PGIS subscales of foot pain, difficulty, activity limitation and the PGIS PF Overall, the PGIC subscales of foot pain, difficulty, activity limitation and the PGIC PF Overall, and the Subject Satisfaction with Treatment Scale.

Pain Intensity Numeric Rating Scale (NRS)-Daily Scale

Daily, each participant will be asked to describe their foot pain in the past 24 hours, on a Pain Intensity NRS, ranging from 0 ("No Pain") to 10 ("Worst Pain Imaginable"). Participants will also be asked to describe their foot pain, immediately before taking rescue medication, on a Pain Intensity NRS, ranging from 0 ("No Pain") to 10 ("Worst Pain Imaginable").

See, for example, FIG. 37 for an exemplary Pain Intensity NRS-Daily Scale.

Pain Intensity Numeric Rating Scale (NRS)—Before Taking Rescue Medication

See, for example, FIG. 38 for an exemplary Pain Intensity NRS-Before Taking Rescue Medication Scale.

Foot Function Index (FFI)

The FFI-PF-May 2021, which comprises 21 questions, will be used in the present study.

Each participant will be asked to complete the FFI, which assesses the impact of foot pathology on 3 domains of pain, difficulty, and activity limitation. The participant will complete the scale prior to evaluation by the investigator.

The Activity Limitation Subscale consists of 3 items and measures limitations in activities in the past week, such as staying off one foot or both feet. It is scored on a 5-point verbal rating scale as follows:

0—Never
1—Rarely
2—Sometimes
3—Often
4—Always

See, for example, FIG. 39 for an exemplary FFI Activity Limitation Subscale.

The Difficulty Subscale consists of 9 items and measures difficulty performing various functional activities in the past week, such as difficulty climbing stairs. It is scored on a 5-point verbal rating scale as follows:

0—No difficulty
1—A little difficulty
2—Some difficulty
3—Much difficulty
4—A lot of difficulty See, for example, FIG. 40 for an exemplary FFI Difficulty Subscale.

The Pain Subscale consists of 9 items and measures the severity of foot pain during the past week in different situations, such as walking barefoot versus walking with shoes. For the pain subscale, if the participant marks "does not wear orthotics" items pertaining to orthotics are not scored and are not included in the total score. It is scored on a 5-point verbal rating scale as follows:

0—None
1—Mild
2—Moderate
3—Severe
4—Extreme

See, for example, FIG. 41 for an exemplary FFI Pain Subscale.

Patient Global Impression of Severity (PGIS)-Foot Pain Subscale

Each participant will be asked to describe the overall severity of foot pain in the past week on a 5-point scale ranging from 0 ("None") to 4 ("Severe").

5 None
6 Minimal
7 Mild
8 Moderate
9 Severe

The Patient Global Impression of Severity (PGIS)-Foot Pain scale is provided below. Please choose the response below that best describes the overall severity of foot pain you experienced in the past week.

☐ None
☐ Minimal
☐ Mild
☐ Moderate
☐ Severe

Patient Global Impression of Severity (PGIS)-Difficulty Subscale

Each participant will be asked to describe the overall difficulty had with your foot or feet doing physical activities (e.g., walking, running, going up and down stairs and curbs) in the past week on a 5-point scale ranging from 0 ("None") to 4 ("Severe").

The Patient Global Impression of Severity (PGIS)-Difficulty scale is provided below. Please choose the response below that best describes the overall difficulty you had with your foot or feet doing physical activities (e.g., walking, running, and going up and down stairs and curbs) in the past week.

☐ None
☐ Minimal
☐ Mild
☐ Moderate
☐ Severe

Patient Global Impression of Severity (PGIS)-Activity Limitation Subscale

Each participant will be asked to describe the activity limitation had with your foot or feet doing physical activities (e.g. staying off one foot or both feet) in the past week on a 5-point scale ranging from 0 ("None") to 4 ("Severe").

Patient Global Impression of Severity (PGIS)-Activity Limitation scale is provided below. Please choose the response below that best describes the overall limitations in your daily activities you experienced in the past week.

☐ None
☐ Minimal
☐ Mild
☐ Moderate
☐ Severe

Patient Global Impression of Severity (PGIS)-PF Overall

Each participant will be asked to describe the severity of plantar fibromatosis in the past week on a 5-point scale ranging from 0 ("None") to 4 ("Severe").

Patient Global Impression of Severity (PGIS)-PF Overall scale is provided below. Please choose the response below that best describes the overall severity of your plantar fibromatosis in the past week.

☐ None
☐ Minimal
☐ Mild
☐ Moderate
☐ Severe

Patient Global Impression of Change (PGIC)-Foot Pain Subscale

Each participant will be asked to describe the overall severity of foot pain in the past week on a 7-point scale, ranging from −3 ("Very Much Worse") to +3 ("Very Much Improvement").

−3 Very Much Worse
−2 Much Worse
−1 Minimally Worse
0 No Change
+1 Minimal Improvement
+2 Much Improvement
+3 Very Much Improvement Participants will be instructed to compare changes in the past week compared to before the start of treatment.

Patient Global Impression of Change (PGIC)-Difficulty Subscale

Each participant will be asked to describe the change in the overall difficulty with the foot or feet doing physical activities (e.g., walking, running, going up and down stairs and curbs) in the past week on a 7-point scale, ranging from −3 ("Very Much Worse") to +3 ("Very Much Improvement"). Participants will be instructed to compare changes in the past week compared to before the start of treatment.

Patient Global Impression of Change (PGIC)-Difficulty is provided below. Please choose the response below that best describes the change in overall difficulty you had with your foot or feet doing physical activities (e.g., walking, running, and going up and down stairs and curbs) in the past week.

☐ Very much improvement
☐ Much improvement
☐ Minimal improvement
☐ No change
☐ Minimally worse
☐ Much worse
☐ Very much worse Patient Global Impression of Change (PGIC)-Activity Limitation Subscale Each participant will be asked to describe the change in the overall limitations in the daily activities experienced in the past week on a 7-point scale, ranging from −3 ("Very Much Worse") to +3 ("Very Much Improvement"). Participants will be instructed to compare changes in the past week compared to before the start of treatment.

Patient Global Impression of Change (PGIC)-Activity Limitation scale is provided below. Please choose the response below that best describes the change in overall limitations in your daily activities you experienced in the past week.

☐ Very much improvement
☐ Much improvement
☐ Minimal improvement
☐ No change
☐ Minimally worse
☐ Much worse
☐ Very much worse Patient Global Impression of Change (PGIC)-PF Overall Each participant will be asked to describe the change in the overall severity of plantar fibromatosis in the past week on a 7-point scale, ranging from −3 ("Very Much Worse") to +3 ("Very Much Improvement"). Participants will be instructed to compare changes in the past week compared to before the start of treatment.

Patient Global Impression of Change (PGIC)-PF Overall scale is provided below. Please choose the response below that best describes the change in overall severity of your plantar fibromatosis in the past week.

☐ Very much improvement
☐ Much improvement
☐ Minimal improvement
☐ No change
☐ Minimally worse
☐ Much worse
☐ Very much worse Subject Satisfaction with Treatment Scale Each participant will be asked to rate his/her satisfaction with treatment of their nodule(s) on a 5-point scale ranging from −2 ("Very Dissatisfied") to +2 ("Very Satisfied") as follows:

−2 Very Dissatisfied
−1 Quite Dissatisfied
0 Neither Satisfied nor Dissatisfied
+1 Quite Satisfied
+2 Very Satisfied The Subject Satisfaction with Treatment scale is provided below. Please rate your satisfaction with treatment of your nodule(s) using a scale that ranges from Very Dissatisfied to Very Satisfied.

(Please specify right or left foot treated):

☐ Right foot ☐ Left foot

Overall, to what extent are you satisfied with your current treatment of your nodule(s)? Please choose one of the following options:

☐ Very Dissatisfied
☐ Quite Dissatisfied
☐ Neither Satisfied nor Dissatisfied
☐ Quite Satisfied
☐ Very Satisfied Investigator Assessments Clinician Global Impression of Change (CGIC) Scale The investigator will determine the degree of improvement with treatment in the treated foot on a 7-point scale ranging from −3 ("Very Much Worse") to +3 ("Very Much Improvement") as follows:

−3 Very Much Worse
−2 Much Worse
−1 Minimally Worse
0 No Change
+1 Minimal Improvement
+2 Much Improvement
+3 Very Much Improvement The Clinician Global Impression of Change Scale is provided below. The following question will ask you to rate the degree of improvement in the participant's treated nodule(s) compared with baseline using a scale that ranges from Very Much Worse to Very Much Improvement.

(Please specify right or left foot treated):

☐ Right foot ☐ Left foot (Please only select one answer):

☐ Very Much Worse
☐ Much Worse
☐ Minimally Worse
☐ No Change
☐ Minimal Improvement
☐ Much Improvement
☐ Very Much Improvement Consistency (Firmness) of the Selected Nodule The investigator or qualified designee will palpate the selected nodule, determine the consistency (firmness) of the nodule, and classify the nodule. For the first treatment, only palpable fibrous nodules that are "Hard" or "Firm Throughout" will be treated. For the second treatment cycle, nodules previously treated on Day 1 that remain palpable are eligible for retreatment. All efforts should be made to ensure the same investigator evaluates the same participant over time. The nodule consistency scale is classified as:

4 Hard (no give) (e.g., marble)
3 Firm throughout (a little resistance) (e.g., pencil eraser)
2 Moderately firm (some resistance) (e.g., gum drop)
1 Soft (no resistance) (e.g., a marshmallow)
0 Non-palpable The Consistency of the Treated Nodule scale is provided below. The following question will ask you to rate the degree of improvement in the consistency of the participant's treated nodule(s) compared with Baseline.

(Please specify right or left foot treated):

☐ Right foot ☐ Left foot
☐ Hard (no give, like a marble)
☐ Firm throughout (a little resistance, like a pencil eraser)
☐ Moderately firm (some resistance like a gum drop)
☐ Soft (no resistance, like a marshmallow)
☐ Non-palpable Durometer Measurements The investigator or qualified designee will use the Type OO Shore Durometer provided to measure the hardness of each of the selected nodule(s), on a scale ranging from 0 to 100, and the nodule hardness measurements will be recorded.

Results

The phase 3 study is contemplated to result in at least a 0.5 point change from Baseline to Week 12 in the weekly mean of the average daily (24-hour) pain (ADP) score as measured on the Pain Intensity NRS, ranging from 0 ("No Pain") to 10 ("Worst Pain Imaginable") for EN3835 vs placebo.

The phase 3 study is contemplated to result in at least a 1 point change from Baseline to Week 12 in the weekly mean of the average daily (24-hour) pain (ADP) score as measured on the Pain Intensity NRS, ranging from 0 ("No Pain") to 10 ("Worst Pain Imaginable") for EN3835 vs placebo.

The phase 3 study is contemplated to result in at least a 1 point change from Baseline to Day 85 in the FFI Difficulty Subscale score (total score on 9 items) of the FFI, ranging from 0 ("No Difficulty") to 4 ("A Lot of Difficulty") for EN3835 vs placebo.

The phase 3 study is contemplated to result in at least a 1 point change from Baseline to Day 85 on the FFI Activity Limitation Subscale score (total score on 3 items) ranging from 0 ("Never") to 4 ("Always") for EN3835 vs placebo.

The phase 3 study is contemplated to result in at least a 0.5 point change from Baseline to Weeks 2, 4, 6, 8, and 12 in the weekly mean of the ADP score as measured on the Pain Intensity NRS, ranging from 0 ("No Pain") to 10 ("Worst Pain Imaginable") for EN3835 vs placebo.

The phase 3 study is contemplated to result in at least a 1 point change from Baseline to Weeks 2, 4, 6, 8, and 12 in the weekly mean of the ADP score as measured on the Pain Intensity NRS, ranging from 0 ("No Pain") to 10 ("Worst Pain Imaginable") for EN3835 vs placebo.

The phase 3 study is contemplated to result in an increase in the proportion of participants treated with EN3835 vs placebo with ≥30% decrease from Baseline to Week 12 in the weekly mean of the ADP score as measured on the Pain Intensity NRS.

The phase 3 study is contemplated to result in an increase in the proportion of participants treated with EN3835 vs placebo with ≥50% decrease from Baseline to Week 12 in the weekly mean of the ADP score as measured on the Pain Intensity NRS.

The phase 3 study is contemplated to result in at least a 1 point change from Baseline to Days 15, 29, 43, 57, and 85 on the FFI Pain Subscale score (total score on 9 items), ranging from 0 ("None") to 4 ("Extreme") for EN3835 vs placebo.

The phase 3 study is contemplated to result in at least a 1 point change from Baseline to Days 15, 29, 43, 57, and 85 in the FFI Difficulty Subscale score (total score on 9 items) of the FFI, ranging from 0 ("No Difficulty") to 4 ("A Lot of Difficulty") for EN3835 vs placebo.

The phase 3 study is contemplated to result in at least a 1 point change from Baseline to Days 15, 29, 43, 57, and 85 on the FFI Activity Limitation Subscale score (total score on 3 items) ranging from 0 ("Never") to 4 ("Always") for EN3835 vs placebo.

The phase 3 study is contemplated to result in at least a 1 point change from Baseline on Days 15, 29, 43, 57, and 85 on the FFI Total score for EN3835 vs placebo. The FFI Total score ranges from 0 to 84, with a higher score indicating worse pain, difficulty, and activity limitation.

The phase 3 study is contemplated to result in at least a 1 point change from Baseline to Days 15, 29, 43, 57, and 85 on the PGIS PF Overall score, a 5-point scale, ranging from 0 ("None") to 4 ("Severe") with EN3835 vs placebo.

The phase 3 study is contemplated to result in at least a 1 point change from Baseline to Days 15, 29, 43, 57, and 85 on the PGIS Foot Pain Subscale, a 5-point scale, ranging from 0 ("None") to 4 ("Severe") with EN3835 vs placebo.

The phase 3 study is contemplated to result in at least a 1 point change from Baseline to Days 15, 29, 43, 57, and 85 on the PGIS Difficulty Subscale, a 5-point scale, ranging from 0 ("None") to 4 ("Severe") with EN3835 vs placebo.

The phase 3 study is contemplated to result in at least a 1 point change from Baseline to Days 15, 29, 43, 57, and 85 on the PGIS Activity Limitation Subscale, a 5-point scale, ranging from 0 ("None") to 4 ("Severe") with EN3835 vs placebo.

The phase 3 study is contemplated to result in an increase in the proportion of participants treated with EN3835 vs placebo reporting "Minimal Improvement" (+1), "Much Improvement" (+2), and "Very Much Improvement" (+3) on the PGIC Overall scale, a 7-point scale ranging from −3 ("Very Much Worse") to +3 ("Very Much Improvement") on Days 15, 29, 43, 57, and 85.

The phase 3 study is contemplated to result in an increase in the proportion of participants treated with EN3835 vs placebo reporting "Minimal Improvement" (+1), "Much Improvement" (+2), and "Very Much Improvement" (+3) on the foot PGIC Foot Pain Subscale, a 7-point scale ranging from −3 ("Very Much Worse") to +3 ("Very Much Improvement") on Days 15, 29, 43, 57, and 85.

The phase 3 study is contemplated to result in an increase in the proportion of participants treated with EN3835 vs placebo reporting "Minimal Improvement" (+1), "Much Improvement" (+2), and "Very Much Improvement" (+3) on the PGIC Difficulty Subscale, a 7-point scale ranging from −3 ("Very Much Worse") to +3 ("Very Much Improvement") on Days 15, 29, 43, 57, and 85.

The phase 3 study is contemplated to result in an increase in the proportion of participants treated with EN3835 vs placebo reporting "Minimal Improvement" (+1), "Much Improvement" (+2), and "Very Much Improvement" (+3) on the PGIC Activity Limitation Subscale, a 7-point scale ranging from −3 ("Very Much Worse") to +3 ("Very Much Improvement") on Days 15, 29, 43, 57, and 85.

The phase 3 study is contemplated to result in decrease in the proportion of participants treated with EN3835 vs placebo that used rescue analgesic medication during the study.

The phase 3 study is contemplated to result in decrease in the amount (mg) of rescue analgesic medication used by participants treated with EN3835 vs placebo during the study.

The phase 3 study is contemplated to result in an increase in the proportion of participants treated with EN3835 vs placebo for whom the investigator reported "Minimal Improvement" (+1), "Much Improvement" (+2), or "Very Much Improvement" (+3) on the CGIC Scale score, a 7-point scale ranging from −3 ("Very Much Worse") to +3 ("Very Much Improvement") on Days 15, 29, 43, 57, and 85.

The phase 3 study is contemplated to result in an increase in the proportion of participants treated with EN3835 vs placebo reporting to be "Quite Satisfied" (+1) and "Very Satisfied" (+2) on the Subject Satisfaction with Treatment Scale, a 5-point scale ranging from −2 ("Very Dissatisfied") to +2 ("Very Satisfied") on Days 15, 29, 43, 57, and 85.

The phase 3 study is contemplated to result in at least a 1 point change from Baseline to Days 15, 29, 43, 57, and 85 in nodule consistency (firmness) of the treated nodules as measured by palpation in participants for EN3835 vs placebo.

The phase 3 study is contemplated to result in at least a 1 point change from Baseline to Days 15, 29, 43 57, and 85 in the nodular hardness of the treated nodules by durometer measurements for EN3835 vs placebo.

The phase 3 study is contemplated to result in at least a 1 point change from Baseline to Days 15, 29, 43 57, and 85 in LSM FFI Foot Pain score with EN3835 vs placebo.

The phase 3 study is contemplated to result in at least a 1 point change from Baseline to Days 15, 29, 43 57, and 85 in combined FFI pain and difficulty score with EN3835 vs placebo.

Example 5—Collagenase *Clostridium histolyticum* (CCH) in Patients with Plantar Fibromatosis (PFI): Post Hoc Analysis of a Phase 2, Double-Blind, Randomized, Placebo-Controlled Study A post hoc analysis of Study 222 was conducted to assess the efficacy of CCH vs placebo in a subgroup of patients.

Methods

The Study 222 full analysis set (FAS) included 172 patients who received ≥1 injection of CCH (n=85) or placebo (n=87) and had ≥1 postinjection FFI Foot Pain subscale measurement. FAS patients with baseline Numeric Rating Scale (NRS) pain score of 10 (i.e., patients with extreme distress or pain) or nodule consistency (firmness as assessed by investigator palpation) of "moderately firm" (i.e., nodules with less collagen content) were excluded from the post hoc subgroup analysis.

Least-squares mean (LSM) change (improvement) from baseline to postinjection day 57 in FFI Total Pain subscale score, combined FFI Pain and Difficulty subscale score, and nodule hardness between subgroup patients treated with CCH and placebo was estimated using analysis of covariance (ANCOVA). Mixed model of repeated measures (MMRM) sensitivity analyses of the change in FFI Foot Pain and combined FFI Pain and Difficulty scores by visit using all observed data from baseline to day 57 were also performed. Differences in the change in nodule consistency and in CGIC score from baseline to day 57 between subgroup patients treated with CCH and placebo were assessed using responder analyses and Cochran-Mantel-Haenszel (CMH) tests. Nodule consistency responders were defined as patients with ≥1 level reduction in nodule consistency from baseline. CGIC responders were defined as patients with a CGIC score of ±1 (minimal improvement),±2 (much improved) or ±3 (very much improved). Safety was evaluated in the Study 222 safety population and included the assessment of the incidence and severity of treatment-related adverse events (TRAEs) and serious adverse events.

Results

The subgroup analyses included 126 patients (CCH, n=61; placebo, n=65) from the FAS population. Demographic and disease characteristics of the subgroup and FAS populations are shown in Table 84.

TABLE 84

Demographic and Clinical Characteristics of the Study 222 Subgroup and FAS Populations

| | Subgroup (n = 126) | | FAS (n = 172) | |
|---|---|---|---|---|
| Characteristic | CCH (n = 61) | Placebo (n = 65) | CCH (n = 85) | Placebo (n = 87) |
| Age, years, mean (SD) | 54.2 (11.07) | 56.5 (11.19) | 54.7 (10.99) | 56.2 (10.61) |
| Sex | 38 (62.3) | 44 (67.7) | 56 (65.9) | 60 (69.0) |
| Female | 38 (62.3) | 44 (67.7) | 56 (65.9) | 60 (69.0) |
| Male | 23 (37.7) | 21 (32.3) | 29 (34.1) | 27 (31.0) |
| Orthotic use | 15 (24.6) | 23 (35.4) | 21 (24.7) | 26 (29.9) |
| Unilateral PFI | 42 (68.9) | 31 (47.7) | 62 (72.9) | 44 (50.6) |
| Nodule hardness, mean (SD) | 48.20 (16.391) | 44.04 (15.331) | 46.66 (16.256) | 42.49 (16.081) |
| Nodule consistency | | | | |
| Hard | 32 (52.6) | 40 (61.5) | 37 (43.5) | 42 (48.3) |
| Firm throughout | 29 (47.5) | 25 (38.5) | 31 (36.5) | 28 (32.2) |
| Moderately firm | 0 | 0 | 17 (20.0) | 17 (19.5) |
| Soft | 0 | 0 | 0 | 0 |
| Nonpalpable | 0 | 0 | 0 | 0 |
| Nodule size (caliper) | | | | |
| Up to 2 cm | 36 (59.0) | 28 (43.1) | 55 (64.7) | 42 (48.3) |
| >2 to ≤4 cm | 24 (39.3) | 36 (55.4) | 28 (32.9) | 43 (49.4) |
| >4 cm | 1 (1.6) | 1 (1.5) | 2 (2.4) | 2 (2.3) |
| FFI Total Pain subscale score, mean (SD) | 24.76 (4.781) | 24.35 (4.839) | 25.43 (5.137) | 24.84 (5.401) |
| NRS pain score, mean (SD) | 7.59 (1.146) | 7.77 (1.101) | 7.95 (1.335) | 7.92 (1.305) |

Data are n (%) unless otherwise indicated.

Nodular hardness was assessed by durometer and is presented as the average hardness of all treated nodules.

Nodular consistency was assessed by investigator palpation and is presented using a worst-case principle (i.e., if any single nodule was assessed as "hard," then a consistency of "hard" was reported).

The FAS included all ITT participants who received ≥1 injection of CCH or placebo and had ≥1 postinjection FFI pain subscale measures.

The subgroup population included all participants in the FAS after exclusion of participants with baseline nodule consistency of "moderately firm" or baseline NRS score of 10.

CCH, collagenase clostridium histolyticum;

FAS, full analysis set;

FFI, Foot Function Index;

ITT, intent-to-treat;

NRS, numerical rating scale;

PFI, plantar fibromatosis.

Figure 18:
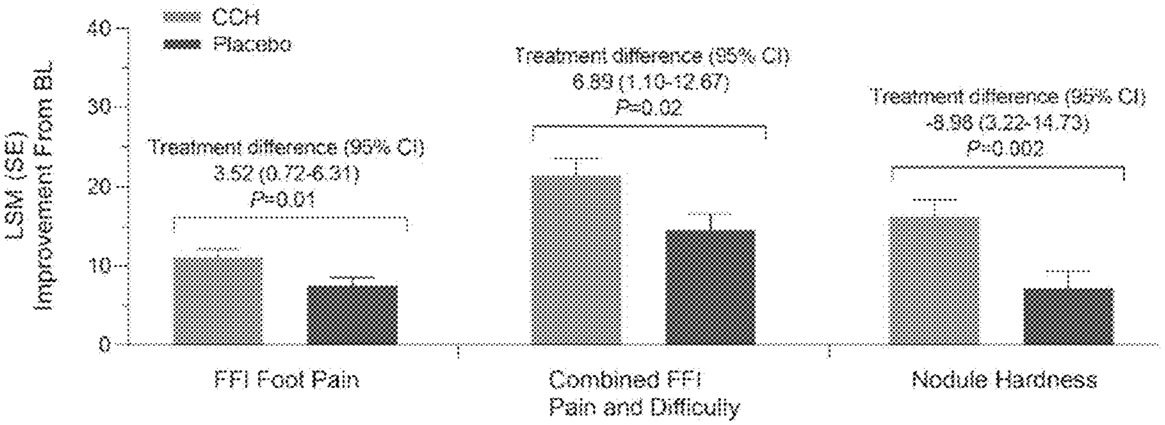
FIG. 18 illustrates the change from baseline to day 57 in FFI foot pain score, combined FFI pain and difficulty score, and nodule hardness in subgroup patients treated with CCH or placebo. LSM changes (improvements) from baseline were estimated using analysis of covariance (ANCOVA). For each end point, treatment differences and associated 95% CIs at day 57 were estimated using ANCOVA with treatment group as a fixed effect and baseline scores as covariates. BL, baseline; CCH, collagenase *Clostridium histolyticum*; FFI, Foot Function Index; LSM least-squares mean.

Subgroup patients treated with CCH demonstrated significantly greater improvement (reduction) from baseline to day 57 in LSM FFI Foot Pain score, combined FFI pain and Difficulty score, and nodule hardness compared with placebo (FIG. 18).

Figure 19A:
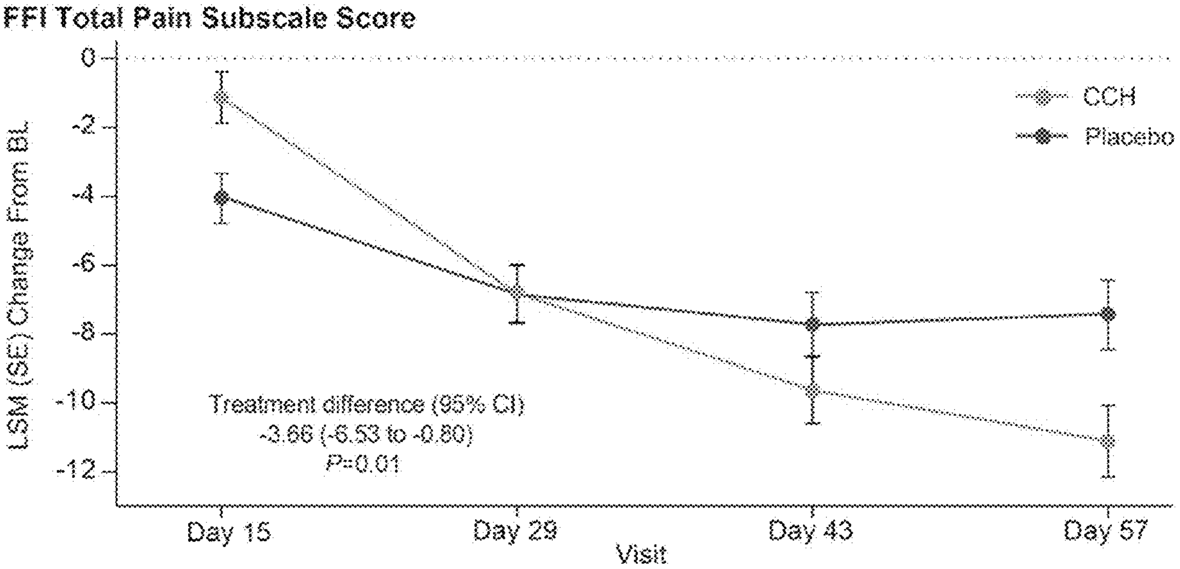
FIG. 19A and FIG. 19B illustrate the change by visit from baseline to day 57 in (FIG. 19A) FFI total pain and (FIG. 19B) combined FFI pain and difficulty subscale scores in the subgroup population. LSM change from baseline to days 15, 29, 43, and 57 for the FFI subscale scores for CCH and placebo as well as treatment effects and 95% CIs at day 57 were derived from a fitted MMRM model with change from baseline to each visit as dependent variables, treatment group and visit as fixed effects, treatment by visit interactions, and baseline FFI subscale score at day 1 as covariates. An unstructured covariance matrix was used to model the within participant observed values. BL, baseline; CCH, collagenase *Clostridium histolyticum*; FFI, Foot Function Index; LSM, least-squares mean; MMRM, mixed model for repeated measures.
Figure 19B:
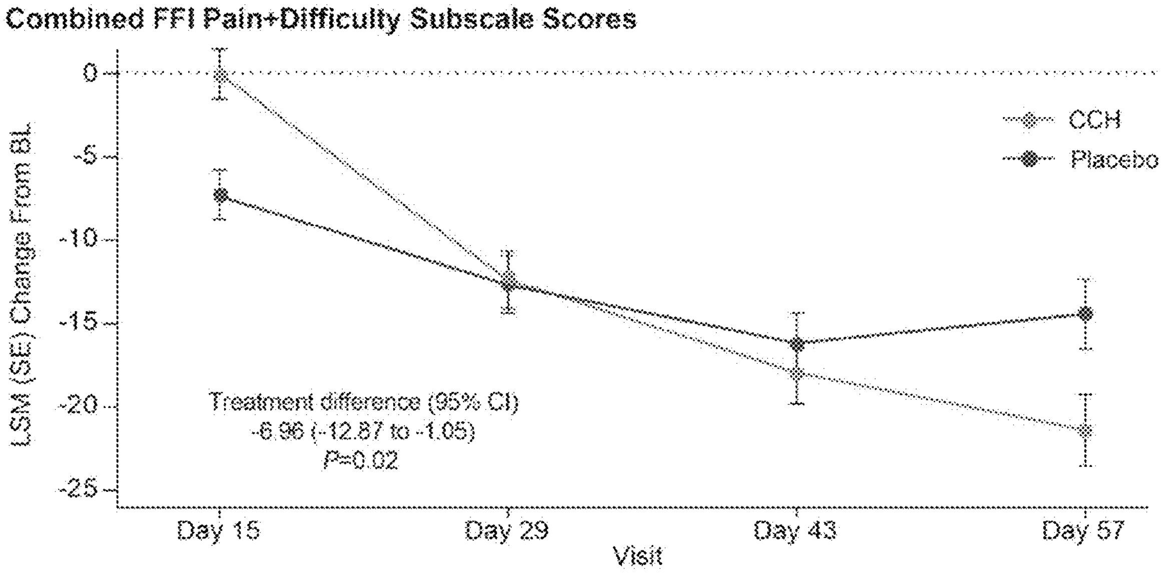

In the sensitivity analyses, subgroup patients treated with CCH demonstrated improvement in FFI Foot Pain and combined FFI Pain and Difficulty scores over 57 days (FIG. 19A and FIG. 19B). At day 57, treatment differences (improvement) estimated by MMRM for both end points significantly favored CCH vs placebo:

FFI Total Pain: 3.66 (95% CI, 0.80-6.53; P=0.01);

Combined FFI Pain and Difficulty: 6.96 (95% CI, 1.05-12.87; P=0.02).

At day 57, there were significantly greater proportions of CGIC score and nodule consistency responders among subgroup patients treated with CCH than with placebo (Table 85).

TABLE 85

Responder Analysis of Nodule Consistency and CGIC Score at Day 57 in the Subgroup Population (n = 126)

| Characteristic | CCH Group | Placebo Group |
|---|---|---|
| Nodule consistency, n | 59 | 61 |
| Responders, n (%)[a] | 52 (88.1) | 38 (62.3) |
| Risk difference, % (95% CI)[b] | 25.8 (11.1-40.5) | — |
| P value[c] | 0.001 | — |
| CGIC score, n | 57 | 61 |
| Responders, n (%)[d] | 43 (75.4) | 34 (55.7) |
| Risk difference, % (95% CI)[b] | 19.7 (3.0-36.4) | — |
| P value[c] | 0.03 | — |

All proportions based on numbers of patients with evaluable data at day 57.

[a]Nodule consistency (firmness by investigator palpation) responders were defined as patients with ≥1-level reduction in nodule consistency for any nodule from baseline at day 57.

[b]Risk difference and 95% CI for the difference in proportion between CCH and placebo.

[c]P value for CCH vs placebo based on CMH test of general association.

[d]CGIC responders were defined as patients with a CGIC score response of +1 (minimal improvement), +2 (much improved), or +3 (very much improved) at day 57.

CCH, collagenase clostridium histolyticum;

CGIC, Clinical Global Impression of Change;

CMH, Cochran-Mantel-Haenszel.

Figure 20:
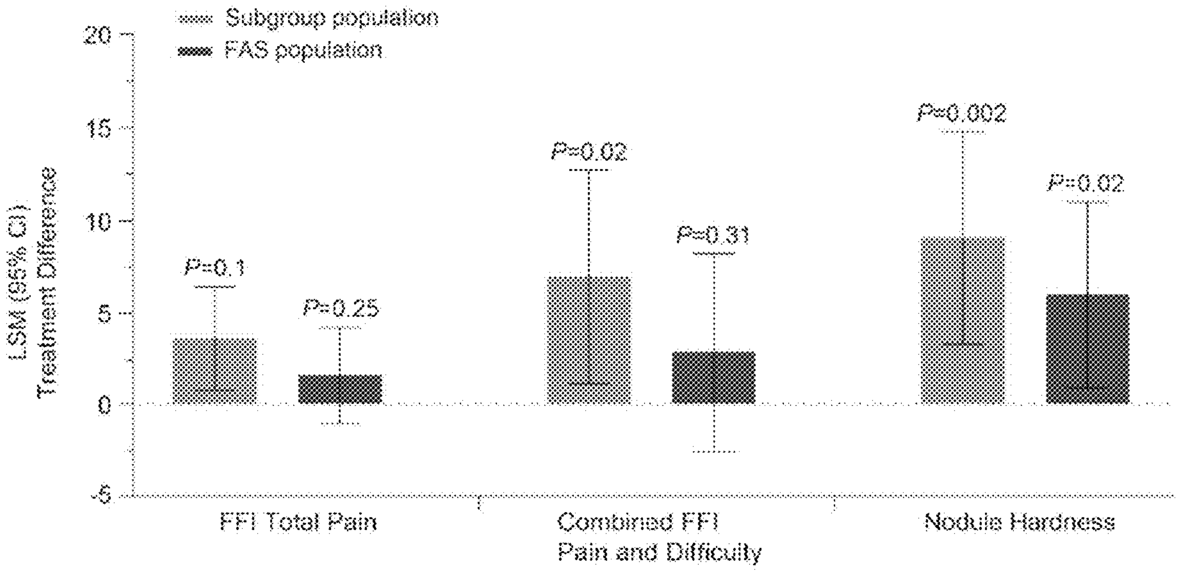
FIG. 20 illustrates the estimated treatment differences for CCH vs placebo at day 57 in the subgroup and FAS populations. For the subgroup population, LSM treatment differences (improvements) and 95% CIs between CCH and placebo were estimated using ANCOVA with treatment group as fixed effect and baseline score as a covariate. For the FAS population, LSM treatment differences and 95% CIs between CCH and placebo were estimated using ANCOVA with treatment group as fixed effect, and with baseline score, maximum of nodule length/nodule width, and the total number of treated nodules as covariates. All ANCOVA analyses were performed on imputed data using a multiple washout model. ANCOVA, analysis of covariance; CCH, collagenase *Clostridium histolyticum*; FAS, full analysis set; FFI, Foot Function Index; LSM, least-squares mean.

The subgroup population demonstrated greater estimated treatment differences (improvements) between CCH and placebo at day 57 for FFI Foot Pain and combined FFI Pain and Difficulty subscale scores, and for nodule hardness compared with the original FAS population (FIG. 20). The estimated risk differences (95% CI) between CCH and placebo for nodule consistency and CGIC score at day 57 were similar for the subgroup and FAS populations:

Nodule consistency: 25.8 (11.1-40.5; P=0.001) vs 22.4 (8.5-36.4; P=0.002);

CGIC score: 19.7 (3.0-36.4; P=0.03) vs 15.4 (1.2-29.7; P=0.04).

Treatment-related adverse events (TRAEs) reported for the Study 222 safety population were consistent with those reported in previous studies of CCH in patients with Dupuytren's contracture (DC) or Peyronie's disease (PD). At least 1 TRAE was reported by 49/87 (56.3%) and 11 (12.6%) of CCH and placebo patients, respectively (Table 86). Most TRAEs were mild to moderate in severity and were related to administration of study drug. There were no serious TRAEs and no reported SAEs in the CCH treatment group.

TABLE 86

Summary of TRAEs in the Overall Study 222 Safety Population

| Safety Outcomes, n (%) | CCH (n = 87) | Placebo (n = 87) |
|---|---|---|
| Patients reporting ≥1 TRAE | 49 (56.3) | 11 (12.6) |
| TRAEs reported by ≥2 patients | | |
| General disorders and administration site conditions | | |
| Injection site pain | 38 (43.7) | 9 (10.3) |
| Injection site bruising | 37 (42.5) | 2 (2.3) |
| Injection site swelling | 25 (28.7) | 3 (3.4) |
| Injection site pruritis | 5 (5.7) | 0 |
| Injection site edema | 4 (4.6) | 0 |
| Injection site discomfort | 2 (2.3) | 0 |
| Injury, poisoning, and procedural complications | | |
| Tendon injury | 3 (3.4) | 0 |
| Fascial rupture | 2 (2.3) | 0 |

TABLE 86-continued

Summary of TRAEs in the Overall Study 222 Safety Population

| Safety Outcomes, n (%) | CCH (n = 87) | Placebo (n = 87) |
|---|---|---|
| Musculoskeletal and connective tissue disorders | | |
| Joint swelling | 1 (1.1) | 1 (1.1) |
| Pain in extremity | 1 (1.1) | 1 (1.1) |

The Study 222 Safety Population consisted of all patients who received ≥1 injection of assigned treatment.
System Organ Class and Preferred Term were coded using MedDRA, version 24.0.
TRAEs were defined as adverse events with the relationship to study drug described by the investigators as "probably related" or "possibly related" or with missing relationship.
TRAE, treatment-related adverse event.

Analysis and Discussion

This post hoc subgroup analysis of phase 2 data identified patients with PFI with a robust response to CCH treatment. After exclusion of Study 222 FAS patients with a baseline NRS pain score of 10 or a baseline nodule consistency of "moderately firm," subgroup patients treated with CCH demonstrated significant treatment differences compared with placebo for FFI Total Pain score, FFI Combined Pain and Difficulty score, nodule hardness, nodule consistency, and CGIC. Subgroup patients treated with CCH also demonstrated larger treatment differences in FFI Total Pain score, FFI Combined Pain and Difficulty score, and nodule hardness (durometer) compared with the corresponding treatment group in the original FAS population. These post hoc results may help in identification of patients with PFI who are more likely to benefit from CCH treatment.

Example 6—A Multi-Center, Open-Label, Extension Study to Evaluate the Long-Term Safety, Efficacy, and Durability of EN3835 in the Treatment and Retreatment of Plantar Fibromatosis-EN3835-306

Study EN3835-306 was conducted to assess the long-term safety, efficacy, and durability of treatment and retreatment with EN3835 in participants with plantar fibromatosis who completed Study EN3835-222. Objectives and Endpoints are provided below.

TABLE 87

Study EN3835-306 Objectives and Endpoints

| Objectives | Endpoints |
|---|---|
| Primary | |
| To assess the long-term safety of treatment with EN3835 for plantar fibromatosis and repeated treatment with EN3835 in plantar fibromatosis. | The proportion of participants reporting AE, during the study assessed by incidence, severity, and duration |
| Secondary | |
| To assess the long-term efficacy of EN3835 in the treatment of plantar fibromatosis in participants treated in Study EN3835-222. | The change from Baseline to Observational Days 60, 120, 180, 270, 360, and 450 on the FFI[a] total score.<br>The change from Baseline to Observational Days 60, 120, 180, 270, 360, and 450 on the FFI subscales (pain, difficulty, and activity limitation).<br>The change from Baseline to Observational Days 60, 120, 180, 270, 360, and 450 in the nodular hardness of the treated nodules by durometer measurements.<br>The change from Baseline to Observational Days 60, 120, 180, 270, 360, and 450 in the nodular consistency of the treated nodules by palpation. |

TABLE 87-continued

Study EN3835-306 Objectives and Endpoints

| Objectives | Endpoints |
| --- | --- |
| | The change from Baseline to Observational Days 60, 120, 180, 270, 360, and 450 on the Pain Intensity NRS.<br>The proportion of participants that meet Treatment Session 1 criteria at Days 180 or 270.<br>The proportion of participants reporting to be "Quite Satisfied" (+1) and "Very Satisfied" (+2) on the Subject Satisfaction with Treatment on Observational Days 60, 120, 180, 270, 360, and 450.<br>The proportion of participants reporting "Minimally Improved" (+1), "Much Improved" (+2) or "Very Much Improved" (+3) on the CGIC Scale on Observational Days 60, 120, 180, 270, 360, and 450. |
| To assess the efficacy of EN3835 in retreatment of plantar fibromatosis in participants that received EN3835 in Study EN3835-222. | The change from Baseline (Retreatment Day 1) with EN3835 to Retreatment Days 15, 29, 43, 57, 117, 197, and 237 on the FFI total score.<br>The change from Baseline (Retreatment Day 1) with EN3835 to Retreatment Days 15, 29, 43, 57, 117, 197, and 237 on the FFI subscales (pain, difficulty, and activity limitation).<br>The change from Baseline (Retreatment Day 1) with EN3835 to Retreatment Days 15, 29, 43, 57, 117, 197, and 237 in the nodular hardness of the treated nodules by durometer measurements.<br>The change from Baseline (Retreatment Day 1) with EN3835 to Retreatment Days 15, 29, 43, 57, 117, 197, and 237 in the nodular consistency of the treated nodules by palpation.<br>The change from Baseline (Retreatment Day 1) with EN3835 to Retreatment Days 15, 29, 43, 57, 117, 197, and 237 on the Pain Intensity NRS.<br>The proportion of participants reporting to be "Satisfied" (+1) and "Very Satisfied (+2) on the Subject Satisfaction with Treatment on Retreatment Days 15, 29, 43, 57, 117, 197, and 237.<br>The proportion of participants for whom the Investigator reports "Minimally Improved" (+1), "Much Improved" (+2) or "Very Much Improved" (+3) on the Clinician Global Impression of Change Scale on Retreatment Days 15, 29, 43, 57, 117, 197, and 237. |
| To assess the efficacy of EN3835 in treatment of plantar fibromatosis in participants treated in this study that received placebo in Study EN3835-222. | The change from Baseline (Treatment Day 1) with EN3835 to Treatment Days 15, 29, 43, 57, 117, 197, and 237 on the FFI total score. |
| | The change from Baseline (Treatment Day 1) with EN3835 to Treatment Days 15, 29, 43, 57, 117, 197, and 237 on the FFI subscales (pain, difficulty, and activity limitation).<br>The change from Baseline (Treatment Day 1) with EN3835 to Treatment Days 15, 29, 43, 57, 117, 197, and 237 in the nodular hardness of the treated nodules by durometer measurements.<br>The change from Baseline (Treatment Day 1) with EN3835 to Treatment Days 15, 29, 43, 57, 117, 197, and 237 in the nodular consistency of the treated nodules by palpation.<br>The change from Baseline (Treatment Day 1) with EN3835 to Treatment Days 15, 29, 43, 57, 117, 197, and 237 on the Pain Intensity NRS. |

TABLE 87-continued

| Study EN3835-306 Objectives and Endpoints | |
|---|---|
| Objectives | Endpoints |
| | The proportion of participants reporting to be "Satisfied" (+1) and "Very Satisfied (+2) on the Subject Satisfaction with Treatment Scale on Treatment Days 15, 29, 43, 57, 117, 197, and 237.<br>The proportion of participants for whom the investigator reports "Minimally Improved" (+1), "Much Improved" (+2) or "Very Much Improved" (+3) on the Clinician Global Impression of Change Scale on Treatment Days 15, 29, 43, 57, 117, 197, and 237. |
| Safety | |
| To assess the long-term safety of treatment with EN3835 for plantar fibromatosis and repeated treatment with EN3835 in plantar fibromatosis. | Presence of anti-Clostridial type I collagenase (AUX-I) and anti-Clostridial type II collagenase (AUX-II) antibody titer levels in EN3835 treated- and retreated participants at the Retreatment/Treatment Day 57 and EOS Visit. |
| To assess the long-term immunogenicity of treatment and retreatment of EN3835 in the treatment of plantar fibromatosis. | Presence of neutralizing antibodies to AUX-I and AUX-II in EN3835 treated- and retreated participants at the Retreatment/Treatment Day 57 and EOS Visit. |

[a]For use in this study, the FFI was adapted for plantar fibromatosis (FFI-PF-May 2021) and is hereafter referred to as the FFI.

Investigational Plan

The purpose of this study was to examine the long-term (15-month) safety, efficacy, and durability of EN3835 in participants with plantar fibromatosis who completed Study EN3835-222. The study also assessed the efficacy and safety of retreatment with up to 2 additional doses of EN3835 (up to maximum of 4 treatments of EN3835 for participants who have received EN3835 in Study EN3835-222). Finally, participants who received placebo in Study EN3835-222 or participants who developed new nodules since being treated could be treated with up to 2 treatments of EN3835. In these participants, the efficacy, safety, and immunogenicity of EN3835 was also assessed.

Overall Study Design and Plan: Description

Figure 21:
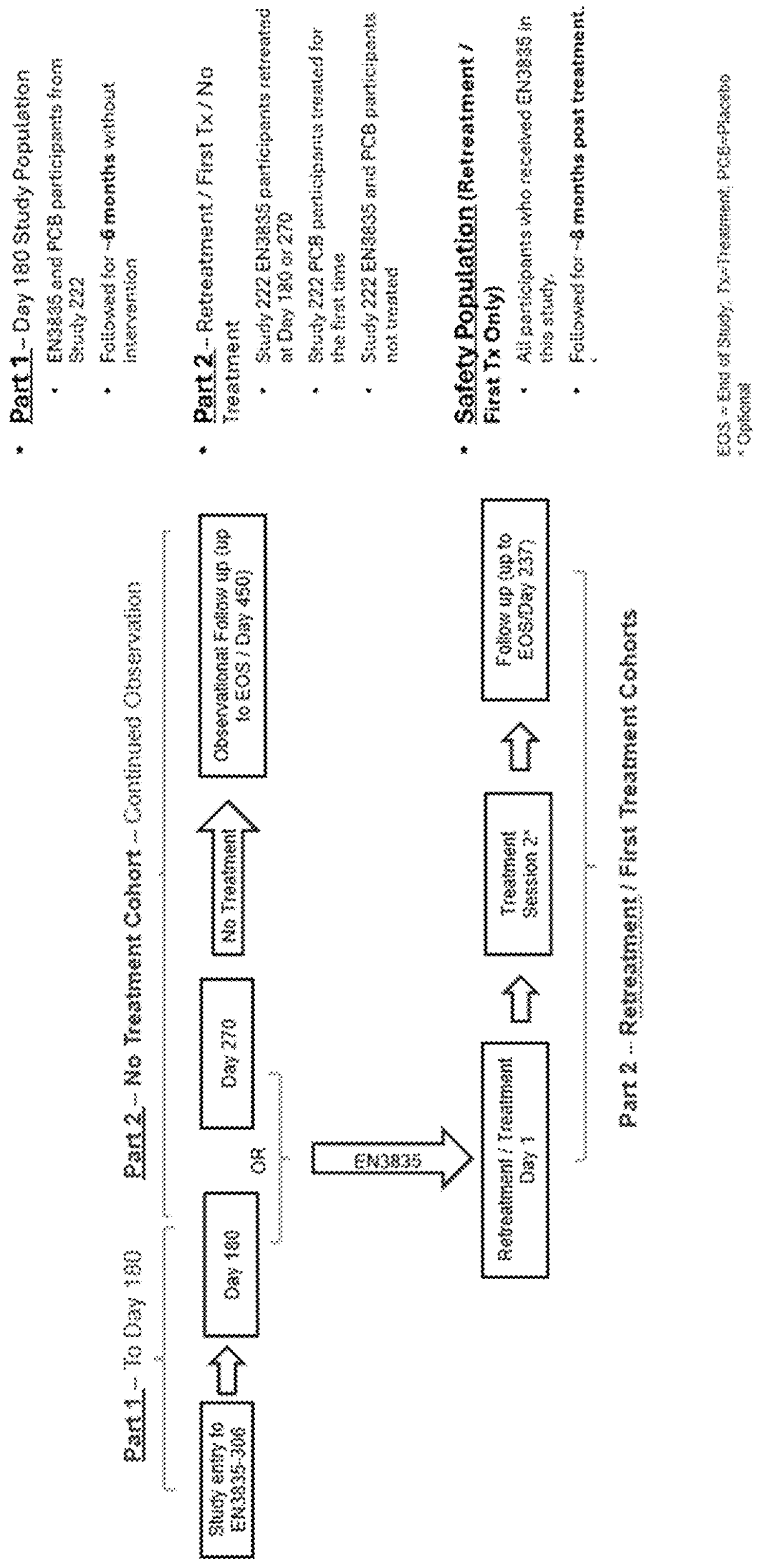
FIG. 21 illustrates the Study 306 study design and patient population.

The Study 306 study design and patient population is provided in FIG. 21.

This was a multi-center, open-label extension study to assess the long-term safety, efficacy, and durability of EN3835 treatment in participants who previously participated in Study EN3835-222. Enrolled participants had the option of:

1. Observation only.
2. Having previously treated nodules retreated (with up to 2 treatments of EN3835) or having new nodules treated (with up to 2 treatments of EN3835).

During this study, all study participants, investigators, and study staff remained blinded to treatment assignment (EN3835 or placebo) from Study EN3835-222. EN3835 was given in an open-label manner in this study.

All participants entered the study on Observational Visit Day 1, which coincided with the EOS visit of Study EN3835-222. After enrolling in the study, participants were observed until the Observational Days 180 or 270 visits (also referred to as Retreatment/Treatment Day 1), at which point, if they fulfilled Treatment Session 1 inclusion criteria and had no exclusion criteria, they had the option of retreating previously treated nodules or treating new nodules with EN3835. Any participant who received EN3835 at the Observational Day 180 Visit could not receive EN3835 at the Observational Day 270 Visit. On Retreatment/Treatment Day 1, participants that met treatment criteria and developed new nodules were also eligible for treatment of these nodules for up to 2 treatment sessions.

Participants observed during the study (did not receive treatment or retreatment) were to attend 6 follow-up visits on Observational Days 60, 120, 180, 270, 360, and 450. Participants who opted to be treated and/or retreated either at Days 180 or 270 (Retreatment/Treatment Day 1), were to attend a total of 7 additional follow-up visits on Retreatment/Treatment Days 15, 29, 43, 57, 117, 197, and 237.

EN3835 was administered intralesionally based on the size of the nodule(s) at the doses described in the Phase 2 protocol (see Table 41, Example 3) to all nodules that were present. The total number of EN3835 injections across all nodules present was not to exceed 3 injections (1.35 mg) in a single foot per treatment when treating participants with unilateral plantar fibromatosis. When treating participants with bilateral plantar fibromatosis, the total number of EN3835 injections across all nodules present was not to exceed 4 injections (1.8 mg) in total per treatment, with each foot receiving a maximum dose of 0.9 mg. All nodules present on each foot were to be treated.

After receiving EN3835, participants were encouraged to resume normal daily activities including walking and bearing weight on the treated foot/feet. Participants returned to the clinic for a total of 7 additional follow-up visits on Retreatment/Treatment Days, 15, 29, 43, 57, 117, 197, and 237. Twenty-eight days after the participant received EN3835 in Treatment Session 1, participants could receive an additional treatment of EN3835 in Treatment Session 2 if Treatment Session 2 criteria were met. Participants then attended 5 follow-up visits.

Throughout the study, the following assessments were conducted: caliper measurements, FFI, nodule hardness measurements using a durometer, Pain Intensity NRS, Subject Satisfaction with Treatment Scale, CGIC Scale, and nodular consistency via palpation. Safety was assessed by evaluating the incidence and duration of TEAEs, AESIs, SAEs, and changes in vital signs and clinical laboratory values.

The number of participants enrolled in Study EN3835-306 was determined by the number of participants who completed Study EN3835-222 and met criteria for study enrollment. Participants entering this study who were observed (and not retreated/treated) during this study completed the study on Day 450 (EOS Visit) during which safety, immunogenicity, and the durability of treatment over 15 months was assessed. Participants entering this study who were retreated/treated, completed the study on Retreatment/Treatment Day 237 (EOS Visit) during which safety, immunogenicity, efficacy, and durability of retreatment/treatment were assessed.

For participants retreated/treated on Day 180, the duration of the study was approximately 417 days (approximately 14 months). For participants retreated/treated on Day 270, the duration of the study was approximately 507 days (approximately 17 months).

Extended Observation Period

In the Extended Observation Population there were 3 (9.7%) participants with PCI high systolic blood pressure values and 1 (3.2%) participant with a PCI low diastolic blood pressure value. None were clinically meaningful.

There were 3 (9.7%) participants with PCI high systolic blood pressure and 1 (3.2%) participant with PCI low diastolic blood pressure. Of the 3 participants with PCI high blood pressure values (participants 1906-0017, 1920-0182, 1920-0383), 1 participant had a medical history of hypertension (participant 1906-0017). There was 1 participant that had an AE of hypertension.

Physical Examination Findings

There were no clinically meaningful changes in physical examination findings during the study in the Extended Population, or the Safety Population. There were no unexpected changes in foot examination findings during the study.

Foot Examination Findings

There were no unexpected changes in foot examination findings during the study in the Day 180 Observation Population, Extended Observation Population, and the Safety Population.

Safety Conclusions

The results of this extension study demonstrated the safety of using EN3835 in treating and retreating plantar nodules. Safety of EN3835 treatment was demonstrated when administered in up to 2 treatments (maximum dose of up to 1.8 mg per treatment) to newly treated participants for up to 237 days after the initial treatment. Safety of EN3835 retreatment was also demonstrated when administered in up to 4 treatments up to 450 days after initial treatment.

Part I—Day 180 Observation Period

In participants observed for up to 180 days after treatment with up to 2 treatments of EN3835 in Study EN3835-222 (no treatment was administered during this part):

- Twenty participants had 29 ongoing AEs from Study EN3835-222, which included 11 EN3835-treated participants with 16 AEs. The most common (≥2%) ongoing AEs in both treatment groups were nodules.
  - Of the ongoing AEs, 9 of 29 AEs were assessed as treatment-related. In EN3835-treated participants, these included 7 TRAEs of injection site pain, bruising, and swelling and joint swelling. In placebo-treated participants, there was 1 TRAE of a new nodule.
- The most common (≥5%) non-serious AEs were nodules with a total of 20 events in 16 participants. There were 7 (10.0%) EN3835-treated participants with 9 nodules
- There were 27 (38.6%) EN3835-treated participants with at least 1 AE. Most AEs affected 1 participant.
- The most common (≥2%) in EN3835-treated participants included nodule and injection site pain, COVID-19, urinary tract infection, and skin abrasion
- Most EN3835-treated participants (24 participants; 88.9%) reported AEs mild to moderate in severity. Severe AEs were not related to treatment.
- There were 2 AESIs of plantar fascial rupture of moderate severity, 1 event in an EN3835-treated participant, that continued from the Study EN3835-222 and 1 event in a placebo-treated participant. Both resolved without further intervention.
- No AEs resulted in study withdrawal or death.
- There were 2 SAEs reported, both in placebo-treated participants (PT: intracranial hematoma and chest pain); both assessed as unrelated.
- There were no unexpected changes in vital signs, physical findings, or foot examination findings.

Part II—Retreatment/Treatment Period

Treatment or No treatment (Pending an assessment at Day 180 or Day 270*)

- Retreatment Cohort—Received EN3835 in Study 222 and offered up to 2 additional treatment cycles (~8 months follow-up)
- First Treatment Cohort—Received Placebo in Study 222 (~8 months follow-up) and/or new nodules
- No Treatment Cohort—Received EN3835 or PCB in Study 222 and did not receive treatment in this study (~15 months observation up to Day 450)

In the Safety Population, 72 participants were retreated/newly treated. On Day 29, forty-seven participants were retreated and observed for up to 237 days after treatment. In those participants:

- The most common (≥5%) ongoing non-serious TEAEs, overall, included injection site reactions of injection site reactions (bruising, pain, swelling) nodules, arthralgias, pain in extremity and SARS-COV-2.
- Overall, TEAEs were most commonly reported in the SOC of General disorders and administration site conditions.
  - In retreated participants, the most common (≥5%) SOCs were General disorders and administration site conditions (15 participants; 57.7%), Musculoskeletal and connective tissue disorders (6 participants; 23.1%), Infections and infestations (3 participants; 11.5%), Skin and subcutaneous tissue disorders (2 participants; 7.7%), and Investigations (2 participants; 7.7%).
  - In newly treated participants the most common (≥5%) SOCs were General disorders and administration site conditions (32 participants; 69.6%), Musculoskeletal and connective tissue disorders (6 participants; 13%), Skin and subcutaneous tissue disorders (4 participants; 8.7%), nervous system disorders (4 participants; 8.7%), Investigations (3 participants; 6.5%), and Injury, poisoning and procedural complications (3 participants; 6.5%).
- The most common TEAEs (≥5%) in all treatment categories were ISRs (bruising, pain, swelling) and nodule. In retreated participants, pain in extremity, arthralgia and SARS-CoV-2 test positive, also met the threshold of most common (≥5%), with each TEAE in 2 (7.7%) participants each.
- In retreated participants 56 (75.6%) TRAEs resolved ≤21 days. In newly treated participants, 89 TRAEs (67.4%) resolved ≤21 days.

TRAEs with a duration ≤21 days included injection site bruising, injection site erythema, injection site hemorrhage, injection site injury, injection site edema, injection site pain, injection site reactions, injection site swelling, ecchymosis, and pain in extremity, fibroma, and nodules.

Most TEAEs (51/57; 91.2%) were mild (Grade 1) to moderate (Grade 2) in severity.

There were 3 SAEs in 2 participants, 1 newly-treated participant with procedural pain post-knee replacement (PT: procedural pain; VT: pain secondary to right knee replacement) and 1 retreated participant (PT gastritis and esophagitis). None were assessed as related to treatment.

There were 2 AESIs of plantar fascial ruptures; in EN3835-treated participants.

There were 3 AEs in 3 participants that led to discontinuation of study intervention. One was an ALT elevation in a placebo-treated participant assessed as unrelated to treatment and 2 were AESIs of plantar fascial tears in newly-treated EN3835 participants assessed as related to treatment.

There were no clinically meaningful shifts in biochemistry or hematology laboratory results or unexpected changes in vital signs, physical findings, or foot examination findings.

At Day 57, after receiving up to 2 treatments of EN3835, almost all (61; 98.4%) participants in all treatment categories tested positive for anti-AUX-I antibodies and almost all (58; 93.5%) participants tested positive for anti-AUX-II antibodies.

At Day 57, 11 (52.4%) and 12 (57.1%) of retreated participants tested positive for neutralizing anti-AUX-I and anti-AUX-II antibodies, respectively.

At Day 237/EOS/ET, almost all (61; 98.4%) participants tested positive for anti-AUX-I antibodies and anti-AUX-II antibodies (56; 90.3%).

At Day 57, six (15.8%) and 7 (20.0%) newly treated participants tested positive for neutralizing anti-AUX-I and anti-AUX-II antibodies, respectively. In retreated participants 11 (52.4%) and 12 (57.1%) tested positive for neutralizing anti-AUX-I and anti-AUX-II antibodies, respectively.

At Day 237 EOS/ET, 6 (15.4%) and 5 (14.7%) newly treated participants tested positive for neutralizing anti-AUX-I and anti-AUX-II antibodies, respectively. In retreated participants 11 (55.0%) and 7 (35.0%) participants tested positive for neutralizing anti-AUX-I and anti-AUX-II antibodies, respectively.

Part II—Extended Observation Period

In participants that opted to be observed (and not treated or treated) for up to 450 days after treatment in Study EN3835-222, There were 10 (32.3%) EN3835-treated participants with AEs.

There were no AE PTs that occurred in more than 1 participant.

Most (90%) EN3835-treated participants reporting AEs mild to moderate in severity. Severe AEs were assessed as unrelated to study intervention administered in Study EN3835-222.

There were 5 SAEs reported in 2 participants: 4 SAEs in a placebo-treated participant (coronavirus infection and pneumonia, acute respiratory failure, and chronic obstructive pulmonary disease) and 1 SAE in an EN3835-treated participant (diabetic encephalopathy).

All SAEs were assessed as not related to study intervention administered in Study EN3835-222.

There were no AEs leading to study withdrawal or death.

There were no clinically meaningful shifts in biochemistry or hematology laboratory results or unexpected changes in vital signs, physical findings, or foot examination findings.

Results

Part I

TABLE 88

Study 306 Part 1 - Disposition (up to Day 180)

| | | Treatment Received in EN3835-222 | | |
|---|---|---|---|---|
| | | EN3835 | PCB | Overall |
| Enrolled Participants | n | 70 | 75 | 145 |
| Completed Day 180 Period | n (%) | 57 (81.4) | 71 (94.7) | 128 (88.3) |
| Discontinued | n (%) | 13 (18.6) | 4 (5.3) | 17 (11.7) |
| Adverse Event | n (%) | 0 (0.0) | 0 (0.0) | 0 (0.0) |
| Lost to Follow-up | n (%) | 6 (8.6) | 1 (1.3) | 7 (4.8) |
| Protocol Violation | n (%) | 0 (0.0) | 0 (0.0) | 0 (0.0) |
| Withdrew Consent | n (%) | 7 (10.0) | 3 (4.0) | 10 (6.9) |
| Day 180 Study Population | n (%) | 70 (100.0) | 75 (100.0) | 145 (100.0) |

TABLE 89

Study 306 Part 1 - Demographics (up to Day 180)

| | | Treatment Received in EN3835-222 | | |
|---|---|---|---|---|
| | | EN3835 (N = 70) n (%) | PCB (N = 75) n (%) | Overall (N = 145) n (%) |
| Age (years) | Mean (SD) | 55.5 (11.2) | 57.5 (9.7) | 56.5 (10.4) |
| Gender | Male | 27 (38.6) | 19 (25.3) | 46 (31.7) |
| | Female | 43 (61.4) | 56 (74.7) | 99 (68.3) |
| Race | Black or African American | 11 (15.7) | 14 (18.7) | 25 (17.2) |
| | Native Hawaiian/ Other Pacific Islander | 0 (0.0) | 1 (1.3) | 1 (0.7) |
| | White | 58 (82.9) | 59 (78.7) | 117 (80.7) |
| | Not Reported/ Multiple | 1 (1.4) | 1 (1.3) | 2 (1.4) |

TABLE 90

Study 306 Part 1 - Overall Summary of Adverse Events (up to Day 180)

| | EN3835 (N = 70) n (%) | PCB (N = 75) n (%) |
|---|---|---|
| Total Number of AEs Reported | 59 | 72 |
| Grade 1 (Mild) | 40 (67.8) | 49 (68.1) |
| Grade 2 (Moderate) | 15 (25.4) | 18 (25.0) |
| Grade 3 (Severe) | 4 (6.8) | 5 (6.9) |
| Grade 4 (Life-Threatening) | 0 (0.0) | 0 (0.0) |
| Grade 5 (Death) | 0 (0.0) | 0 (0.0) |
| Number of Participants Reporting: | | |
| At least one AE | 27 (38.6) | 37 (49.3) |
| At least one Serious AE | 0 (0.0) | 2 (2.7) |
| At least one ongoing AE from the EN3835-222 | 11 (15.7) | 9 (12.0) |

TABLE 90-continued

| Study 306 Part 1 - Overall Summary of Adverse Events (up to Day 180) | EN3835 (N = 70) n (%) | PCB (N = 75) n (%) |
|---|---|---|
| At least one Grade 3+ AE | 3 (4.3) | 3 (4.0) |
| No Grade 3+ AEs, but at least one Grade 2 AE | 8 (11.4) | 12 (16.0) |
| No Grade 3/Grade 2 AEs, but at least one Grade 1 AE | 16 (22.9) | 22 (29.3) |
| At least one AE Leading to Withdrawal from Study | 0 (0.0) | 0 (0.0) |
| At least one AE Leading to Drug Interruption/Discontinuation | 0 (0.0) | 0 (0.0) |
| Number of Participants with any AEs Resulting in Death | 0 | 0 |

Most adverse events (AEs) were mild (Grade 1) to moderate (Grade 2)
55/59 for EN3835 (93.2%)
67/72 for PCB (93.1%)
No AEs led to study withdrawal
No AEs led to drug interruption/discontinuation
2 serious AEs on PCB, not related to treatment
No Deaths

TABLE 91

| Study 306 Part 1 - Ongoing AEs From Study 222 (up to Day 180) | EN3835 (N = 70) n (%) | PCB (N = 75) n (%) |
|---|---|---|
| Number of Participants at least one AE: | 11 (15.7) | 9 (12.0) |
| System Organ Class/Preferred Term ≥2% | | |
| General disorders and administration site conditions | 7 (10.0) | 3 (4.0) |
| Nodule* | 2 (2.9) | 3 (4.0) |
| Injection site pain | 3 (4.3) | 0 (0.0) |
| Injection site bruising | 2 (2.9) | 0 (0.0) |
| Injection site swelling | 2 (2.9) | 0 (0.0) |

*New nodules observed after Day 1 of treatment (in study 222), were captured as AE's

TABLE 92

| Part 1 - Ongoing Adverse Events of Special Interest From Study 222 (up to Day 180) | Severity | EN3835 (N = 70) n (%) | PCB (N = 75) n (%) |
|---|---|---|---|
| Number of Participants at least one AESI*: | | 1 (1.4) | 1 (1.3) |
| System Organ Class Preferred Term | | | |
| Injury, poisoning and procedural complications | | 1 (1.4) | 1 (1.3) |
| Fascial rupture** | Grade 2 | 1 (1.4) | 1 (1.3) |

Figure 22:
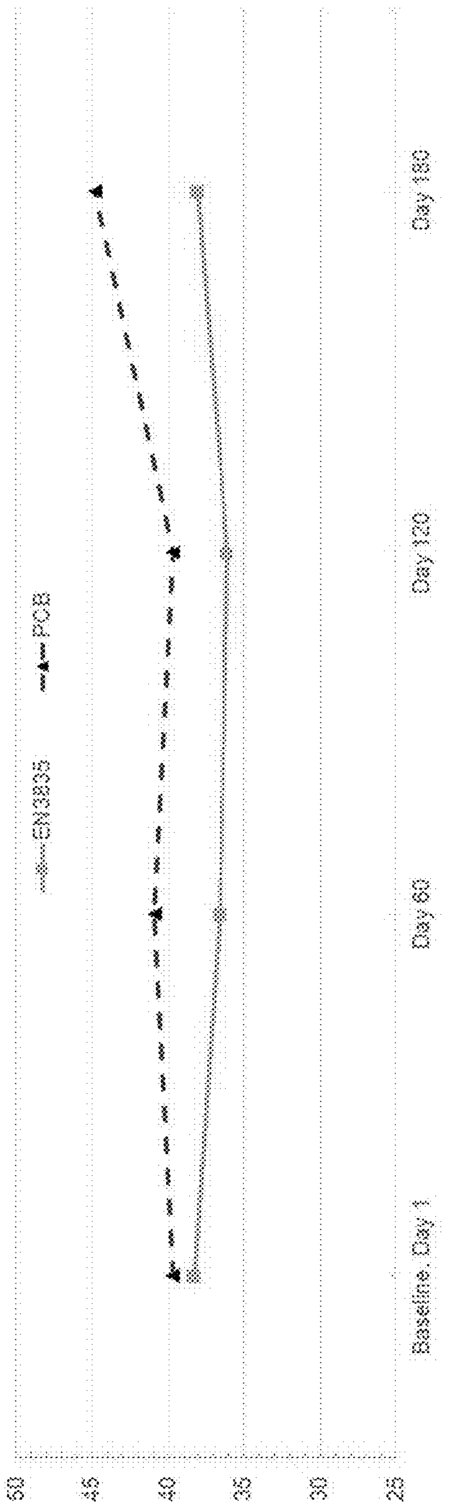
FIG. 22 illustrates Study 306 Part 1-FFI Composite Scores (Up To Day 180).

*AESI - Adverse Event of Special Interest
Fascial Rupture = Partial plantar tears PT Term Adverse Events of Special Interest EN3835 participant with a fascial rupture of moderate severity (Grade 2) assessed as probably related to study intervention which recovered/resolved with a duration of 189 days PCB participant with a fascial rupture of moderate severity (Grade 2) assessed as not related to study intervention which recovered/resolved with a duration of 78 days As shown in FIG. 22**, the treatment effects of EN3835 as measured by FFI were persistent.

Figure 23:
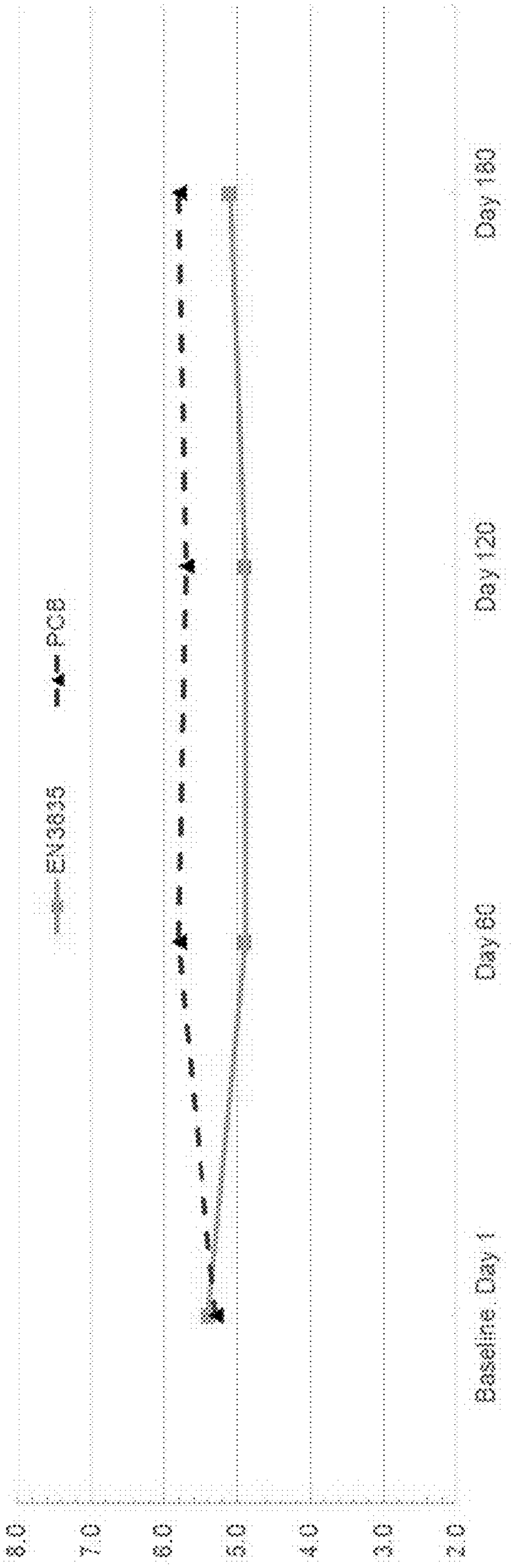
FIG. 23 illustrates Study 306 Part 1-Pain Intensity NRS Scores (Up To Day 180).

As shown in FIG. 23, pain improvements following EN3835 treatment as measured by pain intensity NRS scores were maintained thru Day 180.

Figure 24:
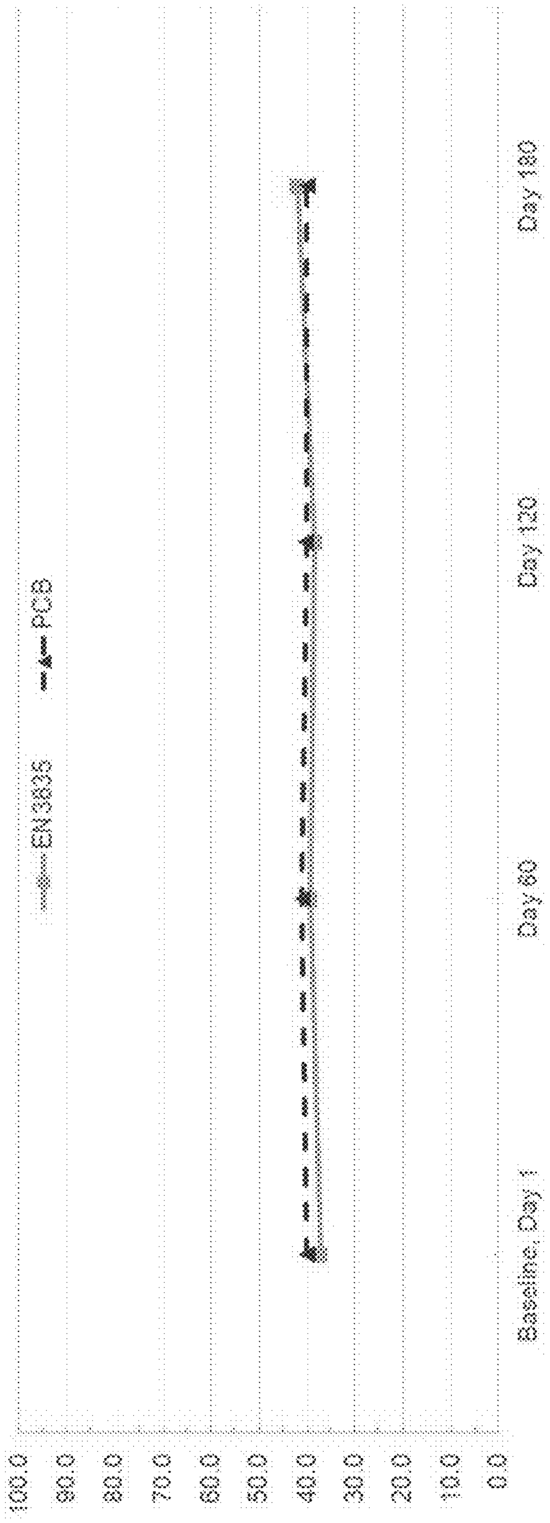
FIG. 24 illustrates Study 306 Part 1-Nodule Hardness (Up To Day 180).

As shown in FIG. 24, there were no appreciable changes in nodule hardness following EN3835 treatment.

Figure 25:
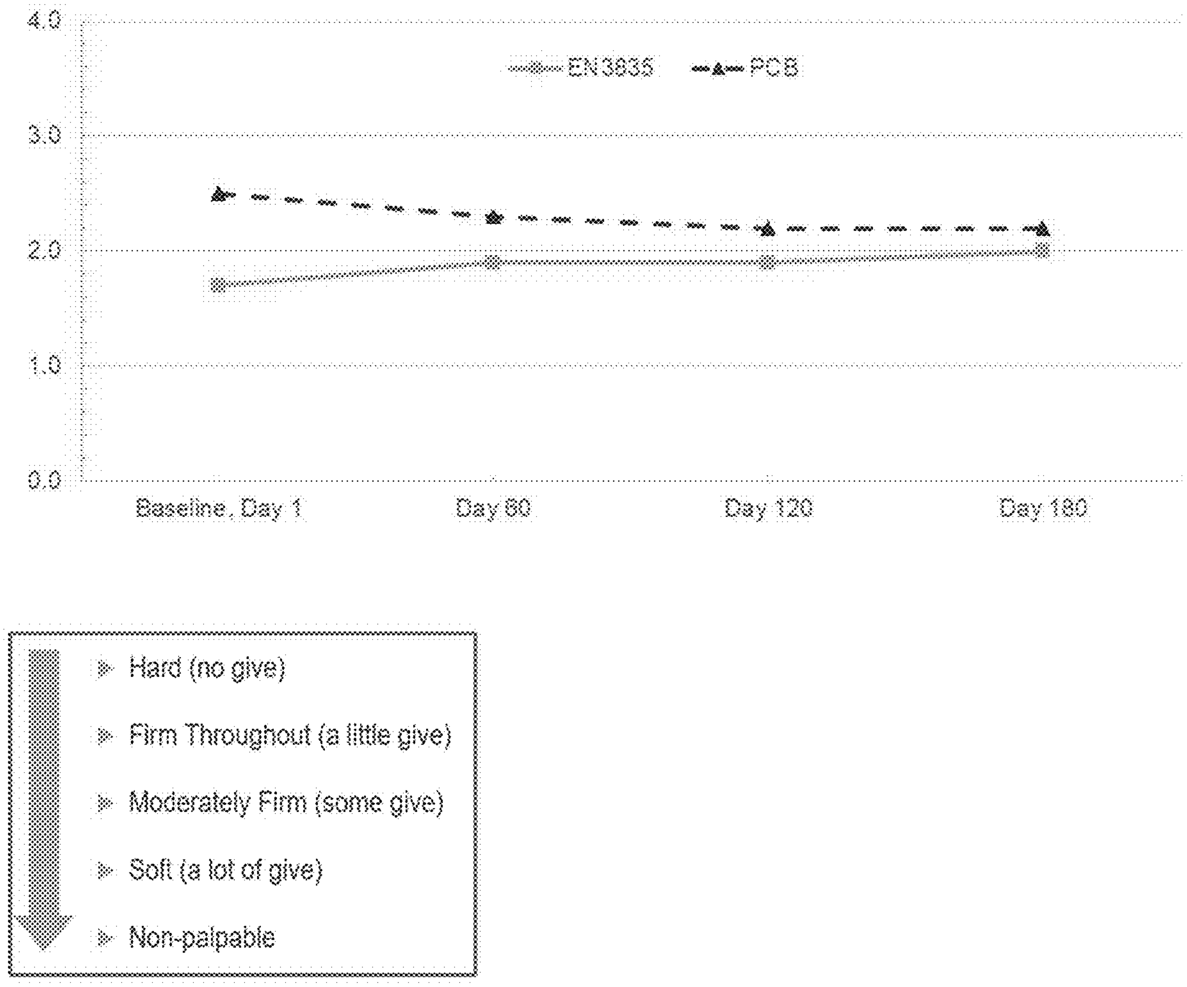
FIG. 25 illustrates Study 306 Part 1-Nodule Consistency (Firmness) (Up To Day 180).

As shown in FIG. 25, nodule consistency remained essentially unchanged (moderately firm) thru Day 180 in EN3835 participants.

Figure 26:
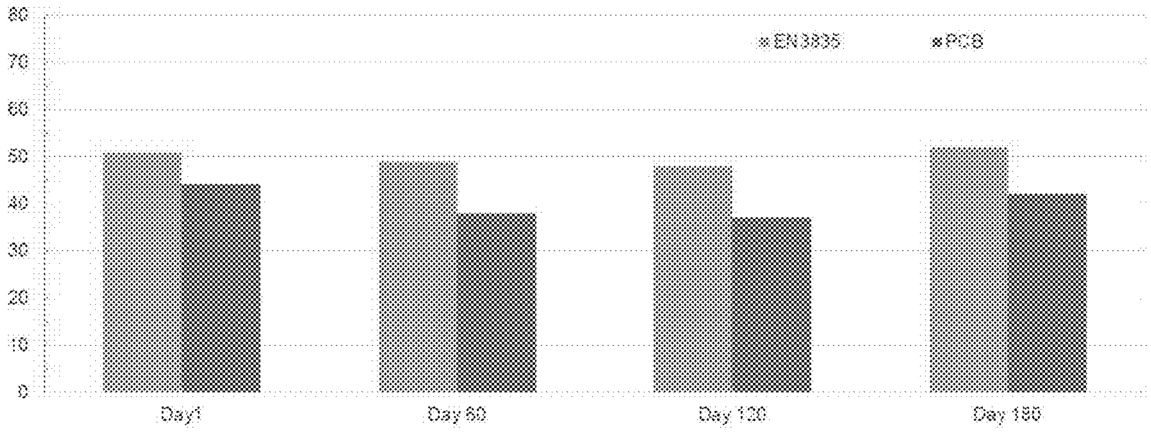
FIG. 26 illustrates Study 306 Part 1—Subject Satisfaction Scale Responders (Up To Day 180).

As shown in FIG. 26, subject satisfaction was maintained thru Day 180.

Figure 27:
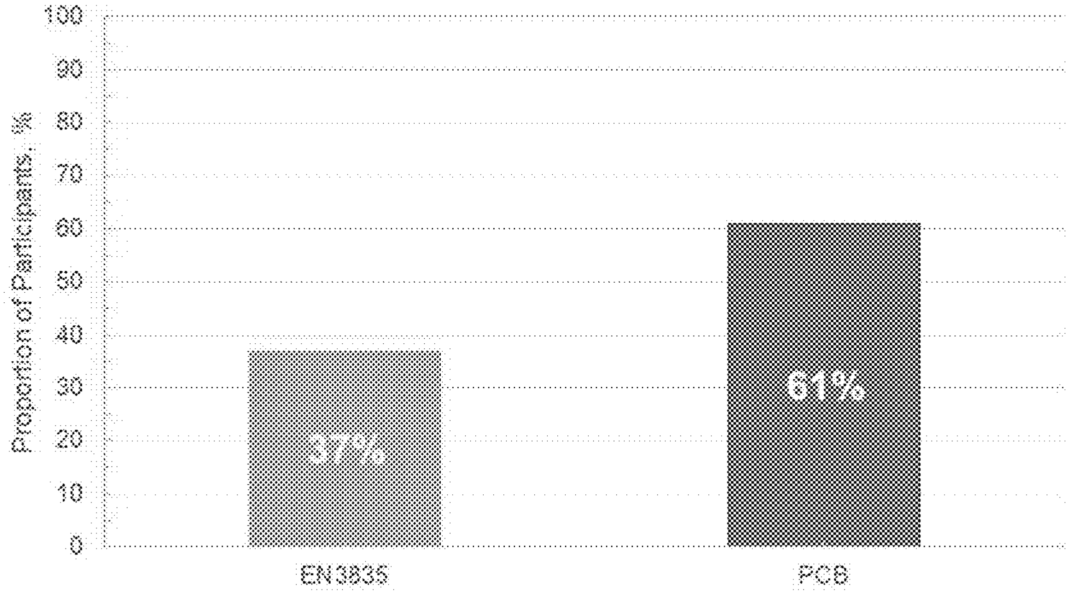
FIG. 27 illustrates Study 306 Part 1—Participants That Met Retreatment/First Treatment Criteria (Up To Day 180).

As shown in FIG. 27:

26 out of 70 (37.1%) participants that received EN3835 in Study 222 met retreatment/first treatment criteria.

46 out of 75 (61.3%) participants that received PCB in Study 222 met retreatment/first treatment criteria.

Part II—Retreatment and First Treatment Cohorts

TABLE 93

| Study 306 Part 2 - Disposition (Retreatment/First Treatment Safety Population) | Statistic | Overall |
|---|---|---|
| Participants eligible for Retreatment/First Treatment | n | 72 |
| Completed | n (%) | 61 (84.7) |
| Discontinued | n (%) | 11 (15.3) |
| Adverse Event | n (%) | 0 (0.0) |
| Lost to Follow-up | n (%) | 1 (1.4) |
| Protocol Violation | n (%) | 0 (0.0) |
| Withdrew Consent | n (%) | 10 (13.9) |
| Safety Population | n (%) | 72 (100.0) |

Safety Population

Overall: 72 participants met retreatment/first treatment criteria (Treatment criteria mimicked that of parent study (Study 222)) and received EN3835 in Study 306

Retreatment: 26 EN3835 participants in Study 222

First Treatment: 46 placebo participants in Study 222

TABLE 94

Study 306 Part 2 - Retreatment Disposition (Retreatment/First Treatment Safety Population)

| Retreatment | Statistic | EN3835 (Retreatment) |
|---|---|---|
| Participants eligible for Retreatment | n | 26* |
| Completed | n (%) | 22 (84.6) |
| Discontinued | n (%) | 4 (15.4) |
| Adverse Event | n (%) | 0 (0.0) |
| Lost to Follow-up | n (%) | 4 (15.4) |
| Protocol Violation | n (%) | 0 (0.0) |
| Withdrew Consent | n (%) | 0 (0.0) |
| Safety Population | n (%) | 26 (100.0) |

*2 participants received treatment in new nodules only

TABLE 95

Study 306 Part 2 - First Treatment Disposition (Retreatment/First Treatment Safety Population)

| First Treatment | Statistic | First Treatment |
|---|---|---|
| Participants eligible for First Treatment | n | 46 |
| Completed | n (%) | 39 (84.8) |
| Discontinued | n (%) | 7 (15.2) |
| Adverse Event | n (%) | 0 (0.0) |
| Lost to Follow-up | n (%) | 1 (2.2) |

TABLE 95-continued

Study 306 Part 2 - First Treatment Disposition (Retreatment/First Treatment Safety Population)

| First Treatment | Statistic | First Treatment |
|---|---|---|
| Protocol Violation | n (%) | 0 (0.0) |
| Withdrew Consent | n (%) | 6 (13.0) |
| Safety Population | n (%) | 46 100.0) |

TABLE 96

Study 306 Part 2 - Demographics (Retreatment/First Treatment Safety Population)

| | | EN3835 Retreatment (N = 26) n (%) | First Treatment (N = 46) n (%) | Overall (N = 72) n (%) |
|---|---|---|---|---|
| Age (years) | Mean (SD) | 54.7 (11.1) | 56.7 (10.0) | 56.0 (10.4) |
| Gender | Male | 9 (34.6) | 11 (23.9) | 20 (27.8) |
| | Female | 17 (65.4) | 35 (76.1) | 52 (72.2) |
| Race | Black or African American | 5 (19.2) | 7 (15.2) | 12 (16.7) |
| | Native Hawaiian or Other Pacific Islander | 0 (0.0) | 1 (2.2) | 1 (1.4) |
| | White | 21 (80.8) | 37 (80.4) | 58 (80.6) |
| | Not Reported | 0 (0.0) | 1 (2.2) | 1 (1.4) |

TABLE 97

Study 306 Part 2 - Overall Treatment Emergent Adverse Events (Retreatment/First Treatment Safety Population)

| | EN3835 Retreatment (N = 26) n (%) | First Treatment (N = 46) n (%) | Overall (N = 72) n (%) |
|---|---|---|---|
| Total Number of TEAEs Reported | 96 | 168 | 264 |
| Grade 1 (Mild) TEAE | 77 (80.2) | 122 (72.6) | 199 (75.4) |
| Grade 2 (Moderate) TEAE | 16 (16.7) | 43 (25.6) | 59 (22.3) |
| Grade 3 (Severe) TEAE | 3 (3.1) | 3 (1.8) | 6 (2.3) |
| Grade 4 (Life-Threatening) TEAE | 0 | 0 (0.0) | 0 (0.0) |
| Grade 5 (Death) TEAE | 0 | 0 (0.0) | 0 (0.0) |
| Number of Participants Reporting | | | |
| At least one TEAE | 19 (73.1) | 38 (82.6) | 57 (79.2) |
| At least one Serious TEAE | 1 (3.8) | 1 (2.2) | 2 (2.8) |
| At least one Grade 3+ TEAE | 2 (7.7) | 3 (6.5) | 5 (6.9) |
| No Grade 3+ TEAEs, but at least one Grade 2 TEAE | 7 (26.9) | 14 (30.4) | 21 (29.2) |
| No Grade 3/Grade 2 TEAEs, but at least one Grade 1 TEAE | 7 (26.9) | 21 (45.7) | 31 (43.1) |
| At least one TEAE Leading to Withdrawal from Study | 0 (0.0) | 0 (0.0) | 0 (0.0) |
| At least one TEAE Leading to Drug Interruption/Discontinuation | 0 (0.0) | 3 (6.5) | 3 (4.2) |
| Number of Participants with any TEAEs Resulting in Death | 0 (0.0) | 0 | 0 |

Most TEAEs were mild (Grade 1) to moderate (Grade 2)
No TEAEs led to study withdrawal
3 TEAEs led to drug interruption/discontinuation
0 for EN3835 Retreatment
3 for First Treatment
Serious TEAEs
1 SAE on EN3835 Retreatment
1 SAE on First Treatment
All SAEs considered not related to study treatment
No Deaths

TABLE 98

Study 306 Part 2 - Common (≥5%) Treatment Emergent Adverse Events (Retreatment/First Treatment Safety Population)

| Treatment-related TEAE | EN3835 Retreatment (N = 26) n (%) | First Treatment (N = 46) n (%) | Overall (N = 72) n (%) |
|---|---|---|---|
| Injection site bruising | 12 (46.2) | 24 (52.2) | 36 (50.0) |
| Injection site pain | 13 (50.0) | 19 (41.3) | 32 (44.4) |
| Injection site swelling | 8 (30.8) | 15 (32.6) | 23 (31.9) |
| Nodule* | 2 (7.7) | 2 (4.3) | 4 (5.6) |

*Nodule - Nodules that were observed after first treatment session were captured as AEs

TABLE 99

Study 306 Part 2 - Adverse Events of Special Interest (Retreatment/First Treatment Safety Population)

| System Organ Class/ Preferred Term | Severity | EN3835 Retreatment (N = 26) n (%) | First Treatment (N = 46) n (%) | Overall (N = 72) n (%) |
|---|---|---|---|---|
| General disorders and administration site conditions Injection site injury* | Grade 1 | 0 (0.0) | 1 (2.2) | 1 (1.4) |
| | Grade 2 | 0 (0.0) | 1 (2.2) | 1 (1.4) |

Figure 28:
FIG. 28 illustrates Study 306 Part 2—FFI Composite Scores (Retreatment/First Treatment Overall Safety Population).

*PT term for Partial Plantar Fascial Tears that were considered an Injection site reaction As shown in FIG. 28, EN3835 treated participants demonstrated improvement in FFI Composite scores.

Figure 29:
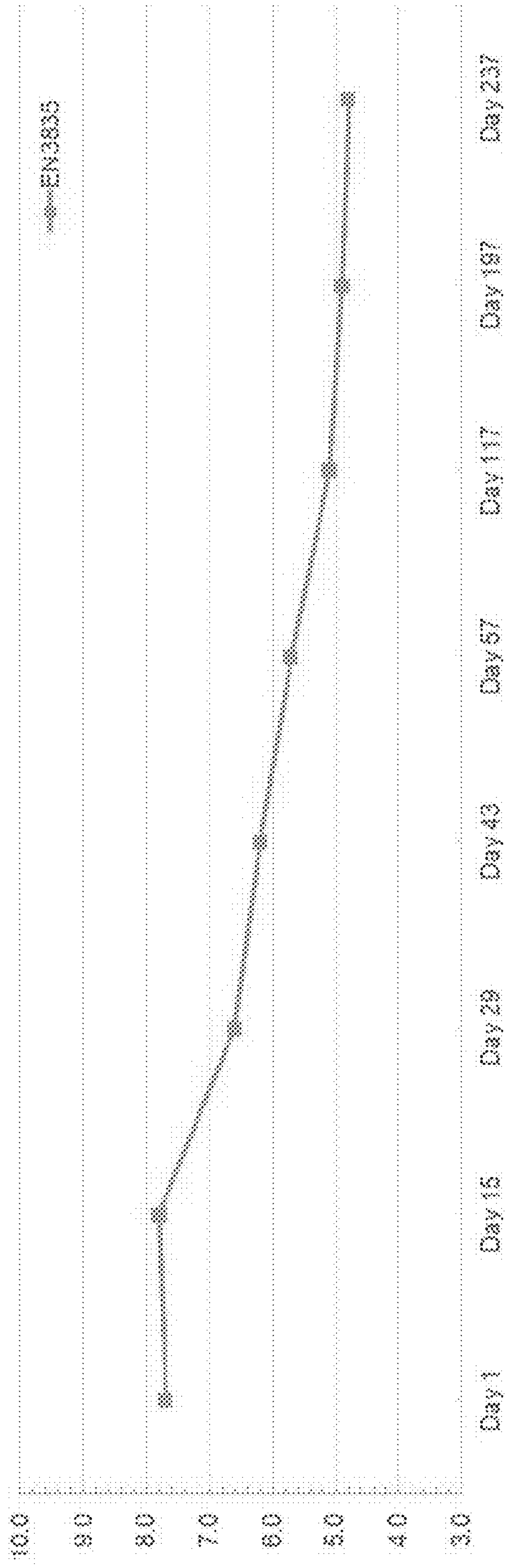
FIG. 29 illustrates Study 306 Part 2—Pain Intensity Numeric Rating Scale (Retreatment/First Treatment Overall Safety Population).

As shown in FIG. 29, EN3835 treated participants demonstrated improvement in NRS pain scores.

Figure 30:
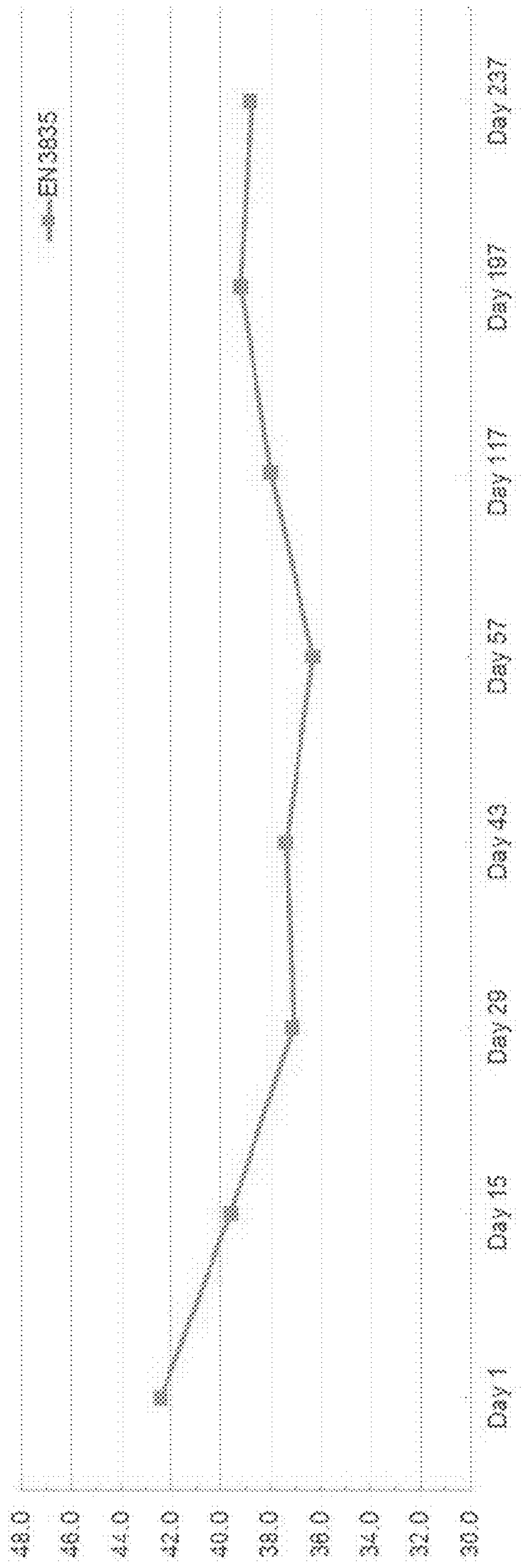
FIG. 30 illustrates Study 306 Part 2—Nodule Hardness (Retreatment/First Treatment Overall Safety Population).

As shown in FIG. 30, EN3835 treated participants demonstrated a small improvement in Nodule Hardness by durometer.

Figure 31:
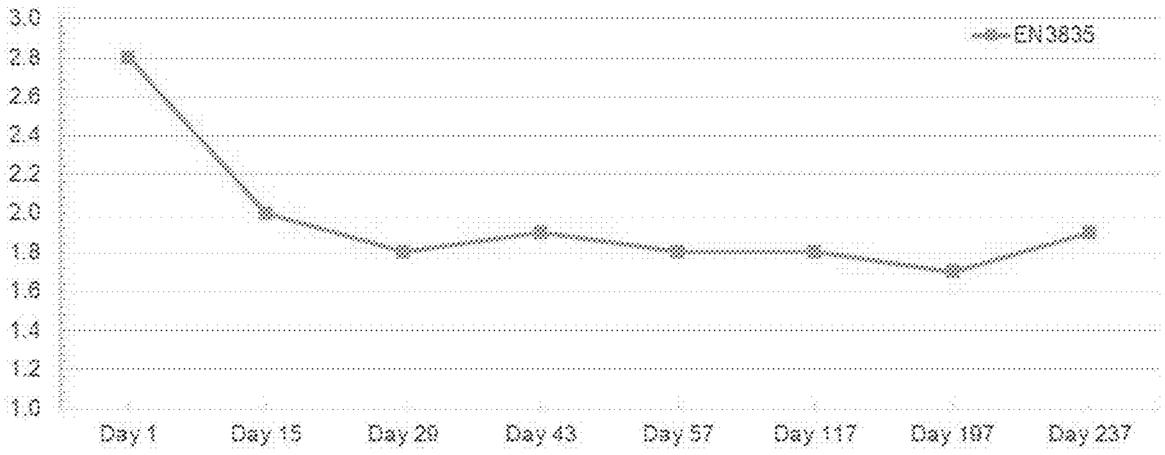
FIG. 31 illustrates Study 306 Part 2—Nodule Consistency (Firmness) (Retreatment/First Treatment Overall Safety Population).
Figure 31:
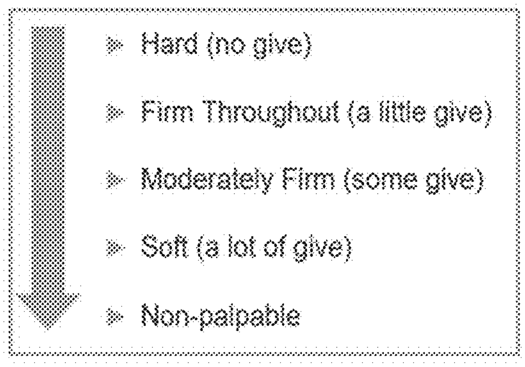

As shown in FIG. 31, EN3835 treated participants demonstrated improvement in Nodule Consistency.

Figure 32:
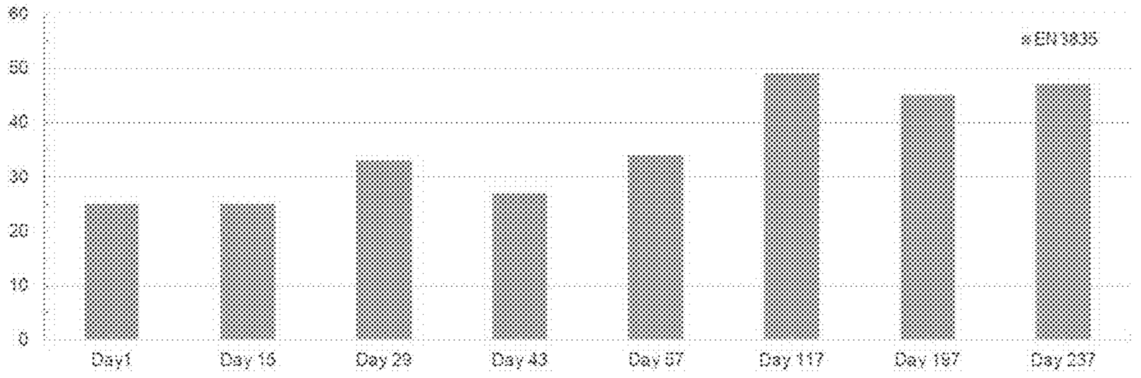
FIG. 32 illustrates Study 306 Part 2—Subject Satisfaction with Treatment (Retreatment/First Treatment Overall Safety Population).

As shown in FIG. 32, EN3835 treated participants demonstrated improvement in subject satisfaction over time.

Part 2—No Treatment/Observation Period EN3835 Participants from Phase 2

TABLE 100

Study 306 Part 2 - Participant Disposition in Open-label Observation Period (No Treatment/Observation Population of EN3835 Participants)

| | | Treatment Received in EN3835-222 EN3835 | Overall* |
|---|---|---|---|
| Participants Completed Day 180 Period | n | 57 | 128 |
| Participants opting to receive Treatment/Retreatment | n (%) | 26 (45.6) | 72 (56.3) |
| Participants continuing to participate in Observation Visits | n (%) | 31 (54.4) | 56 (43.8) |
| Completed | n (%) | 25 (80.6) | 45 (80.4) |
| Discontinued | n (%) | 6 (19.4) | 11 (19.6) |
| Adverse Event | n (%) | 0 (0.0) | 0 (0.0) |
| Lost to Follow-up | n (%) | 1 (3.2) | 3 (5.4) |
| Protocol Violation | n (%) | 0 (0.0) | 0 (0.0) |
| Withdrew Consent | n (%) | 5 (16.1) | 7 (12.5) |
| Open-label Observation Population | n (%) | 31 (100.0) | 56 (100.0) |

*Overall includes PCB, but table focuses on EN3835 only

TABLE 101

Study 306 Part 2 - Participant Demographics
(No Treatment/Observation Population of EN3835 Participants)

| | | Treatment Received in EN3835-222 EN3835 (N = 31) n (%) | Overall* (N = 56) n (%) |
|---|---|---|---|
| Age (years) | Mean (SD) | 57.1 (11.0) | 58.1 (10.3) |
| Gender | Male | 12 (38.7) | 19 (33.9) |
| | Female | 19 (61.3) | 37 (66.1) |
| Race | Black or African American | 2 (6.5) | 7 (12.5) |
| | White | 29 (93.5) | 49 (87.5) |

*Overall includes PCB, but table focuses on EN3835 only

TABLE 102

Study 306 Part 2 - Overall
Summary of AEs during Open-label Observatic Period
(No Treatment/Observation Population of EN3835 Participants)

| | EN3835 (N = 31) n (%) |
|---|---|
| Total Number of AEs Reported | 14 |
| Grade 1 (Mild) | 10 (71.4) |
| Grade 2 (Moderate) | 3 (21.4) |
| Grade 3 (Severe) | 1 (7.1) |
| Grade 4 (Life-Threatening) | 0 (0.0) |
| Grade 5 (Death) | 0 (0.0) |
| Number of Participants Reporting: | |
| At least one AE | 10 (32.3) |
| At least one Serious AE | 1 (3.2) |
| At least one Grade 3+ AE | 1 (3.2) |
| No Grade 3+ AEs, but at least one Grade 2 AE | 2 (6.5) |
| No Grade 3/Grade 2 AEs, but at least one Grade 1 AE | 7 (22.6) |
| At least one AE Leading to Withdrawal from Study | 0 (0.0) |
| At least one AE Leading to Drug Interruption/Discontinuation | 0 (0.0) |
| Number of Participants with any AEs Resulting in Death | 0 |

Most AEs were mild (Grade 1) to moderate (Grade 2)
13/14 (92.8%)
No AEs led to study withdrawal
No AEs led to drug interruption/discontinuation
2 Serious AEs:
1 on EN3835 (Based on treatment received in Study EN3835-222)
1 on PCB (Based on treatment received in Study EN3835-222)
No AESIs
No Deaths

TABLE 103

Study 306 Part 2 - Common
AEs (≥2%) during Open-label Observation Period
(No Treatment/Observation Population of EN3835 Participants)

| | EN3835 (N = 31) n (%) |
|---|---|
| Number of Participants at least one AE | 10 (32.3), 14 |
| System Organ Class Preferred Term (≥2%) | |
| Infections and infestations | 3 (9.7), 4 |
| COVID-19 | 1 (3.2), 2 |
| Vascular disorders | 1 (3.2), 1 |
| Hypertension | 1 (3.2), 1 |

Participants with Ongoing AEs
No ongoing AEs
AESI
No AESIs reported

Figure 33:
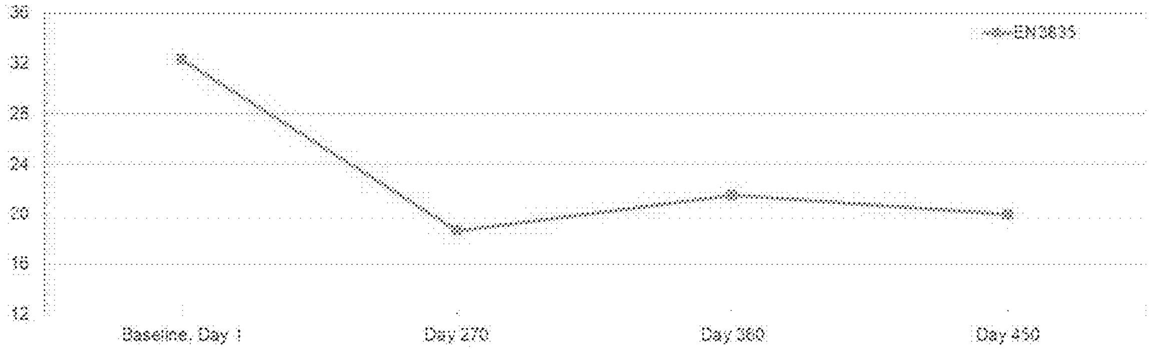
FIG. 33 illustrates Study 306 Part 2—FFI Composite Scores During Open-label Observation Period (No Treatment/Observation Population of EN3835 Participants).

As shown in FIG. 33, the treatment effects of EN3835 as measured by FFI composite scores were persistent with some improvement through Day 450.

Figure 34:
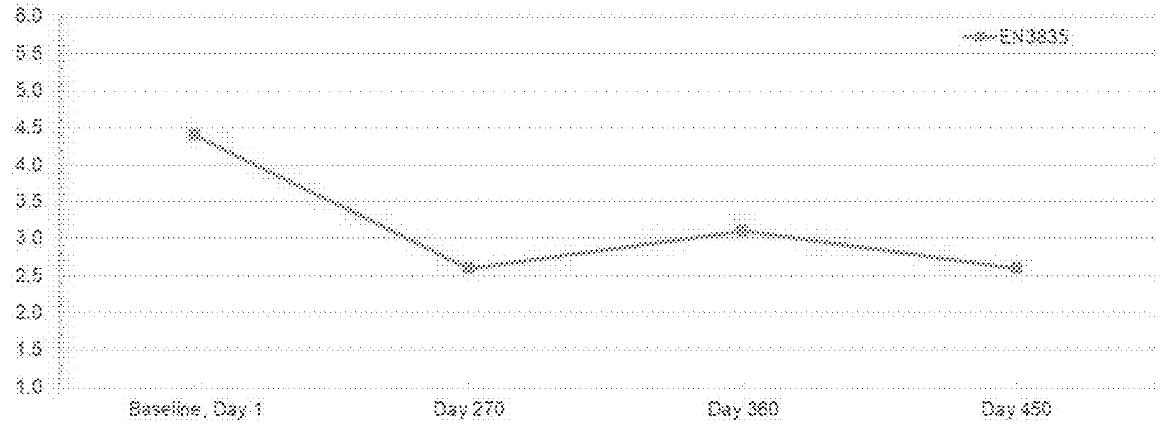
FIG. 34 illustrates Study 306 Part 2—PI-NRS Scores During Open-label Observation Period (No Treatment/Observation Population of EN3835 Participants).

As shown in FIG. 34, the treatment effects of EN3835 as measured by PI-NRS scores were persistent with some improvement through Day 450.

Figure 35:
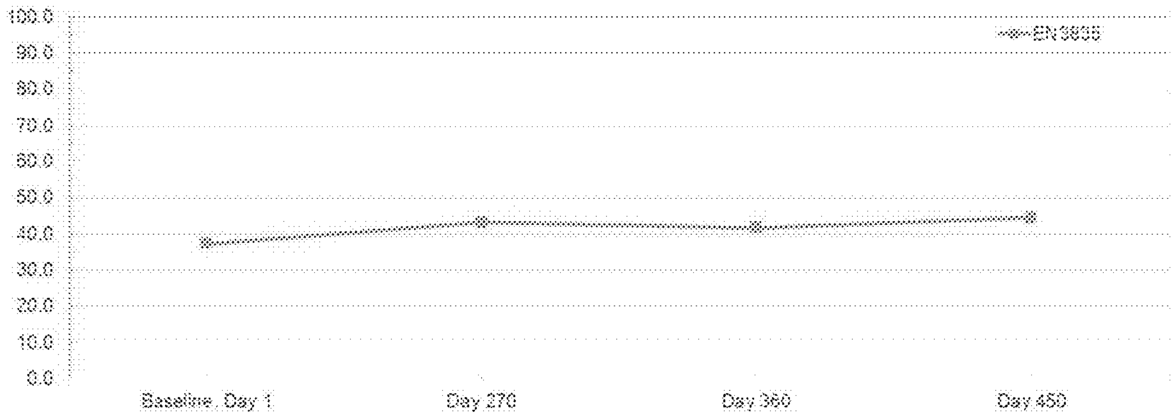
FIG. 35 illustrates Study 306 Part 2—Nodule Hardness during Open-label Observation Period (No Treatment/Observation Population of EN3835 Participants).

As shown in FIG. 35, nodule hardness by durometer in EN3835 treated patients was essentially unchanged through Day 450.

Figure 36:
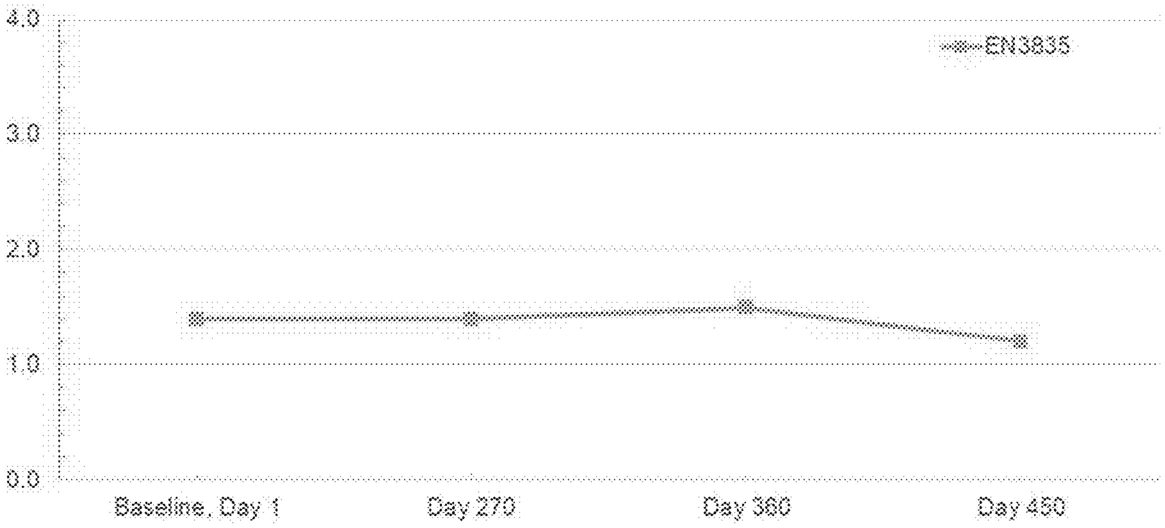
FIG. 36 illustrates Study 306 Part 2—Nodule Consistency During Open-label Observation Period (No Treatment/Observation Population of EN3835 Participants).
Figure 36:
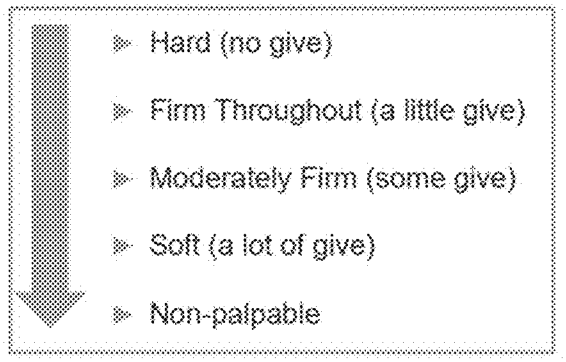

As shown in FIG. 36, no demonstrable worsening of nodule firmness in EN3835 treated participants was observed through Day 450.

Summary

Primary Endpoint (Safety): The study data demonstrates EN3835 was well tolerated and safe in the long-term for PFI participants. Participants treated in this study (Retreated and First treatment with EN3835) have a similar safety profile as seen in Study 222

Secondary Endpoints (Efficacy): Study data demonstrated persistent long-term treatment effect in participants treated with EN3835 in parent phase 2 study (EN3835-222). Study data demonstrated a similar treatment effect in participants retreated with EN3835 in this study. First Treatment participants experienced effects consistent with Study 222.

Discussion and Overall Conclusions

This study was a Phase 2, multicenter, open-label, 15-month extension study designed to evaluate the long-term safety, efficacy, and durability of EN3835 in the treatment and retreatment of plantar fibromatosis. Participants with unilateral or bilateral plantar fibromatosis that had completed the parent study (Study EN3835-222) had the option of being observed for up to 450 days or having previously treated nodules retreated (with up to 2 treatment sessions of EN3835) or having new nodules treated (with up to 2 treatment sessions of EN3835). The safety of EN3835 retreatment was demonstrated when administered in up to 4 treatments for up to 417 days during this study. Safety of EN3835 was also demonstrated when administered in up to 2 treatments (maximum dose of 1.8 mg per treatment) to newly treated participants for up to 237 days after the initial treatment. A persistent efficacy response was sustained at 450 days after EN3835 treatment. Throughout the study, participants and investigators continued to be blinded to the treatment received in the parent study.

EN3835 was well tolerated, with long term safety demonstrated in treated and retreated participants. During the study, there were no deaths or withdrawals from the study. While there were 6 participants with SAEs during the study, distributed equally between EN3835-and placebo treated participants, none were assessed as related to treatment Most AEs (>90%) in participants observed, treated, or retreated were mild to moderate in severity. In participants treated or retreated during the study, TEAEs were transient, resolving in <21 days. There was no increase in the frequency or severity of TEAEs in participants retreated with up to 4 treatments of EN3835. The most common TRAEs were ISRs of bruising, pain and swelling.

During the study, there were 3 AESIs of partial plantar fascial tears in EN3835-treated participants. In 1 participant, this was an ongoing AESI from the parent study. In participants newly treated with EN3835, there were 2 (2.7%) participants with AESIs of partial plantar fascial tears of mild and moderate severity that resolved or were resolving without further intervention. These events resulted in EN3835 discontinuation. There was no relationship between EN3835 dose administered or re-exposure and likelihood of having a tear. No new safety concerns were identified. Immunogenicity findings were consistent with findings observed in other studies of EN3835 in plantar fibromatosis. The safety profile in participants treated and retreated with EN3835 in this study was consistent with safety findings observed in the clinical development program for plantar fibromatosis in Studies EN3835-105 and -222.

The efficacy and durability of effect of administering up to 2 treatments of EN3835 was evaluated for up to 180 days after initial treatment in participants enrolling into this extension study. A persistent treatment effect was demonstrated in participants treated with EN3835 in Study EN3835-222. Improvements in the FFI Total Scales scores, and the subscales scores of activity limitation, difficulty, and pain, and scores on the Pain Intensity NRS were sustained at 180 days after treatment. More than half of all participants were responders as assessed on the Subject Satisfaction with Treatment and CGIC Scales. Mean (SD) nodule consistency scores were consistent with Baseline scores. Improvements on these scales occurred despite nodules becoming harder over time. There were no appreciable changes in nodule hardness following EN3835 treatment.

At Days 180 or 270, there were fewer EN3835-treated participants (26 participants; 37.1%) eligible to receive retreatment than placebo-treated participants (46 participants; 61.3%), demonstrating the efficacy of a treatment. Effectiveness was demonstrated for up to 237 days in participants opting to be treated in this study in an open-label manner with up to 2 treatments of EN3835) or retreated with up to 4 treatments of EN3835. Improvements in the FFI Total Score and subscales scores of activity limitation, difficulty, and pain, and scores on the Pain Intensity NRS were demonstrated in participants treated and retreated during the study. Changes on these scales were similar in magnitude and consistent amongst participants newly treated with EN3835, retreated with EN3835, and with the changes observed in treated participants at Day 57 of Study EN3835-222. Improvement in nodular consistency and nodule hardness as demonstrated. Participant satisfaction with treatment and the CGIC was indicated in treated and retreated participants, with the highest scores in retreated participants.

In participants that did not meet criteria for retreatment, and chose to be observed, a durable response of EN3835 was demonstrated on the FFI Total Scales scores, and the subscales scores of activity limitation, difficulty, and pain, and scores on the Pain Intensity NRS were sustained at 450 days after treatment. More than half of all EN3835 and placebo-treated participants treated were responders on the Subject Satisfaction with Treatment scale and more than two-thirds of EN3835 and placebo-treated participants were responders (ie, response "Minimal Improvement", "Much Improvement" or "Very Much Improvement") on the CGIC Scale. Mean (SD) nodule consistency scores were consistent with Baseline scores. Nodule hardness as measured by durometer in EN3835-treated participants was essentially unchanged. There was no demonstrable worsening of nodule consistency in EN3835 treated participants through Day 450.

In summary, the study results demonstrate the long-term safety, efficacy, and durability of retreatment and treatment with EN3835 in participants with plantar fibromatosis.

Primary Endpoint (Safety):

- EN3835 was well tolerated and demonstrated long-term safety in PFI participants.
- Participants retreated and "first treated" with EN3835 demonstrated a similar safety profile as seen in the clinical program to date.

Secondary Endpoints (Efficacy):

- A persistent treatment effect was seen in participants treated with EN3835 in Study 222.
- Retreatment with EN3835 resulted in a similar treatment effect in comparison to Study 222.
- First Treatment participants experienced effects consistent with Study 222.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

What is claimed:

1. A method of treating moderate to severe plantar fibromatosis in a subject or a population of subjects, the method comprising:

intralesionally injecting a pharmaceutical formulation comprising collagenase into one or more plantar fibromatosis nodules in one or both of the subject's feet or the population of subjects' feet to thereby treat the plantar fibromatosis, wherein the subject or the population of subjects have a baseline numerical rating scale (NRS) score of ≥5 and <10 and one or more plantar fibromatosis nodules assessed at baseline by palpation to be hard or firm throughout or during the 7 days prior to treatment, an average daily pain (ADP) score on the Pain Intensity NRS of 5 to 9 and one or more plantar fibromatosis nodules assessed at baseline by palpation to be hard or firm throughout, wherein the dose of collagenase administered per nodule comprises about 0.45 mg to about 1.35 mg, and the treating comprises:

an improvement from baseline in nodule consistency;

a reduction from baseline in the nodular hardness;

or a combination thereof.

2. The method of claim 1, wherein the reduction or improvement occurs at Day 85 or earlier.

3. The method of claim 1, wherein the reduction or improvement is an at least 1 point reduction from baseline in nodule hardness on a nodule hardness scale as measured by durometer or an at least 1 point improvement from baseline in nodule consistency on a nodule consistency scale as measured by palpation.

4. The method of claim 1, wherein the collagenase comprises collagenase I activity, collagenase II activity, or a mixture of collagenase I activity and collagenase II activity.

5. The method of claim 1, wherein the plantar fibromatosis nodule is less than or equal to 4 cm in size.

6. The method of claim 5, comprising administering a single injection of the collagenase to any nodule that is less than 2 cm in size.

7. The method of claim 5, comprising administering two injections of the collagenase to any nodule that is greater than 2 cm but less than 4 cm in size.

8. The method of claim 7, wherein each of the two injections comprises 0.3 mg of the collagenase.

9. The method of claim 1, wherein the collagenase has a concentration of about 0.6 mg/ml to about 2.25 mg/ml.

10. The method of claim 1, wherein the collagenase has a potency of about 500 SRC units/mg to about 30,000 SRC units/mg.

11. The method of claim 1, wherein about 5 SRC units to about 180,000 SRC units of collagenase are administered per nodule.

12. The method of claim 1, wherein the collagenase has a potency of about 10,000 GPA units/mg to about 400,000 GPA units/mg.

13. The method of claim 1, wherein about 1,000 GPA units to about 2,400,000 GPA units of collagenase are administered per nodule.

* * * * *

SEQUENCE LISTING

```
Sequence total quantity: 2
SEQ ID NO: 1            moltype = AA  length = 1008
FEATURE                 Location/Qualifiers
source                  1..1008
                        mol_type = protein
                        organism = synthetic construct
DOMAIN                  9..278
                        note = Activator domain
DOMAIN                  288..680
                        note = Peptidase domain
DOMAIN                  685..770
                        note = Collagen recruitment domain (PKD and CBD)
DOMAIN                  775..832
                        note = Collagen recruitment domain (PKD and CBD)
DOMAIN                  894..951
                        note = Collagen recruitment domain (PKD and CBD)
```

-continued

```
SEQUENCE: 1
IANTNSEKYD FEYLNGLSYT ELTNLIKNIK WNQINGLFNY STGSQKFFGD KNRVQAIINA  60
LQESGRTYTA NDMKGIETFT EVLRAGFYLG YYNDGLSYLN DRNFQDKCIP AMIAIQKNPN  120
FKLGTAVQDE VITSLGKLIG NASANAEVVN NCVPVLKQFR ENLNQYAPDY VKGTAVNELI  180
KGIEFDFSGA AYEKDVKTMP WYGKIDPFIN ELKALGLYGN ITSATEWASD VGIYYLSKFG  240
LYSTNRNDIV QSLEKAVDMY KYGKIAFVAM ERITWDYDGI GSNGKKVDHD KFLDDAEKHY  300
LPKTYTFDNG TFIIRAGEKV SEEKIKRLYW ASREVKSQFH RVVGNDKALE VGNADDVLTM  360
KIFNSPEEYK FNTNINGVST DNGGLYIEPR GTFYTYERTP QQSIFSLEEL FRHEYTHYLQ  420
ARYLVDGLWG QGPFYEKNRL TWFDEGTAEF FAGSTRTSGV LPRKSILGYL AKDKVDHRYS  480
LKKTLNSGYD DSDWMFYNYG FAVAHYLYEK DMPTFIKMNK AILNTDVKSY DEIIKKLSDD  540
ANKNTEYQNH IQELADKYQG AGIPLVSDDY LKDHGYKKAS EVYSEISKAA SLTNTSVTAE  600
KSQYFNTFTL RGTYTGETSK GEFKDWDEMS KKLDGTLESL AKNSWSGYKT LTAYFTNYRV  660
TSDNKVQYDV VFHGVLTDNA DISNNKAPIA KVTGPSTGAV GRNIEFSGKD SKDEDGKIVS  720
YDWDFGDGAT SRGKNSVHAY KKTGTYNVTL KVTDDKGATA TESFTIEIKN EDTTTPITKE  780
MEPNDDIKEA NGPIVEGVTV KGDLNGSDDA DTFYFDVKED GDVTIELPYS GSSNFTWLVY  840
KEGDDQNHIA SGIDKNNSKV GTFKATKGRH YVFIYKHDSA SNISYSLNIK GLGNEKLKEK  900
ENNDSSDKAT VIPNFNTTMQ GSLLGDDSRD YYSFEVKEEG EVNIELDKKD EFGVTWTLHP  960
ESNINDRITY GQVDGNKVSN KVKLRPGKYY LLVYKYSGSG NYELRVNK            1008

SEQ ID NO: 2           moltype = AA  length = 991
FEATURE                Location/Qualifiers
source                 1..991
                       mol_type = protein
                       organism = synthetic construct
DOMAIN                 18..290
                       note = Activator domain
DOMAIN                 301..691
                       note = Peptidase domain
DOMAIN                 695..780
                       note = Collagen recruitment domain (PKD and CBD)
DOMAIN                 784..843
                       note = Collagen recruitment domain (PKD and CBD)
DOMAIN                 873..930
                       note = Collagen recruitment domain (PKD and CBD)
SEQUENCE: 2
AVDKNNATAA VQNESKRYTV SYLKTLNYYD LVDLLVKTEI ENLPDLFQYS SDAKEFYGNK  60
TRMSFIMDEI GRRAPQYTEI DHKGIPTLVE VVRAGFYLGF HNKELNEINK RSFKERVIPS  120
ILAIQKNPNF KLGTEVQDKI VSATGLLAGN ETAPPEVVNN FTPIIQDCIK NMDRYALDDL  180
KSKALFNVLA APTYDITEYL RATKEKPENT PWYGKIDGFI NELKKLALYG KINDNNSWII  240
DNGIYHIAPL GKLHSNNKIG IETLTEVMKI YPYLSMQHLQ SADQIERHYD SKDAEGNKIP  300
LDKFKKEGKE KYCPKTYTFD DGKVIIKAGA RVEEEKVKRL YWASKEVNSQ FFRVYGIDKP  360
LEEGNPDDIL TMVIYNSPEE YKLNSVLYGY DTNNGGMYIE PDGTFFTYER KAEESTYTLE  420
ELFRHEYTHY LQGRYAVPGQ WGRTKLYDND RLTWYEEGGA ELFAGSTRTS GILPRKSIVS  480
NIHNTTRNNR YKLSDTVHSK YGASFEFYNY ACMFMDYMYN KDMGILNKLN DLAKNNDVDG  540
YDNYIRDLSS NHALNDKYQD HMQERIDNYE NLTVPFVADD YLVRHAYKNP NEIYSEISEV  600
AKLKDAKSEV KKSQYFSTFT LRGSYTGGAS KGKLEDQKAM NKFIDDSLKK LDTYSWSGYK  660
TLTAYFTNYK VDSSNRVTYD VVFHGYLPNE GDSKNSLPYG KINGTYKGTE KEKIKFSSEG  720
SFDPDGKIVS YEWDFGDGNK SNEENPEHSY DKVGTYTVKL KVTDDKGESS VSTTTAEIKD  780
LSENKLPVIY MHVPKSGALN QKVVFYGKGT YDPDGSIAGY QWDFGDGSDF SSEQNPSHVY  840
TKKGEYTVTL RVMDSSGQMS EKTMKIKITD PVYPIGTEKE PNNSKETASG PIVPGIPVSG  900
TIENTSDQDY FYFDVITPGE VKIDINKLGY GGATWVVYDE NNNAVSYATD DGQNLSGKFK  960
ADKPGRYYIH LYMFNGSYMP YRINIEGSVG R                               991
```